United States Patent
Ogawa et al.

(10) Patent No.: US 6,956,033 B2
(45) Date of Patent: Oct. 18, 2005

(54) 3,4-DIHYDROISOQUINOLINE DERIVATIVE COMPOUND AND A PHARMACEUTICAL AGENT COMPRISING IT AS ACTIVE INGREDIENT

(75) Inventors: Mikio Ogawa, Mishima-gun (JP); Yoshikazu Takaoka, Mishima-gun (JP); Akira Ohhata, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 109 days.

(21) Appl. No.: 10/333,591

(22) PCT Filed: Jul. 30, 2001

(86) PCT No.: PCT/JP01/06541

§ 371 (c)(1),
(2), (4) Date: May 15, 2003

(87) PCT Pub. No.: WO02/10135

PCT Pub. Date: Feb. 7, 2002

(65) Prior Publication Data

US 2004/0077643 A1 Apr. 22, 2004

(30) Foreign Application Priority Data

Aug. 1, 2000 (JP) .................................. 2000-232911

(51) Int. Cl.$^7$ .................. C07D 401/02; A61K 31/47
(52) U.S. Cl. .................. 514/230.5; 514/307; 546/139; 546/146; 544/105
(58) Field of Search .............. 514/230.5, 307; 546/139, 146; 544/105

(56) References Cited

U.S. PATENT DOCUMENTS

| | | | |
|---|---|---|---|
| 5,532,237 A | 7/1996 | Gallant et al. | |
| 6,017,919 A | 1/2000 | Inaba et al. | |

FOREIGN PATENT DOCUMENTS

| | | | |
|---|---|---|---|
| FR | 2 783 246 A | 3/2000 | |
| GB | 1122212 A | 8/1965 | |
| GB | 1122212 A | 7/1968 | |
| WO | WO 97/29079 A1 | 8/1997 | |
| WO | WO 98/41519 A1 | 9/1998 | |

OTHER PUBLICATIONS

Partial European Search Report dated Jul. 21, 2004.

Mikhailovskii, A.G. et al., Reaction of Enamines of the Isocholine and Phenanthridine Series with Oxalyl Chloride, (1994), vol. 30, No. 7, pp. 946–949.

A.G. Mikhailovsky, et al., "Reaction of Isoquinoline and Phernanthridine Enamines with Oxalyl Chloride", (1994), No. 7, pp. 946 to 949.

*Primary Examiner*—Zinna Northington Davis
(74) *Attorney, Agent, or Firm*—Sughrue Mion, PLLC

(57) ABSTRACT

A 3,4-dihydroisoquinoline derivative compound of formula (I) or a non-toxic salt thereof and a pharmaceutical agent comprising it as active ingredient (wherein all symbols have the same meaning as described in the specification). The compound of formula (I) has agonizing activity on CB2 receptor and therefore it is useful for the prophylaxis and/or treatment of various diseases such as asthma, nasal allergy, atopic dermatitis, autoimmune diseases, rheumatoid arthritis, immune dysfunction, postoperative pain, carcinomatous pain, etc.

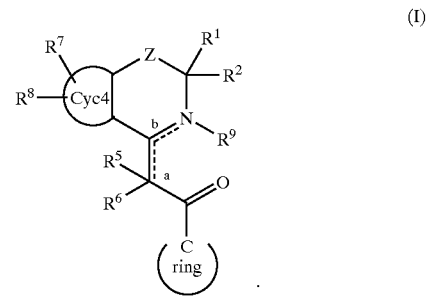

(I)

14 Claims, No Drawings

3,4-DIHYDROISOQUINOLINE DERIVATIVE COMPOUND AND A PHARMACEUTICAL AGENT COMPRISING IT AS ACTIVE INGREDIENT

TECHNICAL FIELD

The present invention relates to a 3,4-dihydroisoquinoline derivative.

More particularly, the present invention relates to
(1) a compound of formula (I)

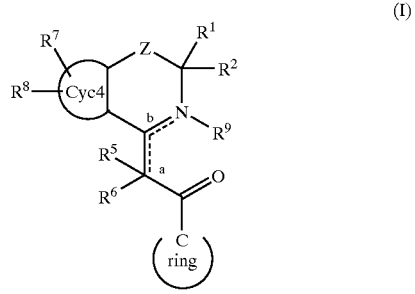

(wherein all symbols have the same meaning as hereafter described) and a non-toxic salt thereof,
(2) a method for the preparation thereof and
(3) a pharmaceutical agent comprising it as active ingredient.

BACKGROUND OF THE INVENTION

The cannabinoid is a generic name of Δ9-tetrahydrocannabinol (abbreviated as Δ9-THC hereafter), which is a main ingredient of marijuana, which is made from hemp, and its analogues (Deway, Pharmacol. Rev., 38, 15–178 (1996)), and it is known as a substance which causes euphoria, sleepiness, hallucination, relief from mental tense, etc (Hollister, Pharmacol. Rev., 38, 1–20 (1986)).

Aside from the previous central effects, it is reported that the reactivity of lymphocytes is decreased in habitual users of marijuana (Naha et al., Science, 183, 419–420 (1974)), that marijuana or Δ9-THC lowers the ability of leucocytes migration and the function of macrophages in vitro (Schwartzfarb et al., J. Clin. Pharmacol., 14, 35–41 (1974); Lopez-Capero et al., J. Leuk. Biol., 39, 679–686 (1986)), and that it lowers the resistance to virus infection (Morahan etc., Infect. Immun., 23, 670–674 (1979)), etc. These facts imply that cannabinoids act not only on central nervous system but also on peripheral system (especially immune system).

The first reported cannabinoid receptor is the CB1 receptor, which was cloned from a rat cerebral cortex cDNA library in 1990 (Matsuda et al., Nature., 346, 561–564 (1990)). Afterwards, the CB2 receptor was cloned from a cDNA library of HL-60, a human promyelogenic leukemia cell line (Murano, et al., Nature., 365, 61–65 (1993)). It was revealed that the CB1 receptors are mainly expressed in brains and CB2 receptors in those cells which are responsible for immunity, e.g. splenic cells.

It had been conceived to adapt cannabinoids to medical care for a long time (Mechiulan, CRC Press, Boca Raton., 1–20 (1986); Razdan et al., Med. Res. Rev., 3, 119–146 (1983)), and some of them have already been used as medical drug such as Cesamet (Ward and Holmes, Drugs., 3, 127–144 (1985)). These are conceived to take effect via the CB1 receptor.

On the other hand, the physiological roles of the CB2 receptor, which is a peripheral receptor, is not revealed enough yet, but it is suggested that a compound which acts specifically on the CB2 receptor (agonist, antagonist) modulates inflammation and/or immune system. Moreover, it is expected that it is effective for an inflammation pain. (Calignano et al., Nature., 394, 277–281 (1998)).

From these evidences, those compounds which act on the CB2 receptor specifically, are useful for the prevention and/or treatment of various diseases such as asthma, nasal allergy, atopic dermatitis, autoimmune diseases, rheumatoid arthritis, immune dysfunction, postoperative pain, carcinomatous pain, etc.

Isoquinoline derivatives are known as follows: for example, in JP63-280069(A), it is disclosed that a compound of formula (A)

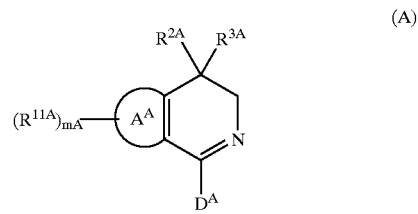

(wherein $A^A$ is benzo or thieno and $R^{2A}$ and $R^{3A}$ are independently hydrogen or (C1~5)alkyl, or taken together with the carbon atom to which they are attached to form 5 or 6 membered carbocycle and $R^{11A}$ is (C1~4)alkyl, halogen, hydroxy and mA is 0, 1, 2 or 3 when $A^A$ is benzo, $D^A$ is $Ib^A$, etc.:

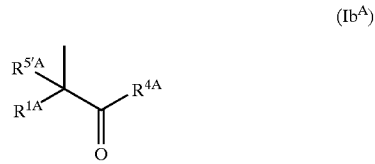

$R^{1A}$ is hydrogen, (C1~10)alkyl etc, $R^{5'A}$ is hydrogen or (C1~4)alkyl, $R^{4A}$ is (C1~4)alkoxy or —$NR^{9A}R^{10A}$ (wherein $R^{9A}$ and $R^{10A}$ are independently hydrogen, C1~12 branched or unbranched alkyl, alkenyl or alkynyl, etc., or $R^{9A}$ and $R^{10A}$ are taken together with the carbon atom to which they are attached to form pyrrolidinyl, piperidinyl, morpholinyl or piperazinyl, etc.)) has cardioprotective activity (groups are extracted for description).

Khim. Geterotsikl. Soedin., 946–949, 7, (1994) discloses a compound of 2-(3,3-dimethyl-3,4-dihydro-(2H)-isoquinoline-1-ylidene)-1-phenylmethan-1-one (Reg No. 163769-77-5).

DISCLOSURE OF THE INVENTION

The present inventors have energetically investigated to find out such compounds that bind to the CB2 receptor specifically, to find out that a 3,4-dihydroisoquinoline derivative of formula (I) accomplishes the purpose, and completed the present invention.

The present invention relates to
(1) a 3,4-dihydroisoquinoline derivative compound of formula (I)

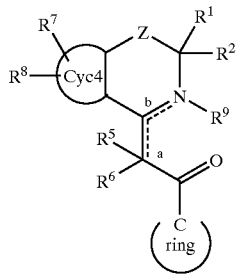

(wherein $R^1$ and $R^2$ are each independently
1) hydrogen, or
2) C1~8 alkyl or
$R^1$ and $R^2$ are taken together with carbon atom to which they are attached to form Cyc1, with proviso that $R^1$ and $R^2$ do not represent hydrogen at the same time.
Z is
1) —$CR^3R^4$—, or
2) —O—,
$R^3$ and $R^4$ are each independently,
1) hydrogen,
2) C1~8 alkyl,
3) C1~8 alkoxy or
4) hydroxy, or
$R^3$ and $R^4$ are taken together with carbon atom to which they are attached to form Cyc1 or —C(O)—,
$R^5$ and $R^6$ are each independently,
1) hydrogen or
2) C1~8 alkyl, or
$R^5$ and $R^6$ are taken together with carbon atom to which they are attached to form Cyc1,
Cyc1 represented by $R^1$ and $R^2$, $R^3$ and $R^4$, $R^5$ and $R^6$ is each independently,
1) C3~10 cycloalkyl or
2) 3~10 membered mono-cyclic heteroring comprising 1~2 of heteroring selected from oxygen, nitrogen or sulfur,
Cyc1 may be substituted with $R^{10}$.
$R^{10}$ is
1) C1~8 alkyl, 2) C1~8 alkoxy, 3) hydroxy, 4) —$COOR^{11}$, 5) keto, 6) —$SO_2R^{12}$, or 7) —$COR^{13}$,
$R^{11}$ is hydrogen or C1~8 alkyl,
$R^{12}$ and $R^{13}$ are, 1) C1~8 alkyl or 2) phenyl which may be substituted with C1~8 alkyl.
$R^7$ and $R^8$ are each independently,
1) hydrogen,
2) C1~8 alkyl,
3) C1~8 alkoxy,
4) hydroxy,
5) cyano,
6) halogen,
7) —$COOR^{14}$,
8) —$CONR^{15}R^{16}$,
9) Cyc2,
10) C2~8 alkenyl,
11) C2~8 alkynyl,
12) —$NR^{51}R^{52}$,
13) nitro,
14) formyl,
15) C2~8 acyl,
16) C1~8 alkyl substituted with hydroxy, C1~8 alkoxy, Cyc2, —$NR^{51}R^{52}$ or —$NR^{53}$— Cyc2, 17) —$NR^{54}COR^{55}$,
18) —$NR^{56}SO_2R^{57}$,
19) —$SO_2NR^{58}R^{59}$,
20) C2~8 alkenyl substituted with —$COOR^{14}$,
21) —CH=N—OH,
22) —(C1~8 alkylene)—$NR^{60}$—(C1~8alkylene)—$R^{61}$ or
23) C1~8 alkylthio.
$R^{14}$ is hydrogen or C1~8 alkyl,
$R^{15}$ and $R^{16}$ are each independently, hydrogen or C1~8 alkyl,
$R^{51}$ and $R^{52}$, $R^{53}$ and $R^{59}$ are each independently, hydrogen or C1~8 alkyl,
$R^{53}$, $R^{54}$, $R^{56}$ and $R^{60}$ are each independently hydrogen or C1~8 alkyl,
$R^{55}$ is hydrogen, C1~alkyl, or C1~8 alkoxy,
$R^{57}$ is C1~8 alkyl,
$R^{61}$ is —$NR^{62}R^{63}$ or hydroxy,
$R^{62}$ and $R^{63}$ are each independently, hydrogen or C1~8 alkyl.

(abbreviated as ring hereafter.)
is Cyc2, but the atom which attaches to carbonyl is carbon.
Cyc2, represented by $R^7$, $R^8$ and Ring, is each independently,
1) C3~15 mono-, bi- or tri-cyclic (fused or spiro) carbocyclic ring or
2) 3~15 membered mono-, bi- or tri-cyclic(fused or spiro) heteroring comprising 1~4 of hetero atom selected from oxygen, nitrogen or sulfur,
Cyc2 may be substituted with 1~5 of $R^{17}$.
$R^{17}$ is
1) C1~8 alkyl, 2) C2~8 alkenyl, 3) C2~8 alkynyl, 4) C1~8 alkoxy, 5) C1~8 alkylthio, 6) hydroxy, 7) halogen, 8) nitro, 9) keto, 10) carboxy, 11) formyl, 12) cyano, 13) —$NR^{18}R^{19}$, 14) phenyl, phenoxy or phenylthio which may be substituted with 1~5 of $R^{20}$, 15) C1~8 alkyl, C2~8 alkenyl, C1~8 alkoxy or C1~8 alkylthio which may be substituted with 1~5 of $R^{21}$, 16) —$OCOR^{22}$, 17) —$CONR^{23}R^{24}$, 18) —$SO_2NR^{25}R^{26}$, 19) —$COOR^{27}$, 20) —$COCOOR^{28}$, 21) —$COR^{29}$, 22) —$COCOR^{30}$, 23) —$NR^{31}COR^{32}$, 24) —$SO_2R^{33}$, 25) —$NR^{34}SO_2R^{35}$, or 26) —$SOR^{64}$.
$R^{18}$ and $R^{19}$, $R^{31}$ and $R^{34}$ are each independently, hydrogen or C1~8 alkyl,
$R^{20}$ and $R^{21}$ are, C1~8 alkyl, C1~8 alkoxy, hydroxy, halogen, nitro, or —$COOR^{36}$,
$R^{22}$ and $R^{64}$ are each independently, C1~8 alkyl,
$R^{23}$ and $R^{24}$, $R^{25}$ and $R^{26}$ are each independently, hydrogen, C1~8 alkyl, or phenyl,
$R^{27}$, $R^{28}$, $R^{29}$, $R^{30}$, $R^{32}$, $R^{33}$ and $R^{35}$ are,
1) C1~8 alkyl, 2) C2~8 alkenyl, 3) C1~8 alkyl substituted with 1–5 of $R^{37}$, 4) diphenylmethyl, 5) triphenylmethyl, 6) Cyc3, 7) C1~8 alkyl or C2~8 alkenyl substituted with Cyc3, 8) C1~8 alkyl substituted with —O-Cyc3, —S-Cyc3 or —$SO_2$— Cyc3.
$R^{36}$ is hydrogen or C1~8 alkyl,
$R^{37}$ is C1~8 alkoxy, C1~8 alkylthio, benzyloxy, halogen, nitro or —$COOR^{38}$,
$R^{38}$ is hydrogen, C1~8 alkyl or C2~8 alkenyl, Cyc3 is
1) C3~15 mono-, bi- or tri-cyclic (fused or spiro) carboring, or
2) 3–15 membered mono-, bi- or tri-cyclic (fused or spiro) heteroring comprising 1~4 of heteroring selected from oxygen, nitrogen or sulfur, Cyc3 may be substituted with 1~5 of $R^{39}$.

$R^{39}$ is
1) C1~8 alkyl, 2) C2~8 alkenyl, 3) C2~8 alkynyl, 4) C1~8 alkoxy, 5) C1~8 alkylthio, 6) hydroxy, 7) halogen, 8) nitro, 9) keto, 10) cyano, 11) benzyl, 12) benzyloxy, 13) C1~8 alkyl, C1~8 alkoxy or C1~8 alkylthio substituted with 1~5 of $R^{40}$, 14) phenyl, phenoxy, phenylthio, phenylsulfonyl or benzoyl, which may be substituted with 1~5 of $R^{41}$, 15) —$OCOR^{42}$, 16) —$SO_2R^{43}$, 17) —$NR^{44}COR^{45}$, 18) —$SO_2NR^{46}R^{47}$, 18) —$COOR^{48}$, or 19) —$NR^{49}R^{50}$.

$R^{40}$ is halogen,
$R^{41}$ is C1~8 alkyl, C1~8 alkoxy, halogen or nitro,
$R^{42}$, $R^{43}$ and $R^{45}$ are C1~8 alkyl,
$R^{44}$ and $R^{48}$ are, hydrogen or C1~8 alkyl,
$R^{46}$ and $R^{47}$, $R^{49}$ and $R^{50}$ are each independently, hydrogen or C1~8 alkyl.

Cyc4 is
1) C5~7 mono-cyclic carboring or
2) 5–7 membered mono-cyclic heteroring comprising 1–2 of heteroatom selected from a group consisting of oxygen, nitrogen or sulfur.

a
-----

(abbreviated as broken line a hereafter.)
and b
-----

(abbreviated as broken line b hereafter)
is
1) a bond or 2) a double bond.
$R^9$ is 1) absent or 2) hydrogen.
with proviso that,
1) when broken line a is a bond, then broken line b is a double bond and $R^9$ is absent,
2) when broken line a is a double bond, then broken line b is a bond and $R^9$ is hydrogen and $R^6$ is absent, and
3) 2-(3,3-dimethyl-3,4-dihydro-(2H)-isoquinolin-1-ylidene)-1-phenylethan-1-one is excluded), or a non-toxic salt thereof,
(2) a method for the preparation thereof and
(3) a pharmaceutical agent comprising them as active ingredient.

In the formula (I), C1~8 alkyl is methyl, ethyl, propyl, butyl, pentyl, hexyl, heptyl, octyl and isomers thereof.

In the formula (I), C2~8 alkenyl is ethenyl, propenyl, butenyl, pentenyl, hexenyl, heptenyl, octenyl and isomers thereof.

In the formula (I), C2~8 alkynyl is ethynyl, propynyl, butynyl, pentynyl, hexynyl, heptynyl, octynyl and isomers thereof.

In the formula (I), C1~18 alkoxy is methoxy, ethoxy, propoxy, butoxy, pentyloxy, hexyloxy, heptyloxy, octyloxy and isomers thereof.

In the formula (I), C1~8 alkylthio is methylthio, ethylthio, propylthio, butylthio, pentylthio, hexylthio, heptylthio, octylthio and isomers thereof.

In the formula (I), halogen is chlorine, bromine, fluorine, iodine atom.

In the formula (I), C3~10 cycloalkyl is cyclopropyl, cyclobutyl, cyclopentyl, cyclohexyl, cycloheptyl, cyclooctyl, cyclononyl, cyclodecyl.

In the formula (I), C2~8 acyl is acetyl, propanoyl, butanoyl, pentanoyl, hexanoyl, heptanoyl, octanoyl and isomers thereof.

In the formula (I), C1~8 alkylene is methylene, ethylene, trimethylene, tetramethylene, pentamethylene, hexamethylene, heptamethylene, octamethylene and isomers thereof.

In the formula (I), C5~7 mono-cyclic carboring is, for example, cyclopentane, cyclohexane, cycloheptane, cyclopentene, cyclohexene, cycloheptene, cyclopentadiene, cyclohexadiene, cycloheptadiene, benzene, etc.

In the formula (I), 5~7 membered mono-cyclic heteroring comprising 1~2 of heteroatom selected from oxygen, notrogen or sulfur is, 5~7 membered mono-cyclic heteroaryl comprising 1–2 of heteroatom selected from oxygen, nitrogen or sulfur or partially or completely saturated ones thereof.

5~7 membered mono-cyclic heteroaryl comprising 1–2 of heteroatom selected from oxygen, nitrogen or sulfur is, for example, pyrrole, imidazole, pyrazole, pyridine, pyrazine, pyrimidine, pyridazine, azepine, diazepine, furan, pyran, oxepin, thiophene, thiain (thiopyran), thiepin, oxazole, isoxazole, thiazole, isothiazole, oxazine, oxazepine, thiazine, thiazepine, etc.

Partially or completely saturated 5~7 membered mono-cyclic heteroaryl comprising 1–2 of heteroatom selected from oxygen, nitrogen or sulfur is, for example, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisooxazole, tetrahydroisooxazole, dihydrothiazole, tetrahydrothiazole, dihydroisothiazole, tetrahydroisothiazole, tetrahydroxazepine, perhydroxazepine, tetrahydrothiazepine, perhydrothiazepine, morpholine, thiomorpholine, dioxolane, dioxane, dithiolane, dithian ring, etc.

In the formula (I), 3–10 membered mono-cyclic heteroring comprising 1–2 of heteroatom selected from 1–2 of oxygen, nitrogen or sulfur is, 3–10 membered mono-cyclic heteroaryl comprising 1–2 of heteroatom selected from 1–2 of oxygen, nitrogen and sulfur and completely saturated one thereof.

Completely saturated 3–10 membered mono-cyclic heteroaryl comprising 1–2 of heteroatom selected from 1–2 of oxygen, nitrogen or sulfur is, for example, pyrrolidine, imidazolidine, pyrazolidine, piperidine, piperazine, perhydropyrimidine, perhydropyridazine, perhydroazepine, perhydrodiazepine, tetrahydrofuran, tetrahydropyran, tetrahydrothiophene, tetrahydrothiain (tetrahydrothiopyran), tetrahydrooxazole, tetrahydroisooxazole, tetrahydrothiazole, tetrahydroisothiazole, perhydroxazepine, perhydrothiaazepine, morpholine, thiomorpholine, dioxolane, dioxane, dithiolane, dithiane ring, etc.

In the formula (I), C3~15 mono-, bi- or tri-cyclic (fused or spiro) carboring is, for example, cyclopropane, cyclobutane, cyclopentane, cyclohexane, cycloheptane, cyclooctane, cyclononane, cyclodecane, cycloundecane, cyclododecane, cyclotridodecane, cyclopentene, cyclohexene, cyloheptene, cyclooctene, cyclopentadiene, cyclohexadiene, cycloheptadiene, cyclooctadiene, benzene, indene, naphthalene, indan, tetrahydronaphthalene, bicyclo [3.3.0]octane, bicyclo[4.3.0]nonane, bicyclo[4.4.0]decane, spiro[4.4]nonane, spiro[4.5]decane, cpiro[5.5]undecane, fluorene, anthracene, 9,10dihydroanthracene, bicyclo[3.1.1] heptane, bicyclo[3.3.1]-2-heptene, adamantane, noradamantane, bicyclo[2.2.2]octane, etc.

In the formula (I), 3~15 membered mono-, bi- or tri-cyclic (fused or spiro) heteroring comprising 1~4 of heteroatom selected from oxygen, nitrogen or sulfur is 3~15 membered mono-, bi- or tri-cyclic (fused or spiro) heteroaryl comprising 1~4 of heteroatom selected from oxygen, nitrogen or sulfur or partially or completely saturated ones thereof.

3~15 membered mono-, bi- or tri-cyclic (fused or spiro) heteroaryl comprising 1~4 of heteroatom selected from oxygen, nitrogen or sulfur is, for example, pyrrole, imidazole, triazole, tetrazole, pyrazole, pyridine, pyrazine, pyrimidine, pyridazine, azepine, diazepine, furan, pyran, oxepin, thiophene, thiaine (thiopyran), thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, pyrazolo[5,4-b]pyridine, benzoxepin, benzoxazepine, benzoxadiazepine, benzodiazepine, benzofurazane, benzothiadiazole, benzotriazole, carbazole, acridine, dibenzofuran, dibenzothiophene, phenothiazine, etc.

Partially or completely saturated 3~15 membered mono-, bi- or tri-cyclic (fused or spiro) heteroaryl comprising 1~4 of heteroatom selected from oxygen, nitrogen or sulfur is, for example, pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiaine (dihydrothiopyran), tetrahydrothiain (tetrahydrothipyran), dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrooxadiazole, tetrahydrooxadiazole (oxadiazolidine), dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, benzodioxane, chroman, benzodithiolane, benzodithiane, 2,4,6-trioxaspiro [bicyclo[3.3.0]octan-3,1'-cyclohexan]1,3-dioxorano[4,5-g] chlomene, 2-oxabicyclo[2.2.1]heptane ring, etc.

Unless otherwise specified, all isomers are included in the present invention. For example, alkyl, alkoxy and alkylene groups include straight-chain and also branched-chain ones. In addition, isomers in double bond(s), ring(s), fused ring(s) (E-, Z-, cis-, trans-isomer), isomers generated from asymmetric carbon(s) etc. (R-, S-, α-, β-isomer, enantiomer, diastereomer), optically active isomers having optical rotation (D-, L-, d-, l-isomer), polar compounds separated by chromatography (more polar compound, less polar compound), equilibrium compounds, mixtures thereof at arbitrary ratios and racemic mixtures are all included in the present invention.

In the present invention, as may be easily understood by those skilled in the art, the symbol: ⫼ indicates that the substituent attached thereto is behind the sheet (α-position) unless specified, ⫽ indicates that the substituent attached thereto is in front of the sheet (β-position) unless specified, ⫾ indicates that the substituent attached thereto is in β-position or α-position or a mixture thereof, and ⫿ indicates that the substituent attached thereto is a mixture of β-position and α-position.

In the compound of formula (I), a compound wherein broken line a is a double bond, broken line b is a single bond, $R^9$ is hydrogen and $R^6$ is absent, i.e. the compound of formula (Ia), and a compound wherein broken line a is a single bond, a broken line b is a double bond, $R^6$ is hydrogen and $R^9$ is absent, i.e. the compound of formula (Ib) are tautomers.

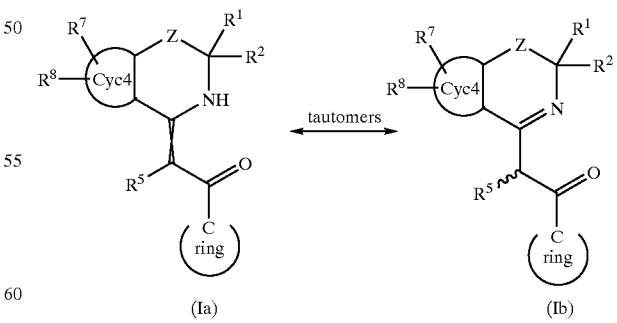

(wherein all symbols have the same meanings as hereinbefore described.)

And the compound of formula (Ia) also includes the compound of formula (Ia') and the compound of formula (Ia") and mixtures thereof.

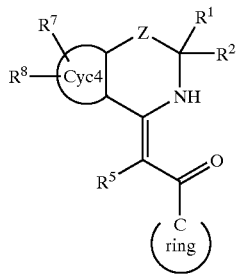

(Ia')

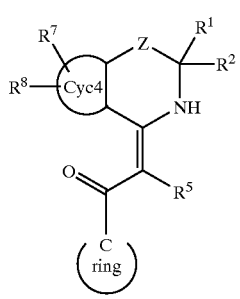

(Ia")

(wherein all symbols have the same meanings as hereinbefore described.)

The compound of formula (I) may be converted to a non-toxic salt by conventional methods.

Non-toxic salts include salts of alkali metals, salts of alkaline-earth metals, ammonium salts, amine salts and acid-addition salts, etc.

Non-toxic and water-soluble salts are preferable. Appropriate salts include salts of alkali metals (potassium, sodium, etc.), salts of alkaline-earth metals (calcium, magnesium, etc.), ammonium salts, pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl) aminomethane, lysine, arginine, N-methyl-D-glucamine, etc.).

Non-toxic and water-soluble acid-addition salts are preferable. Appropriate acid-addition salts include, salts of inorganic acid, e.g. hydrochloride, hydrobromide, hydroiodide, sulfate, phosphate, nitrate, or salts of organic acid, e.g. acatate, lactate, tartarate, benzoate, citrate, methanesulfonate, ethanesulfonate, benzenesulfonate, toluenesulfonate, isethionate, glucronate, gluconate, etc.

The compound of formula (I) and its salt may be converted to a solvate thereof.

Non-toxic and water-soluble solvates are preferable. Appropriate ones are solvates of water and alcohol solvent (e.g. ethanol etc.)

In the formula (I), $R^1$ and $R^2$ are preferably C1~8 alkyl, and more preferably methyl.

In the formula (I), Z is —$CR^3R^4$— or —O—.

In the formula (I), $R^3$ and $R^4$ are preferably, hydrogen or C1~8 alkyl, and more preferably hydrogen or methyl.

In the formula (I), $R^5$ and $R^6$ are preferably, hydrogen.

In the formula (I), Cyc4 is preferably C5~7 mono-cyclic carboring and more preferably benzene ring.

In the formula (I), ring is preferably C3~15 mono- or bi-cyclic carboring or 3~15 membered mono- or bi-cyclic heteroring and more preferably benzene, cyclohexane, cycloheptane, adamantan, naphthalene, quinoline, isoquinoline, piperidine or pyridine.

In the compound of formula (I), the following compounds are preferable; the compound of formula (Ia'-1)

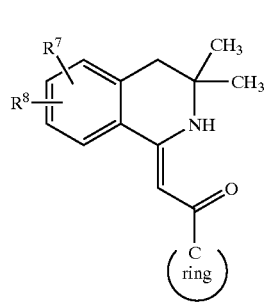

(Ia'-1)

(wherein all symbols have the same meaning as hereinbefore described.), the compound of formula (Ia'-2)

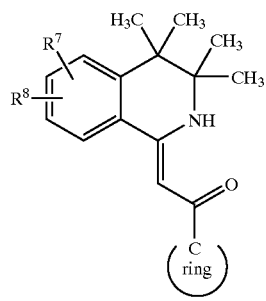

(Ia'-2)

(wherein all symbols have the same meaning as hereinbefore described.), the compound of formula (Ia'-3)

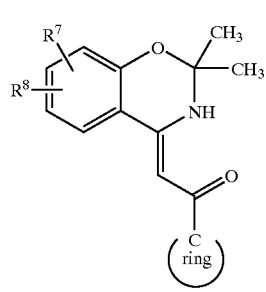

(Ia'-3)

(wherein all symbols have the same meaning as hereinbefore described.), the compound of formula (Ia'-4)

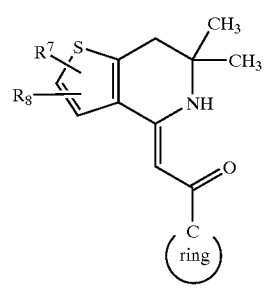

(Ia'-4)

(wherein all symbols have the same meaning as hereinbefore described.).

Concretely preferable ones are, the compounds described in the tables 1~8, the compounds of the examples and non-toxic salt thereof, acid-addition salts thereof and solvates thereof.

In the following tables, Me is methyl, Et is ethyl, Boc is t-butoxycarbonyl and the other symbols have the same meanings as hereinbefore described.

TABLE 1

(Ia'-1-1)

| No. | R$^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |

TABLE 1-continued (Ia'-1-1)

| No. | R$^{17}$ |
|---|---|
| 51 | 4-OEt |
| 52 | 2-CHO |
| 53 | 3-CHO |
| 54 | 4-CHO |

TABLE 2

(Ia'-1-2)

| No. | R$^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF3 |
| 20 | 3-CF3 |
| 21 | 4-CF3 |
| 22 | 2-OCF3 |
| 23 | 3-OCF3 |
| 24 | 4-OCF3 |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |

TABLE 2-continued (Ia'-1-2)

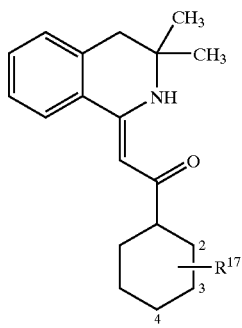

| No. | R<sup>17</sup> |
|---|---|
| 32 | 3-acetyl |
| 33 | 4-acetyl |
| 34 | 2-mesyl |
| 35 | 3-mesyl |
| 36 | 4-mesyl |
| 37 | 2-NH2 |
| 38 | 3-NH2 |
| 39 | 4-NH2 |
| 40 | 2-NO2 |
| 41 | 3-NO2 |
| 42 | 4-NO2 |
| 43 | 2-CH2OH |
| 44 | 3-CH2OH |
| 45 | 4-CH2OH |
| 46 | 2-CH2NH2 |
| 47 | 3-CH2NH2 |
| 48 | 4-CH2NH2 |
| 49 | 2-OEt |
| 50 | 3-OEt |
| 51 | 4-OEt |
| 52 | 2-CHO |
| 53 | 3-CHO |
| 54 | 4-CHO |

TABLE 3

(Ia'-1-3)

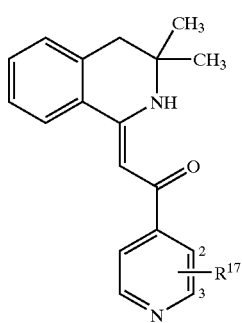

| No. | R$^{17}$ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |

TABLE 3-continued (Ia'-1-3)

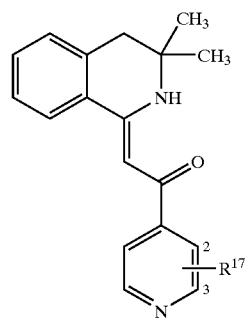

| No. | R$^{17}$ |
|---|---|
| 13 | 2-CF$_3$ |
| 14 | 3-CF$_3$ |
| 15 | 2-OCF$_3$ |
| 16 | 3-OCF$_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH$_2$ |
| 26 | 3-NH$_2$ |
| 27 | 2-NO$_2$ |
| 28 | 3-NO$_2$ |
| 29 | 2-CH$_2$OH |
| 30 | 3-CH$_2$OH |
| 31 | 2-CH$_2$NH$_2$ |
| 32 | 3-CH$_2$NH$_2$ |
| 33 | 2-OEt |
| 34 | 3-OEt |
| 35 | 2-CHO |
| 36 | 3-CHO |

TABLE 4

(Ia'-1-4)

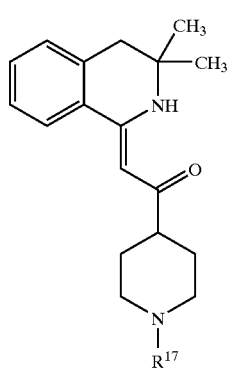

| No. | R$^{17}$ |
|---|---|
| 1 | Me |
| 2 | Boc |
| 3 |  |

TABLE 4-continued
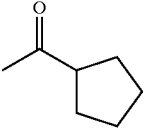
(Ia'-1-4)
| No. | R[17] |
|---|---|
| 4 | acetyl |
| 5 | 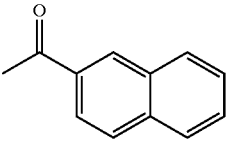 |
| 6 | benzoyl |
| 7 | 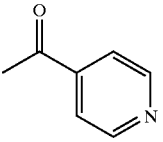 |
| 8 | 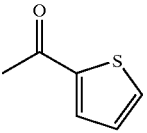 |
| 9 | 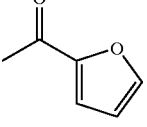 |
| 10 | 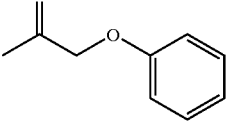 |
| 11 | 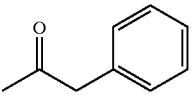 |
| 12 | 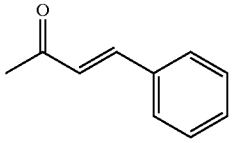 |
TABLE 4-continued
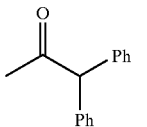
(Ia'-1-4)
| No. | R[17] |
|---|---|
| 13 | 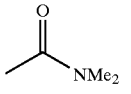 |
| 14 | 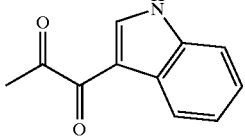 |
| 15 | 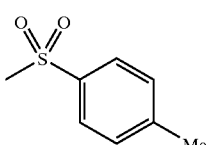 |
| 16 | 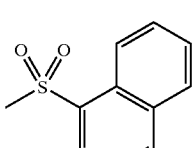 |
| 17 | mesyl |
| 18 | 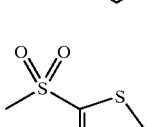 |
| 19 | 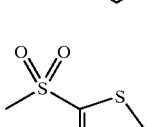 |
| 20 | 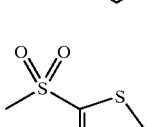 |

TABLE 4-continued (Ia'-1-4)

| No. | R¹⁷ |
|-----|-----|
| 21  | (methylsulfonyl-furan) |
| 22  | (methylsulfonyl-styrene) |

TABLE 5

(Ia'-1-5)

| No. | R⁷ |
|-----|-----|
| 1   | 6-Me |
| 2   | 7-Me |
| 3   | 6-OMe |
| 4   | 7-OMe |
| 5   | 6-SMe |
| 6   | 7-SMe |
| 7   | 6-OH |
| 8   | 7-OH |
| 9   | 6-F |
| 10  | 7-F |
| 11  | 6-Cl |
| 12  | 7-Cl |
| 13  | 6-CF₃ |
| 14  | 7-CF₃ |
| 15  | 6-OCF₃ |
| 16  | 7-OCF₃ |
| 17  | 6-CN |
| 18  | 8-CN |
| 19  | 6-COOH |
| 20  | 7-COOH |

TABLE 5-continued (Ia'-1-5)

| No. | R⁷ |
|-----|-----|
| 21  | 6-acetyl |
| 22  | 7-acetyl |
| 23  | 6-mesyl |
| 24  | 7-mesyl |
| 25  | 6-NH₂ |
| 26  | 7-NH₂ |
| 27  | 6-NO₂ |
| 28  | 7-NO₂ |
| 29  | 6-CH₂OH |
| 30  | 7-CH₂OH |
| 31  | 6-CH₂NH₂ |
| 32  | 7-CH₂NH₂ |
| 33  | 6-OEt |
| 34  | 7-OEt |
| 35  | 6-CHO |
| 36  | 7-CHO |

TABLE 6

(Ia'-1-6)

| No. | R⁷ |
|-----|-----|
| 1   | 6-Me |
| 2   | 7-Me |
| 3   | 6-OMe |
| 4   | 7-OMe |
| 5   | 6-SMe |
| 6   | 7-SMe |
| 7   | 6-OH |
| 8   | 7-OH |
| 9   | 6-F |
| 10  | 7-F |
| 11  | 6-Cl |
| 12  | 7-Cl |
| 13  | 6-CF₃ |
| 14  | 7-CF₃ |
| 15  | 6-OCF₃ |
| 16  | 7-OCF₃ |
| 17  | 6-CN |
| 18  | 8-CN |
| 19  | 6-COOH |
| 20  | 7-COOH |

TABLE 6-continued (Ia'-1-6)

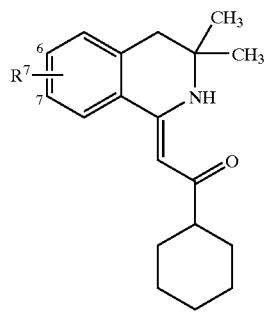

| No. | R⁷ |
|---|---|
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 7

(Ia'-1-7)

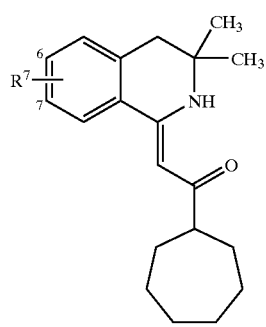

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |

TABLE 7-continued (Ia'-1-7)

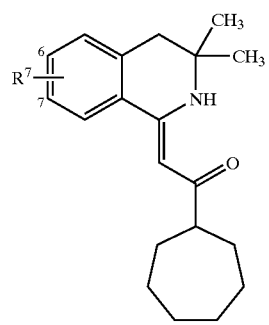

| No. | R⁷ |
|---|---|
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 8

(Ia'-1-8)

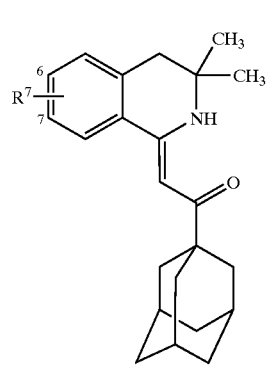

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |

TABLE 8-continued (Ia'-1-8)

| No. | R⁷ |
|---|---|
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

TABLE 9

(Ia'-2-1)

| No. | R¹⁷ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |

TABLE 9-continued (Ia'-2-1)

| No. | R¹⁷ |
|---|---|
| 16 | 2-Cl |
| 17 | 3-Cl |
| 18 | 4-Cl |
| 19 | 2-CF3 |
| 20 | 3-CF3 |
| 21 | 4-CF3 |
| 22 | 2-OCF3 |
| 23 | 3-OCF3 |
| 24 | 4-OCF3 |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-$NH_2$ |
| 38 | 3-$NH_2$ |
| 39 | 4-$NH_2$ |
| 40 | 2-$NO_2$ |
| 41 | 3-$NO_2$ |
| 42 | 4-$NO_2$ |
| 43 | 2-$CH_2OH$ |
| 44 | 3-$CH_2OH$ |
| 45 | 4-$CH_2OH$ |
| 46 | 2-$CH_2NH_2$ |
| 47 | 3-$CH_2NH_2$ |
| 48 | 4-$CH_2NH_2$ |
| 49 | 2-OEt |
| 50 | 3-OEt |
| 51 | 4-OEt |
| 52 | 2-CHO |
| 53 | 3-CHO |
| 54 | 4-CHO |

TABLE 10

(Ia'-2-2)

| No. | R¹⁷ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF₃ |
| 20 | 3-CF₃ |
| 21 | 4-CF₃ |
| 22 | 2-OCF₃ |
| 23 | 3-OCF₃ |
| 24 | 4-OCF₃ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH₂ |
| 38 | 3-NH₂ |
| 39 | 4-NH₂ |
| 40 | 2-NO₂ |
| 41 | 3-NO₂ |
| 42 | 4-NO₂ |
| 43 | 2-CH₂OH |
| 44 | 3-CH₂OH |
| 45 | 4-CH₂OH |
| 46 | 2-CH₂NH₂ |
| 47 | 3-CH₂NH₂ |
| 48 | 4-CH₂NH₂ |
| 49 | 2-OEt |
| 50 | 3-OEt |
| 51 | 4-OEt |
| 52 | 2-CHO |
| 53 | 3-CHO |
| 54 | 4-CHO |

TABLE 11

(Ia'-2-3)

| No. | R¹⁷ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF₃ |
| 14 | 3-CF₃ |
| 15 | 2-OCF₃ |
| 16 | 3-OCF₃ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH₂ |
| 26 | 3-NH₂ |
| 27 | 2-NO₂ |
| 28 | 3-NO₂ |
| 29 | 2-CH₂OH |
| 30 | 3-CH₂OH |
| 31 | 2-CH₂NH₂ |
| 32 | 3-CH₂NH₂ |
| 33 | 2-OEt |
| 34 | 3-OEt |
| 35 | 2-CHO |
| 36 | 3-CHO |

TABLE 12
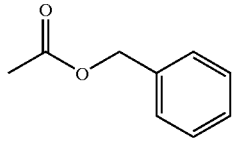
(Ia'-2-4)
| No. | R¹⁷ |
|---|---|
| 1 | Me |
| 2 | Boc |
| 3 | 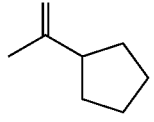 |
| 4 | acetyl |
| 5 | 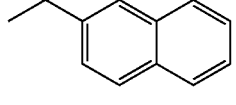 |
| 6 | benzoyl |
| 7 | 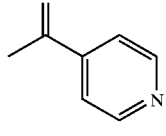 |
| 8 | 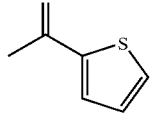 |
| 9 | 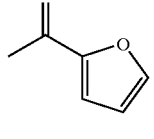 |
| 10 | 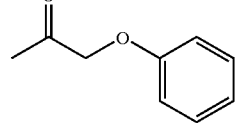 |
TABLE 12-continued
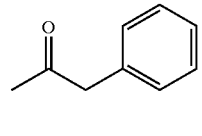
(Ia'-2-4)
| No. | R¹⁷ |
|---|---|
| 11 | 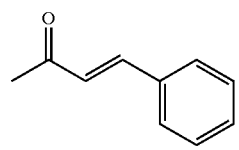 |
| 12 | 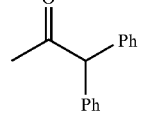 |
| 13 | 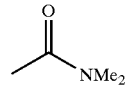 |
| 14 | 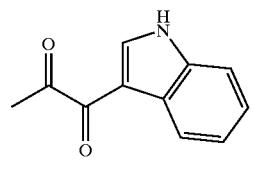 |
| 15 |  |
| 16 |  |

TABLE 12-continued (Ia'-2-4)

| No. | R$^{17}$ |
|---|---|
| 17 | mesyl |
| 18 | [4-methylphenylsulfonyl structure] |
| 19 | [1-naphthylsulfonyl structure] |
| 20 | [2-thienylsulfonyl structure] |
| 21 | [2-furylsulfonyl structure] |
| 22 | [styrylsulfonyl structure] |

TABLE 13

(Ia'-2-5)

| No. | R$^7$ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 14
(Ia'-2-6)
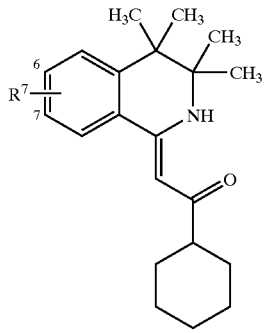
| No. | $R^7$ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |
TABLE 15
(Ia'-2-7)
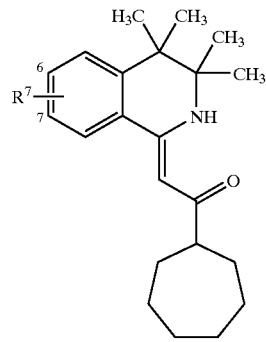
| No. | $R^7$ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

TABLE 16

(Ia'-2-8)

[Structure: 4,4,3,3-tetramethyl-1,2,3,4-tetrahydroisoquinoline with =CH-C(=O)-adamantyl substituent at position 1, R⁷ on aromatic ring]

| No. | R⁷ |
|-----|------|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 17

(Ia'-3-1)

[Structure: 2,2-dimethyl-2H-benzo[e][1,3]oxazine with =CH-C(=O)-phenyl(R¹⁷) substituent]

| No. | R¹⁷ |
|-----|------|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 18

(Ia'-3-2)

| No. | R$^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 19

(Ia'-3-3)

| No. | R$^{17}$ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF$_3$ |
| 14 | 3-CF$_3$ |
| 15 | 2-OCF$_3$ |
| 16 | 3-OCF$_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH$_2$ |
| 26 | 3-NH$_2$ |
| 27 | 2-NO$_2$ |
| 28 | 3-NO$_2$ |
| 29 | 2-CH$_2$OH |
| 30 | 3-CH$_2$OH |
| 31 | 2-CH$_2$NH$_2$ |
| 32 | 3-CH$_2$NH$_2$ |
| 33 | 2-OEt |
| 34 | 3-OEt |
| 35 | 2-CHO |
| 36 | 3-CHO |

TABLE 20
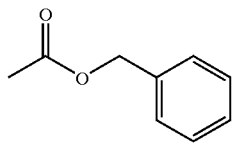
(Ia'-3-4)
| No. | R17 |
|---|---|
| 1 | Me |
| 2 | Boc |
| 3 | 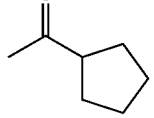 |
| 4 | acetyl |
| 5 | 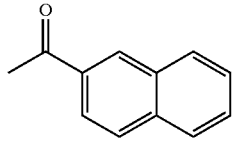 |
| 6 | benzoyl |
| 7 | 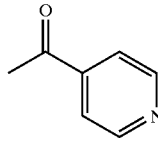 |
| 8 | 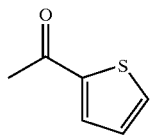 |
| 9 | 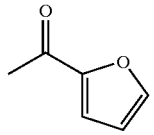 |
| 10 | 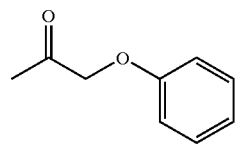 |
TABLE 20-continued
(Ia'-3-4)
| No. | R17 |
|---|---|
| 11 | 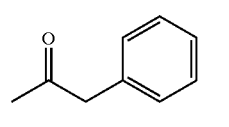 |
| 12 | 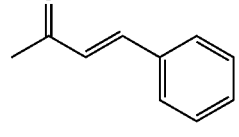 |
| 13 | 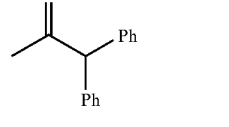 |
| 14 | 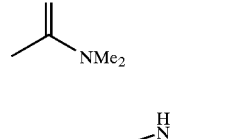 |
| 15 | 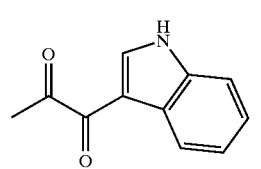 |
| 16 | 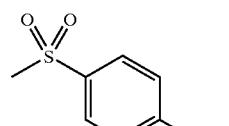 |
| 17 | mesyl |
| 18 | (tosyl structure) |

TABLE 20-continued (Ia'-3-4)

| No. | R¹⁷ |
|---|---|
| 19 | (methylsulfonyl-naphthalene) |
| 20 | (methylsulfonyl-thiophene) |
| 21 | (methylsulfonyl-furan) |
| 22 | (methylsulfonyl-styrene) |

TABLE 21

(Ia'-3-5)

| No. | R⁷ |
|---|---|
| 1 | 6-Me |
| 2 | 7-Me |
| 3 | 6-OMe |
| 4 | 7-OMe |
| 5 | 6-SMe |

TABLE 21-continued (Ia'-3-5)

| No. | R⁷ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF₃ |
| 14 | 7-CF₃ |
| 15 | 6-OCF₃ |
| 16 | 7-OCF₃ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH₂ |
| 26 | 7-NH₂ |
| 27 | 6-NO₂ |
| 28 | 7-NO₂ |
| 29 | 6-CH₂OH |
| 30 | 7-CH₂OH |
| 31 | 6-CH₂NH₂ |
| 32 | 7-CH₂NH₂ |
| 33 | 6-OEt |
| 34 | 7-OEt |
| 35 | 6-CHO |
| 36 | 7-CHO |

TABLE 22

(Ia'-3-6)

| No. | R⁷ |
|---|---|
| 1 | 6-Me |
| 2 | 7-Me |
| 3 | 6-OMe |
| 4 | 7-OMe |
| 5 | 6-SMe |

TABLE 22-continued (Ia'-3-6)

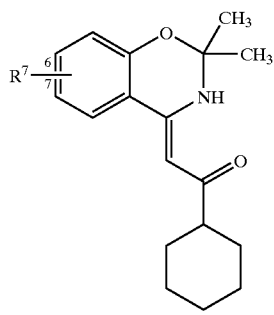

| No. | R⁷ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 23

(Ia'-3-7)

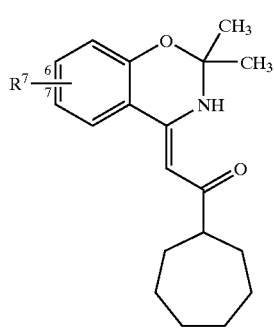

| No. | R⁷ |
|---|---|
| 1 | 6-Me |
| 2 | 7-Me |
| 3 | 6-OMe |
| 4 | 7-OMe |
| 5 | 6-SMe |

TABLE 23-continued (Ia'-3-7)

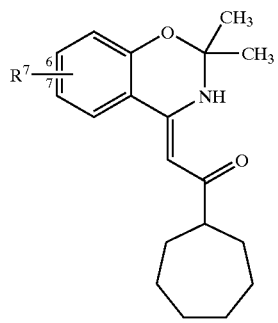

| No. | R⁷ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 24

(Ia'-3-8)

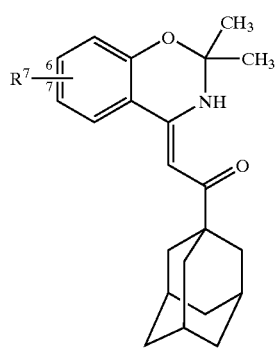

| No. | R⁷ |
|---|---|
| 1 | 6-Me |
| 2 | 7-Me |
| 3 | 6-OMe |
| 4 | 7-OMe |

TABLE 24-continued

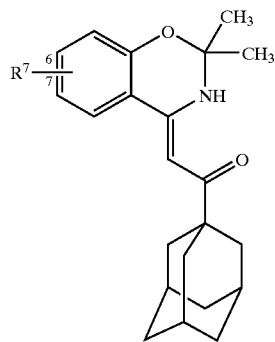

(Ia'-3-8)

| No. | R⁷ |
|---|---|
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 25

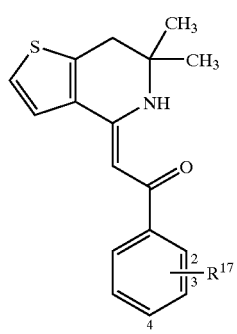

(Ia'-4-1)

| No. | R¹⁷ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 26

(Ia'-4-2)

| No. | R¹⁷ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF₃ |
| 20 | 3-CF₃ |
| 21 | 4-CF₃ |
| 22 | 2-OCF₃ |
| 23 | 3-OCF₃ |
| 24 | 4-OCF₃ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH₂ |
| 38 | 3-NH₂ |
| 39 | 4-NH₂ |
| 40 | 2-NO₂ |
| 41 | 3-NO₂ |
| 42 | 4-NO₂ |
| 43 | 2-CH₂OH |
| 44 | 3-CH₂OH |
| 45 | 4-CH₂OH |
| 46 | 2-CH₂NH₂ |
| 47 | 3-CH₂NH₂ |
| 48 | 4-CH₂NH₂ |
| 49 | 2-OEt |
| 50 | 3-OEt |
| 51 | 4-OEt |
| 52 | 2-CHO |
| 53 | 3-CHO |
| 54 | 4-CHO |

TABLE 27

(Ia'-4-3)

| No. | R¹⁷ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF₃ |
| 14 | 3-CF₃ |
| 15 | 2-OCF₃ |
| 16 | 3-OCF₃ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH₂ |
| 26 | 3-NH₂ |
| 27 | 2-NO₂ |
| 28 | 3-NO₂ |
| 29 | 2-CH₂OH |
| 30 | 3-CH₂OH |
| 31 | 2-CH₂NH₂ |
| 32 | 3-CH₂NH₂ |
| 33 | 2-OEt |
| 34 | 3-OEt |
| 35 | 2-CHO |
| 36 | 3-CHO |

TABLE 28

(Ia'-4-4)

[Structure: 6,6-dimethyl-thieno[3,2-c]pyridine with =CH-C(=O)- linker to 4-piperidinyl bearing N-R¹⁷]

| No. | R¹⁷ |
|---|---|
| 1 | Me |
| 2 | Boc |
| 3 | -C(=O)-O-CH₂-phenyl (benzyloxycarbonyl) |
| 4 | acetyl |
| 5 | -C(=O)-cyclopentyl |
| 6 | benzoyl |
| 7 | -C(=O)-(2-naphthyl) |
| 8 | -C(=O)-(4-pyridyl) |
| 9 | -C(=O)-(2-thienyl) |
| 10 | -C(=O)-(2-furyl) |
| 11 | -C(=O)-CH₂-O-phenyl |
| 12 | -C(=O)-CH₂-phenyl |
| 13 | -C(=O)-CH=CH-phenyl |
| 14 | -C(=O)-CH(Ph)₂ |
| 15 | -C(=O)-NMe₂ |
| 16 | -C(=O)-C(=O)-(1H-indol-3-yl) |
| 17 | mesyl |
| 18 | -S(=O)₂-(4-methylphenyl) |

TABLE 28-continued
(Ia'-4-4)
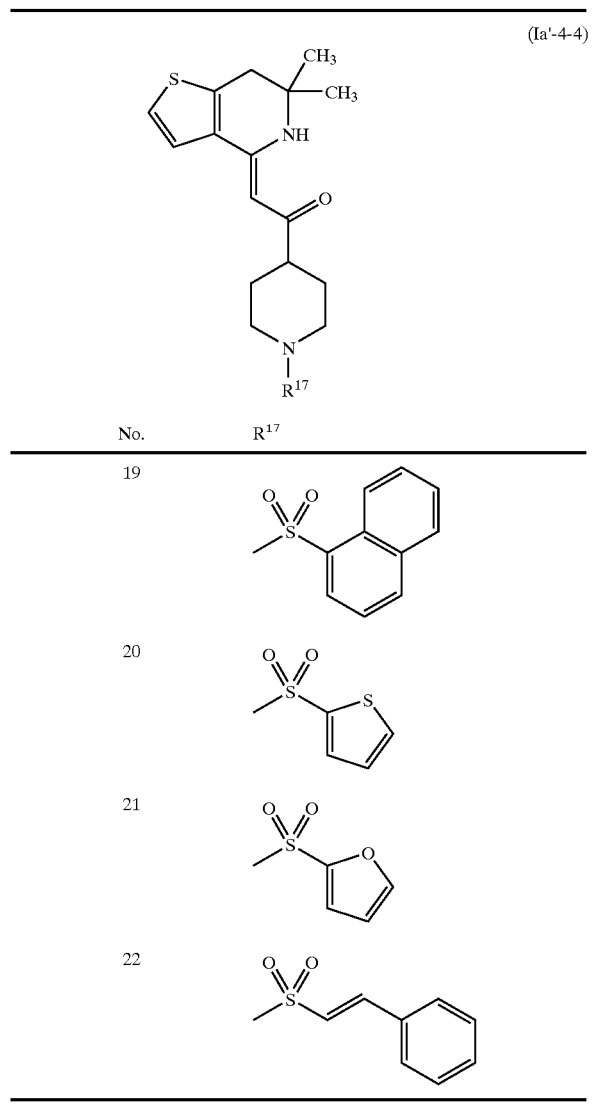
| No. | R17 |
|---|---|
| 19 | |
| 20 | |
| 21 | |
| 22 | |
TABLE 29
(Ia'-4-5)
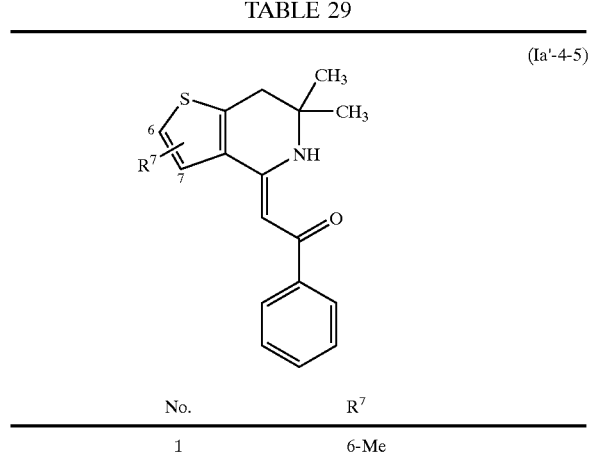
| No. | R7 |
|---|---|
| 1 | 6-Me |
| 2 | 7-Me |
| 3 | 6-OMe |
| 4 | 7-OMe |
| 5 | 6-SMe |
TABLE 29-continued
(Ia'-4-5)
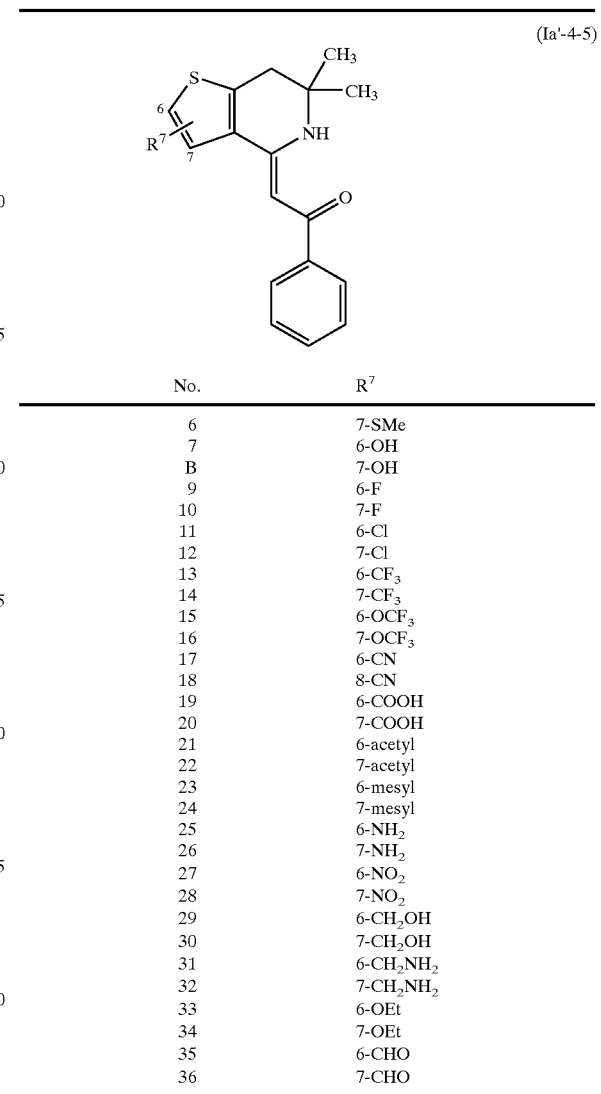
| No. | R7 |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |
TABLE 30
(Ia'-4-6)
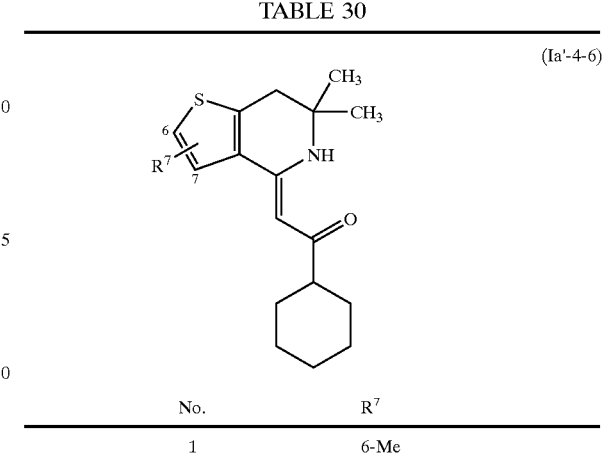
| No. | R7 |
|---|---|
| 1 | 6-Me |
| 2 | 7-Me |
| 3 | 6-OMe |
| 4 | 7-OMe |
| 5 | 6-SMe |

TABLE 30-continued

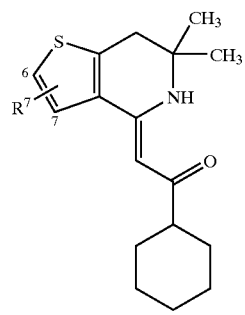

(Ia'-4-6)

| No. | $R^7$ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

TABLE 31

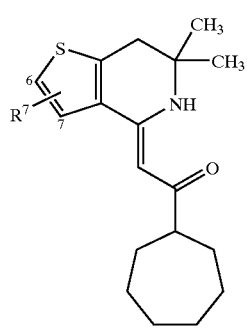

(Ia'-4-7)

| No. | $R^7$ |
|---|---|
| 1 | 6-Me |
| 2 | 7-Me |
| 3 | 6-OMe |
| 4 | 7-OMe |
| 5 | 6-SMe |

TABLE 31-continued

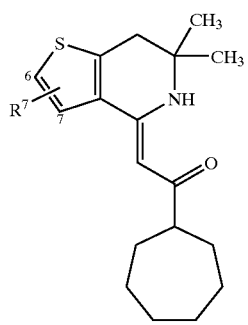

(Ia'-4-7)

| No. | $R^7$ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

TABLE 32

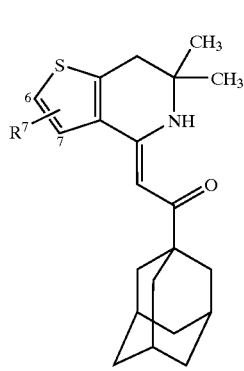

(Ia'-4-8)

| No. | $R^7$ |
|---|---|
| 1 | 6-Me |
| 2 | 7-Me |
| 3 | 6-OMe |

TABLE 32-continued (Ia'-4-8)

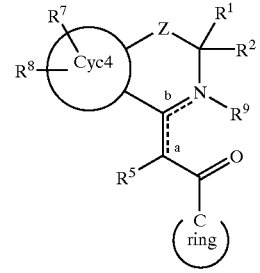

| No. | $R^7$ |
|---|---|
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

The Method for the Preparation of the Compound of the Present Invention

The compound of formula (I) of the present invention may be prepared according to the following methods or the methods described in the examples.

[1] Among the compound of formula (I) of the present invention, a compound wherein $R^6$ is hydrogen, i.e. the compound of formula (IA)

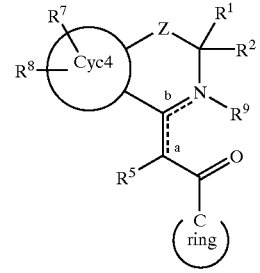

(IA)

(wherein all symbols have the same meaning as hereinbefore described.) may be prepared according to the method of [a], [b] or [c].

[a] The compound of formula (IA) may be prepared by subjecting to a reaction the compound of formula (II)

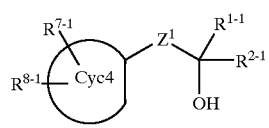

(II)

(wherein $Z^1$ is —$CR^{3-1}R^{4-1}$— or —O—, $R^{1-1}$, $R^{2-1}$, $R^{3-1}$, $R^{4-1}$, $R^{7-1}$ and $R^{8-1}$ are the same meaning as $R^1$, $R^2$, $R^3$, $R^4$, $R^7$ and $R^8$ respectively, and hydroxy, amino or carboxy included in a group of $R^{1-1}$, $R^{2-1}$, $R^{3-1}$, $R^{4-1}$, $R^{7-1}$ or $R^{8-1}$ is protected if necessary.) and the compound of formula (III)

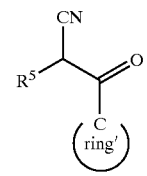

(III)

(wherein

(hereafter represented by ring') is the same meaning as ring, but hydroxy, amino or carboxy included in ring' is protected if necessary.) to give a compound of formula (IA')

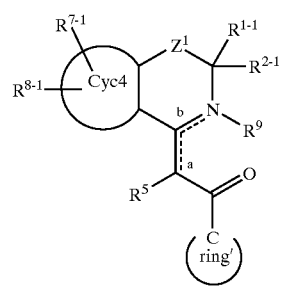

(IA')

(wherein all symbols have the same meaning as hereinbefore.), optionally followed by subjecting to a deprotection reaction of protective groups.

The reaction of the compound of formula (II) and the compound of formula (III) is known, for example, it is carried out by subjecting to a reaction the compound of formula (II) and the compound of formula (III) at a temperature between −20~100° C. in concentrated sulfuric acid.

Deprotection reaction may be carried out by following methods.

Deprotection reactions of protective groups of carboxy, hydroxy or amino is known, for example,
(1) a deprotection reaction under alkaline conditions,
(2) a deprotection reaction under acidic conditions,
(3) a deprotection reaction by hydration,
(4) a deprotection reaction of silyl group, etc are known.

To describe these methods concretely,
1) a deprotection reaction under alkaline conditions is, for example, carried out in an organic solvent (methanol, tetrahydrofuran, dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), or carbonates (sodium carbonate, potassium carbonate, etc.) or a solution thereof or a mixture thereof at a temperature between 0 and 40° C.

(2) a deprotection reaction under acidic conditions is, for example, carried out in or without an organic solvent (methylene chloride, chloroform, dioxane, ethyl acetate, anisole, etc.), using an organic acid (acetic acid, trifluoroacetic acid, methanesulfonic acid, etc.) or an inorganic acid (hydrochloric acid, sulfuric acid, etc.) or a mixture thereof (hydrobromic acid/acetic acid, etc.) at a temperature between 0 and 100° C.

(3) a deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitrites (acetonitrile etc.), amides (dimethylformamide etc.), water, ethyl acetate, acetic acid or a mixture of more than two from above etc.) in the presence of a catalyst (palladium-carbon, palladium black, palladium hydroxide, platinum oxide, Raney nickel, etc.) under atmosphere of hydrogen of normal or suppressed pressure, or in the presence of ammonium formate at a temperature between 0 and 200° C.

As easily understood by those skilled in the art, the compounds of the present invention may be easily prepared by these reactions.

(4) Deprotection reaction of silyl group is, for example, carried out in an organic solbent which is miscible with water (tetrahydrofuran, acetonitrile, etc.) using tetrabutylammoniumfluoride at a temperature between 0 and 40° C.

Protective groups for carboxy are, for example, methyl, ethyl, t-butyl, benzyl.

Protective groups for hydroxy are, for example, methoxymethyl, 2-tetrahydropyranyl, t-butyidimethylsilyl, t-butyldiphenylsilyl, acetyl, benzyl.

Protective groups for amino are, for example, benzyloxycarbonyl, t-butoxycarbonyl, trifluoroacetyl, 9-fluorenylmethoxycarbonyl.

Protective groups for carboxy, hydroxy or amino are not limited to above listed, but other groups may also be used instead, if easily and selectively eliminated. For example, the groups described in T. W. Greene, Protective Groups in Organic Synthesis 3rd edition, Wiley, New York, 1999 may be used.

As easily understood by those skilled in the art, the target compounds of the present invention may be easily prepared by these reactions.

[b] The compound of formula (IA) may be prepared by subjecting to a reaction a compound of formula (IV)

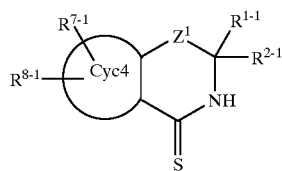

(wherein all symbols have the same meaning as hereinbefore.) and a compound of formula (V)

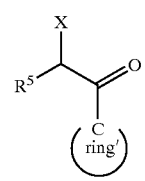

(wherein X is a halogen atom and the other symbols have the same meaning as hereinbefore.) to give the compound of formula (IA'), as depicted above, optionally followed by subjecting to deprotection reaction of protective groups.

The reaction of the compound of formula (IV) and the compound of formula (V) is known, for example, it is carried out by subjecting to a reaction in an organic solvent (xylene, toluene, benzene, acetonitrile, tetrahydrofuran, methylene chloride, chloroform, etc.) in the presence of phosphine reagent (triphenylphosphine, tributylphosphine, etc.) or phosphite reagent (trimethylphosphite, triethylphosphite, tripropylphosphite, tributylphosphite, etc.) and a base (triethylamine, diisopropylamine, dimethylaminopyridine, etc.) at a temperature between 30° C. and refluxing temperature.

Deprotection reaction of protective groups may be carried out as hereinbefore described.

[c] Among the compound of formula (IA), a compound wherein $R^5$ is hydrogen, i.e. a compound of formula (IA-1)

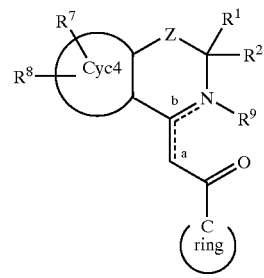

(wherein all symbols have the same meaning as hereinbefore) may be prepared by subjecting to a reaction a compound of formula (VI) and a compound of formula (VII) to give a compound of formula (IA'-1)

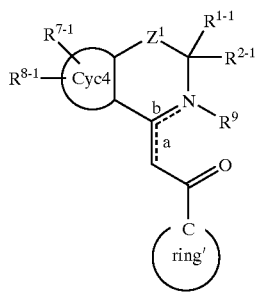

(IA'-1)

(wherein all symbols have the same meaning as hereinbefore described), optionally followed by deprotection reaction of protective groups.

The reaction of the compound of formula (VI) and the compound of formula (VII) is known, for example, it is carried out in an inert organic solvent (tetrahydrofuran (THF), diethyl ether, benzene, etc.) in the presence of a base (lithium isopropylamine (LDA), lithium hexamethyldisilazide (LHMDS), n-butyl lithium, t-butyl lithium, etc.) at a temperature between −78° C. and room temperature.

Deprotection reaction of protective groups may be carried out as hereinbefore described.

[2] Among the compound of formula (I) of the present invention, a compound wherein $R^5$ and $R^6$ are C1~8 alkyl, or $R^5$ and $R^6$ are taken together with carbon atom to which they are attached to form Cyc1, i.e. the compound of formula (IB)

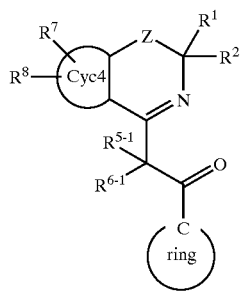

(IB)

(wherein $R^{5-1}$ and $R^{6-1}$ are independently, C1–8 alkyl, or $R^{5-1}$ and $R^{6-1}$ are taken together with the carbon atom to which they are attached to form Cyc1, and the other symbols have the same meaning as hereinbefore described) may be prepared according to the following method.

The compound of formula (IB) may be prepared according to a reaction the compound of (IA'-1) above depicted, and the compound of formula (VIII)

$$R^{65}\text{—X} \qquad \text{(VIII)}$$

(wherein $R^{65}$ is C1–8 alkyl and X is the same meaning as above described.) or a compound of formula (IX)

$$\text{X—Y—X} \qquad \text{(IX)}$$

(wherein Y is —$(CH_2)_m$— (wherein m is an integer of 2~9) and carbon atom in —$(CH_2)_m$— may be replaced by 1–2 of heteroatom selected from oxygen, nitrogen and sulfur, and when it is replaced by nitrogen, it is protected if necessary. Y may be substituted with $R^{10-1}$ ($R^{10-1}$ is the same meaning as $R^{10}$, with proviso that hydroxy included in $R^{10-1}$ is protected if necessary) and X is the same meaning as hereinbefore described.) to give the compound of formula (IB')

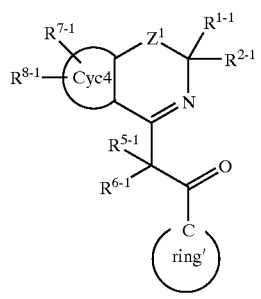

(IB')

(wherein all symbols have the same meaning as hereinbefore described), optionally followed by subjecting to deprotection reaction of protective groups.

The reaction of the compound of formula (IA'-1) and the compound of formula (VIII) or the compound of formula (IX) is known, for example, it is carried out in an inert organic solvent (e.g. tetrahydrofuran, diethyl ether, dimethylformamide, benzene, dioxane, etc.) in the presence of a base (sodium hydroxide, LDA, n-butyl lithium, t-butyl lithium, etc.), optionally in the presence of sodium iodide, at a temperature of −20° C. and refluxing temperature.

Deprotection reaction of protective groups may be carried out as hereinbefore described.

[3] Among the compound of formula (I), a compound wherein $R^7$ is Cyc2, i.e. the compound of formula (IC)

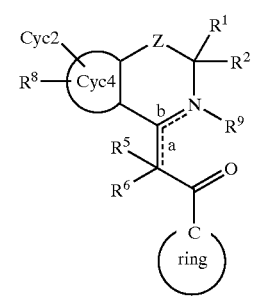

(IC)

(wherein all symbols have the same meaning as hereinbefore described.) may be prepared according to the following methods.

The compound of formula (IC) may be prepared by subjecting to a reaction the compound of formula (X)

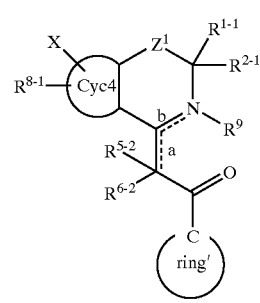

(X)

(wherein $R^{5-2}$ and $R^{6-2}$ are the same meaning as $R^5$ and $R^6$ respectively, but hydroxy and amino included in $R^{1-2}$ and $R^{6-2}$ are protected if necessary, and the other symbols have the same meaning as hereinbefore described.) and the compound of formula (XI)

$$Cyc2'—R^{66} \quad (XI)$$

(wherein $R^{66}$ is —B(OH)$_2$ and —B(C$_{1\sim8}$ alkyl)$_2$ and Cyc2' is the same meaning as Cyc2, with proviso that hydroxy, amino or carboxy included in Cyc2' are protected if necessary) to give the compound of formula (IC')

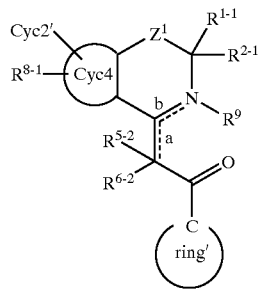

(IC')

(wherein all symbols have the same meaning as hereinbefore described.), optionally followed by subjecting to deprotection reaction of protective groups.

The reaction of the compound of formula (X) and the compound of formula (XI) is known, for example, it is carried out in an organic solvent (benzene, acetonitrile, dimethoxyethane, acetone, etc.) in the presence of a base (sodium ethylate, sodium hydroxide, potassium hydroxide, triethylamine, sodium carbonate, sodium bicarbonate, potassium carbonate, cesium carbonate, thallium carbonate, potassium phosphate, cesium fluoride, barium hydroxide, tetrabutyl ammonium fluoride, etc.) and a catalyst (tetrakis (triphenylphosphine)palladium (PdCl$_2$(PPh$_3$)$_2$), palladium acetate (Pd(OAc)2), palladium black, 1,1'-bis (diphenylphosphinoferrocene) dichloropalladium (PdCl$_2$ (dppf)$_2$), dichlorodiallylpalladium (PdCl$_2$(allyl)$_2$), palladium phenylbis(triphenylphosphine)iodide (PhPdI(PPh$_3$)$_2$), etc.) at a temperature between room temperature and 120° C.

Deprotection reaction of protective groups may be carried out as hereinbefore described.

[4] Among the compound of formula (I) of the present invention, a compound wherein at least one of ring is amide or a group which include amide, i.e. the compound of formula (ID)

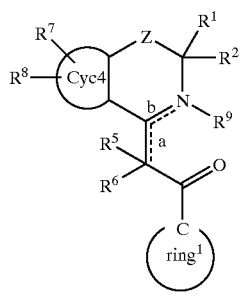

(ID)

(wherein ring$^1$ is the same meaning as ring, with proviso that at least one of ring$^1$ is amide or a group which contains amide, and the other symbols have the same meaning as hereinbefore.) may be prepared according to the following method.

The compound of formula (ID) may be prepared by subjecting to a reaction the compound of formula (XII)

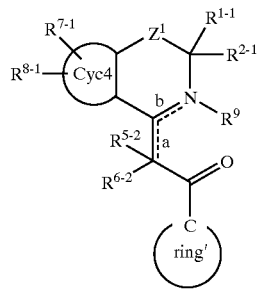

(XII)

(wherein ring1' is the same meaning as ring, with proviso that at least one of ring1' is amino or a group which contains amino, and the other amino, hydroxy or carboxy is protected if necessary, and the other symbols have the same meaning as hereinbefore) and carboxylic acid or a corresponding compound which possess acid halide, optionally subjected to an amidation deprotection reaction of protective groups.

Methods for amidation reaction are known, for example,
(1) a method using acid halide,
(2) a method using mixed anhydride,
(3) a method using a condensing agent, etc.

To explain these methods concretely,
(1) The method using acid halide is, for example, carried out by subjecting to a reaction carboxylic acid in an organic solvent (chloroform, methylene chloride, diethyl ether, tetrahydrofuran, etc.) or without a solvent, and acid-halogenating agent (oxalyl chloride, thionyl chloride, etc.) at a temperature between −20° C. and refluxing temperature, and then subjecting to a reaction thus obtained acid halide in the presence of tertiary amine (pyridine, triethylamine, dimethylaniline, dimethylaminopyridine, etc.) at a temperature between 0 and 40° C. And it is also carried out by subjecting to a reaction with an acid halide by using an alkaline aqueous solution (sodium bicarbonate or sodium hydroxide, etc.) in organic solvent (dioxane, tetrahydrofuran, etc.) at a temperature between 0 and 40° C.

(2) The method using mixed anhydride is, for example, carried out by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, etc.) carboxylic acid with acid halide (pivaloyl chloride, tosyl chloride, mesylchloride, etc.) or acid derivative (chloroethyl formate, chloroisobutyl formate, etc.) at a temperature between −20 and 40° C., and then subjecting to a reaction thus obtained mixed anhydride with amine at a temperature between 0 and 40° C.

(3) The method using a condensing agent is carried out, for example, in an inert organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, N-methylmorpholine, etc.), using a condensing reagent (1,3-dichlorohexylcarbodiimide (DCC), 1-ethyl-3-[3-(dimethylamino)propyl]carbodiimide (EDC), 1,1'-carbonyldiimizazole (CDI), 2-chloro-1-methylpyridinium iodide, etc.) in the presence or absence of 1-hydroxybenzotriazole, by subjecting to a reaction carboxylic acid and amine at a temperature between 0 and 40° C.

These reactions (1), (2) and (3) are desirably carried out under atmosphere of an inert gas (argon, nitrogen, etc.) under anhydrous conditions.

Deprotection reaction of protective groups may be carried out in the same methods as described hereinbefore described.

[5] In the compound of formula (I) of the present invention, a compound wherein at least one group represented by ring is sulfonamide or a group which contains it, i.e., the compound of formula (IE)

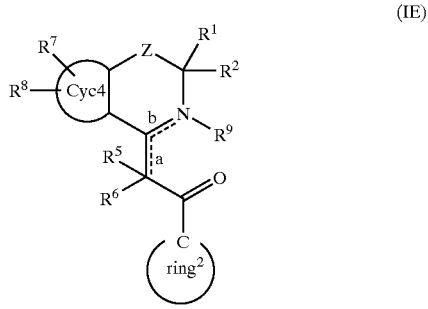

(IE)

(wherein ring$^2$ is the same meaning as ring, with proviso that at least one group represented by ring$^2$ is sulfonamide or a group which contains it, and the other symbols have the same meanings as hereinbefore described.) may be prepared by the following methods.

The compound of formula (IE) may be prepared by subjecting to a sulfonamidation reaction the compound of formula (XIII)

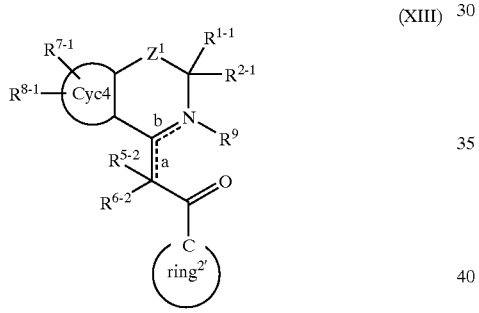

(XIII)

(wherein ring$^{2'}$ is the same meaning as ring, with proviso that at least one of groups represented by ring$^{2'}$ is amino or a group comprising amino and the other amino, hydroxy or carboxy is protected if necessary and the other symbols have the same meaning as above.) and a sulfonic acid or a corresponding compound having sulfonyl halide, optionally followed by subjecting to a deprotection reaction of protective groups.

Sulfonamidation is known, for example, it is carried out in an inert organic solvent (chloroform, dichloromethane, dichloroethane, diethyl ether, tetrahydrofuran, etc.) or without a solvent, by subjecting to a reaction sulfonic acid with acid halide (oxalyl chloride, thionyl chloride, phosphine pentachloride, phosphine trichloride, etc.) at a temperature between −20° C. and refluxing temperature to give sulfonyl halide, followed by subjecting it to a reaction with an amine in the presence of a tertiary amine (isopropylethylamine, pyrlidine, triethylamine, dimethylaniline, dimethylaminopyridine, etc.) at a temperature between 0 and 40° C.

Deprotection reaction of protective groups may be carried out in the same methods as described hereinbefore described.

The compounds of formula (II), (III), (IV), (V), (VI), (VII), (VIII), (IX) and (XI) may be prepared by known methods or are commercially available.

For example, the compound of formula (IV) may be prepared according to the following reaction scheme 1.

In the reaction scheme 1, LDA is lithium diisopropylamide, DPPA is diphenylphosphoryl azide, Et$_3$N is triethylamine, PPA is polyphosphoric acid and the other symbols have the same meaning as hereinbefore described.

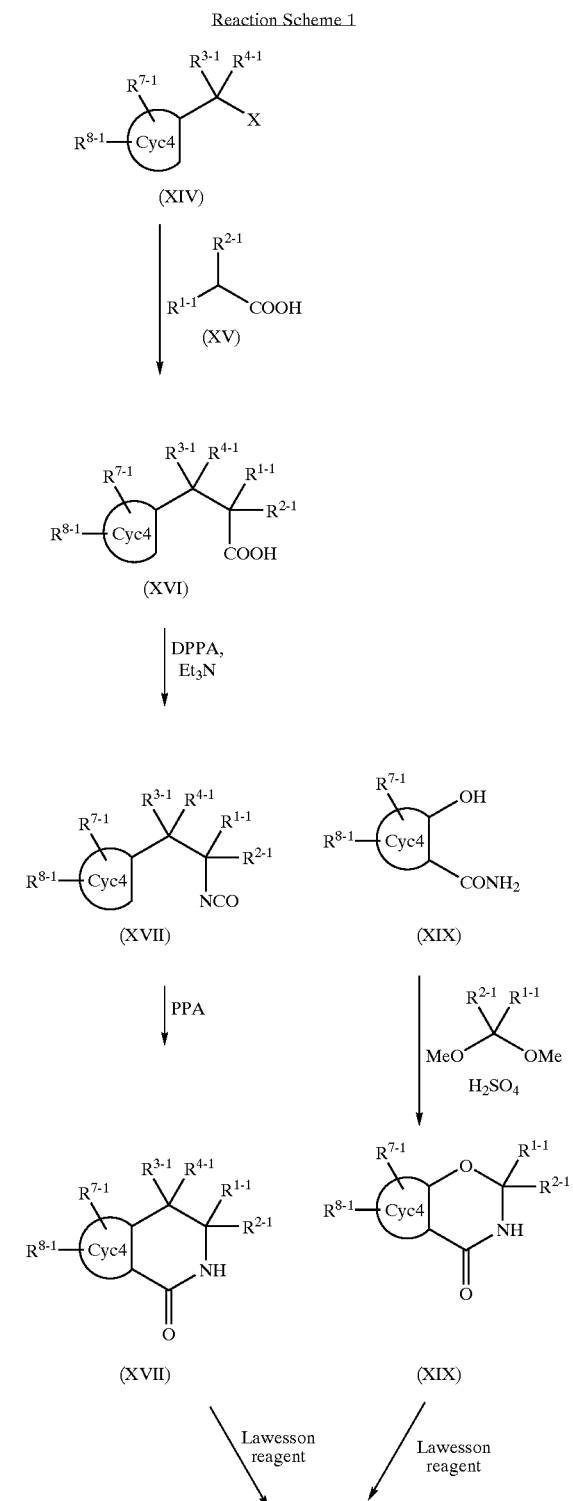

Reaction Scheme 1

-continued

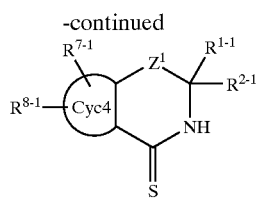

In the reaction scheme 1, the compounds of formula (XIV), (XV), (XIX) and (XX), which are used as starting materials, are known or may be prepared by known methods easily.

In each reaction of the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Pharmacological Effect]

It was confirmed by the following experiment that the compound of formula (I) of the present invention has CB2 receptor agonist activity.

In vitro Signaling Assay

Method for the Experiment:

Human CB2 receptors expressed CHO cells were used for the assays. Cells were dispersed seeded in 96-well plates in a density of $5\times10^4$ cells/well, and were subjected to experiment the next day. After removing the culture media 1 mM isobutylmethylxanthine (IBMX) solution was added, and cells were incubated for 10 minutes at room temperature. Next, a mixture of 10 $\mu$M forskolin and the compound of the present invention was added. After additional incubation for 15 minutes at room temperature, the culture supernatant was discarded and 200 $\mu$l of lysis reagent (attached to a cAMP EIA) was added. The amounts of cAMP of the lysate were determined by a cAMP EIA kit (Amersham) under conditions of the forskolin-induced cAMP production. The compound of the present invention was dissolved in DMSO and the solution was diluted to adjust the final concentration of DMSO to 0.1%. $IC_{50}$ values were calculated from the inhibitory ratio of the compound of the present invention toward the amount of the forskolin-induced cAMP production. By the same experiment using CHO cells, it was confirmed that this inhibitory effect toward cAMP production by the compound was mediated via the human CB2 receptors.

The results are shown in table 33.

TABLE 33

| Example No. | $IC_{50}$(nM) |
|---|---|
| 1 | 2.4 |
| 1(11) | 0.4 |
| 1(33) | 0.8 |

[Toxicity]

The toxicity of the compound of the present invention of formula (I) is low enough to use as a medical drug.

[Application to Medical Treatment]

The compound of the present invention, since it acts on the CB2 receptor specifically, is thought to be useful for the prevention and/or treatment of various diseases, for example, asthma, nasal allergy, atopic dermatitis, autoimmune diseases, rheumatoid arthritis, postoperative pain, carcinomatous pain, etc.

For the purpose described above, the compounds of formula (I), of the present invention, non-toxic salts thereof or solvates thereof may normally be administered systemically or topically, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of formula (I) of the present invention may be administered in the form of solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) may be admixed with at least one inert diluent (e.g. lactose, mannitol, glucose, hydroxypropyl cellulose, microcrystalline cellulose, starch, polyvinyl pyrrolidone or magnesium metasilicate aluminate). The compositions may also comprise, as is normal practice, additional substances other than inert diluents: e.g. lubricating agents (e.g. magnesium stearate), disintegrating agents (e.g. cellulose calcium glycolate), stabilizing agents (e.g. lactose), and agents to assist dissolution (e.g. glutamic acid or aspartic acid). The tablets or pills may, if desired, be coated with a film of gastric or enteric material (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable emulsions, solutions, syrups and elixirs. In such compositions, one or more of the active compound(s) may be contained in inert diluent(s) commonly used in the art (e.g. purified water or ethanol). Besides inert diluents, such compositions may also comprise adjutants (e.g. wetting agents or suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (e.g. sodium sulfite hydride), isotonic buffers (e.g. sodium chloride, sodium citrate or citric acid). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions and suspensions include distilled water for injection and physiological salt solution. Non-aqueous solutions and suspensions may include propylene glycol, polyethylene glycol, vegetable oil such as olive oil, alcohol such as ethanol or POLYSORBATE80 (registered trade mark). Sterile aqueous and inaqueous solutions, suspensions and emulsions may be used as mixture. Injections may comprise additional ingredients e.g. preserving agents, wetting agents, emulsifying agents, dispersing agents, stabilizing agents, assisting agents such as agents to assist dissolution (e.g. glutamic acid or aspartic acid). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

Other compositions for parenteral administration include liquids for external use, and ointment, endermic liniments, suppositories for rectal administration and pessaries for vaginal administration which comprise one or more of the active compound(s) and may be prepared by methods known per se.

BEST MODE FOR CARRYING OUT THE INVENTION

The following reference examples and examples illustrate the present invention, but the present invention are not limit to them.

The solvents in parentheses show the eluting or developing solvents and the ratios of the solvents used are by volume in chromatographic separations or TLC.

The solvents in parentheses in NMR show the solvents used in measurement.

REFERENCE EXAMPLE 1

3-cyclohexyl-3-oxo-propanenitrile

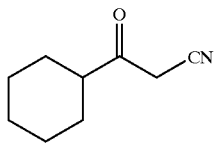

To a solution of sodium amide (1.87 g) in tetrahydrofuran (1.87 g) was added acetonitrile (2.72 ml) at −50~−40° C. dropwise and then was added cyclohexanecarboxylic acid methyl ester (2.86 ml) and the mixture was stirred for 1 hour at −20° C. The reaction mixture was poured into cool hydrochloric acid and was extracted with ethyl acetate. The extract was washed with water and a saturated aqueous solution of sodium chloride successively, and was dried over anhydrous magnesium sulfate and then concentrated under reduced pressure. The residue was purified by column chromatography on silica gel (hexane:ethyl acetate=4:1) to give the title compound (0.91 g) having the following physical data.

TLC: Rf 0.33 (ethyl acetate:hexane=1:3);

NMR (CDCl$_3$): δ 3.50 (s, 2H), 2.55 (m, 1H), 2.00–1.60 (m, 5H), 1.50–1.10 (m, 5H).

EXAMPLE 1

(Z)-2-(3,3-dimethyl-3,4-dihydro-(2H)-isoquinolin-1-ylidene)-1-cyclohexylethan-1-one

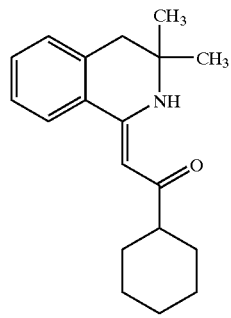

To a concentrated sulfuric acid was added the compound prepared in reference example 1 (890 mg) and to the mixture was added a solution of 2-methyl-1-phenylpropan-2-ol (1061 mg) in benzene (1 ml) at 0° C. and the mixture was stirred for 30 minutes at 60° C. The reaction mixture was neutralized with an aqueous solution of sodium hydroxide under cooling with ice, and the mixture was extracted with ethyl acetate. The extract was washed with water and a saturated aqueous solution of sodium chloride successively, dried over anhydrous magnesium sulfate and was concentrated under reduced pressure. The residue was purified by column chromatography on silica gel (hexane:ethyl acetate= 9:1) to give the compound of the present invention (1170 mg) having the following physical data.

TLC: Rf 0.36 (ethyl acetate:hexane=1:5);

NMR (CDCl$_3$): δ 11.32 (br., 1H), 7.71 (dd, J=8.0, 1.5 Hz, 1H), 7.39 (ddd, J=8.0, 8.0, 1.5 Hz, 1H), 7.28 (ddd, J=8.0, 8.0, 1.5 Hz, 1H), 7.16 (dd, J=8.0, 1.5 Hz, 1H), 5.64 (s, 1H), 2.84 (s, 2H), 2.39 (m, 1H), 2.00–1.20 (m, 10H), 1.29 (s, 6H).

EXAMPLE 1(1)~EXAMPLE 1(81)

By the same procedure as described in example 1 using the compound prepared in reference example 1 or a corresponding nitrile derivative, and 2-methyl-1-phenylpropan-2-ol or a corresponding alcohol derivative, the following compounds of the present invention were given.

EXAMPLE 1(1)

(Z)-2-(3,3-dimethyl-3,4-dihydro-(2H)-isoquinolin-1-ylidene)-1-(4-methoxycarbonylphenyl)ethan-1-one

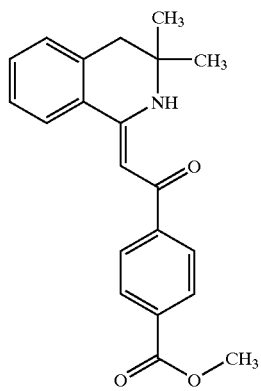

TLC: Rf 0.18 (ethyl acetate:hexane=1:5);

NMR (CDCl$_3$): δ 11.95 (br., 1H), 8.10 (d, J=8.0 Hz, 2H), 7.99 (d, J=8.0 Hz, 2H), 7.83 (d, J=7.5 Hz, 1H), 7.45 (dd, J=7.5, 7.5 Hz, 1H), 7.35 (dd, J=7.5, 7.5 Hz, 1H), 7.22 (d, J=7.5 Hz, 1H), 6.33 (s, 1H), 3.94 (s, 3H), 2.91 (s, 2H), 1.37 (s, 6H).

EXAMPLE 1(2)

(Z)-2-(3,3-dimethyl-3,4-dihydro-(2H)-isoquinolin-1-ylidene)-1-cyclopentylethan-1-one

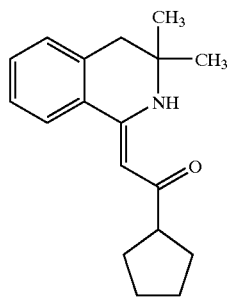

TLC: Rf 0.38 (ethyl acetate:hexane=1:5);

NMR (CDCl$_3$): δ 11.27 (br., 1H), 7.70 (m, 1H), 7.45–7.10 (m, 3H), 5.66 (s, 1H), 2.84 (s, 2H), 2.83 (m, 1H), 2.00–1.50 (m, 8H), 1.29 (s, 6H).

EXAMPLE 1(3)

(Z)-2-(3,3-dimethyl-3,4-dihydro-(2H)-isoquinolin-1-ylidene)-1-(2-methylphenyl)ethan-1-one

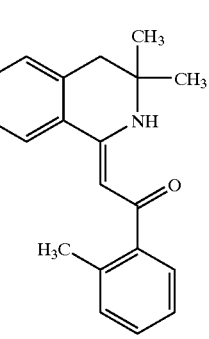

TLC: Rf 0.33 (ethyl acetate:hexane=1:4);

NMR (CDCl$_3$): δ 11.58 (br., 1H), 7.70 (d, J=8.0 Hz, 1H), 7.50–7.15 (m, 7H), 5.90 (s, 1H), 2.91 (s, 2H), 2.51 (s, 3H), 1.37 (s, 6H).

EXAMPLE 1(4)

(Z)-2-(3,3-dimethyl-3,4-dihydro-(2H)-isoquinolin-1-ylidene)-1-(3-methylphenyl)ethan-1-one

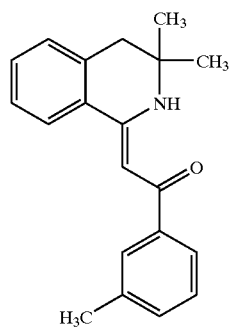

TLC: Rf 0.33 (ethyl acetate:hexane=1:4);

NMR (CDCl$_3$): δ 11.84 (br., 1H), 7.90–7.70 (m, 3H), 7.50–7.15 (m, 5H), 6.32 (s, 1H), 2.90 (s, 2H), 2.42 (s, 3H), 1.36 (s, 6H).

EXAMPLE 1(5)

(Z)-2-(3,3-dimethyl-3,4-dihydro-(2H)-isoquinolin-1-ylidene)-1-(4-methylphenyl)ethan-1-one

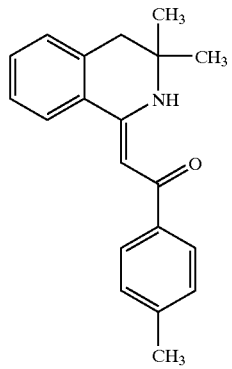

TLC: Rf 0.33 (ethyl acetate:hexane=1:4);

NMR (CDCl$_3$): δ 11.80 (br., 1H), 7.86 (d, J=8.0 Hz, 2H), 7.83 (m, 1H), 7.50–7.20 (m, 3H), 7.24 (d, J=8.0 Hz, 2H), 6.33 (s, 1H), 2.90 (s, 2H), 2.40 (s, 3H), 1.36 (s, 6H).

EXAMPLE 1(6)

(Z)-2-(3,3-dimethyl-3,4-dihydro-(2H)-isoquinolin-1-ylidene)-1-(furan-2-yl)ethan-1-one

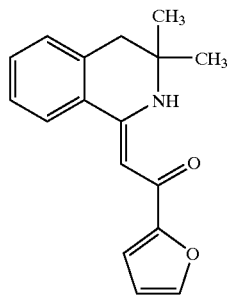

TLC: Rf 0.37 (ethyl acetate:hexane=1:3);

NMR (CDCl$_3$): δ 11.59 (br., 1H), 7.84 (m, 1H), 7.49 (dd, J=2.0, 1.0 Hz, 1H), 7.50–7.15 (m, 3H), 7.04 (dd, J=3.5, 1.0 Hz, 1H), 6.49 (dd, J=3.5, 2.0 Hz, 1H), 6.30 (s, 1H), 2.90 (s, 2H), 1.34 (s, 6H).

EXAMPLE 1(7)

(Z)-2-(3,3-dimethyl-3,4-dihydro-(2H)-isoquinolin-1-ylidene)-1-(2-chlorophenyl)ethan-1-one

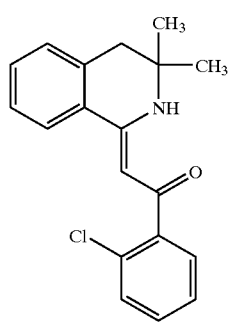

TLC: Rf 0.25 (hexane:ethyl acetate=5:1);

NMR (CDCl$_3$): δ 11.55 (br, 1H), 7.72 (d, J=7.5 Hz, 1H), 7.57–7.52 (m, 1H), 7.45–7.38 (m, 2H), 7.33–7.26 (m, 3H), 7.21 (dd, J=7.5, 1.0 Hz, 1H), 5.97 (s, 1H), 2.92 (s, 2H), 1.38 (s, 6H).

EXAMPLE 1(8)

(Z)-2-(3,3-dimethyl-3,4-dihydro-(2H)-isoquinolin-1-ylidene)-1-(thiophen-2-yl)ethan-1-one

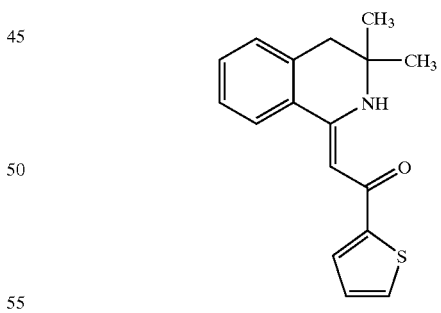

TLC: Rf 0.54 (ethyl acetate:hexane=1:2);

NMR (CDCl$_3$): δ 11.51 (br., 1H), 7.81 (d, J=7.0 Hz, 1H), 7.64 (d, J=3.0 Hz, 1H), 7.50–7.30 (m, 3H), 7.21 (d, J=7.0 Hz, 1H), 7.10 (dd, J=3.0, 3.0 Hz, 1H), 6.21 (s, 1H), 2.89 (s, 2H), 1.34 (s, 6H).

EXAMPLE 1(9)

(Z)-2-(3,3-dimethyl-3,4-dihydro-(2H)-isoquinolin-1-ylidene)-1-(3-chlorophenyl)ethan-1-one

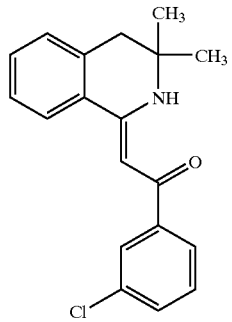

TLC: Rf 0.46 (hexane:ethyl acetate=3:1);

NMR (CDCl$_3$): δ 11.85 (br, 1H), 7.92–7.91 (m, 1H), 7.84–7.80 (m, 2H), 7.47–7.34 (m, 4H), 7.22 (d, J=7.0 Hz, 1H), 6.26 (s, 1H), 2.91 (s, 2H), 1.37 (s, 6H).

EXAMPLE 1(10)

(Z)-2-(3,3-dimethyl-3,4-dihydro-(2H)-isoquinolin-1-ylidene)-1-cyclobutylethan-1-one

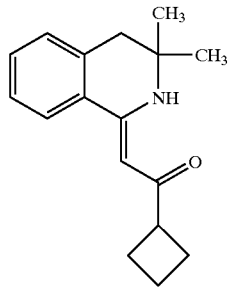

TLC: Rf 0.43 (ethyl acetate:hexane=1:3);

NMR (CDCl$_3$): δ 11.34 (br., 1H), 7.69 (d, J=7.0 Hz, 1H), 7.45–7.20 (m, 2H), 7.16 (d, J=7.0 Hz, 1H), 5.56 (s, 1H), 3.26 (m, 1H), 2.84 (s, 2H), 2.45–1.70 (m, 6H), 1.30 (s, 6H).

EXAMPLE 1(11)

(Z)-2-(3,3-dimethyl-3,4-dihydro-(2H)-isoquinolin-1-ylidene)-1-cycloheptylethan-1-one

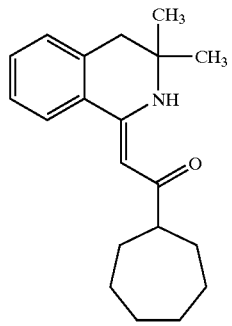

TLC: Rf 0.50 (ethyl acetate:hexane=1:3);

NMR (CDCl$_3$): δ 11.23 (br., 1H), 6.70 (d, J=8.0 Hz, 1H), 7.45–7.20 (m, 2H), 7.16 (d, J=8.0 Hz, 1H), 5.60 (s, 1H), 2.84 (s, 2H), 2.45 (m, 1H), 2.00–1.30 (m, 12H), 1.29 (s, 6H).

EXAMPLE 1(12)

(Z)-2-(3,3-dimethyl-3,4-dihydro-(2H)-isoquinolin-1-ylidene)-1-(4-chlorophenyl)ethan-1-one

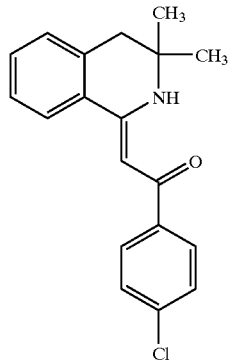

TLC: Rf 0.48 (hexane:ethyl acetate=3:1);

NMR (CDCl$_3$): δ 11.82 (br, 1H), 7.91–7.87 (m, 2H), 7.81 (d, J=8.0 Hz, 1H), 7.47–7.32 (m, 4H), 7.22 (dd, J=7.5, 1.0 Hz, 1H), 6.27 (s, 1H), 2.91 (s, 2H), 1.37 (s, 6H).

EXAMPLE 1(13)

(Z)-2-(3,3-dimethyl-3,4-dihydro-(2H)-isoquinolin-1-ylidene)-1-(adamantan-1-yl)ethan-1-one

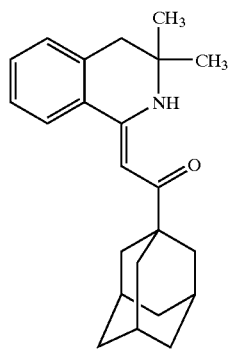

TLC: Rf 0.34 (ethyl acetate:hexane=1:5);

NMR (CDCl$_3$): δ 11.48 (br., 1H), 7.72 (d, J=8.0 Hz, 1H), 7.45–7.25 (m, 2H), 7.16 (d, J=8.0 Hz, 1H), 5.79 (s, 1H), 2.84 (s, 2H), 2.05 (m, 3H), 1.91 (m, 6H), 1.75 (m, 6H), 1.29 (s, 6H).

EXAMPLE 1(14)

(Z)-2-(3,3,5-trimethyl-3,4-dihydro-(2H)-isoquinolin-1-ylidene)-1-phenylethan-1-one

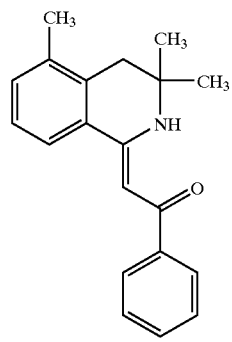

TLC: Rf 0.24 (ethyl acetate:hexane=1:5);

NMR (CDCl$_3$): δ 11.92 (br., 1H), 7.95 (m, 2H), 7.71 (d, J=7.5 Hz, 1H), 7.50–7.40 (m, 3H), 7.32 (d, J=7.5 Hz, 1H), 7.23 (dd, J=7.5, 7.5 Hz, 1H), 6.32 (s, 1H), 2.83 (s, 2H), 2.32 (s, 3H), 1.37 (s, 6H).

EXAMPLE 1(15)

(Z)-2-(3,3,6-trimethyl-3,4-dihydro-(2H)-isoquinolin-1-ylidene)-1-phenylethan-1-one

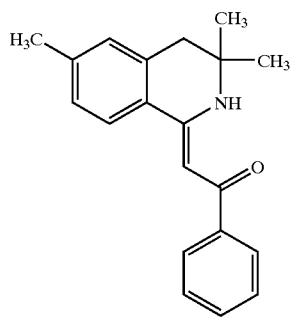

TLC: Rf 0.27 (ethyl acetate:hexane=1:5);

NMR (CDCl$_3$): δ 11.83 (br., 1H), 7.95 (m, 2H), 7.71 (d, J=8.0 Hz, 1H), 7.50–7.40 (m, 3H), 7.13 (d, J=8.0 Hz, 1H), 7.01 (s, 1H), 6.30 (s, 1H), 2.85 (s, 2H), 2.39 (s, 3H), 1.35 (s, 6H).

EXAMPLE 1(16)

(Z)-2-(3,3-dimethyl-3,4-dihydro-(2H)-isoquinolin-1-ylidene)-1-(naphthalen-2-yl)ethan-1-one

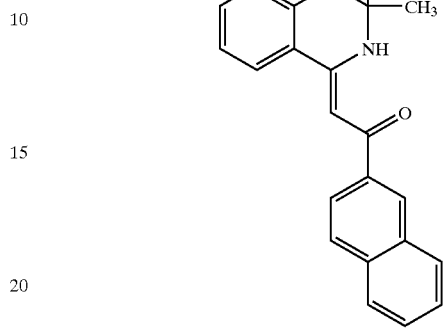

TLC: Rf 0.26 (ethyl acetate:hexane=1:5);

NMR (CDCl$_3$): δ 11.95 (br., 1H), 8.46 (s, 1H), 8.07 (dd, J=8.5, 1.0 Hz, 1H), 8.00–7.80 (m, 4H), 7.60–7.20 (m, 5H), 6.49 (s, 1H), 2.93 (s, 2H), 1.39 (s, 6H).

EXAMPLE 1(17)

(Z)-2-(3,3-dimethyl-3,4-dihydro-(2H)-isoquinolin-1-ylidene)-1-(4-methoxyphenyl)ethan-1-one

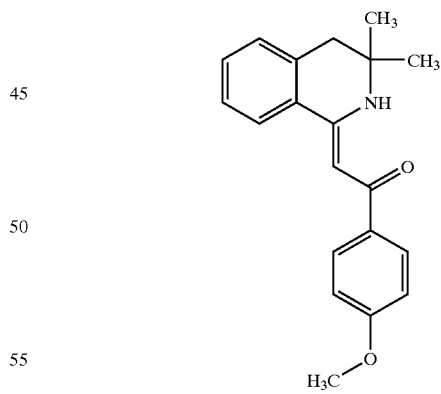

TLC: Rf 0.28 (hexane:ethyl acetate=3:1);

NMR (CDCl$_3$): δ 11.74 (br, 1H), 7.98–7.91 (m, 2H), 7.83 (d, J=7.0 Hz, 1H), 7.45–7.29 (m, 2H), 7.21 (d, J=7.5 Hz, 1H), 6.97–6.91 (m, 2H), 6.31 (s, 1H), 3.86 (s, 3H), 2.89 (s, 2H), 1.35 (s, 6H).

EXAMPLE 1(18)

(Z)-2-(3,3-dimethyl-3,4-dihydro-(2H)-isoquinolin-1-ylidene)-1-(3-methoxyphenyl)ethan-1-one

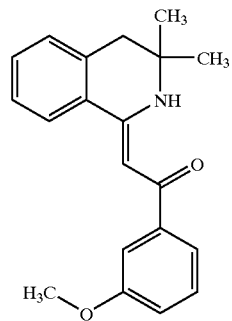

TLC: Rf 0.48 (hexane:ethyl acetate=2:1);

NMR (CDCl$_3$): δ 11.83 (br, 1H), 7.83 (d, J=8.0 Hz, 1H), 7.55–7.29 (m, 5H), 7.22 (d, J=7.5 Hz, 1H), 7.03–6.97 (m, 1H), 6.32 (s, 1H), 3.88 (s, 3H), 2.91 (s, 2H), 1.37 (s, 6H).

EXAMPLE 1(19)

(Z)-2-(3,3-dimethyl-3,4-dihydro-(2H)-isoquinolin-1-ylidene)-1-(4-fluorophenyl)ethan-1-one

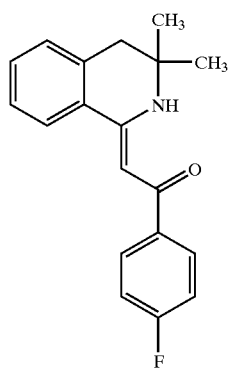

TLC: Rf 0.52 (hexane:ethyl acetate=2:1);

NMR (CDCl$_3$): δ 11.78 (br, 1H), 7.98–7.91 (m, 2H), 7.81 (d, J=7.5 Hz, 1H), 7.47–7.30 (m, 2H), 7.21 (d, J=7.0 Hz, 1H), 7.14–7.05 (m, 2H), 6.27 (s, 1H), 2.90 (s, 2H), 1.36 (s, 6H).

EXAMPLE 1(20)

(Z)-2-(3,3,7-trimethyl-3,4-dihydro-(2H)-isoquinolin-1-ylidene)-1-phenylethan-1-one

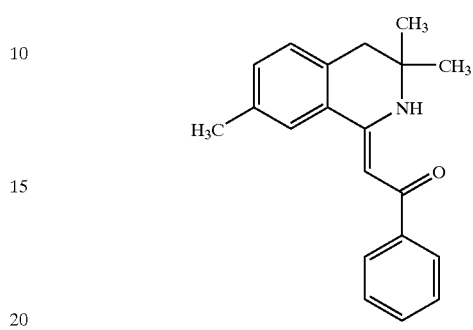

TLC: Rf 0.38 (ethyl acetate:hexane=1:3);

NMR (CDCl$_3$): δ 11.84 (br., 1H), 7.96 (m, 2H), 7.62 (s, 1H), 7.50–7.40 (m, 3H), 7.24 (d, J=7.5 Hz, 1H), 7.10 (d, J=7.5 Hz, 1H), 6.32 (s, 1H), 2.85 (s, 2H), 2.42 (s, 3H), 1.35 (s, 6H).

EXAMPLE 1(21)

(Z)-2-(3,3-dimethyl-3,4-dihydro-(2H)-isoquinolin-1-ylidene)-1-(naphthalen-1-yl)ethan-1-one

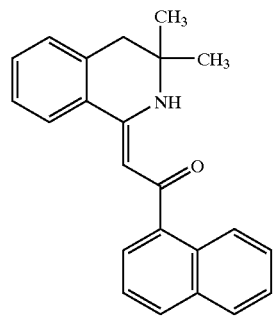

TLC: Rf 0.27 (ethyl acetate:hexane=1:5);

NMR (CDCl$_3$): δ 11.78 (br., 1H), 8.50 (m, 1H), 7.90–7.80 (m, 2H), 7.75–7.65 (m, 2H), 7.55–7.15 (m, 6H), 6.09 (s, 1H), 2.94 (s, 2H), 1.41 (s, 6H).

EXAMPLE 1(22)

(Z)-2-(3,3-dimethyl-3,4-dihydro-(2H)-isoquinolin-1-ylidene)-1-(2-methoxyphenyl)ethan-1-one

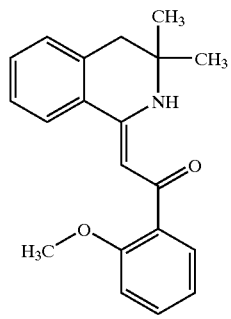

TLC: Rf 0.38 (hexane:ethyl acetate=2:1);

NMR (CDCl$_3$): δ 11.69 (br, 1H), 7.74 (d, J=8.0 Hz, 1H), 7.67 (dd, J=8.0, 2.0 Hz, 1H), 7.43–7.29 (m, 3H), 7.19 (dd, J=7.0, 0.5 Hz, 1H), 7.03–6.95 (m, 2H), 6.27 (s, 1H), 3.91 (s, 3H), 2.89 (s, 2H), 1.36 (s, 6H).

EXAMPLE 1(23)

(Z)-2-(3,3-dimethyl-3,4-dihydro-(2H)-isoquinolin-1-ylidene)-1-(2-fluorophenyl)ethan-1-one

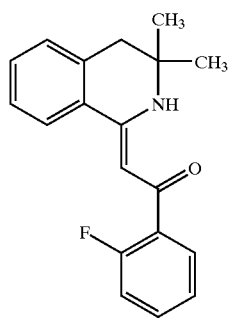

TLC: Rf 0.59 (hexane:ethyl acetate=2:1);

NMR (CDCl$_3$): δ 11.79 (br, 1H), 7.86 (ddd, J=8.0, 8.0, 2.0 Hz, 1H), 7.79 (d, J=7.0 Hz, 1H), 7.45–7.30 (m, 3H), 7.24–7.18 (m, 2H), 7.10 (ddd, J=11.5, 8.0, 1.0 Hz, 1H), 6.30 (s, 1H), 2.91 (s, 2H), 1.37 (s, 6H).

EXAMPLE 1(24)

(Z)-2-(3,3-dimethyl-3,4-dihydro-(2H)-isoquinolin-1-ylidene)-1-(3-fluorophenyl)ethan-1-one

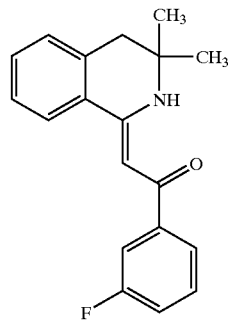

TLC: Rf 0.63 (hexane:ethyl acetate=2:1);

NMR (CDCl$_3$): δ 11.84 (br, 1H), 7.82 (d, J=8.0 Hz, 1H), 7.72 (d, J=8.0 Hz, 1H), 7.63 (d, J=10.0 Hz, 1H), 7.47–7.33 (m, 3H), 7.22 (d, J=7.5 Hz, 1H), 7.17–7.10 (m, 1H), 6.27 (s, 1H), 2.91 (s, 2H), 1.37 (s, 6H).

EXAMPLE 1(25)

A mixture of (Z)-2-(3,3-dimethyl-3,4-dihydro-(2H)-isoquinolin-1-ylidene)-2-methyl-1-phenylethan-1-one and 2-(3,3-dimethyl-3,4-dihydroisoquinolin-1-yl)-1-phenylpropan-1-one Mixture of

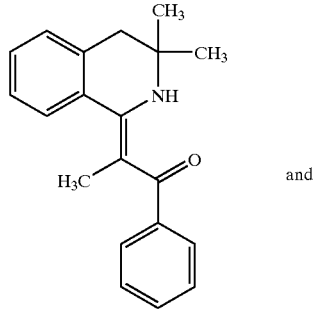

A and

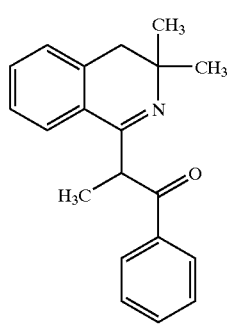

B

A and B were given as a mixture (A:B=5:4).

TLC: Rf 0.29 (ethyl acetate:hexane=1:5);

NMR (CDCl$_3$): δ 13.05 (br., 1H of A), 7.92 (m, 2H of A), 7.81 (m, 1H of A), 7.60–7.10 (m, 6H of A and 9H of B), 4.80 (q, J=7.0 Hz, 1H of B), 2.84 (s, 2H of A), 2.58 (s, 2H of B), 2.56 (d, J=7.0 Hz, 3H of B), 2.10 (s, 3H of A), 1.27 (s, 6H of A), 1.08 (s, 3H of B), 0.97 (s, 3H of B).

EXAMPLE 1(26)

(Z)-2-(spiro[3,4-dihydro-(2H)-isoquinolin-3,1'-cyclohexane]-1-ylidene)-1-phenylethan-1-one

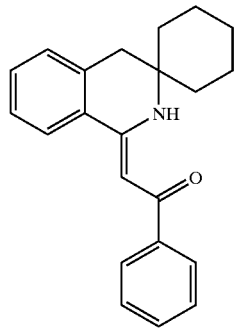

TLC: Rf 0.58 (hexane:ethyl acetate=3:1);

NMR (CDCl$_3$): δ 12.21 (br, 1H), 7.99–7.94 (m, 2H), 7.82 (d, J=7.0 Hz, 1H), 7.47–7.28 (m, 5H), 7.21 (d, J=7.0 Hz, 1H), 6.35 (s, 1H), 2.91 (s, 2H), 1.80–1.30 (m, 10H).

EXAMPLE 1(27)

(Z)-2-(spiro[3,4-dihydro-(2H)-isoquinolin-3,1'-cyclopentan]-1-ylidene)-1-phenylethan-1-one

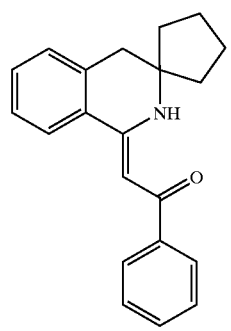

TLC: Rf 0.54 (hexane:ethyl acetate=3:1);

NMR (CDCl$_3$): δ 12.03 (br, 1H), 7.98–7.93 (m, 2H), 7.82 (d, J=7.5 Hz, 1H), 7.47–7.29 (m, 5H), 7.23 (d, J'=7.5 Hz, 1H), 6.34 (s, 1H), 2.98 (s, 2H), 1.95–1.62 (m, 8H).

EXAMPLE 1(28)

(Z)-2-(spiro[3,4-dihydro-(2H)-isoquinolin-3,1'-cycloheptan]-1-ylidene)-1-phenylethan-1-one

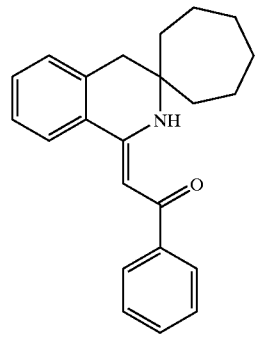

TLC: Rf 0.41 (hexane:ethyl acetate=5:1);

NMR (CDCl$_3$): δ 12.16 (br, 1H), 7.99–7.94 (m, 2H), 7.82 (d, J=7.5 Hz, 1H), 7.47–7.29 (m, 5H), 7.20 (d, J=7.0 Hz, 1H), 6.33 (s, 1H), 2.92 (s, 2H), 1.91–1.45 (m, 12H).

EXAMPLE 1(29)

(Z)-2-(3,3-diethyl-3,4-dihydro-(2H)-isoquinolin-1-ylidene)-1-phenylethan-1-one

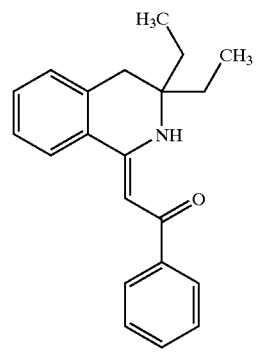

TLC: Rf 0.35 (hexane:ethyl acetate=5:1);

NMR (CDCl$_3$): δ 11.98 (br, 1H), 7.99–7.94 (m, 2H), 7.82 (d, J=7.5 Hz, 1H), 7.45–7.29 (m, 5H), 7.21 (d, J=7.0 Hz, 1H), 6.36 (s, 1H), 2.90 (s, 2H), 1.70–1.58 (m, 4H), 0.95 (t, J=7.5 Hz, 6H).

EXAMPLE 1(30)

(Z)-2-(3,3-dimethyl-3,4-dihydro-(2H)-isoquinolin-1-ylidene)-1-(3-methoxycarbonylphenyl)ethan-1-one

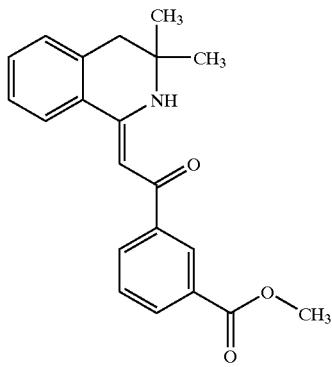

TLC: Rf 0.19 (ethyl acetate:hexane=1:5);

NMR (CDCl$_3$): δ 11.91 (br., 1H), 8.60 (dd, J=1.5, 1.5 Hz, 1H), 8.20–8.10 (m, 2H), 7.86 (dd, J=8.5, 1.5 Hz, 1H), 7.60–7.20 (m, 4H), 6.36 (s, 1H), 3.95 (s, 3H), 2.92 (s, 2H), 1.38 (s, 6H).

EXAMPLE 1(31)

(Z)-2-(spiro[3,4-dihydro-(2H)-isoquinolin-3,1'-cyclobutan]-1-ylidene)-1-phenylethan-1-one

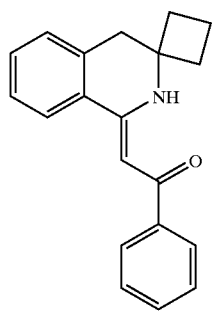

TLC: Rf 0.35 (hexane:ethyl acetate=5:1);

NMR (CDCl$_3$): δ 11.99 (br, 1H), 7.97–7.94 (m, 2H), 7.80 (d, J=7.5 Hz, 1H), 7.47–7.41 (m, 4H), 7.37–7.26 (m, 2H), 6.34 (s, 1H), 3.09 (s, 2H), 2.33–2.23 (m, 2H), 2.18–2.09 (m, 2H), 1.96–1.79 (m, 2H).

EXAMPLE 1(32)

(Z)-2-(3,3-dimethyl-3,4-dihydro-(2H)-isoquinolin-1-ylidene)-1-(quinolin-6-yl)ethan-1-one

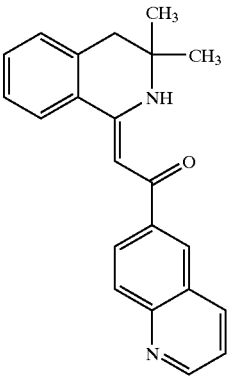

TLC: Rf 0.22 (ethyl acetate:hexane=1:1);

NMR (CDCl$_3$): δ 11.99 (br., 1H), 8.95 (dd, J=4.0, 1.5 Hz, 1H), 8.44 (d, J=1.5 Hz, 1H), 8.30 (dd, J=9.0, 1.5 Hz, 1H), 8.27 (m, 1H), 8.15 (d, J=9.0 Hz, 1H), 7.90 (m, 1H), 7.50–7.20 (m, 4H), 6.47 (s, 1H), 2.94 (s, 2H), 1.40 (s, 6H).

EXAMPLE 1(33)

(Z)-2-(spiro[3,4-dihydro-(2H)-isoquinolin-3,4'-3,4,5,6-tetrahydropyran]-1-ylidene)-1-phenylethan-1-one

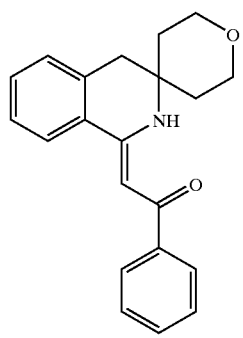

TLC: Rf 0.49 (hexane:ethyl acetate=1:1);

NMR (CDCl$_3$): δ 12.41 (br, 1H), 7.99–7.94 (m, 2H), 7.83 (d, J=7.0 Hz, 1H), 7.48–7.23 (m, 6H), 6.39 (s, 1H), 3.90–3.84 (m, 4H), 2.96 (s, 2H), 1.80–1.73 (m, 4H).

EXAMPLE 1(34)

(Z)-2-(spiro[3,4-dihydro-(2H)-isoquinolin-3,4'-1'-methylpiperidin]-1-ylidene)-1-phenylethan-1-one

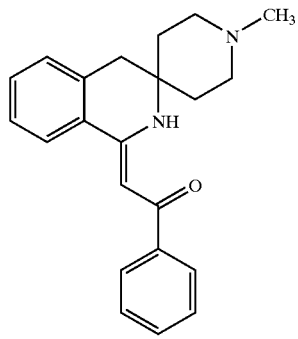

TLC: Rf 0.27 (chloroform:methanol=10:1);

NMR (CDCl₃): δ 12.22 (br, 1H), 7.98–7.95 (m, 2H), 7.82 (d, J=7.5 Hz, 1H), 7.46–7.41 (m, 4H), 7.34 (t, J=7.5 Hz, 1H), 7.24 (d, J=7.5 Hz, 1H), 6.36 (s, 1H), 2.92 (s, 2H), 2.73–2.69 (m, 2H), 2.53–2.45 (m, 2H), 2.38 (s, 3H), 1.81–1.77 (m, 4H).

EXAMPLE 1(35)

(Z)-2-(3,3-dimethyl-3,4-dihydro-(2H)-isoquinolin-1-ylidene)-1-(2-trifluoromethylphenyl)ethan-1-one

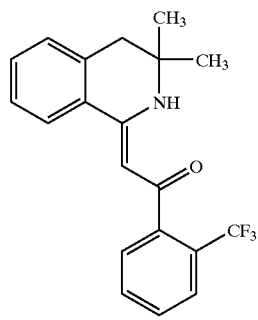

TLC: Rf 0.19 (ethyl acetate:hexane=1:5);

NMR (CDCl₃): δ 11.42 (br., 1H), 7.75–7.15 (m, 8H), 5.82 (s, 1H), 2.92 (s, 2H), 1.38 (s, 6H).

EXAMPLE 1(36)

(Z)-2-(3,3-dimethyl-3,4-dihydro-(2H)-isoquinolin-1-ylidene)-1-(3-trifluoromethylphenyl)ethan-1-one

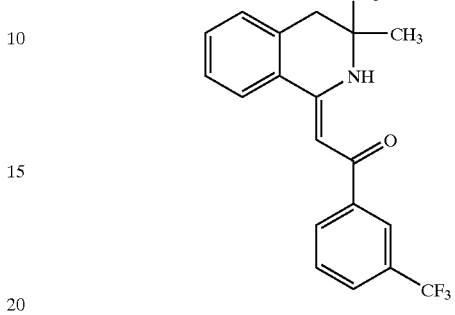

TLC: Rf 0.47 (ethyl acetate:hexane=1:3);

NMR (CDCl₃): δ 11.92 (br., 1H), 8.21 (s, 1H), 8.12 (d, J=8.0 Hz, 1H), 7.85 (d, J=7.5 Hz, 1H), 7.70 (d, J=8.0 Hz, 1H), 7.57 (d, J=7.5 Hz, 1H), 7.55–7.20 (m, 3H), 6.31 (s, 1H), 2.93 (s, 2H), 1.39 (s, 6H).

EXAMPLE 1(37)

(Z)-2-(3,3-dimethyl-3,4-dihydro-(2H)-isoquinolin-1-ylidene)-1-(4-trifluoromethylphenyl)ethan-1-one

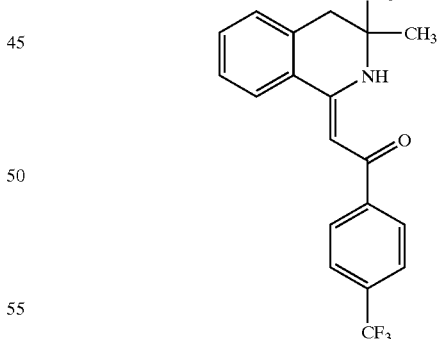

TLC: Rf 0.27 (ethyl acetate:hexane=1:5);

NMR (CDCl₃): δ 11.93 (br., 1H), 8.03 (d, J=8.0 Hz, 2H), 7.83 (m, 1H), 7.69 (d, J=8.0 Hz, 2H), 7.50–7.20 (m, 3H), 6.30 (s, 1H), 2.92 (s, 2H), 1.38 (s, 6H).

EXAMPLE 1(38)

(Z)-2-(3,3,6,8-tetramethyl-3,4-dihydro-(2H)-isoquinolin-1-ylidene)-1-phenylethan-1-one

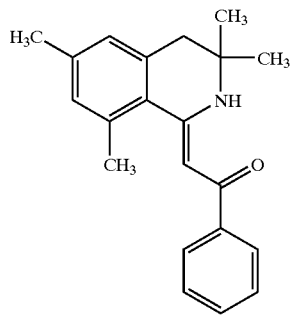

TLC: Rf 0.46 (ethyl acetate:hexane=1:3);

NMR (CDCl$_3$): δ 12.06 (br., 1H), 7.88 (m, 2H), 7.50–7.35 (m, 3H), 7.03 (s, 1H), 6.86 (s, 1H), 6.11 (s, 1H), 2.79 (s, 2H), 2.65 (s, 3H), 2.34 (s, 3H), 1.30 (s, 6H).

EXAMPLE 1(39)

(Z)-2-(3,3-dimethyl-3,4-dihydro-(2H)-isoquinolin-1-ylidene)-1-(pyridin-3-yl)ethan-1-one

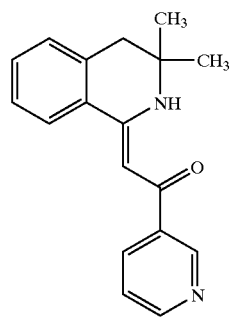

TLC: Rf 0.36 (ethyl acetate:hexane=2:1);

NMR (CDCl$_3$): δ 11.89 (br., 1H), 9.16 (dd, J=2.0, 0.5 Hz, 1H), 8.66 (dd, J=5.0, 2.0 Hz, 1H), 8.22 (ddd, J=8.0, 2.0, 2.0 Hz, 1H), 7.83 (m, 1H), 7.50–7.20 (m, 4H), 6.29 (s, 1H), 2.92 (s, 2H), 1.38 (s, 6H).

EXAMPLE 1(40)

(Z)-2-(3,3-dimethyl-3,4-dihydro-(2H)-isoquinolin-1-ylidene)-1-(pyridin-4-yl)ethan-1-one

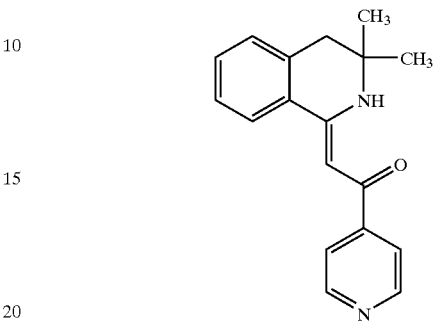

TLC: Rf 0.34 (ethyl acetate:hexane=2:1);

NMR (CDCl$_3$): δ 11.98 (br., 1H), 8.72 (d, J=6.0 Hz, 2H), 7.82 (m, 1H), 7.75 (d, J=6.0 Hz, 2H), 7.50–7.20 (m, 3H), 6.29 (s, 1H), 2.92 (s, 2H), 1.38 (s, 6H).

EXAMPLE 1(41)

(Z)-2-(8-methoxy-3,3-dimethyl-3,4-dihydro-(2H)-isoquinolin-1-ylidene)-1-phenylethan-1-one

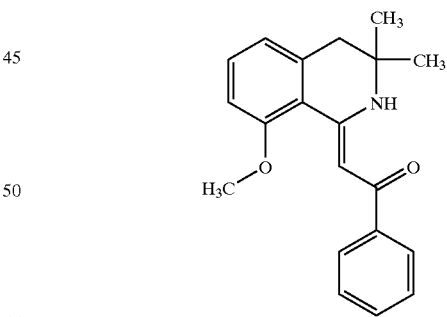

TLC: Rf 0.36 (ethyl acetate:hexane=1:3);

NMR (CDCl$_3$): δ 12.28 (br., 1H), 7.93 (m, 2H), 7.50–7.35 (m, 3H), 7.35 (dd, J=7.0, 7.0 Hz, 1H), 6.96 (s, 1H), 6.92 (d, J=7.0 Hz, 1H), 6.81 (d, J=7.0 Hz, 1H), 3.97 (s, 3H), 2.85 (s, 2H), 1.34 (s, 6H).

EXAMPLE 1(42)

(Z)-2-(6-methoxy-3,3-dimethyl-3,4-dihydro-(2H)-isoquinolin-1-ylidene)-1-phenylethan-1-one

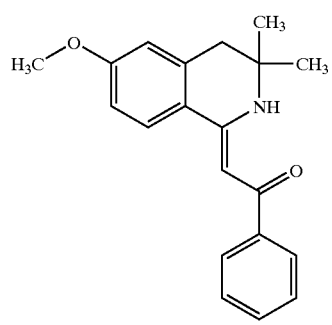

TLC: Rf 0.28 (ethyl acetate:hexane=1:3);

NMR (CDCl$_3$): δ 11.84 (br., 1H), 7.93 (m, 2H), 7.77 (d, J=9.0 Hz, 1H), 7.50–7.35 (m, 3H), 6.85 (dd, J=9.0, 2.5 Hz, 1H), 6.72 (d, J=2.5 Hz, 1H), 6.25 (s, 1H), 3.87 (s, 3H), 2.86 (s, 2H), 1.36 (s, 6H).

EXAMPLE 1(43)

(Z)-2-(spiro[3,4-dihydro-(2H)-isoquinolin-3,4'-piperidin]-1-ylidene)-1-phenylethan-1-one

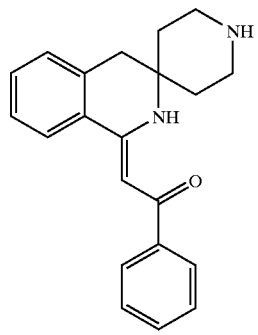

TLC: Rf 0.14 (water:methanol:chloroform=1:10:50);

NMR (CDCl$_3$): δ 12.40 (s, 1H), 7.96 (m, 2H), 7.82 (d, J=7.5 Hz, 1H), 7.50–7.20 (m, 6H), 6.39 (s, 1H), 3.12 (m, 4H), 2.96 (s, 2H), 1.83 (m, 4H).

EXAMPLE 1(44)

(Z)-2-(3,3-dimethyl-3,4-dihydro-(2H)-isoquinolin-1-ylidene)-1-(2,6-dimethylphenyl)ethan-1-one

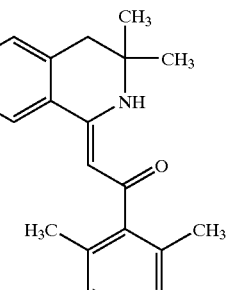

TLC: Rf 0.24 (ethyl acetate:hexane=1:5);

NMR (CDCl$_3$): δ 11.52 (br., 1H), 7.64 (d, J=7.5 Hz, 1H), 7.45–6.95 (m, 6H), 5.71 (s, 1H), 2.92 (s, 2H), 2.33 (s, 6H), 1.38 (s, 6H).

EXAMPLE 1(45)

(Z)-2-(spiro[3,4-dihydro-(2H)-isoquinolin-3,1'-4'-ethoxycarbonylcyclohexane]-1-ylidene)-1-phenylethan-1-one

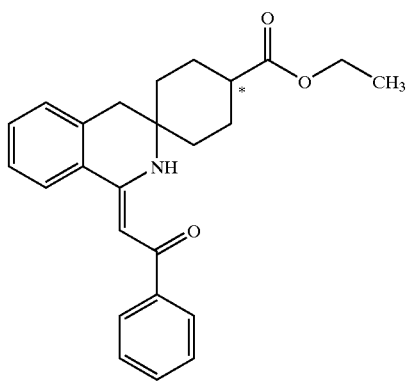

TLC: Rf 0.50 (hexane:ethyl acetate=2:1);

NMR (CDCl$_3$): δ 12.04 (br, 1H), 7.98–7.93 (m, 2H), 7.82 (d, J=8.0 Hz, 1H), 7.46–7.20 (m, 6H), 6.35 (s, 1H), 4.15 (q, J=7.0 Hz, 2H), 2.98 (s, 2H), 2.55–2.42 (m, 1H), 2.03–1.50 (m, 8H), 1.27 (t, J=7.0 Hz, 3H).

(This compound has two stereo isomers by the existence of carbon* to which ethoxycarbonyl group is attached. This compound corresponds to less polar compound on thin layer silica gel. And more polar compound corresponding to this compound is described in example 1 (46)).

EXAMPLE 1(46)

(Z)-2-(spiro[3,4-dihydro-(2H)-isoquinolin-3,1'-4'-ethoxycarbonylcyclohexane]-1-ylidene)-1-phenylethan-1-one

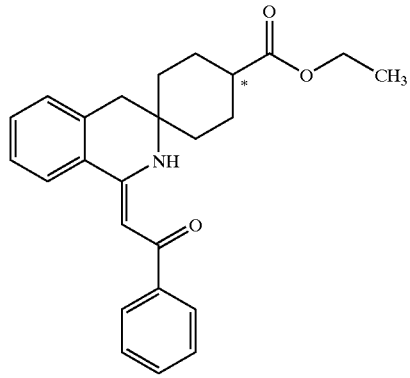

TLC: Rf 0.36 (hexane:ethyl acetate=2:1);

NMR (CDCl$_3$): δ 12.26 (br, 1H), 7.98–7.90 (m, 2H), 7.82 (d, J=7.0 Hz, 1H), 7.57–7.27 (m, 5H), 7.21 (d, J=6.5 Hz, 1H), 6.34 (s, 1H), 4.15 (q, J=7.0 Hz, 2H), 2.89 (s, 2H), 2.34–2.25 (m, 1H), 1.98–1.40 (m, 8H), 1.27 (t, J=7.0 Hz, 3H).

(This compound has two stereo isomers by the existence of carbon* to which ethoxycarbonyl group is attached. This compound corresponds to more polar compound on thin layer silica gel. And less polar compound corresponding to this compound is described in example 1 (45)).

EXAMPLE 1(47)

(Z)-2-(3,3-dimethyl-3,4-dihydro-(2H)-isoquinolin-1-ylidene)-1-cyclododecylethan-1-one

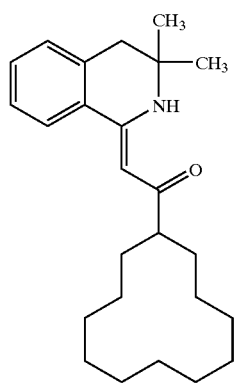

TLC: Rf 0.35 (ethyl acetate:hexane=1:5);

NMR (CDCl$_3$): δ 11.32 (br., 1H), 7.72 (m, 1H), 7.45–7.10 (m, 3H), 5.61 (s, 1H), 2.84 (m, 2H), 2.55 (m, 1H), 1.70–1.20 (m, 22H), 1.29 (s, 6H).

EXAMPLE 1(48)

(Z)-2-(3,3-dimethyl-3,4-dihydro-(2H)-isoquinolin-1-ylidene)-1-(4-t-butylphenyl)ethan-1-one

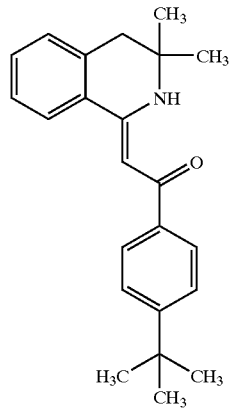

TLC: Rf 0.26 (ethyl acetate:hexane=1:5);

NMR (CDCl$_3$): δ 11.78 (br., 1H), 7.89 (d, J=8.5 Hz, 2H), 7.82 (m, 1H), 7.45 (d, J=8.5 Hz, 2H), 7.45–7.15 (m, 3H), 6.33 (s, 1H), 2.90 (m, 2H), 1.36 (s, 6H), 1.35 (s, 9H).

EXAMPLE 1(49)

(Z)-2-(spiro[3,4-dihydro-(2H)-isoquinolin-3,1'-4'-oxocyclohexane]-1-ylidene)-1-phenylethan-1-one

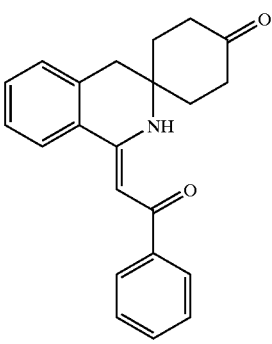

TLC: Rf 0.38 (ethyl acetate:hexane=1:1);

NMR (CDCl$_3$): δ 12.63 (br., 1H), 7.96 (m, 2H), 7.87 (m, 1H), 7.50–7.20 (m, 6H), 6.45 (s, 1H), 3.04 (s, 2H), 2.77 (m, 2H), 2.39 (m, 2H), 2.17 (m, 2H), 1.93 (m, 2H).

EXAMPLE 1(50)

(Z)-2-(3,3-dimethyl-3,4-dihydro-(2H)-isoquinolin-1-ylidene)-1-(piperidin-4-yl)ethan-1-one

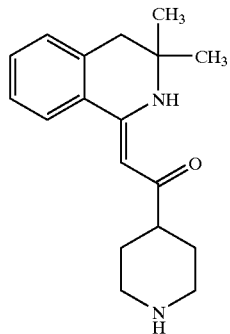

TLC: Rf 0.18 (water:methanol:chloroform=1:10:50);

NMR (CDCl$_3$): δ 11.31 (br., 1H), 7.70 (m, 1H), 7.45–7.15 (m, 3H), 5.64 (s, 1H), 3.17 (dt, J=12.0, 3.5 Hz, 2H), 2.85 (s, 2H), 2.67 (dt, J=3.5, 12.0 Hz, 2H), 2.42 (tt, J=12.0, 4.0 Hz, 1H), 1.86 (m, 2H), 1.68 (m, 2H), 1.30 (s, 6H).

EXAMPLE 1(51)

(Z)-2-(3,3-dimethyl-3,4-dihydro-(2H)-isoquinolin-1-ylidene)-1-(4-isopropylphenyl)ethan-1-one

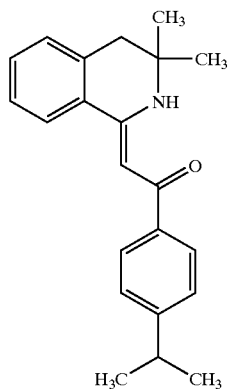

TLC: Rf 0.38 (hexane:ethyl acetate=4:1);

NMR (CDCl$_3$): δ 11.78 (s, 1H), 7.88 (d, J=8.0 Hz, 2H), 7.86–7.80 (m, 1H), 7.44–7.18 (m, 3H), 7.28 (d, J=8.0 Hz, 2H), 6.32 (s, 1H), 3.02–2.81 (m, 1H), 2.89 (s, 2H), 1.36 (s, 6H), 1.28 (d, J=8.0 Hz, 6H).

EXAMPLE 1(52)

(Z)-2-(3,3-dimethyl-3,4-dihydro-(2H)-isoquinolin-1-ylidene)-1-cyclooctylethan-1-one

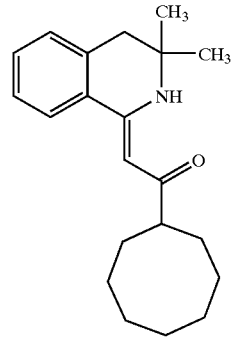

TLC: Rf 0.42 (ethyl acetate:hexane=1:5);

NMR (CDCl$_3$): δ 11.21 (br., 1H), 7.71 (d, J=7.5 Hz, 1H), 7.45–7.20 (m, 2H), 7.16 (d, J=7.5 Hz, 1H), 5.60 (s, 1H), 2.84 (s, 2H), 2.51 (m, 1H), 2.00–1.40 (m, 14H), 1.29 (s, 6H).

EXAMPLE 1(53)

(Z)-2-(3,3-dimethyl-3,4-dihydro-(2H)-isoquinolin-1-ylidene)-1-(1-methylcyclohexyl)ethan-1-one

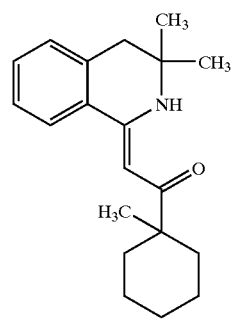

TLC: Rf 0.44 (ethyl acetate:hexane=1:5);

NMR (CDCl$_3$): δ 11.36 (br., 1H), 7.70 (m, 1H), 7.45–7.10 (m, 3H), 5.83 (s, 1H), 2.84 (s, 2H), 2.10–1.95 (m, 2H), 1.65–1.20 (m, 8H), 1.30 (s, 6H), 1.15 (s, 3H).

EXAMPLE 1(54)

(Z)-2-(3,3-dimethyl-3,4-dihydro-(2H)-isoquinolin-1-ylidene)-1-(4-ethyphenyl)ethan-1-one

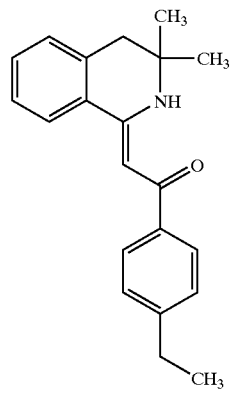

TLC: Rf 0.35 (hexane:ethyl acetate=4:1);

NMR (CDCl₃): δ 11.80 (bs, 1H), 7.90–7.80 (m, 3H), 7.46–7.18 (m, 5H), 6.33 (s, 1H), 2.89 (s, 2H), 2.70 (q, J=7.8 Hz, 2H), 1.36 (s, 6H), 1.27 (t, J=7.8 Hz, 3H).

EXAMPLE 1(55)

(Z)-2-(3,3-dimethyl-3,4-dihydro-(2H)-isoquinolin-1-ylidene)-1-(4-butylphenyl)ethan-1-one

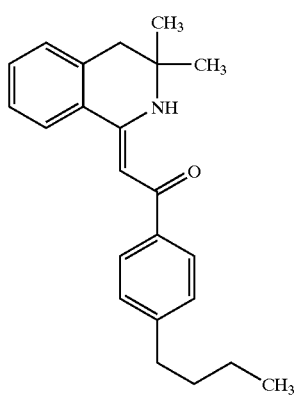

TLC: Rf 0.20 (hexane:ethyl acetate=4:1);

NMR (CDCl₃): δ 11.79 (bs, 1H), 7.89–7.81 (m, 3H), 7.46–7.19 (m, 5H), 6.33 (s, 1H), 2.90 (s, 2H), 2.66 (t, J=7.4 Hz, 2H), 1.63 (m, 2H), 1.39 (m, 2H), 1.36 (s, 6H), 0.93 (t, J=7.4 Hz, 3H).

EXAMPLE 1(56)

(Z)-2-(3,3-dimethyl-3,4-dihydro-(2H)-isoquinolin-1-ylidene)-1-(1-phenylcyclohexyl)ethan-1-one

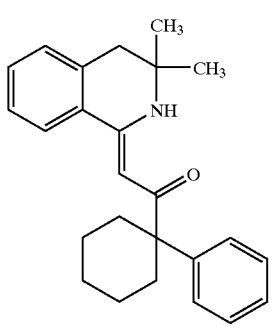

TLC: Rf 0.37 (ethyl acetate:hexane=1:5);

NMR (CDCl₃): δ 11.12 (br., 1H), 7.50–7.10 (m, 9H), 5.55 (s, 1H), 2.78 (s, 2H), 2.45–2.30 (m, 2H), 2.15–2.00 (m, 2H), 1.80–1.30 (m, 6H), 1.26 (s, 6H).

EXAMPLE 1(57)

(Z)-2-(3,3-dimethyl-3,4-dihydro-(2H)-isoquinolin-1-ylidene)-1-(4-propylphenyl)ethan-1-one

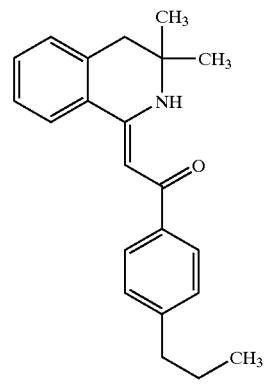

TLC: Rf 0.33 (hexane:ethyl acetate=4:1);

NMR (CDCl₃): δ 11.79 (bs, 1H), 7.87 (d, J=8.0 Hz, 2H), 7.82 (m, 1H), 7.46–7.19 (m, 3H), 7.24 (d, J=8.0 Hz, 2H), 6.33 (s, 1H), 2.90 (s, 2H), 2.64 (t, J=7.4 Hz, 2H), 1.69 (m, 2H), 1.36 (s, 6H), 0.95 (t, J=7.4 Hz, 3H).

EXAMPLE 1(58)

2-(3,3-dimethyl-3,4-dihydroisoquinolin-1-yl)-1-phenylbutan-1-one

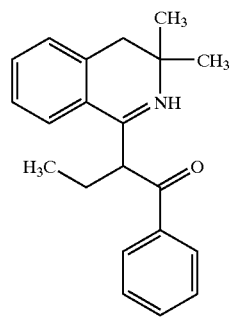

TLC: Rf 0.42 (hexane:ethyl acetate=4:1);

NMR (CDCl$_3$): δ 7.95–7.91 (m, 2H), 7.59–7.10 (m, 7H), 4.60 (m, 1H), 2.57 (s, 2H), 2.21 (m, 1H), 1.98 (m, 1H), 1.09 (s, 3H), 1.02 (t, J=8.0 Hz, 3H), 1.00 (s, 3H).

EXAMPLE 1(59)

2-(3,3-dimethyl-3,4-dihydroisoquinolin-1-yl)-1-phenylpentan-1-one

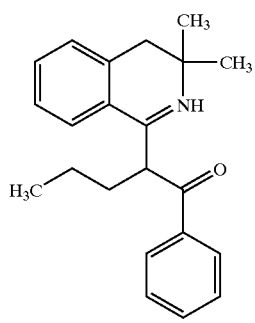

TLC: Rf 0.44 (hexane:ethyl acetate=4:1);

NMR (CDCl$_3$): δ 8.06–7.91 (m, 3H), 7.59–7.24 (m, 5H), 7.11 (m, 1H), 4.69 (dd, J=7.5, 6.0 Hz, 1H), 2.61 (s, 2H), 2.20 (m, 1H), 1.85 (m, 1H), 1.40 (m, 2H), 1.05 (s, 3H), 1.00 (s, 3H), 0.98 (t, J=8.0 Hz, 3H).

EXAMPLE 1(60)

(Z)-cis-2-(3,3-dimethyl-3,4-dihydro-(2H)-isoquinolin-1-ylidene)-1-(2-methylcyclohexyl)ethan-1-one

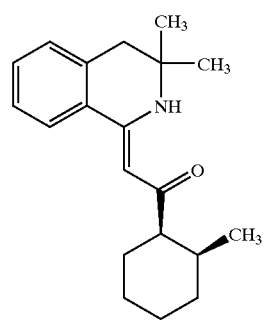

TLC: Rf 0.37 (ethyl acetate:hexane=1:5);

NMR (CDCl$_3$): δ 11.25 (br., 1H), 7.70 (m, 1H), 7.45–7.10 (m, 3H), 5.65 (s, 1H), 2.83 (s, 2H), 2.50 (dt, J=11.0, 4.5 Hz, 1H), 2.28 (m, 1H), 1.90–1.10 (m, 8H), 1.29 (s, 3H), 1.28 (s, 3H), 0.90 (d, J=7.0 Hz, 3H).

EXAMPLE 1(61)

(Z)-trans-2-(3,3-dimethyl-3,4-dihydro-(2H)-isoquinolin-1-ylidene)-1-(2-methylcyclohexyl)ethan-1-one

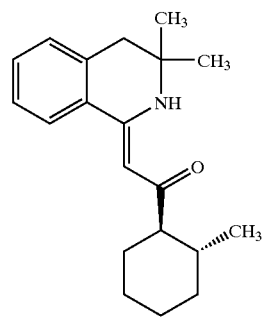

TLC: Rf 0.35 (ethyl acetate:hexane=1:5);

NMR (CDCl$_3$): δ 11.38 (br., 1H), 7.71 (m, 1H), 7.45–7.10 (m, 3H), 5.60 (s, 1H), 2.84 (s, 2H), 2.00–0.90 (m, 10H), 1.30 (s, 6H), 0.88 (d, J=7.5 Hz, 3H).

EXAMPLE 1(62)

(Z)-trans-2-(3,3-dimethyl-3,4-dihydro-(2H)-isoquinolin-1-ylidene)-1-(3-methylcyclohexyl)ethan-1-one

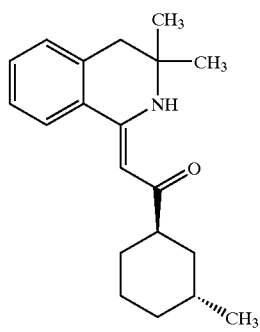

TLC: Rf 0.39 (ethyl acetate:hexane=1:5);

NMR (CDCl$_3$): δ 11.27 (br., 1H), 7.71 (m, 1H), 7.45–7.10 (m, 3H), 5.68 (s, 1H), 2.84 (s, 2H), 2.59 (m, 1H), 2.10–1.10 (m, 9H), 1.29 (s, 6H), 0.98 (d, J=7.0 Hz, 3H).

EXAMPLE 1(63)

(Z)-cis-2-(3,3-dimethyl-3,4-dihydro-(2H)-isoquinolin-1-ylidene)-1-(3-methylcyclohexyl)ethan-1-one

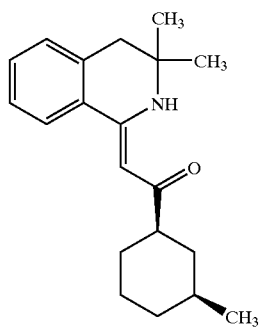

TLC: Rf 0.34 (ethyl acetate:hexane=1:5);

NMR (CDCl$_3$): δ 11.34 (br., 1H), 7.71 (m, 1H), 7.45–7.10 (m, 3H), 5.64 (s, 1H), 2.84 (s, 2H), 2.39 (m, 1H), 1.95–0.80 (m, 9H), 1.29 (s, 6H), 0.92 (d, J=6.5 Hz, 3H).

EXAMPLE 1(64)

(Z)-cis-2-(3,3-dimethyl-3,4-dihydro-(2H)-isoquinolin-1-ylidene)-1-(4-methylcyclohexyl)ethan-1-one

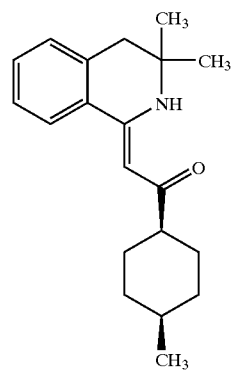

TLC: Rf 0.43 (ethyl acetate:hexane=1:5);

NMR (CDCl$_3$): δ 11.30 (br., 1H), 7.70 (m, 1H), 7.45–7.10 (m, 3H), 5.68 (s, 1H), 2.84 (s, 2H), 2.38 (m, 1H), 2.00–1.30 (m, 9H), 1.29 (s, 6H), 0.97 (d, J=7.0 Hz, 3H).

EXAMPLE 1(65)

(Z)-trans-2-(3,3-dimethyl-3,4-dihydro-(2H)-isoquinolin-1-ylidene)-1-(4-methylcyclohexyl)ethan-1-one

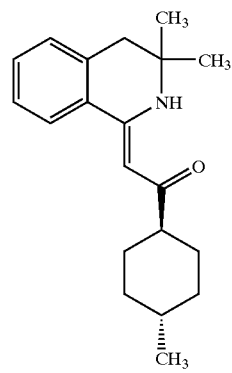

TLC: Rf 0.37 (ethyl acetate:hexane=1:5);

NMR (CDCl$_3$): δ 11.33 (br., 1H), 7.70 (m, 1H), 7.45–7.10 (m, 3H), 5.64 (s, 1H), 2.84 (s, 2H), 2.24 (tt, J=12.0, 3.5 Hz, 1H), 2.00–0.90 (m, 9H), 1.29 (s, 6H), 0.90 (d, J=6.5 Hz, 3H).

EXAMPLE 1(66)

(Z)-2-(3,3-dimethyl-3,4-dihydro-(2H)-isoquinolin-1-ylidene)-1-(3,5-dimethylisoxazol-4-yl)ethan-1-one

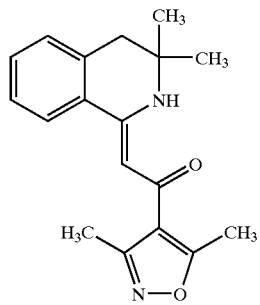

TLC: Rf 0.25 (hexane:ethyl acetate=4:1);

NMR (CDCl$_3$): δ 11.55 (bs, 1H), 7.68 (d, J=7.8 Hz, 1H), 7.49–7.20 (m, 3H), 5.80 (s, 1H), 2.90 (s, 2H), 2.66 (s, 3H), 2.50 (s, 3H), 1.36 (s, 6H).

EXAMPLE 1(67)

(Z)-2-(3,3-dimethyl-3,4-dihydro-(2H)-isoquinolin-1-ylidene)-1-(4-trifluoromethoxyphenyl)ethan-1-one

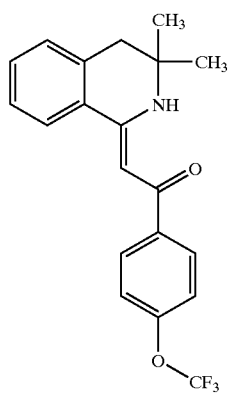

TLC: Rf 0.54 (hexane:ethyl acetate=3:1);

NMR (CDCl$_3$): δ 11.83 (br, 1H), 8.00–7.95 (m, 2H), 7.82 (d, J=7.5 Hz, 1H), 7.45 (t, J=7.5 Hz, 1H), 7.35 (t, J=7.5 Hz, 1H), 7.27–7.21 (m, 3H), 6.27 (s, 1H), 2.91 (s, 2H), 1.37 (s, 6H).

EXAMPLE 1(68)

(Z)-2-(6-chloro-3,3-dimethyl-3,4-dihydro-(2H)-isoquinolin-1-ylidene)-1-phenylethan-1-one

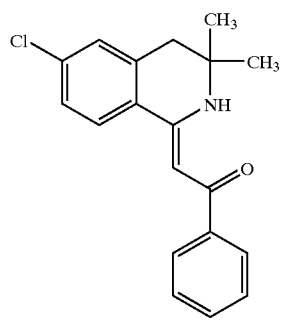

TLC: Rf 0.50 (hexane:ethyl acetate=3:1);

NMR (CDCl$_3$): δ 11.82 (br, 1H), 7.95–7.92 (m, 2H), 7.75 (d, J=8.0 Hz, 1H), 7.47–7.40 (m, 3H), 7.32 (dd, J=8.0, 2.0 Hz, 1H), 7.22 (d, J=2.0 Hz, 1H), 6.23 (br, 1H), 2.88 (s, 2H), 1.37 (s, 6H).

EXAMPLE 1(69)

(Z)-2-(5-chloro-3,3-dimethyl-3,4-dihydro-(2H)-isoquinolin-1-ylidene)-1-phenylethan-1-one

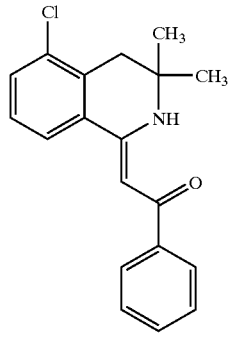

TLC: Rf 0.61 (hexane:ethyl acetate=3:1);

NMR (CDCl$_3$): δ 11.83 (br, 1H), 7.96–7.92 (m, 2H), 7.77 (d, J=8.0 Hz, 1H), 7.52 (d, J=8.0 Hz, 1H), 7.48–7.42 (m, 3H), 7.32–7.26 (m, 1H), 6.31 (br, 1H), 3.03 (s, 2H), 1.39 (s, 6H).

EXAMPLE 1(70)

(Z)-2-(7-chloro-3,3-dimethyl-3,4-dihydro-(2H)-isoquinolin-1-ylidene)-1-phenylethan-1-one

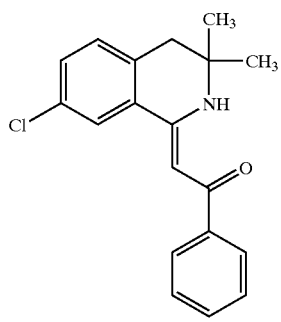

TLC: Rf 0.48 (hexane:ethyl acetate=3:1);

NMR (CDCl$_3$): δ 11.81 (br, 1H), 7.97–7.93 (m, 2H), 7.78 (d, J=2.0 Hz, 1H), 7.48–7.43 (m, 3H), 7.41 (dd, J=8.0, 2.0 Hz, 1H), 7.17 (d, J=8.0 Hz, 1H), 6.23 (br, 1H), 2.88 (s, 2H), 1.37 (s, 6H).

EXAMPLE 1(71)

(Z)-2-(3,3-dimethyl-3,4-dihydro-(2H)-isoquinolin-1-ylidene)-1-(5-methyl-2-phenyloxazol-4-yl)ethan-1-one

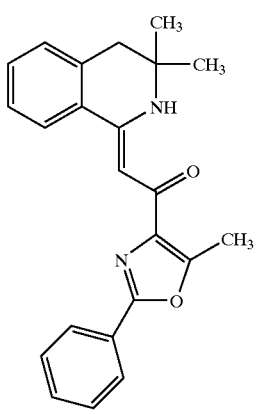

TLC: Rf 0.37 (hexane:ethyl acetate=4:1);

NMR (CDCl$_3$): δ 11.65 (bs, 1H), 8.11–8.08 (m, 2H), 7.96 (d, J=7.6 Hz, 1H), 7.49–7.36 (m, 5H), 7.20 (d, J=7.6 Hz, 1H), 6.72 (bs, 1H), 2.91 (s, 2H), 2.79 (s, 3H), 1.38 (s, 6H).

EXAMPLE 1(72)

(Z)-2-(7-fluoro-3,3-dimethyl-3,4-dihydro-(2H)-isoquinolin-1-ylidene)-1-phenylethan-1-one

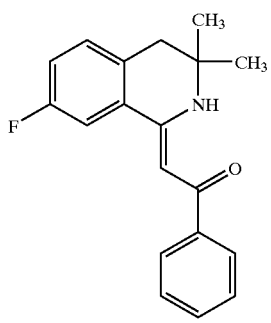

TLC: Rf 0.45 (hexane:ethyl acetate=3:1);

NMR (CDCl$_3$): δ 11.80 (br, 1H), 7.96–7.93 (m, 2H), 7.51 (dd, J=9.5, 2.5 Hz, 1H), 7.48–7.41 (m, 3H), 7.22–7.11 (m, 2H), 6.24 (br, 1H), 2.87 (s, 2H), 1.37 (s, 6H).

EXAMPLE 1(73)

(Z)-2-(6-fluoro-3,3-dimethyl-3,4-dihydro-(2H)-isoquinolin-1-ylidene)-1-phenylethan-1-one

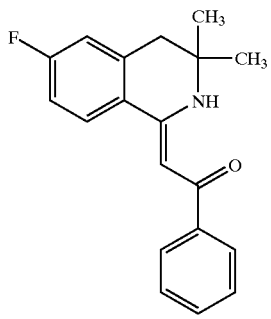

TLC: Rf 0.45 (hexane:ethyl acetate=3:1);

NMR (CDCl$_3$): δ 11.83 (br, 1H), 7.96–7.92 (m, 2H), 7.82 (dd, J=8.5, 5.5 Hz, 1H), 7.48–7.40 (m, 3H), 7.04 (ddd, J=8.5, 8.5, 3.0 Hz, 1H), 6.94 (dd, J=8.5, 3.0 Hz, 1H), 6.23 (br, 1H), 2.90 (s, 2H), 1.38 (s, 6H).

EXAMPLE 1(74)

(Z)-2-(5-fluoro-3,3-dimethyl-3,4-dihydro-(2H)-isoquinolin-1-ylidene)-1-phenylethan-1-one

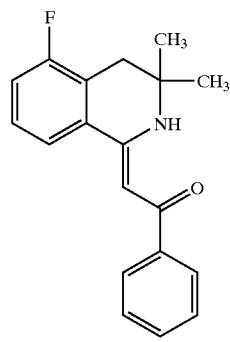

TLC: Rf 0.54 (hexane:ethyl acetate=3:1);

NMR (CDCl$_3$): δ 11.80 (br, 1H), 7.96–7.93 (m, 2H), 7.65 (d, J=8.0 Hz, 1H), 7.47–7.40 (m, 3H), 7.35–7.30 (m, 1H), 7.19 (dd, J=8.0, 8.0 Hz, 1H), 6.31 (br, 1H), 2.93 (s, 2H), 1.39 (s, 6H).

EXAMPLE 1(75)

(Z)-2-(3,3-dimethyl-3,4-dihydro-(2H)-isoquinolin-1-ylidene)-1-(4-methyl-2-phenylthiazol-5-yl)ethan-1-one

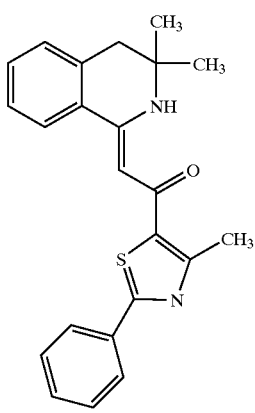

TLC: Rf 0.37 (hexane:ethyl acetate=4:1);

NMR (CDCl$_3$): δ 11.56 (bs, 1H), 8.00–7.97 (m, 2H), 7.77 (d, J=7.8 Hz, 1H), 7.46–7.42 (m, 4H), 7.36 (m, 1H), 7.22 (d, J=7.5 Hz, 1H), 6.08 (s, 1H), 2.91 (s, 2H), 2.85 (s, 3H), 1.37 (s, 6H).

EXAMPLE 1(76)

(Z)-2-(3,3-dimethyl-3,4-dihydro-(2H)-isoquinolin-1-ylidene)-1-(4-pentylbicyclo[2.2.2]octan-1-yl)ethan-1-one

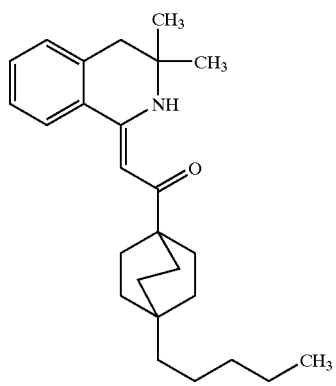

TLC: Rf 0.54 (hexane:ethyl acetate=4:1);

NMR (CDCl$_3$): δ 11.39 (bs, 1H), 7.70 (d, J=7.5 Hz, 1H), 7.36 (m, 1H), 7.28 (m, 1H), 7.16 (d, J=7.5 Hz, 1H), 5.73 (s, 1H), 2.83 (s, 2H), 1.81–1.76 (m, 6H), 1.56 (s, 2H), 1.44–1.38 (m, 6H), 1.28 (s, 6H), 1.23–1.16 (m, 4H), 1.11–1.07 (m, 2H), 0.88 (t, J=7.0 Hz, 3H).

EXAMPLE 1(77)

(Z)-trans-2-(3,3-dimethyl-3,4-dihydro-(2H)-isoquinolin-1-ylidene)-1-(4-t-butylcyclohexyl)ethan-1-one

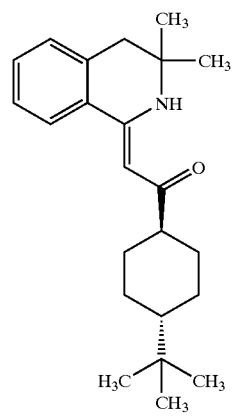

TLC: Rf 0.52 (hexane:ethyl acetate=4:1);

NMR (CDCl$_3$): δ 11.32 (bs, 1H), 7.71 (d, J=7.8 Hz, 1H), 7.39 (m, 1H), 7.33 (m, 1H), 7.17 (d, J=7.2 Hz, 1H), 5.64 (s, 1H), 2.84 (s, 2H), 2.05 (m, 1H), 1.92 (m, 2H), 1.86 (m, 2H), 1.45 (m, 2H), 1.28 (s, 6H), 1.18–1.01 (m, 3H), 0.86 (s, 9H).

EXAMPLE 1(78)

(Z)-2-(3,3,4,4-tetramethyl-3,4-dihydro-(2H)-isoquinolin-1-ylidene)-1-phenylethan-1-one

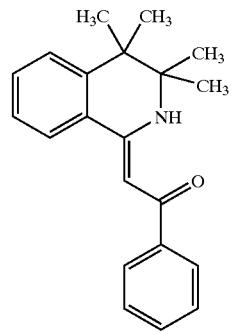

TLC: Rf 0.35 (ethyl acetate:hexane=1:5);

NMR (CDCl$_3$): δ 11.80 (br, 1H), 7.96 (m, 2H), 7.81 (m, 1H), 7.55–7.40 (m, 5H), 7.32 (m, 1H), 6.30 (br., 1H), 1.50–1.00 (m, 12H).

EXAMPLE 1(79)

(Z)-2-(spiro[3,3-dimethyl-3,4-dihydro-(2H)-isoquinolin-4,1'-cyclohexane]-1-ylidene)-1-phenylethan-1-one

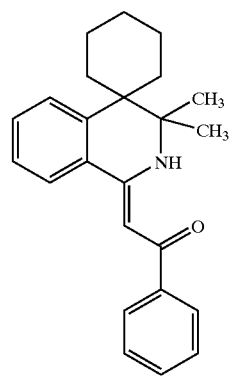

TLC: Rf 0.45 (ethyl acetate:hexane=1:5);

NMR (CDCl$_3$): δ 12.22 (br, 1H), 7.99 (m, 2H), 7.81 (m, 1H), 7.50–7.40 (m, 5H), 7.32 (m, 1H), 6.32 (br., 1H), 2.20–1.00 (m, 16H).

EXAMPLE 1(80)

(Z)-2-(6,7-dimethoxy-3,3-dimethyl-3,4-dihydro-(2H)-isoquinolin-1-ylidene)-1-phenylethan-1-one

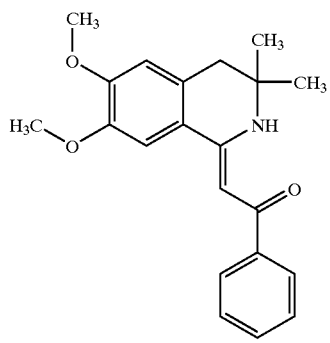

TLC: Rf 0.59 (hexane:ethyl acetate=1:1);

NMR (DMSO-d$_6$): δ 11.91 (br, 1H), 8.00–7.97 (m, 2H), 7.48–7.41 (m, 4H), 6.91 (s, 1H), 6.36 (s, 1H), 3.88 (s, 3H), 3.83 (s, 3H), 2.84 (s, 2H), 1.28 (s, 6H).

EXAMPLE 1(81)

(Z)-2-(spiro[3,3-dimethyl-3,4-dihydro-(2H)-isoquinolin-4,1'-cyclopentan]-1-ylidene)-1-phenylethan-1-one

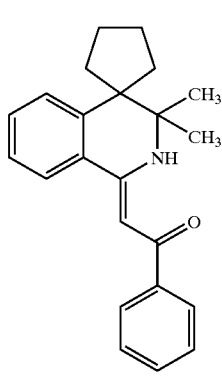

TLC: Rf 0.49 (ethyl acetate:hexane=1:3);

NMR (CDCl$_3$): δ 11.92 (br, 1H), 7.97 (m, 2H), 7.84 (d, J=8.0 Hz, 1H), 7.55–7.30 (m, 6H), 6.33 (br., 1H), 2.00–1.10 (m, 14H).

EXAMPLE 2

2-(3,3-dimethyl-3,4-dihydroisoquinolin-1-yl)-1-cyclopentylethan-1-one hydrochloride

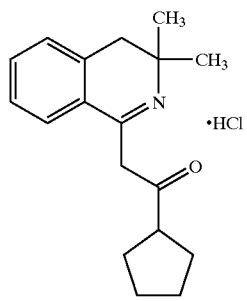

To a solution of the compound prepared in example 1 (2) (1132 mg) in dioxane (5 ml) was added a solution of 4M hydrochloric acid in dioxane (2 ml) dropwise. The residue was washed with hexane to give the compound of the present invention (1212 mg)having the following physical data.

TLC: Rf 0.38 (ethyl acetate:hexane=1:5);

NMR (CDCl$_3$): δ 14.48 (br., 1H), 7.68 (dd, J=7.5, 7.5 Hz, 1H), 7.62 (d, J=7.5 Hz, 1H), 7.46 (dd, J=7.5, 7.5 Hz, 1H), 7.34 (d, J=7.5 Hz, 1H), 4.35 (br., 2H), 3.26 (m, 1H), 3.06 (s, 2H), 2.20–1.55 (m, 8H), 1.59 (s, 6H).

EXAMPLE 2(1)~EXAMPLE 2(5)

By the same procedure as described in example 2 using the compound prepared in example 1(11), example 1(25), example 1(50), example 1(58) and example 1(59) in place of the compound prepared in example 1(2), the compounds of the present invention were given.

EXAMPLE 2(1)

2-(3,3-dimethyl-3,4-dihydroisoquinolin-1-yl)-1-cycloheptylethan-1-one hydrochloride

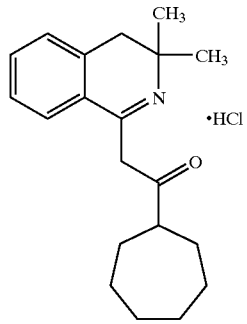

TLC: Rf 0.40 (ethyl acetate:hexane=1:5);
NMR (CDCl$_3$): δ 7.67 (dd, J=7.5, 7.5 Hz, 1H), 7.61 (d, J=7.5 Hz, 1H), 7.45 (dd, J=7.5, 7.5 Hz, 1H), 7.34 (d, J=7.5 Hz, 1H), 4.75 (br., 2H), 3.05 (s, 2H), 2.93 (m, 1H), 2.06 (m, 2H), 1.85–1.50 (m, 10H), 1.58 (s, 6H).

EXAMPLE 2(2)

2-(3,3-dimethyl-3,4-dihydroisoquinolin-1-yl)-1-phenylpropan-1-one hydrochloride

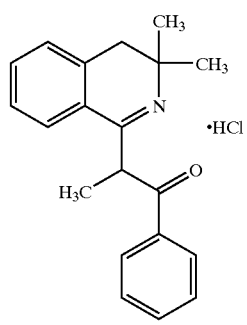

TLC: Rf 0.29 (ethyl acetate:hexane=1:5);

NMR (CDCl$_3$): δ 8.13 (m, 2H), 7.78 (d, J=8.0 Hz, 1H), 7.60 (ddd, J=8.0, 8.0, 1.0 Hz, 1H), 7.55–7.35 (m, 4H), 7.24 (d, J=8.0 Hz, 1H), 6.31 (q, J=7.0 Hz, 1H), 3.03 (d, J=16.5 Hz, 1H), 2.85 (d, J=16.5 Hz, 1H), 1.81 (d, J=7.0 Hz, 3H), 1.71 (s, 3H), 1.46 (s, 3H).

EXAMPLE 2(3)

(Z)-2-(3,3-dimethyl-3,4-dihydro-(2H)-isoquinolin-1-ylidene)-1-(piperidin-4-yl)ethan-1-one 2hydrochloride

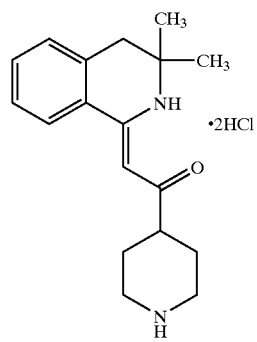

TLC: Rf 0.18 (water:methanol:chloroform=1:10:50);

NMR (DMSO-d$_6$): δ 11.19 (br., 1H), 9.02 (br., 1H), 8.75 (br., 1H), 7.80 (d, J=7.5 Hz, 1H), 7.47 (dd, J=7.5, 7.5 Hz, 1H), 7.34 (dd, J=7.5, 7.5 Hz, 1H), 7.29 (d, J=7.5 Hz, 1H), 5.73 (s, 1H), 3.25 (m, 2H), 2.95–2.80 (m, 4H), 2.56 (m, 1H), 1.95–1.65 (m, 4H), 1.22 (s, 6H).

EXAMPLE 2(4)

2-(3,3-dimethyl-3,4-dihydroisoquinolin-1-yl)-1-phenylbutan-1-one hydrochloride

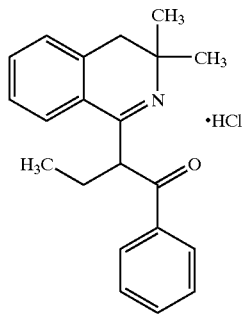

TLC: Rf 0.77 (hexane:ethyl acetate=1:1);

NMR (CDCl$_3$): δ 8.21–8.16 (m, 2H), 7.87 (d, J=8.0 Hz, 1H), 7.65–7.34 (m, 5H), 7.25 (d, J=8.6 Hz, 1H), 6.20 (dd, J=6.2, 5.8 Hz, 1H), 3.00 (d, J=16.6 Hz, 1H), 2.86 (d, J=16.6 Hz, 1H), 2.56 (m, 1H), 2.13 (m, 1H), 1.70 (s, 3H), 1.48 (s, 3H), 1.15 (t, J=7.4 Hz, 3H).

EXAMPLE 2(5)

2-(3,3-dimethyl-3,4-dihydroisoquinolin-1-yl)-1-phenylpentan-1-one hydrochloride

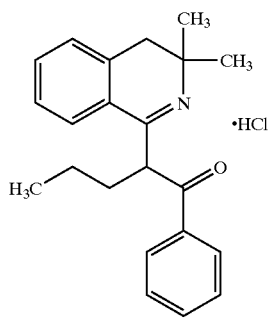

TLC: Rf 0.36 (hexane:ethyl acetate=4:1);

NMR (CDCl$_3$): δ 8.20 (m, 2H), 7.88 (d, J=7.6 Hz, 1H), 7.64–7.35 (m, 5H), 7.24 (d, J=7.0 Hz, 1H), 6.24 (dd, J=6.0, 6.2 Hz, 1H), 3.01 (d, J=16.8 Hz, 1H), 2.83 (d, J=16.8 Hz, 1H), 2.48 (m, 1H), 1.99 (m, 1H), 1.80 (m, 1H), 1.71 (s, 3H), 1.45 (s, 3H), 1.35 (m, 1H), 0.99 (t, J=7.4 Hz, 3H).

REFERENCE EXAMPLE 2

1,3,3-trimethyl-3,4-dihydroisoquinolin

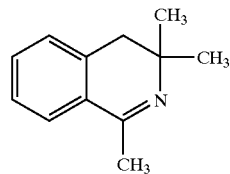

To conc. sulfuric acid (10 ml) was added a solution of 2-methyl-1-phenylpropan-2-ol (7.0 g) and acetonitrile (1.62 ml) in benzene (7.0 ml) dropwise and the mixture was stirred for 24 hours at room temperature. The mixture was neutralized by adding to a mixture of ice and a saturated aqueous solution of sodium bicarbonate dropwise, and it was extracted with ethyl acetate twice. The extract was dried over anhydrous magnesium sulfate and was concentrated under reduced pressure. The residue was dissolved in ether and was extracted with 1N hydrochloric acid and 2N hydrochloric acid. The extract was washed with ether and to the mixture was added 5N aqueous solution of sodium hydroxide and was extracted with ether twice. The extract was washed with water and a saturated aqueous solution of sodium chloride successively, and dried over anhydrous magnesium sulfate and was concentrated under reduced pressure to give the title compound (2.53 g) having the following physical data.

TLC: Rf 0.22 (hexane:ethyl acetate=2:1);

NMR (CDCl$_3$): δ 7.48 (dd, J=7.5, 1.5 Hz, 1H), 7.35 (dt, J=1.5, 7.5 Hz, 1H), 7.30–7.25 (m, 1H), 7.14 (d, J=7.5 Hz, 1H), 2.69 (s, 2H), 2.38 (s, 3H), 1.20 (s, 6H).

EXAMPLE 3

(Z)-2-(3,3-dimethyl-3,4-dihydro-(2H)-isoquinolin-1-ylidene)-1-(3-cyanophenyl)ethan-1-one

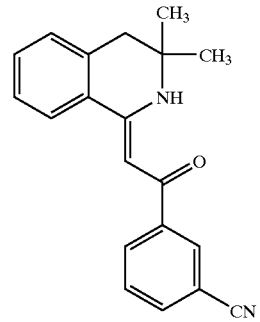

To a solution of diisopropylamine (0.43 ml) in tetrahydrofuran (5 ml) was added n-butyl lithium (1.6M hexane solution, 2.15 ml) dropwise and the mixture was stirred for 30 minutes at 0° C. To the reaction mixture was added the compound prepared in reference example 2 (478 mg) in tetrahydrofuran (2 ml) dropwise for 90 minutes at −78° C. To the reaction mixture was added a solution of tetrahydrofuran (2 ml) of 3-cyanobenzoylchloride (571 mg) and the mixture was stirred with warming to −10° C. over a period of 90 minutes. To the reaction mixture was added water and was extracted with ether twice. The extract was washed with 1N hydrochloric acid, water and a saturated aqueous solution successively, dried over anhydrous magnesium sulfate and was concentrated under reduced pressure. The residue was purified by column chromatography on silica gel (hexane:ethyl acetate=30:1→10:1) to give the compound of the present invention (61 mg) having the following physical data.

TLC: Rf 0.49 (hexane:ethyl acetate=2:1);

NMR (CDCl$_3$): δ 11.89 (br, 1H), 8.22 (dd, J=1.5, 1.5 Hz, 1H), 8.17 (ddd, J=7.5, 1.5, 1.5 Hz, 1H), 7.83 (d, J=7.0 Hz, 1H), 7.71 (ddd, J=7.5, 1.5, 1.5 Hz, 1H), 7.55 (dd, J=7.5, 7.5 Hz, 1H), 7.47 (t, J=7.0 Hz, 1H), 7.38 (t, J=7.0 Hz, 1H), 7.24 (d, J=7.0 Hz, 1H), 6.25 (s, 1H), 2.93 (s, 2H), 1.38 (s, 6H).

EXAMPLE 3(1)~EXAMPLE 3(4)

By the same procedure as described in example 3 using 4-cyanobenzoylchloride, 2-trifluoromethoxybenzoylchloride, 2-cyanobenzoyl chloride, or 3-trifluoromethylbenzoyl chloride in place of 3-cyanobenzoylchloride, the following compounds of the present invention were given.

EXAMPLE 3(1)

(Z)-2-(3,3-dimethyl-3,4-dihydro-(2H)-isoquinolin-1-ylidene)-1-(4-cyanophenyl)ethan-1-one

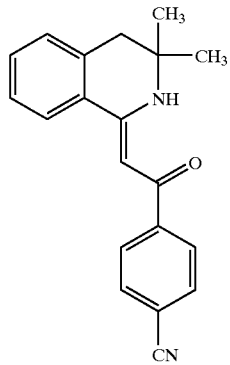

TLC: Rf 0.47 (hexane:ethyl acetate=2:1);

NMR (CDCl$_3$): δ 11.96 (br, 1H), 8.02 (d, J=8.5 Hz, 2H), 7.81 (d, J=7.5 Hz, 1H), 7.72 (d, J=8.5 Hz, 2H), 7.47 (t, J=7.5 Hz, 1H), 7.36 (t, J=7.5 Hz, 1H), 7.24 (d, J=7.5 Hz, 1H), 6.28 (s, 1H), 2.92 (s, 2H), 1.38 (s, 6H).

EXAMPLE 3(2)

(Z)-2-(3,3-dimethyl-3,4-dihydro-(2H)-isoquinolin-1-ylidene)-1-(2-trifluoromethoxyphenyl)ethan-1-one

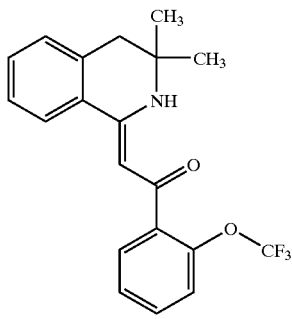

TLC: Rf 0.69 (hexane:ethyl acetate=2:1);

NMR (CDCl$_3$): δ 11.65 (br, 1H), 7.79–7.72 (m, 2H), 7.45–7.25 (m, 5H), 7.21 (d, J=7.5 Hz, 1H), 6.12 (s, 1H), 2.92 (s, 2H), 1.38 (s, 6H).

EXAMPLE 3(3)

(Z)-2-(3,3-dimethyl-3,4-dihydro-(2H)-isoquinolin-1-ylidene)-1-(2-cyanophenyl)ethan-1-one

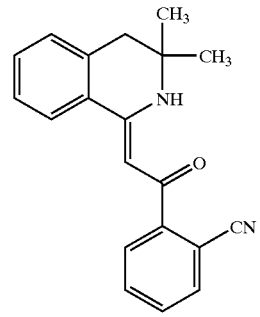

TLC: Rf 0.44 (hexane:ethyl acetate=2:1);

NMR (CDCl$_3$): δ 11.76 (br, 1H), 7.87 (dd, J=7.5, 1.5 Hz, 1H), 7.81 (d, J=7.0 Hz, 1H), 7.76 (dd, J=7.5, 1.5 Hz, 1H), 7.62 (dt, J=1.5, 7.5 Hz, 1H), 7.52–7.42 (m, 2H), 7.34 (t, J=7.0 Hz, 1H), 7.22 (d, J=7.0 Hz, 1H), 6.21 (s, 1H), 2.92 (s, 2H), 1.39 (s, 6H).

EXAMPLE 3(4)

(Z)-2-(3,3-dimethyl-3,4-dihydro-(2H)-isoquinolin-1-ylidene)-1-(3-trifluoromethoxyphenyl)ethan-1-one

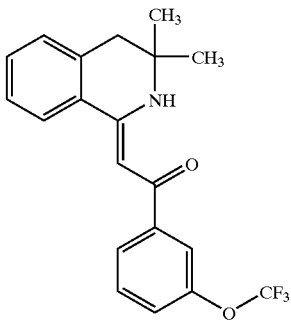

TLC: Rf 0.53 (hexane:ethyl acetate=3:1);

NMR (CDCl₃): δ 11.87 (br, 1H), 7.88–7.80 (m, 3H), 7.48–7.43 (m, 2H), 7.36 (t, J=7.5 Hz, 1H), 7.31–7.27 (m, 1H), 7.23 (d, J=7.5 Hz, 1H), 6.27 (s, 1H), 2.92 (s, 2H), 1.38 (s, 6H).

EXAMPLE 4

(Z)-2-(3,3-dimethyl-3,4-dihydro-(2H)-isoquinolin-1-ylidene)-1-(4-carboxyphenyl)ethan-1-one

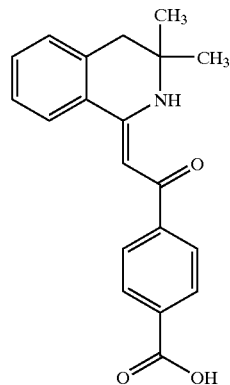

To a mixture of methanol (5 ml) and tetrahydrofuran (5 ml) was added the compound prepared in example 1 (1) (662 mg), and to the mixture was added 2N aqueous solution of sodium hydroxide (5 ml) at room temperature and the mixture was stirred for 3 hours at room temperature. The reaction mixture was neutralized by hydrochloric acid and the mixture was stirred overnight. The aggregate that appeared was filtered and was dried. It was washed with a mixture (hexane:ethyl acetate=1:1) to give the compound of the present invention (575 mg) having the following physical data.

TLC: Rf 0.29 (methanol:chloroform=1:10);

NMR (DMSO-d₆): δ 13.12 (br., 1H), 11.94 (s, 1H), 8.09 (d, 7.0 Hz, 1H), 8.09 (d, J=8.5 Hz, 2H), 7.99 (d, J=8.5 Hz, 2H), 7.52 (dd, J=7.0, 7.0 Hz, 1H), 7.39 (dd, J=7.0, 7.0 Hz, 1H), 7.33 (d, J=7.0 Hz, 1H), 6.50 (s, 1H), 2.94 (s, 2H), 1.29 (s, 6H).

EXAMPLE 4(1)~EXAMPLE 4(3)

By the same procedure as described in example 4 using the compounds prepared in example 1 (30), example 1 (45) or example 1 (46) in place of the compound prepared in example 1 (1), the following compounds of the present invention were given.

EXAMPLE 4(1)

(Z)-2-(3,3-dimethyl-3,4-dihydro-(2H)-isoquinolin-1-ylidene)-1-(3-carboxyphenyl)ethan-1-one

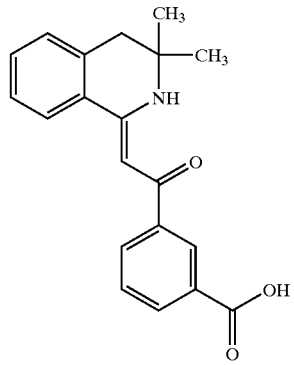

TLC: Rf 0.37 (methanol:chloroform=1:10);

NMR (DMSO-d₆): δ 13.10 (br., 1H), 11.90 (s, 1H), 8.47 (dd, J=1.5, 1.5 Hz, 1H), 8.25 (d, J=8.0 Hz, 1H), 8.10–8.00 (m, 2H), 7.65–7.30 (m, 4H), 6.47 (s, 1H), 2.94 (s, 2H), 1.29 (s, 6H).

EXAMPLE 4(2)

(Z)-2-(spiro[3,4-dihydro-(2H)-isoquinolin-3,1'-4'-carboxycyclohexane]-1-ylidene)-1-phenylethan-1-one

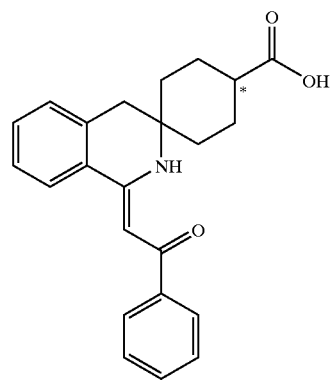

TLC: Rf 0.35 (chloroform:methanol:water=10:1:0.1);

NMR (CDCl₃): δ 12.08 (br, 1H), 7.97–7.94 (m, 2H), 7.83 (d, J=7.5 Hz, 1H), 7.47–7.41 (m, 4H), 7.35 (t, J=7.5 Hz, 1H), 7.22 (d, J=7.5 Hz, 1H), 6.36 (s, 1H), 2.99 (s, 2H), 2.63–2.56 (m, 1H), 2.06–1.95 (m, 2H), 1.95–1.75 (m, 4H), 1.75–1.60 (m, 2H).

(This compound has two stereo isomers by the existence of carbon* to which carboxy group is attached. This compound corresponds to less polar compound on thin layer silica gel. And more polar compound corresponding to this compound is described in example 4 (3)).

EXAMPLE 4(3)

(Z)-2-(spiro[3,4-dihydro-(2H)-isoquinolin-3,1'-4'-carboxycyclohexane]-1-ylidene)-1-phenylethan-1-one

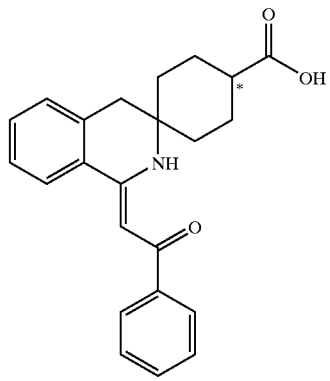

TLC: Rf 0.32 (chloroform:methanol:water=10:1:0.1);

NMR (CDCl$_3$): δ 12.32 (br, 1H), 7.95–7.92 (m, 2H), 7.82 (d, J=7.5 Hz, 1H), 7.44–7.42 (m, 4H), 7.34 (t, J=7.5 Hz, 1H), 7.22 (d, J=7.5 Hz, 1H), 6.33 (s, 1H), 2.90 (s, 2H), 2.40–2.29 (m, 1H), 2.02–1.91 (m, 6H), 1.52–1.43 (m, 2H).

This compound has two stereo isomers by the existence of carbon* to which carboxy group is attached. This compound corresponds to more polar compound on thin layer silica gel. And the less polar compound corresponding to this compound is described in example 4 (2)).

EXAMPLE 5

(Z)-2-(3,3-dimethyl-3,4-dihydro-(2H)-isoquinolin-1-ylidene)-1-(3-hydroxyphenyl)ethan-1-one

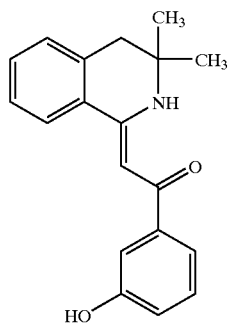

To the compound prepared in example 1 (18) (200 mg) was added 47% hydrobromic acid (3 ml) and the mixture was stirred for 1 hour at 115° C. The reaction mixture was allowed to cool and was neutralized by addition of a saturated aqueous solution of sodium bicarbonate and then was extracted with ethyl acetate twice. The extract was washed with water, dried over anhydrous magnesium sulfate and then concentrated under reduced pressure. The residue was purified by column chromatography on silica gel (hexane:ethyl acetate=3:1→1:1) to give the compound of the present invention (147 mg) having the following physical data.

TLC: Rf 0.48 (hexane:ethyl acetate=1:1);

NMR (CDCl$_3$): δ 11.78 (br, 1H), 7.81 (d, J=8.0 Hz, 1H), 7.53–7.25 (m, 5H), 7.21 (d, J=7.5 Hz, 1H), 6.95 (dd, J=8.0, 3.0 Hz, 1H), 6.30 (s, 1H), 6.13 (br, 1H), 2.90 (s, 2H), 1.36 (s, 6H).

EXAMPLE 5(1)~EXAMPLE 5(3)

By the same procedure as described in example 5 using the compound prepared in example 1(17), example 1(22) or example 1(42) in place of the compound prepared in example 1(18), the following compounds of the present invention were given.

EXAMPLE 5(1)

(Z)-2-(3,3-dimethyl-3,4-dihydro-(2H)-isoquinolin-1-ylidene)-1-(4-hydroxyphenyl)ethan-1-one

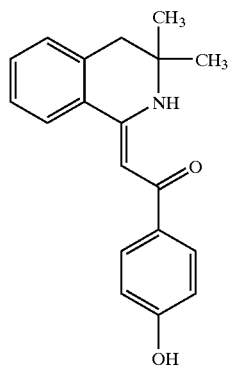

TLC: Rf 0.19 (hexane:ethyl acetate=2:1);

NMR (CDCl$_3$): δ 11.72 (br, 1H), 7.91–7.87 (m, 2H), 7.82 (d, J=7.0 Hz, 1H), 7.42 (t, J=7.0 Hz, 1H), 7.33 (t, J=7.0 Hz, 1H), 7.21 (d, J=7.0 Hz, 1H), 6.90–6.85 (m, 2H), 6.29 (s, 1H), 2.89 (s, 2H), 1.35 (s, 6H).

EXAMPLE 5(2)

(Z)-2-(3,3-dimethyl-3,4-dihydro-(2H)-isoquinolin-1-ylidene)-1-(2-hydroxyphenyl)ethan-1-one

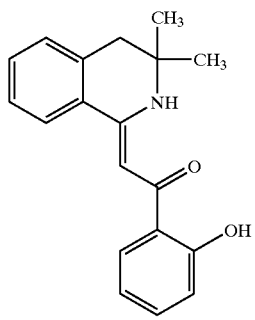

TLC: Rf 0.70 (hexane:ethyl acetate=2:1);

NMR (CDCl$_3$): δ 11.34 (br, 1H), 7.83 (d, J=7.0 Hz, 1H), 7.76 (dd, J=8.0, 1.5 Hz, 1H), 7.46 (dt, J=1.5, 8.0 Hz, 1H), 7.40–7.31 (m, 2H), 7.23 (d, J=7.5 Hz, 1H), 6.94 (dd, J=8.0, 1.0 Hz, 1H), 6.83 (dt, J=1.0, 8.0 Hz, 1H), 6.34 (s, 1H), 2.91 (s, 2H), 1.38 (s, 6H).

EXAMPLE 5(3)

(Z)-2-(6-hydroxy-3,3-dimethyl-3,4-dihydro-(2H)-isoquinolin-1-ylidene)-1-phenylethan-1-one

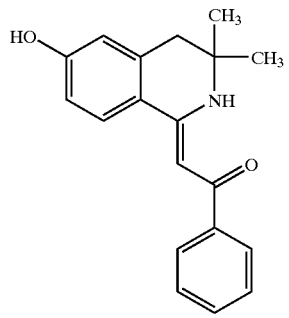

TLC: Rf 0.18 (ethyl acetate:hexane=1:2);

NMR (DMSO-$d_6$): δ 11.84 (s, 1H), 10.15 (s, 1H), 8.00–7.85 (m, 3H), 7.50–7.35 (m, 3H), 6.73 (dd, J=8.5, 2.5 Hz, 1H), 6.67 (d, J=2.5 Hz, 1H), 6.30 (s, 1H), 2.82 (s, 2H), 1.27 (s, 6H).

EXAMPLE 6

2-(3,3-dimethyl-3,4-dihydroisoquinolin-1-yl)-2-methyl-1-phenylpropan-1-one

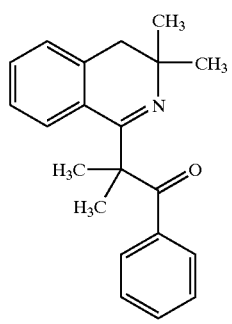

To a solution of (Z)-2-(3,3-dimethyl-3,4-dihydro-(2H)-isoquinolin-1-ylidene)-1-phenylethan-1-one(277 mg; see Khim. Geterotsikl. Soedin., 7, 946–949 (1994)) in tetrahydrofuran (5 ml) were added 62.7% sodium hydride (77 mg) and methyl iodide (0.14 ml) successively at 0° C. and the mixture was warmed to room temperature and the mixture was stirred for two hours. To the reaction mixture were added water and saturated aqueous solution of ammonium chloride successively and was extracted with ethyl acetate. The extract was dried over anhydrous magnesium sulfate and was concentrated under reduced pressure. The residue was purified by column chromatography on silica gel (hexane:ethyl acetate=10:1) to give the compound of the present invention (110 mg) having the following physical data.

TLC: Rf 0.62 (ethyl acetate:hexane=1:5);

NMR (CDCl$_3$): δ 8.03 (m, 2H), 7.37 (tt, J=7.5, 2.0 Hz, 1H), 7.26 (m, 2H), 7.20–7.00 (m, 4H), 2.65 (s, 2H), 1.64 (s, 6H), 1.23 (s, 6H).

EXAMPLE 6(1)~EXAMPLE 6(3)

By the same procedure as described in example 6, using 1,4-dibromobutane, 1,5-dibromopentane or 2-bromo-1-(2-bromoethoxy)ethane in place of methyl iodide, the following compounds of the present invention were given.

EXAMPLE 6(1)

1-(3,3-dimethyl-3,4-dihydroisoquinolin-1-yl) cyclopentylphenyl ketone

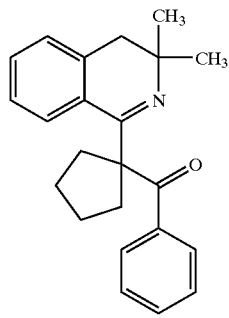

TLC: Rf 0.66 (ethyl acetate:hexane=1:5);

NMR (CDCl$_3$): δ 7.97 (m, 2H), 7.40–6.90 (m, 7H), 2.57 (s, 2H), 2.70–2.30 (m, 4H), 1.73 (m, 4H), 1.19 (s, 6H).

EXAMPLE 6(2)

1-(3,3-dimethyl-3,4-dihydroisoquinolin-1-yl) cyclohexylphenyl ketone

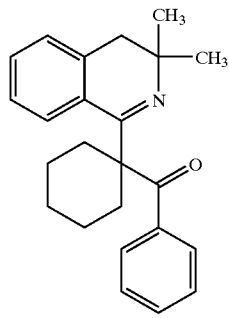

TLC: Rf 0.70 (ethyl acetate:hexane=1:5);

NMR (CDCl$_3$): δ 8.09 (m, 2H), 7.40–7.00 (m, 7H), 2.66 (s, 2H), 2.40–2.05 (m, 4H), 1.80–1.30 (m, 6H), 1.24 (s, 6H).

EXAMPLE 6(3)

4-(3,3-dimethyl-3,4-dihydroisoquinolin-1-yl)-3,4,5,6-tetrahydropyran-4-ylphenyl ketone

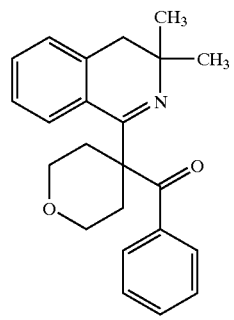

TLC: Rf 0.41 (ethyl acetate:hexane=1:5);

NMR (CDCl$_3$): δ 8.11 (m, 2H), 7.45–7.00 (m, 7H), 3.80 (m, 4H), 2.68 (s, 2H), 2.40 (m, 4H), 1.26 (s, 6H).

EXAMPLE 7

(Z)-2-(spiro[3,4-dihydro-(2H)-isoquinolin-3,1'-4'-hydroxycyclohexane]-1-ylidene)-1-phenylethan-1-one

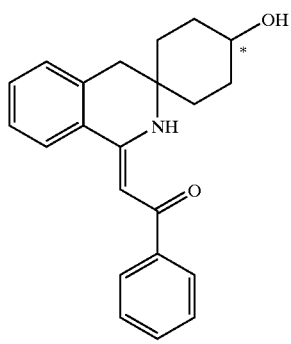

To a solution of the compound prepared in example 1 (49) (52 mg) in methanol (3 ml) was added sodium borohydride (6 mg) at room temperature and the mixture was stirred at room temperature for 10 minutes. The reaction mixture was added to water and was extracted with ethyl acetate. The extract was washed with a saturated aqueous solution of sodium chloride and dried over anhydrous magnesium sulfate and was concentrated under reduced pressure. The residue was purified by thin layer chromatography on silica gel (hexane:ethyl acetate=5:1) to give the compound of the present invention (less polar 11 mg, more polar 33 mg).

This compound has two stereo isomers by the existence of carbon* to which hydroxy group is attached. Less polar compound means one at less polar position on thin layer silica gel, and more polar compound means one at more polar position thereon.

[Less Polar]

TLC: Rf 0.33 (ethyl acetate:hexane=2:1);

NMR (CDCl$_3$): δ 12.19 (br., 1H), 7.95 (m, 2H), 7.82 (m, 1H), 7.50–7.20 (m, 6H), 6.36 (s, 1H), 4.02 (m, 1H), 2.97 (s, 2H), 2.10–1.55 (m, 8H).

[More Polar]

TLC: Rf 0.28 (ethyl acetate:hexane=2:1);

NMR (CDCl$_3$): δ 12.34 (br., 1H), 7.96 (m, 2H), 7.83 (m, 1H), 7.50–7.20 (m, 6H), 6.37 (s, 1H), 3.66 (m, 1H), 2.89 (s, 2H), 2.00–1.40 (m, 8H).

EXAMPLE 8

(Z)-2-(3,3-dimethyl-3,4-dihydro-(2H)-isoquinolin-1-ylidene)-1-(1-acetylpiperidin-4-yl)ethan-1-one

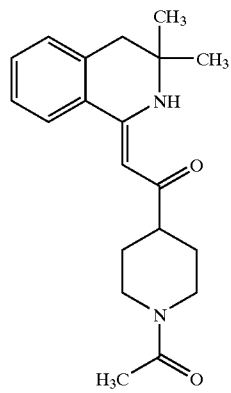

To a solution of the compound prepared in example 2(3) (77 mg) and triethylamine (0.15 ml) in dichloromethane (5 ml) was added acetyl chloride (0.02 ml) at room temperature and the mixture was stirred for 30 minutes at room temperature. The reaction mixture was added to water and was extracted with ethyl acetate. The extract was washed with a saturated aqueous solution of sodium bicarbonate, water and a saturated aqueous solution of sodium chloride successively, dried over anhydrous magnesium sulfate and was concentrated under reduced pressure to give the compound of the present invention (65 mg) having the following physical data.

TLC: Rf 0.72 (water:methanol:chloroform=1:10:50);

NMR (CDCl$_3$): δ 11.33 (br., 1H), 7.69 (m, 1H), 7.45–7.15 (m, 3H), 5.62 (s, 1H), 4.65 (m, 1H), 3.88 (m, 1H), 3.11 (m, 1H), 2.85 (s, 2H), 2.75–2.40 (m, 2H), 2.11 (s, 3H), 2.00–1.60 (m, 4H), 1.31 (s, 6H).

EXAMPLE 8(1)~EXAMPLE 8(3)

By the same procedure as described in example 8 using the compound prepared in example 2(3) or a corresponding amine derivative, and a halide derivative corresponding to acetyl chloride, the following compounds of the present invention were given.

EXAMPLE 8(1)

(Z)-2-(spiro[3,4-dihydro-(2H)-isoquinolin-3,4'-1'-acetylpiperidin]-1-ylidene)-1-phenylethan-1-one

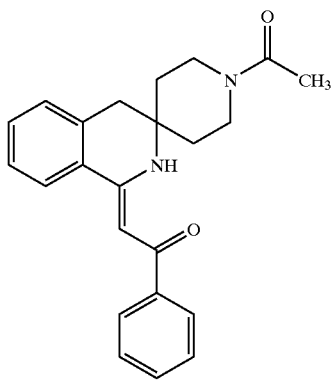

TLC: Rf 0.53 (water:methanol:chloroform=1:10:100);

NMR (CDCl₃): δ 12.47 (s, 1H), 7.96 (m, 2H), 7.84 (d, J=7.5 Hz, 1H), 7.50–7.20 (m, 6H), 6.42 (s, 1H), 4.35 (m, 1H), 3.80–3.45 (m, 2H), 3.24 (m, 1H), 2.94 (s, 2H), 2.11 (s, 3H), 1.90–1.50 (m, 4H).

EXAMPLE 8(2)

(Z)-2-(3,3-dimethyl-3,4-dihydro-(2H)-isoquinolin-1-ylidene)-1-(1-t-butoxycarbonylpiperidin-4-yl)ethan-1-one

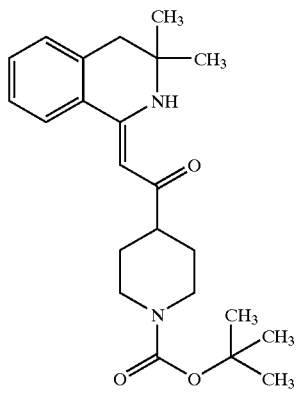

TLC: Rf 0.34 (ethyl acetate:hexane=1:2);

NMR (CDCl₃): δ 11.32 (br., 1H), 7.69 (m, 1H), 7.45–7.15 (m, 3H), 5.62 (s, 1H), 4.17 (m, 2H), 2.85 (s, 2H), 2.77 (m, 2H), 2.42 (tt, J=11.5, 3.5 Hz, 1H), 1.84 (m, 2H), 1.66 (m, 2H), 1.47 (s, 9H), 1.30 (s, 6H).

EXAMPLE 8(3)

(Z)-2-(3,3-dimethyl-3,4-dihydro-(2H)-isoquinolin-1-ylidene)-1-(1-mesylpiperidin-4-yl)ethan-1-one

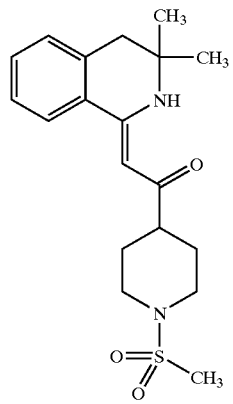

TLC: Rf 0.34 (ethyl acetate:hexane=2:1);

NMR (CDCl₃): δ 11.35 (br., 1H), 7.68 (m, 1H), 7.45–7.15 (m, 3H), 5.61 (s, 1H), 3.85 (m, 2H), 2.90–2.70 (m, 2H), 2.86 (s, 2H), 2.81 (s, 3H), 2.42 (m, 1H), 2.05–1.80 (m, 4H), 1.32 (s, 6H).

EXAMPLE 9

(Z)-2-(6-phenyl-3,3-dimethyl-3,4-dihydro-(2H)-isoquinolin-1-ylidene)-1-phenylethan-1-one

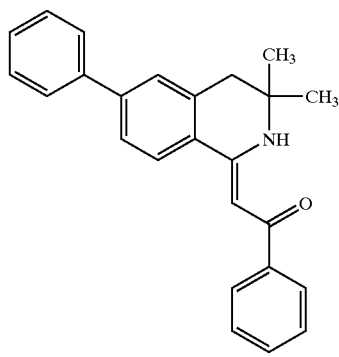

Under atmosphere of argon, a solution of the compound prepared in example 1(68) (312 mg) in dimethoxyethane (10 ml) was degassed and to the mixture were added tetrakis(triphenylphosphine)palladium (58 mg), a saturated aqueous solution of sodium bicarbonate (2.5 ml) and benzeneboronic acid and the mixture was refluxed for 3 days. The reaction mixture was allowed to cool and thereto was added water, and the mixture was extracted with ethyl acetate twice. The extract was washed with water and a saturated aqueous solution of sodium chloride and was dried over anhydrous magnesium sulfate and was concentrated under reduced pressure. The residue was purified by thin layer column chromatography on silica gel (hexane:ethyl acetate=5:1) to give the compound of the present invention (121 mg) having the following physical data.

TLC: Rf 0.39 (hexane:ethyl acetate=3:1);

NMR (CDCl₃): δ 11.82 (br, 1H), 7.99–7.96 (m, 2H), 7.89 (d, J=8.0 Hz, 1H), 7.66–7.63 (m, 2H), 7.58 (dd, J=8.0, 2.0 Hz, 1H), 7.51–7.38 (m, 7H), 6.36 (br, 1H), 2.98 (s, 2H), 1.41 (s, 6H).

EXAMPLE 9(1)

(Z)-2-(6-(pyridin-3-yl)-3,3-dimethyl-3,4-dihydro-(2H)-isoquinolin-1-ylidene)-1-phenylethan-1-one

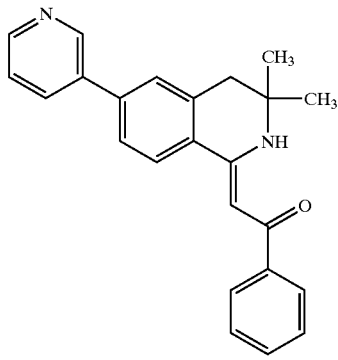

By the same procedure as described in example 9 using diethyl(3-pyridyl)borane in place of benzeneboronic acid, the compound of the present invention having the following physical data was given.

TLC: Rf 0.31 (hexane:ethyl acetate=1:1);

NMR (CDCl$_3$): δ 11.81 (br, 1H), 8.91 (d, J=1.5 Hz, 1H), 8.65 (dd, J=5.0, 1.5 Hz, 1H), 7.98–7.93 (m, 4H), 7.57 (dd, J=8.0, 2.0 Hz, 1H), 7.48–7.41 (m, 5H), 6.38 (s, 1H), 2.99 (s, 2H), 1.41 (s, 6H).

EXAMPLE 10

(Z)-2-(3,3-dimethyl-3,4-dihydro-(2H)-isoquinolin-1-ylidene)-1-(4-hydroxymethylphenyl)ethan-1-one

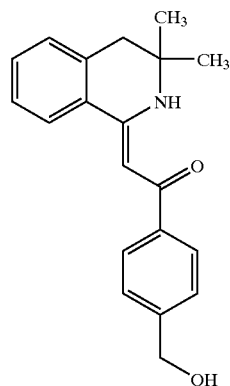

To a suspension of lithium aluminum hydride (95 mg) in anhydrous tetrahydrofuran (9 ml) was added the compound prepared in example 1(1) (317 mg) in anhydrous tetrahydrofuran (6 ml) and the mixture was stirred for 1 hour at room temperature. To the reaction mixture was added a saturated aqueous solution of sodium sulfate (1.0 ml) and was stirred. The residue was purified by column chromatography on silica gel (hexane:ethyl acetate=3:1→1:1) to give the compound of the present invention (251 mg) having the following physical data.

TLC: Rf 0.33 (hexane:ethyl acetate=1:1);

NMR (CDCl$_3$): δ 11.84 (br, 1H), 7.95 (d, J=8.0 Hz, 2H), 7.83 (d, J=7.0 Hz, 1H), 7.46–7.41 (m, 3H), 7.35 (t, J=7.0 Hz, 1H), 7.22 (d, J=7.0 Hz, 1H), 6.33 (s, 1H), 4.76 (s, 2H), 2.91 (s, 2H), 1.75 (br, 1H), 1.37 (s, 6H).

EXAMPLE 10(1)

(Z)-2-(3,3-dimethyl-3,4-dihydro-(2H)-isoquinolin-1-ylidene)-1-(3-hydroxymethylphenyl)ethan-1-one

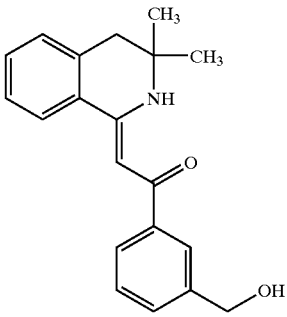

By the same procedure as described in example 10 using the compound prepared in example 1(30) in place of the compound prepared in example 1(1), the following compound of the present invention was given.

TLC: Rf 0.33 (hexane:ethyl acetate=1:1);

NMR (CDCl$_3$): δ 11.86 (br, 1H), 7.94 (s, 1H), 7.90–7.83 (m, 2H), 7.49–7.41 (m, 3H), 7.35 (t, J=7.0 Hz, 1H), 7.22 (d, J=7.0 Hz, 1H), 6.34 (s, 1H), 4.77 (s, 2H), 2.91 (s, 2H), 1.77 (br, 1H), 1.37 (s, 6H).

REFERENCE EXAMPLE 3

3-(4-isopropylphenyl)-2,2-dimethylpropanoic acid

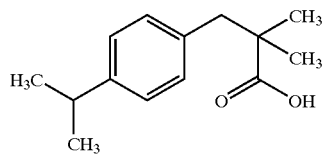

in tetrahydrofuran (40 ml) was dissolved in diisopropylamine (3.08 ml) and to the mixture was added n-butyl lithium (13.8 ml; 1.6 M hexane solution) at −78° C. and thereto was added isobutylbutyric acid (0.93 ml) dropwise and the mixture was stirred for 1 hour at 30° C. To the reaction mixture was added a solution of 4-isopropylbenzyl chloride (2.19 g) in tetrahydrofuran (10 ml) at −78° C. and the mixture was stirred at room temperature for 2 hours. The reaction mixture was poured to cool hydrochloric acid and was extracted with ethyl acetate. The extract was concentrated. The residue was purified by column chromatography on silica gel (hexane:ethyl acetate=5:1) to give the title compound (1.73 g) having the following physical data.

TLC: Rf 0.32 (ethyl acetate:hexane=1:4);

NMR (CDCl$_3$): δ 7.15–7.05 (m, 4H), 2.88 (m, 1H), 2.86 (s, 2H), 1.23 (d, J=7.0 Hz, 6H), 1.20 (s, 6H).

REFERENCE EXAMPLE 4

2-methyl-1-(4-isopropylphenyl)propane-2-isocyanate

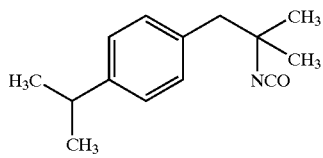

The compound prepared in reference example 3 (1.71 g), diphenylphosphoryl azide (2.15 g) and triethylamine (1.2 ml) were added to dioxane (20 ml) and the mixture was refluxed for 1 hour. The reaction mixture was allowed to cool and was poured to ice-water and was extracted with ether. The extract was washed with a saturated aqueous solution of sodium chloride and was dried over anhydrous magnesium sulfate and was concentrated to give a crude product of the title compound (1.70 g). It was used in the next reaction without purification.

REFERENCE EXAMPLE 5

3,3-dimethyl-7-isopropyl-3,4-dihydro-(2H)-isoquinolin-1-one

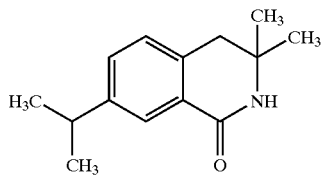

To the compound prepared in reference example 4 (1.70 g) was added polyphosphoric acid (100 g) and the mixture was stirred for 2 hours at room temperature. To the reaction mixture was added ice-water and was extracted with ethyl acetate. The extract was washed with water, a saturated aqueous solution of sodium bicarbonate and a saturated aqueous solution of sodium chloride, dried over anhydrous magnesium sulfate and was concentrated. The residue was purified by column chromatography on silica gel (hexane:ethyl acetate=3:2) to give the title compound (60 mg) having the following physical data.

TLC: Rf 0.36 (ethyl acetate:hexane=1:1);

NMR (CDCl$_3$): δ 7.94 (d, J=2.0 Hz, 1H), 7.31 (dd, J=8.0, 2.0 Hz, 1H), 7.10 (d, J=8.0 Hz, 1H), 5.73 (br., 1H), 2.95 (m, 1H), 2.89 (s, 2H), 1.31 (s, 6H), 1.27 (d, J=7.0 Hz, 6H).

REFERENCE EXAMPLE 6

3,3-dimethyl-7-isopropyl-3,4-dihydro-(2H)-isoquinolin-1-thione

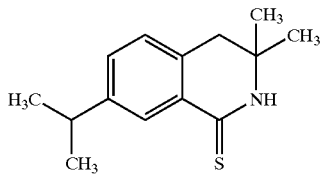

The compound prepared in reference example 5 (52 mg) and Lawesson reagent (48 mg) were added to toluene (5 ml) and the mixture was refluxed for 1 hour. The reaction mixture was allowed to cool and was purified by column chromatography on silica gel (hexane:ethyl acetate=9:1) to give the title compound (48 mg) having the following physical data.

TLC: Rf 0.35 (chloroform:hexane=1:4);

NMR (CDCl$_3$): δ 8.39 (d, J=2.0 Hz, 1H), 7.97 (br., 1H), 7.33 (dd, J=7.5, 2.0 Hz, 1H), 7.05 (d, J=7.5 Hz, 1H), 2.98 (m, 1H), 2.90 (s, 2H), 1.34 (s, 6H), 1.28 (d, J=7.0 Hz, 6H).

REFERENCE EXAMPLE 7

3,3-dimethyl-4-oxa-3,4-dihydro-(2H)-isoquinolin-1-one

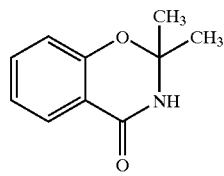

To chloroform (30 ml) was added 2-hydroxybenzamide (2.74 g) and acetonedimethylacetal (2.6 ml) and to the mixture was added concentrated sulfuric acid at room temperature and the mixture was refluxed for 8 hours. The reaction mixture was allowed to cool and filtered. The filtrate was concentrated. To the residue was added ether and was washed with 2N aqueous solution of sodium hydroxide, water and a saturated aqueous solution of sodium chloride successively and dried over anhydrous magnesium sulfate and concentrated to give the title compound (1.62 g) having the following physical data.

TLC: Rf 0.45 (ethyl acetate:hexane=1:1);

NMR (CDCl$_3$): δ 7.92 (dd, J=7.5, 1.5 Hz, 1H), 7.45 (ddd, J=8.0, 7.5, 1.5 Hz, 1H), 7.15 (br, 1H), 7.07 (ddd, J=7.5, 7.5, 1.0 Hz, 1H), 6.92 (dd, J=8.0, 1.0 Hz, 1H), 1.66 (s, 6H).

REFERENCE EXAMPLE 8

3,3-dimethyl-4-oxa-3,4-dihydro-(2H)-isoquinolin-1-thione

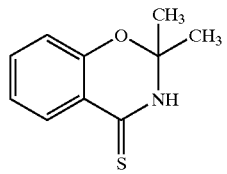

To toluene (70 ml) were added the compound prepared in reference example 7 (1.20 g) and Lawesson reagent (1.37 g) and the mixture was refluxed for 2 hours. The reaction mixture was purified by column chromatography on silica gel (hexane:ethyl acetate=5:1) to give the title compound (1.34 g) having the following physical data.

TLC: Rf 0.45 (ethyl acetate:hexane=1:3);

NMR (CDCl$_3$): δ 8.45 (br, 1H), 8.31 (dd, J=8.0, 1.5 Hz, 1H), 7.46 (ddd, J=8.0, 7.5, 1.5 Hz, 1H), 7.07 (ddd, J=8.0, 7.5, 1.0 Hz, 1H), 6.89 (dd, J=8.0, 1.0 Hz, 1H), 1.66 (s, 6H).

EXAMPLE 11

(Z)-2-(7-isopropyl-3,3-dimethyl-3,4-dihydro-(2H)-isoquinolin-1-ylidene)-1-phenylethan-1-one

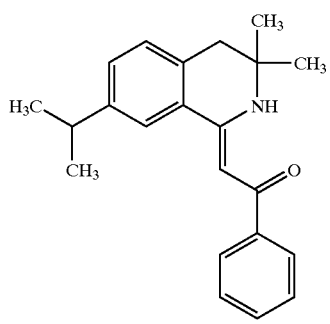

The compound prepared in reference example 6 (45 mg) was dissolved in xylene (5 ml) and to the mixture was added benzoylmethyl bromide (46 mg) and the mixture was stirred for 1.5 hours. To the reaction mixture was added triethylamine (0.04 ml) and the mixture was stirred for 15 minutes. To the reaction mixture was added triphenylphosphine (61 mg) and the mixture was stirred for 15 minutes and to the mixture was added triethylamine (0.04 ml) and the mixture was refluxed for 1 hour. The reaction mixture was allowed to cool and was purified by column chromatography on silica gel (hexane:ethyl acetate=20:1) to give the compound of the present invention (58 mg) having the following physical data.

TLC: Rf 0.19 (ethyl acetate:hexane=1:10);

NMR (CDCl$_3$): δ 11.88 (br., 1H), 7.96 (m, 2H), 7.64 (d, J=1.5 Hz, 1H), 7.50–7.40 (m, 3H), 7.30 (dd, J=8.0, 1.5 Hz, 1H), 7.14 (d, J=8.0 Hz, 1H), 6.32 (s, 1H), 2.98 (m, 1H), 2.86 (s, 2H), 1.36 (s, 6H), 1.30 (d, J=7.0 Hz, 6H).

EXAMPLE 11(1)–EXAMPLE 11(203)

By the same procedure as described in example 11 using the compound prepared in reference example 6 or a corresponding derivative and benzoylmethyl bromide or a corresponding derivative, the following compound of the present invention were given.

EXAMPLE 11(1)

(Z)-2-(3,3-dimethyl-4-oxa-3,4-dihydro-(2H)-isoquinolin-1-ylidene)-1-phenylethan-1-one

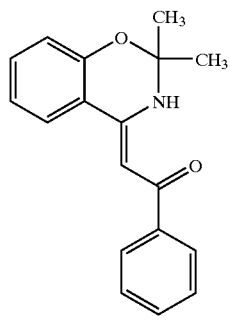

TLC: Rf 0.22 (chloroform:hexane=1:1);

NMR (CDCl$_3$): δ 11.65 (br., 1H), 7.94 (m, 2H), 7.74 (d, J=7.5, 1.5 Hz, 1H), 7.50–7.40 (m, 4H), 7.07 (ddd, J=7.5, 7.5, 1.0 Hz, 1H), 6.96 (dd, J=7.5, 1.0 Hz, 1H), 6.34 (s, 1H), 1.67 (s, 6H).

EXAMPLE 11(2)

(Z)-2-(7-methoxy-3,3-dimethyl-3,4-dihydro-(2H)-isoquinolin-1-ylidene)-1-phenylethan-1-one

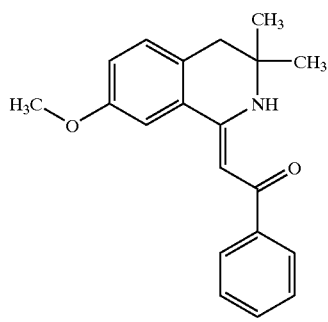

TLC: Rf 0.20 (ethyl acetate:hexane=1:5);

NMR (CDCl$_3$): δ 11.82 (br., 1H), 7.94 (m, 2H), 7.50–7.40 (m, 3H), 7.34 (d, J=2.5 Hz, 1H), 7.13 (d, J=8.0 Hz, 1H), 6.98 (dd, J=8.0, 2.5 Hz, 1H), 6.28 (s, 1H), 3.87 (s, 3H), 2.83 (s, 2H), 1.35 (s, 6H).

EXAMPLE 11(3)

(Z)-2-(7-ethyl-3,3-dimethyl-3,4-dihydro-(2H)-isoquinolin-1-ylidene)-1-phenylethan-1-one

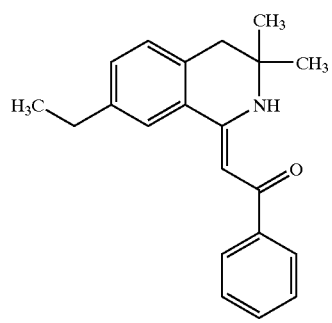

TLC: Rf 0.31 (ethyl acetate:hexane=1:5);

NMR (CDCl$_3$): δ 11.86 (br., 1H), 7.96 (m, 2H), 7.63 (s, 1H), 7.50–7.40 (m, 3H), 7.27 (m, 1H), 7.12 (d, J=8.0 Hz, 1H), 6.32 (s, 1H), 2.86 (s, 2H), 2.71 (q, J=7.5 Hz, 2H), 1.36 (s, 6H), 1.29 (t, J=7.5 Hz, 3H).

EXAMPLE 11(4)

(Z)-2-(7-t-butyl-3,3-dimethyl-3,4-dihydro-(2H)-isoquinolin-1-ylidene)-1-phenylethan-1-one

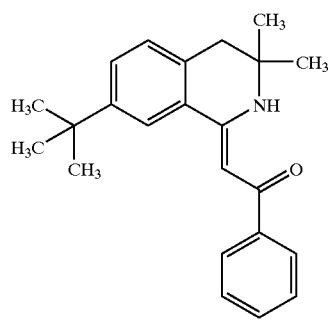

TLC: Rf 0.37 (ethyl acetate:hexane=1:5);

NMR (CDCl$_3$): δ 11.90 (br., 1H), 7.95 (m, 2H), 7.81 (d, J=2.0 Hz, 1H), 7.50–7.40 (m, 4H), 7.14 (d, J=8.0 Hz, 1H), 6.32 (s, 1H), 2.86 (s, 2H), 1.38 (s, 9H), 1.36 (s, 6H).

EXAMPLE 11(5)

(Z)-2-(7-propyl-3,3-dimethyl-3,4-dihydro-(2H)-isoquinolin-1-ylidene)-1-phenylethan-1-one

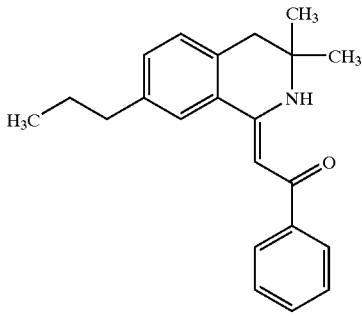

TLC: Rf 0.34 (ethyl acetate:hexane=1:5);

NMR (CDCl$_3$): δ 11.86 (br., 1H), 7.96 (m, 2H), 7.61 (d, J=1.5 Hz, 1H), 7.50–7.40 (m, 3H), 7.24 (dd, J=8.0, 1.5 Hz, 1H), 7.11 (d, J=8.0 Hz, 1H), 6.32 (s, 1H), 2.86 (s, 2H), 2.65 (t, J=7.5 Hz, 2H), 1.69 (m, 2H), 1.36 (s, 6H), 0.98 (t, J=7.5 Hz, 3H).

EXAMPLE 11(6)

(Z)-2-(7-butyl-3,3-dimethyl-3,4-dihydro-(2H)-isoquinolin-1-ylidene)-1-phenylethan-1-one

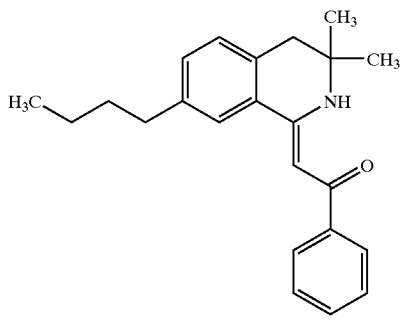

TLC: Rf 0.27 (ethyl acetate:hexane=1:5);

NMR (CDCl$_3$): δ 11.86 (br., 1H), 7.96 (m, 2H), 7.61 (d, J=2.0 Hz, 1H), 7.50–7.40 (m, 3H), 7.25 (dd, J=8.0, 2.0 Hz, 1H), 7.11 (d, J=8.0 Hz, 1H), 6.31 (s, 1H), 2.86 (s, 2H), 2.67 (t, J=7.5 Hz, 2H), 1.65 (m, 2H), 1.39 (m, 2H), 1.36 (s, 6H), 0.96 (t, J=7.5 Hz, 3H).

EXAMPLE 11(7)

(Z)-2-(7-bromo-3,3-dimethyl-3,4-dihydro-(2H)-isoquinolin-1-ylidene)-1-phenylethan-1-one

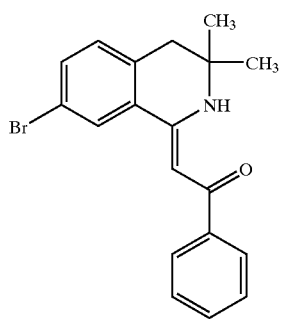

TLC: Rf 0.27 (ethyl acetate:hexane=1:5);

NMR (CDCl$_3$): δ 11.75 (br., 1H), 8.00–7.90 (m, 3H), 7.54 (dd, J=8.0, 2.0 Hz, 1H), 7.50–7.40 (m, 3H), 7.10 (d, J=8.0 Hz, 1H), 6.26 (s, 1H), 2.85 (s, 2H), 1.36 (s, 6H).

EXAMPLE 11(8)

(Z)-2-(7-chloro-3,3-dimethyl-4-oxa-3,4-dihydro-(2H)-isoquinolin-1-ylidene)-1-cycloheptylethan-1-one

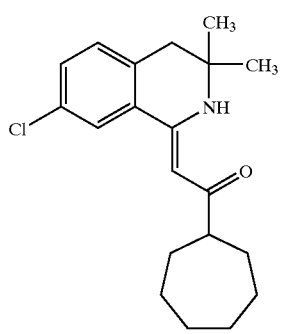

TLC: Rf 0.46 (ethyl acetate:hexane=1:5);

NMR (CDCl$_3$): δ 10.98 (br., 1H), 7.56 (d, J=2.5 Hz, 1H), 7.31 (dd, J=8.5, 2.5 Hz, 1H), 6.86 (d, J=2.5 Hz, 1H), 5.55 (s, 1H), 2.49 (m, 1H), 1.95–1.40 (m, 12H), 1.58 (s, 6H).

EXAMPLE 11(9)

(Z)-2-(7-chloro-3,3-dimethyl-4-oxa-3,4-dihydro-(2H)-isoquinolin-1-ylidene)-1-cyclohexylethan-1-one

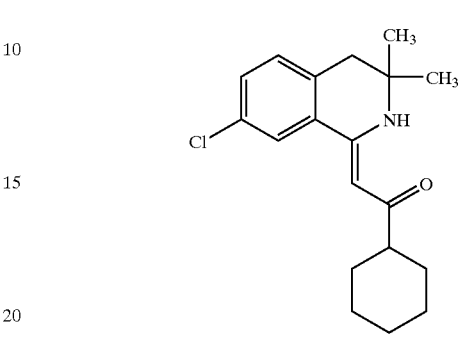

TLC: Rf 0.42 (ethyl acetate:hexane=1:5);

NMR (CDCl$_3$): δ 11.07 (br., 1H), 7.57 (d, J=2.5 Hz, 1H), 7.32 (dd, J=8.5, 2.5 Hz, 1H), 6.86 (d, J=8.5 Hz, 1H), 5.59 (s, 1H), 2.32 (m, 1H), 1.95–1.15 (m, 10H), 1.59 (s, 6H).

EXAMPLE 11(10)

(Z)-2-(7-chloro-3,3-dimethyl-4-oxa-3,4-dihydro-(2H)-isoquinolin-1-ylidene)-1-(2-methoxyphenyl)ethan-1-one

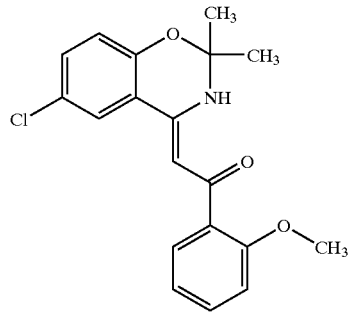

TLC: Rf 0.20 (ethyl acetate:hexane=1:5);

NMR (CDCl$_3$): δ 11.40 (br., 1H), 7.65 (dd, J=7.5, 2.0 Hz, 1H), 7.60 (d, J=2.5 Hz, 1H), 7.39 (m, 1H), 7.33 (dd, J=8.5, 2.5 Hz, 1H), 7.05–6.95 (m, 2H), 6.89 (d, J=8.5 Hz, 1H), 6.25 (s, 1H), 3.93 (s, 3H), 1.65 (s, 6H).

EXAMPLE 11(11)

(Z)-2-(7-chloro-3,3-dimethyl-4-oxa-3,4-dihydro-(2H)-isoquinolin-1-ylidene)-1-(4-cyanophenyl)ethan-1-one

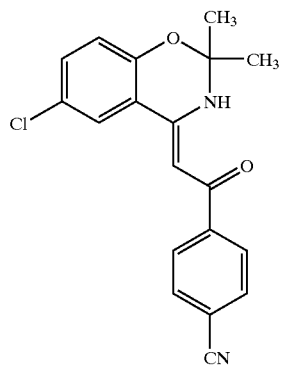

TLC: Rf 0.19 (ethyl acetate:hexane=1:5);

NMR (CDCl$_3$): δ 11.67 (br., 1H), 8.01 (d, J=9.0 Hz, 2H), 7.75 (d, J=9.0 Hz, 2H), 7.67 (d, J=2.5 Hz, 1H), 7.40 (dd, J=8.5, 2.5 Hz, 1H), 6.93 (d, J=8.5 Hz, 1H), 6.21 (s, 1H), 1.68 (s, 6H).

EXAMPLE 11(12)

(Z)-2-(3,3,7-trimethyl-4-oxa-3,4-dihydro-(2H)-isoquinolin-1-ylidene)-1-cyclohexylethan-1-one

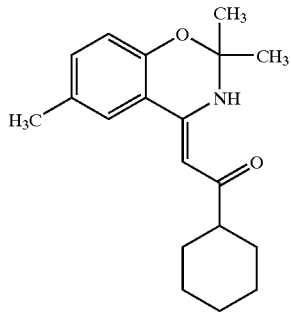

TLC: Rf 0.39 (ethyl acetate:hexane=1:5);

NMR (CDCl$_3$): δ 11.15 (br., 1H), 7.40 (d, J=1.5 Hz, 1H), 7.18 (dd, J=8.5, 1.5 Hz, 1H), 6.81 (d, J=8.5 Hz, 1H), 5.62 (s, 1H), 2.33 (s, 3H), 2.31 (m, 1H), 1.95–1.15 (m, 10H), 1.58 (s, 6H).

EXAMPLE 11(13)

(Z)-2-(7-methoxy-3,3-dimethyl-4-oxa-3,4-dihydro-(2H)-isoquinolin-1-ylidene)-1-cyclohexylethan-1-one

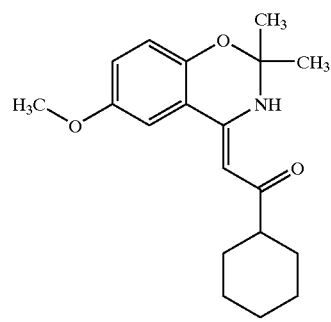

TLC: Rf 0.31 (ethyl acetate:hexane=1:5);

NMR (CDCl$_3$): δ 11.14 (br., 1H), 7.08 (d, J=3.0 Hz, 1H), 6.96 (dd, J=9.0, 3.0 Hz, 1H), 6.85 (d, J=9.0 Hz, 1H), 5.57 (s, 1H), 3.83 (s, 3H), 2.32 (m, 1H), 1.95–1.15 (m, 10H), 1.58 (s, 6H).

EXAMPLE 11(14)

(Z)-2-(7-fluoro-3,3-dimethyl-4-oxa-3,4-dihydro-(2H)-isoquinolin-1-ylidene)-1-cyclohexylethan-1-one

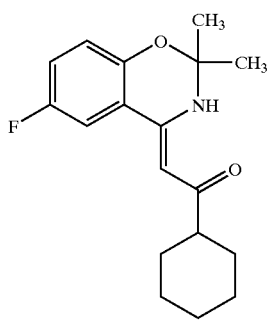

TLC: Rf 0.41 (ethyl acetate:hexane=1:5);

NMR (CDCl$_3$): δ 11.07 (br., 1H), 7.29 (dd, J=9.0, 3.0 Hz, 1H), 7.08 (ddd, J=9.0, 8.0, 3.0 Hz, 1H), 6.88 (dd, J=9.0, 5.0 Hz, 1H), 5.56 (s, 1H), 2.32 (m, 1H), 1.95–1.15 (m, 10H), 1.59 (s, 6H).

EXAMPLE 11(15)

(Z)-2-(3,3,7-trimethyl-4-oxa-3,4-dihydro-(2H)-isoquinolin-1-ylidene)-1-(2-methoxyphenyl)ethan-1-one

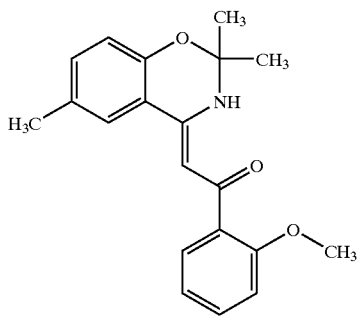

TLC: Rf 0.38 (ethyl acetate:hexane=1:3);

NMR (CDCl$_3$): δ 11.48 (br., 1H), 7.64 (dd, J=7.5, 1.5 Hz, 1H), 7.42 (d, J=2.0 Hz, 1H), 7.37 (ddd, J=8.0, 7.5, 1.5 Hz, 1H), 7.19 (dd, J=8.0, 2.0 Hz, 1H), 7.01 (ddd, J=7.5, 7.5, 1.0 Hz, 1H), 6.97 (dd, J=8.0, 1.0 Hz, 1H), 6.83 (d, J=8.0 Hz, 1H), 6.23 (s, 1H), 3.92 (s, 3H), 2.32 (s, 3H), 1.65 (s, 6H).

EXAMPLE 11(16)

(Z)-2-(7-methoxy-3,3-dimethyl-4-oxa-3,4-dihydro-(2H)-isoquinolin-1-ylidene)-1-(2-methoxyphenyl)ethan-1-one

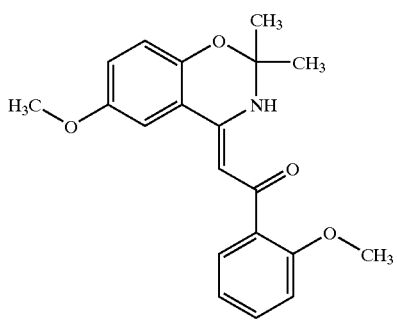

TLC: Rf 0.31 (ethyl acetate:hexane=1:3);

NMR (CDCl$_3$): δ 11.46 (br., 1H), 7.66 (dd, J=7.5, 2.0 Hz, 1H), 7.38 (ddd, J=8.0, 7.5, 2.0 Hz, 1H), 7.12 (d, J=3.0 Hz, 1H), 7.05–6.95 (m, 3H), 6.87 (d, J=8.0 Hz, 1H), 6.23 (s, 1H), 3.91 (s, 3H), 3.81 (s, 3H), 1.64 (s, 6H).

EXAMPLE 11(17)

(Z)-2-(7-fluoro-3,3-dimethyl-4-oxa-3,4-dihydro-(2H)-isoquinolin-1-ylidene)-1-(2-methoxyphenyl)ethan-1-one

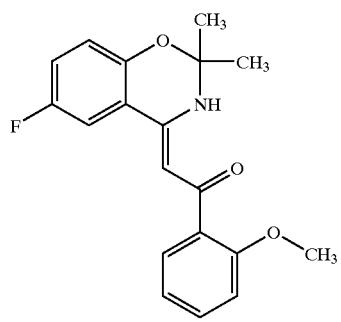

TLC: Rf 0.40 (ethyl acetate:hexane=1:3);

NMR (CDCl$_3$): δ 11.40 (br., 1H), 7.67 (dd, J=7.5, 2.0 Hz, 1H), 7.39 (ddd, J=8.0, 7.5, 2.0 Hz, 1H), 7.32 (dd, J=9.0, 3.0 Hz, 1H), 7.10 (ddd, J=9.0, 8.0, 3.0 Hz, 1H), 7.02 (ddd, J=7.5, 7.5, 1.5 Hz, 1H), 6.98 (dd, J=8.0, 1.5 Hz, 1H), 6.90 (dd, J=9.0, 4.5 Hz, 1H), 6.25 (s, 1H), 3.93 (s, 3H), 1.65 (s, 6H).

EXAMPLE 11(18)

(Z)-2-(3,3,7-trimethyl-4-oxa-3,4-dihydro-(2H)-isoquinolin-1-ylidene)-1-cycloheptylethan-1-one

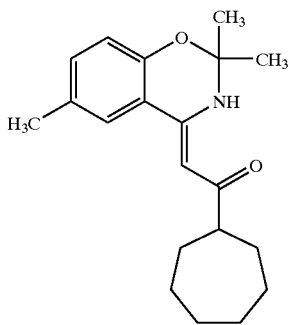

TLC: Rf 0.49 (ethyl acetate:hexane=1:4);

NMR (CDCl$_3$): δ 11.07 (br., 1H), 7.39 (d, J=1.5 Hz, 1H), 7.17 (dd, J=8.0, 1.5 Hz, 1H), 6.81 (d, J=8.0 Hz, 1H), 5.58 (s, 1H), 2.48 (m, 1H), 2.33 (s, 3H), 2.00–1.40 (m, 12H), 1.59 (s, 6H).

EXAMPLE 11(19)

(Z)-2-(7-methoxy-3,3-dimethyl-4-oxa-3,4-dihydro-(2H)-isoquinolin-1-ylidene)-1-cycloheptylethan-1-one

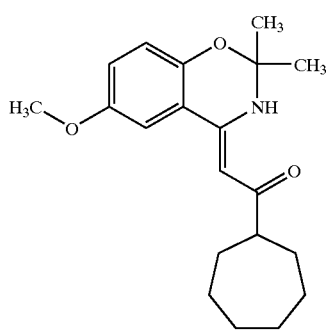

TLC: Rf 0.43 (ethyl acetate:hexane=1:4);

NMR (CDCl$_3$): δ 11.06 (br., 1H), 7.07 (d, J=3.0 Hz, 1H), 6.96 (dd, J=9.0, 3.0 Hz, 1H), 6.85 (d, J=9.0 Hz, 1H), 5.54 (s, 1H), 3.83 (s, 3H), 2.49 (m, 1H), 2.00–1.40 (m, 12H), 1.58 (s, 6H).

EXAMPLE 11(20)

(Z)-2-(7-fluoro-3,3-dimethyl-4-oxa-3,4-dihydro-(2H)-isoquinolin-1-ylidene)-1-cycloheptylethan-1-one

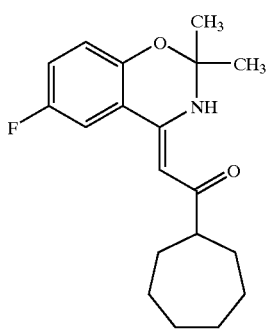

TLC: Rf 0.53 (ethyl acetate:hexane=1:4);

NMR (CDCl$_3$): δ 10.98 (br., 1H), 7.29 (dd, J=9.0, 3.0 Hz, 1H), 7.08 (ddd, J=9.0, 8.0, 3.0 Hz, 1H), 6.87 (dd, J=9.0, 5.0 Hz, 1H), 5.53 (s, 1H), 2.48 (m, 1H), 2.00–1.40 (m, 12H), 1.59 (s, 6H).

EXAMPLE 11(21)

(Z)-2-(3,3,7-trimethyl-4-oxa-3,4-dihydro-(2H)-isoquinolin-1-ylidene)-1-(4-cyanophenyl)ethan-1-one

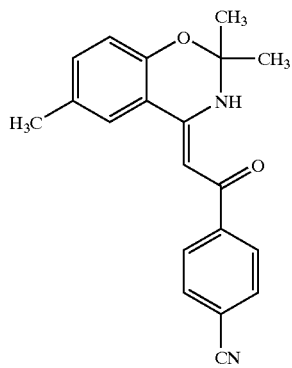

TLC: Rf 0.26 (ethyl acetate:hexane=1:5);

NMR (CDCl$_3$): δ 11.74 (br., 1H), 8.02 (d, J=8.0 Hz, 2H), 7.74 (d, J=8.0 Hz, 2H), 7.49 (d, J=1.5 Hz, 1H), 7.26 (dd, J=8.0, 1.5 Hz, 1H), 6.87 (d, J=8.0 Hz, 1H), 6.24 (s, 1H), 2.38 (s, 3H), 1.67 (s, 6H).

EXAMPLE 11(22)

(Z)-2-(7-methoxy-3,3-dimethyl-4-oxa-3,4-dihydro-(2H)-isoquinolin-1-ylidene)-1-(4-cyanophenyl)ethan-1-one

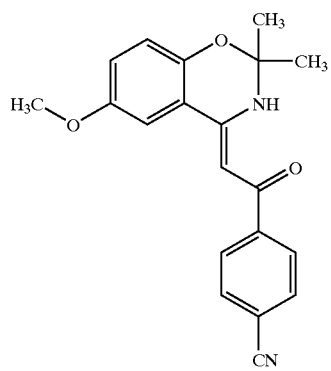

TLC: Rf 0.16 (ethyl acetate:hexane=1:5);

NMR (CDCl$_3$): δ 11.72 (br., 1H), 8.00 (d, J=8.0 Hz, 2H), 7.74 (d, J=8.0 Hz, 2H), 7.17 (d, J=3.0 Hz, 1H), 7.04 (dd, J=9.0, 3.0 Hz, 1H), 6.92 (d, J=9.0 Hz, 1H), 6.19 (s, 1H), 3.86 (s, 3H), 1.67 (s, 6H).

EXAMPLE 11(23)

(Z)-2-(7-fluoro-3,3-dimethyl-4-oxa-3,4-dihydro-(2H)-isoquinolin-1-ylidene)-1-(4-cyanophenyl)ethan-1-one

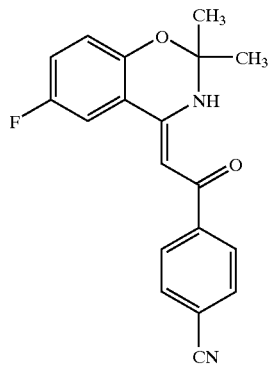

TLC: Rf 0.24 (ethyl acetate:hexane=1:5);

NMR (CDCl$_3$): δ 11.66 (br., 1H), 8.01 (d, J=8.5 Hz, 2H), 7.75 (d, J=8.5 Hz, 2H), 7.40 (dd, J=9.0, 3.0 Hz, 1H), 7.17 (ddd, J=9.0, 8.0, 3.0 Hz, 1H), 6.95 (dd, J=9.0, 4.5 Hz, 1H), 6.18 (s, 1H), 1.68 (s, 6H).

EXAMPLE 11(24)

(Z)-2-(3,3-dimethyl-4-oxa-3,4-dihydro-(2H)-isoquinolin-1-ylidene)-1-(2-methoxyphenyl)ethan-1-one

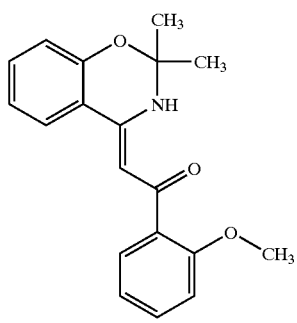

TLC: Rf 0.29 (hexane:ethyl acetate=3:1);

NMR (CDCl$_3$): δ 11.49 (br, 1H), 7.68–7.63 (m, 2H), 7.42–7.35 (m, 2H), 7.05–6.93 (m, 4H), 6.30 (s, 1H), 3.92 (s, 3H), 1.66 (s, 6H).

EXAMPLE 11(25)

(Z)-2-(3,3-dimethyl-4-oxa-3,4-dihydro-(2H)-isoquinolin-1-ylidene)-1-(4-cyanophenyl)ethan-1-one

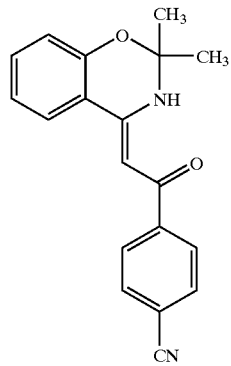

TLC: Rf 0.36 (hexane:ethyl acetate=3:1);

NMR (CDCl$_3$): δ 11.75 (br, 1H), 8.03–7.99 (m, 2H), 7.75–7.71 (m, 3H), 7.46 (dt, J=1.5, 8.0 Hz, 1H), 7.09 (t, J=8.0 Hz, 1H), 6.98 (d, J=8.0 Hz, 1H), 6.27 (s, 1H), 1.69 (s, 6H).

EXAMPLE 11(26)

(Z)-2-(3,3-dimethyl-4-oxa-3,4-dihydro-(2H)-isoquinolin-1-ylidene)-1-cycloheptylethan-1-one

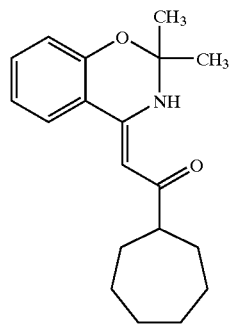

TLC: Rf 0.59 (hexane:ethyl acetate=3:1);

NMR (CDCl$_3$): δ 11.08 (br, 1H), 7.61 (dd, J=8.0, 1.5 Hz, 1H), 7.37 (ddd, J=8.0, 7.5, 1.5 Hz, 1H), 7.01 (ddd, J=8.0, 7.5, 1.0 Hz, 1H), 6.91 (dd, J=8.0, 1.0 Hz, 1H), 5.61 (s, 1H), 2.53–2.43 (m, 1H), 1.94–1.85 (m, 2H), 1.82–1.45 (m, 16H).

EXAMPLE 11(27)

(Z)-2-(3,3-dimethyl-4-oxa-3,4-dihydro-(2H)-isoquinolin-1-ylidene)-1-cyclohexylethan-1-one

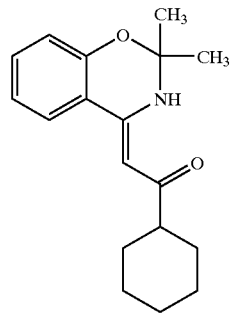

TLC: Rf 0.56 (hexane:ethyl acetate=3:1);

NMR (CDCl₃): δ 11.16 (br, 1H), 7.61 (dd, J=8.0, 1.5 Hz, 1H), 7.37 (ddd, J=8.0, 7.5, 1.5 Hz, 1H), 7.01 (ddd, J=8.0, 7.5, 1.0 Hz, 1H), 6.91 (dd, J=8.0, 1.0 Hz, 1H), 5.64 (s, 1H), 2.31 (tt, J=11.5, 3.5 Hz, 1H), 1.89–1.79 (m, 4H), 1.71–1.67 (m, 1H), 1.61 (s, 6H), 1.49–1.19 (m, 5H).

EXAMPLE 11(28)

(Z)-2-(3,3,7-trimethyl-4-oxa-3,4-dihydro-(2H)-isoquinolin-1-ylidene)-1-phenylethan-1-one

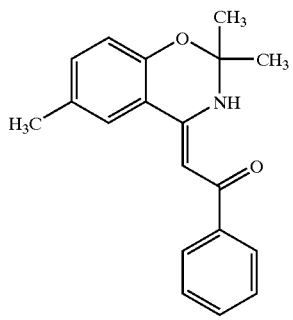

TLC: Rf 0.35 (ethyl acetate:hexane=1:5);

NMR (CDCl₃): δ 11.65 (br., 1H), 7.95 (m, 2H), 7.51 (d, J=1.5 Hz, 1H), 7.50–7.40 (m, 3H), 7.23 (m, 1H), 6.86 (d, J=9.0 Hz, 1H), 6.31 (s, 1H), 2.37 (s, 3H), 1.66 (s, 6H).

EXAMPLE 11(29)

(Z)-2-(7-methoxy-3,3-dimethyl-4-oxa-3,4-dihydro-(2H)-isoquinolin-1-ylidene)-1-phenylethan-1-one

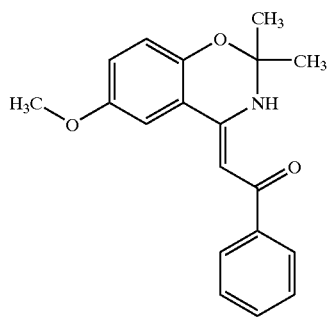

TLC: Rf 0.31 (ethyl acetate:hexane=1:5);

NMR (CDCl₃): δ 11.62 (br., 1H), 7.94 (m, 2H), 7.50–7.40 (m, 3H), 7.20 (d, J=3.0 Hz, 1H), 7.01 (dd, J=9.0, 3.0 Hz, 1H), 6.90 (d, J=9.0 Hz, 1H), 6.26 (s, 1H), 3.86 (s, 3H), 1.65 (s, 6H).

EXAMPLE 11(30)

(Z)-2-(7-chloro-3,3-dimethyl-4-oxa-3,4-dihydro-(2H)-isoquinolin-1-ylidene)-1-phenylethan-1-one

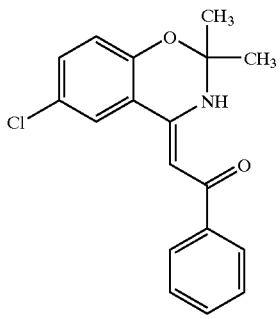

TLC: Rf 0.31 (ethyl acetate:hexane=1:5);

NMR (CDCl₃): δ 11.56 (br., 1H), 7.95 (m, 2H), 7.70 (d, J=2.5 Hz, 1H), 7.50–7.40 (m, 3H), 7.36 (dd, J=8.5, 2.5 Hz, 1H), 6.91 (d, J=8.5 Hz, 1H), 6.28 (s, 1H), 1.66 (s, 6H).

EXAMPLE 11(31)

(Z)-2-(7-fluoro-3,3-dimethyl-4-oxa-3,4-dihydro-(2H)-isoquinolin-1-ylidene)-1-phenylethan-1-one

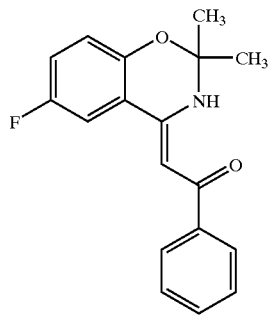

TLC: Rf 0.31 (ethyl acetate:hexane=1:5);

NMR (CDCl$_3$): δ 11.55 (br., 1H), 7.93 (m, 2H), 7.50–7.40 (m, 3H), 7.41 (dd, J=9.0, 3.0 Hz, 1H), 7.13 (ddd, J=9.0, 8.0, 3.0 Hz, 1H), 6.92 (dd, J=9.0, 4.5 Hz, 1H), 6.25 (s, 1H), 1.66 (s, 6H).

EXAMPLE 11(32)

(Z)-2-(7-methoxy-3,3-dimethyl-3,4-dihydro-(2H)-isoquinolin-1-ylidene)-1-cyclohexylethan-1-one

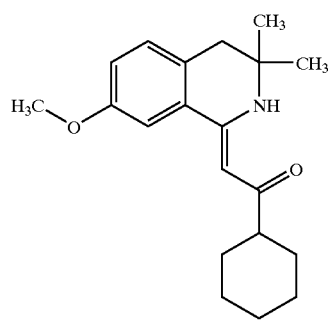

TLC: Rf 0.28 (ethyl acetate:hexane=1:5);

NMR (CDCl$_3$): δ 11.31 (br., 1H), 7.22 (d, J=2.5 Hz, 1H), 7.08 (d, J=8.5 Hz, 1H), 6.94 (dd, J=8.5, 2.5 Hz, 1H), 5.58 (s, 1H), 3.86 (s, 3H), 2.77 (s, 2H), 2.30 (m, 1H), 1.95–1.20 (m, 10H), 1.28 (s, 6H).

EXAMPLE 11(33)

(Z)-2-(7-methoxy-3,3-dimethyl-3,4-dihydro-(2H)-isoquinolin-1-ylidene)-1-cycloheptylethan-1-one

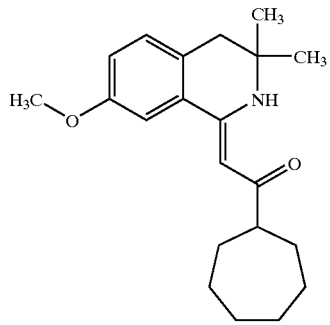

TLC: Rf 0.29 (ethyl acetate:hexane=1:5);

NMR (CDCl$_3$): δ 11.23 (br., 1H), 7.21 (d, J=2.5 Hz, 1H), 7.08 (d, J=8.5 Hz, 1H), 6.94 (dd, J=8.5, 2.5 Hz, 1H), 5.55 (s, 1H), 3.86 (s, 3H), 2.77 (s, 2H), 2.46 (m, 1H), 2.00–1.40 (m, 12H), 1.28 (s, 6H).

EXAMPLE 11(34)

(Z)-2-(7-methoxy-3,3-dimethyl-3,4-dihydro-(2H)-isoquinolin-1-ylidene)-1-(2-methoxyphenyl)-1-one

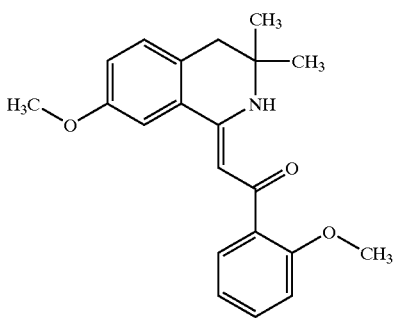

TLC: Rf 0.23 (ethyl acetate:hexane=1:3);

NMR (CDCl$_3$): δ 11.67 (br., 1H), 7.67 (dd, J=7.5, 2.0 Hz, 1H), 7.36 (ddd, J=8.0, 7.5, 2.0 Hz, 1H), 7.26 (d, J=2.5 Hz, 1H), 7.11 (d, J=8.0 Hz, 1H), 7.05–6.90 (m, 3H), 6.22 (s, 1H), 3.91 (s, 3H), 3.84 (s, 3H), 2.82 (s, 2H), 1.35 (s, 6H).

EXAMPLE 11(35)

(Z)-2-(7-methoxy-3,3-dimethyl-3,4-dihydro-(2H)-isoquinolin-1-ylidene)-1-(4-cyanophenyl)-1-one

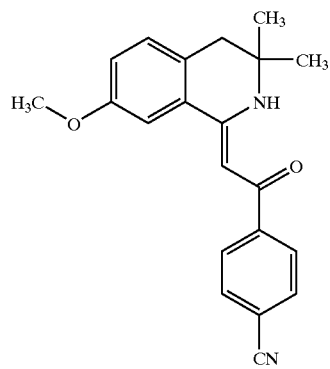

TLC: Rf 0.29 (ethyl acetate:hexane=1:3);

NMR (CDCl$_3$): δ 11.95 (br., 1H), 8.00 (d, J=8.5 Hz, 2H), 7.72 (d, J=8.5 Hz, 2H), 7.31 (d, J=2.5 Hz, 1H), 7.16 (d, J=8.5 Hz, 1H), 7.02 (dd, J=8.5, 2.5 Hz, 1H), 6.21 (s, 1H), 3.88 (s, 3H), 2.85 (s, 2H), 1.37 (s, 6H).

EXAMPLE 11(36)

(Z)-2-(7-t-butyl-3,3-dimethyl-3,4-dihydro-(2H)-isoquinolin-1-ylidene)-1-cyclohexylethan-1-one

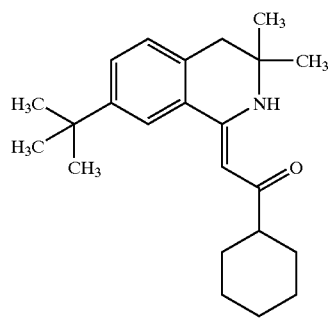

TLC: Rf 0.34 (ethyl acetate:hexane=1:5);

NMR (CDCl$_3$): δ 11.41 (br., 1H), 7.69 (d, J=2.0 Hz, 1H), 7.42 (dd, J=8.0, 2.0 Hz, 1H), 7.10 (d, J=8.0 Hz, 1H), 5.61 (s, 1H), 2.79 (s, 2H), 2.33 (m, 1H), 1.95–1.20 (m, 10H), 1.36 (s, 9H), 1.29 (s, 6H).

EXAMPLE 11(37)

(Z)-2-(7-t-butyl-3,3-dimethyl-3,4-dihydro-(2H)-isoquinolin-1-ylidene)-1-cycloheptylethan-1-one

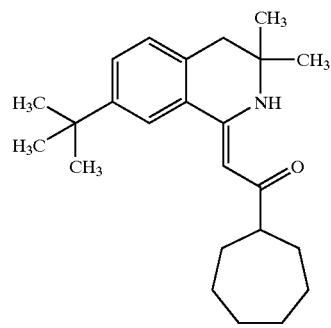

TLC: Rf 0.34 (ethyl acetate:hexane=1:5);

NMR (CDCl$_3$): δ 11.33 (br., 1H), 7.69 (d, J=2.0 Hz, 1H), 7.42 (dd, J=8.0, 2.0 Hz, 1H), 7.09 (d, J=8.0 Hz, 1H), 5.58 (s, 1H), 2.79 (s, 2H), 2.49 (m, 1H), 2.00–1.40 (m, 12H), 1.36 (s, 9H), 1.28 (s, 6H).

EXAMPLE 11(38)

(Z)-2-(7-t-butyl-3,3-dimethyl-3,4-dihydro-(2H)-isoquinolin-1-ylidene)-1-(2-methoxyphenyl)ethan-1-one

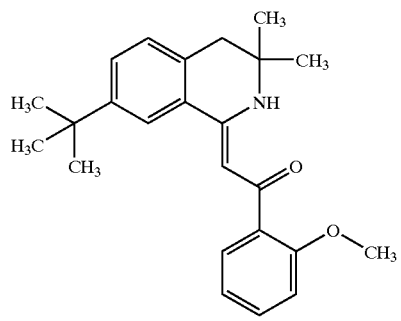

TLC: Rf 0.33 (ethyl acetate:hexane=1:3);

NMR (CDCl$_3$): δ 11.71 (br., 1H), 7.77 (d, J=2.0 Hz, 1H), 7.72 (dd, J=7.5, 2.0 Hz, 1H), 7.44 (dd, J=8.0, 2.0 Hz, 1H), 7.37 (ddd, J=8.0, 7.5, 2.0 Hz, 1H), 7.12 (d, J=8.0 Hz, 1H), 7.02 (ddd, J=7.5, 7.5, 1.0 Hz, 1H), 6.98 (dd, J=8.0, 1.0 Hz, 1H), 6.34 (s, 1H), 3.93 (s, 3H), 2.85 (s, 2H), 1.35 (s, 6H), 1.34 (s, 9H).

EXAMPLE 11(39)

(Z)-2-(7-t-butyl-3,3-dimethyl-3,4-dihydro-(2H)-isoquinolin-1-ylidene)-1-(4-cyanophenyl)ethan-1-one

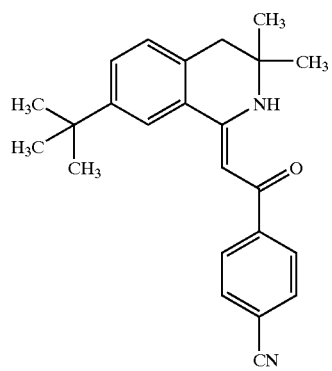

TLC: Rf 0.40 (ethyl acetate:hexane=1:3);

NMR (CDCl$_3$): δ 12.03 (br., 1H), 8.01 (d, J=8.5 Hz, 2H), 7.78 (d, J=2.0 Hz, 1H), 7.74 (d, J=8.5 Hz, 2H), 7.50 (d, J=8.0, 2.0 Hz, 1H), 7.17 (d, J=8.0 Hz, 1H), 6.25 (s, 1H), 2.88 (s, 2H), 1.38, (s, 9H), 1.38 (s, 6H).

EXAMPLE 11(40)

(Z)-2-(7-fluoro-3,3-dimethyl-3,4-dihydro-(2H)-isoquinolin-1-ylidene)-1-(4-cyanophenyl)ethan-1-one

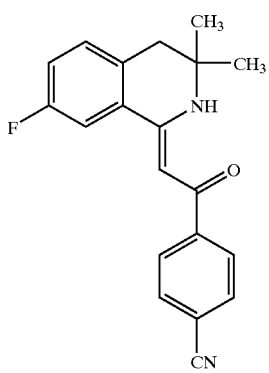

TLC: Rf 0.33 (hexane:ethyl acetate=2:1);

NMR (CDCl$_3$): δ 11.89 (br, 1H), 8.03–7.99 (m, 2H), 7.76–7.72 (m, 2H), 7.50 (dd, J=9.5, 2.5 Hz, 1H), 7.22–7.14 (m, 2H), 6.19 (s, 1H), 2.89 (s, 2H), 1.38 (s, 6H).

EXAMPLE 11(41)

(Z)-2-(7-chloro-3,3-dimethyl-3,4-dihydro-(2H)-isoquinolin-1-ylidene)-1-(4-cyanophenyl)ethan-1-one

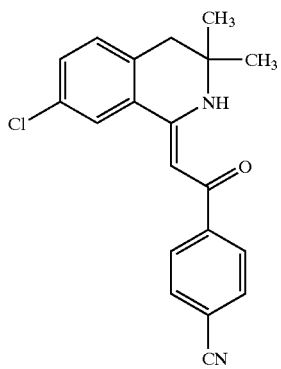

TLC: Rf 0.33 (hexane:ethyl acetate=2:1);

NMR (CDCl$_3$): δ 11.89 (br, 1H), 8.04–8.01 (m, 2H), 7.77–7.73 (m, 3H), 7.43 (dd, J=8.0, 2.0 Hz, 1H), 7.19 (d, J=8.0 Hz, 1H), 6.21 (s, 1H), 2.89 (s, 2H), 1.38 (s, 6H).

EXAMPLE 11(42)

(Z)-2-(7-fluoro-3,3-dimethyl-3,4-dihydro-(2H)-isoquinolin-1-ylidene)-1-(2-methoxyphenyl)ethan-1-one

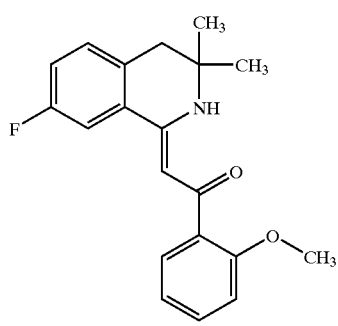

TLC: Rf 0.40 (hexane:ethyl acetate=2:1);

NMR (CDCl$_3$): δ 11.61 (br, 1H), 7.68 (dd, J=8.0, 2.0 Hz, 1H), 7.45–7.34 (m, 2H), 7.19–7.07 (m, 2H), 7.04–6.96 (m, 2H), 6.22 (s, 1H), 3.92 (s, 3H), 2.85 (s, 2H), 1.35 (s, 6H).

EXAMPLE 11(43)

(Z)-2-(7-chloro-3,3-dimethyl-3,4-dihydro-(2H)-isoquinolin-1-ylidene)-1-(2-methoxyphenyl)ethan-1-one

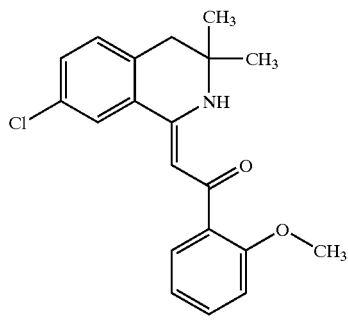

TLC: Rf 0.40 (hexane:ethyl acetate=2:1);

NMR (CDCl$_3$): δ 11.59 (br, 1H), 7.70 (d, J=2.0 Hz, 1H), 7.66 (dd, J=8.0, 2.0 Hz, 1H), 7.40–7.34 (m, 2H), 7.14 (d, J=8.0 Hz, 1H), 7.04–6.96 (m, 2H), 6.22 (s, 1H), 3.92 (s, 3H), 2.85 (s, 2H), 1.35 (s, 6H).

EXAMPLE 11(44)

(Z)-2-(7-fluoro-3,3-dimethyl-3,4-dihydro-(2H)-isoquinolin-1-ylidene)-1-cyclohexylethan-1-one

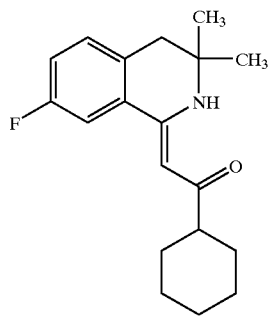

TLC: Rf 0.52 (hexane:ethyl acetate=2:1);

NMR (CDCl$_3$): δ 11.24 (br, 1H), 7.39 (dd, J=10.0, 2.5 Hz, 1H), 7.16–7.05 (m, 2H), 5.56 (s, 1H), 2.80 (s, 2H), 2.36–2.25 (m, 1H), 1.90–1.79 (m, 4H), 1.71–1.68 (m, 1H), 1.50–1.20 (m, 11H).

EXAMPLE 11(45)

(Z)-2-(7-fluoro-3,3-dimethyl-3,4-dihydro-(2H)-isoquinolin-1-ylidene)-1-cycloheptylethan-1-one

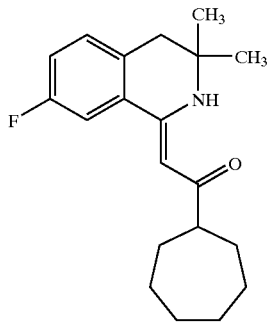

TLC: Rf 0.55 (hexane:ethyl acetate=2:1);

NMR (CDCl$_3$): δ 11.16 (br, 1H), 7.39 (dd, J=9.5, 2.5 Hz, 1H), 7.16–7.05 (m, 2H), 5.52 (s, 1H), 2.80 (s, 2H), 2.50–2.42 (m, 1H), 1.95–1.88 (m, 2H), 1.82–1.45 (m, 10H), 1.29 (s, 6H).

EXAMPLE 11(46)

(Z)-2-(7-chloro-3,3-dimethyl-3,4-dihydro-(2H)-isoquinolin-1-ylidene)-1-cyclohexylethan-1-one

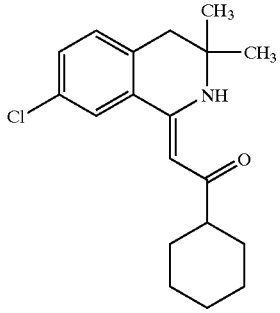

TLC: Rf 0.52 (hexane:ethyl acetate=2:1);

NMR (CDCl$_3$): δ 11.23 (br, 1H), 7.67 (d, J=2.0 Hz, 1H), 7.35 (dd, J=8.0, 2.0 Hz, 1H), 7.12 (d, J=8.0 Hz, 1H), 5.58 (s, 1H), 2.80 (s, 2H), 2.31 (tt, J=11.5, 3.0 Hz, 1H), 1.90–1.80 (m, 4H), 1.71–1.68 (m, 1H), 1.51–1.20 (m, 11H).

EXAMPLE 11(47)

(Z)-2-(7-chloro-3,3-dimethyl-3,4-dihydro-(2H)-isoquinolin-1-ylidene)-1-cycloheptylethan-1-one

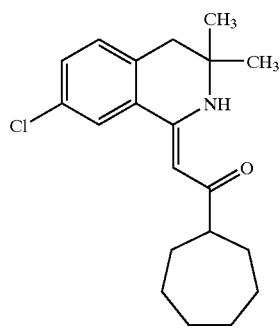

TLC: Rf 0.55 (hexane:ethyl acetate=2:1);

NMR (CDCl$_3$): δ 11.15 (br, 1H), 7.67 (d, J=2.0 Hz, 1H), 7.35 (dd, J=8.0, 2.0 Hz, 1H), 7.11 (d, J=8.0 Hz, 1H), 5.54 (s, 1H), 2.80 (s, 2H), 2.48 (tt, J=9.5, 4.0 Hz, 1H), 1.95–1.88 (m, 2H), 1.82–1.47 (m, 10H), 1.28 (s, 6H).

EXAMPLE 11(48)

(Z)-2-(3,3,7-trimethyl-3,4-dihydro-(2H)-isoquinolin-1-ylidene)-1-cyclohexylethan-1-one

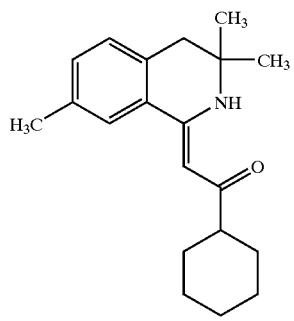

TLC: Rf 0.30 (ethyl acetate:hexane=1:5);

NMR (CDCl$_3$): δ 11.32 (br., 1H), 7.51 (s, 1H), 7.19 (m, 1H), 7.05 (d, J=8.0 Hz, 1H), 5.62 (s, 1H), 2.79 (s, 2H), 2.38 (s, 3H), 2.30 (m, 1H), 1.95–1.20 (m, 10H), 1.28 (s, 6H).

EXAMPLE 11(49)

(Z)-2-(3,3,7-trimethyl-3,4-dihydro-(2H)-isoquinolin-1-ylidene)-1-cycloheptylethan-1-one

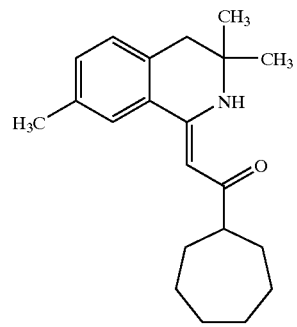

TLC: Rf 0.34 (ethyl acetate:hexane=1:5);

NMR (CDCl$_3$): δ 11.23 (br., 1H), 7.50 (s, 1H), 7.18 (m, 1H), 7.05 (d, J=7.5 Hz, 1H), 5.59 (s, 1H), 2.78 (s, 2H), 2.46 (m, 1H), 2.38 (s, 3H), 2.00–1.40 (m, 12H), 1.28 (s, 6H).

EXAMPLE 11(50)

(Z)-2-(3,3,7-trimethyl-3,4-dihydro-(2H)-isoquinolin-1-ylidene)-1-(2-methoxyphenyl)ethan-1-one

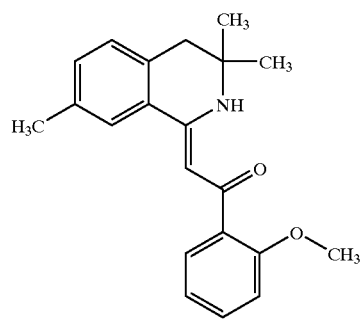

TLC: Rf 0.34 (ethyl acetate:hexane=1:3);

NMR (CDCl$_3$): δ 11.67 (br., 1H), 7.65 (dd, J=7.5, 2.0 Hz, 1H), 7.54 (s, 1H), 7.35 (ddd, J=8.0, 7.5, 2.0 Hz, 1H), 7.20 (m, 1H), 7.07 (d, J=7.5 Hz, 1H), 7.00 (ddd, J=8.0, 8.0, 1.0 Hz, 1H), 6.96 (dd, J=8.0, 1.0 Hz, 1H), 6.22 (s, 1H), 3.91 (s, 3H), 2.84 (s, 2H), 2.37 (s, 3H), 1.34 (s, 6H).

EXAMPLE 11(51)

(Z)-2-(3,3,7-trimethyl-3,4-dihydro-(2H)-isoquinolin-1-ylidene)-1-(4-cyanophenyl)ethan-1-one

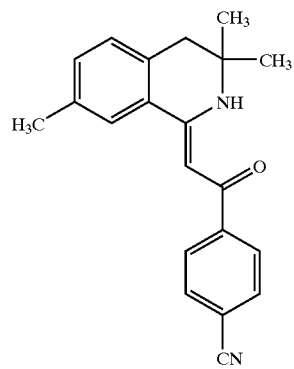

TLC: Rf 0.40 (ethyl acetate:hexane=1:3);

NMR (CDCl$_3$): δ 11.96 (br., 1H), 8.03 (d, J=8.5 Hz, 2H), 7.73 (d, J=8.5 Hz, 2H), 7.60 (s, 1H), 7.27 (m, 1H), 7.12 (d, J=7.5 Hz, 1H), 6.26 (s, 1H), 2.87 (s, 2H), 2.43, (s, 3H), 1.37 (s, 6H).

EXAMPLE 11(52)

(Z)-2-(3,3-dimethyl-3,4-dihydro-(2H)-isoquinolin-1-ylidene)-1-(2-nitrophenyl)ethan-1-one

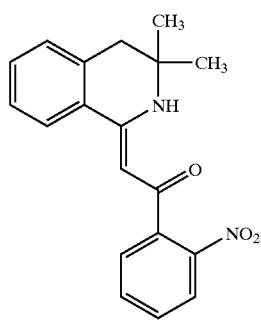

TLC: Rf 0.41 (hexane:ethyl acetate=2:1);

NMR (CDCl$_3$): δ 11.40 (br, 1H), 7.85 (d, J=7.5 Hz, 1H), 7.69 (d, J=7.5 Hz, 1H), 7.64–7.57 (m, 2H), 7.52–7.41 (m, 2H), 7.33–7.27 (m, 1H), 7.21 (d, J=7.5 Hz, 1H), 5.86 (s, 1H), 2.92 (s, 2H), 1.37 (s, 6H).

EXAMPLE 11(53)

(Z)-2-(3,3-dimethyl-3,4-dihydro-(2H)-isoquinolin-1-ylidene)-1-(3-nitrophenyl)ethan-1-one

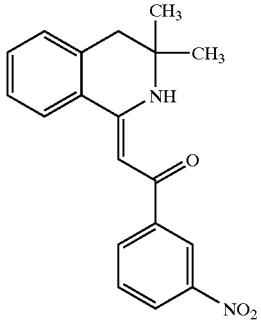

TLC: Rf 0.53 (hexane:ethyl acetate=2:1);

NMR (CDCl$_3$): δ 11.94 (br, 1H), 8.77 (dd, J=2.0, 2.0 Hz, 1H), 8.32–8.27 (m, 2H), 7.86 (dd, J=7.5, 1.0 Hz, 1H), 7.62 (dd, J=8.0, 8.0 Hz, 1H), 7.48 (ddd, J=7.5, 7.5, 1.0 Hz, 1H), 7.39 (ddd, J=7.5, 7.5, 1.0 Hz, 1H), 7.27–7.23 (m, 1H), 6.32 (s, 1H), 2.94 (s, 2H), 1.39 (s, 6H).

EXAMPLE 11(54)

(Z)-2-(3,3-dimethyl-3,4-dihydro-(2H)-isoquinolin-1-ylidene)-1-(4-nitrophenyl)ethan-1-one

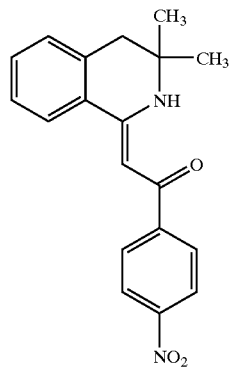

TLC: Rf 0.56 (hexane:ethyl acetate=2:1);

NMR (CDCl$_3$): δ 12.00 (br, 1H), 8.30–8.26 (m, 2H), 8.09–8.05 (m, 2H), 7.83 (dd, J=7.5, 1.0 Hz, 1H), 7.48 (ddd, J=7.5, 7.5, 1.0 Hz, 1H), 7.37 (ddd, J=7.5, 7.5, 1.0 Hz, 1H), 7.27–7.23 (m, 1H), 6.30 (s, 1H), 2.93 (s, 2H), 1.39 (s, 6H).

EXAMPLE 11(55)

(Z)-2-(3,3-dimethyl-3,4-dihydro-(2H)-isoquinolin-1-ylidene)-1-(2,5-dimethoxyphenyl)ethan-1-one

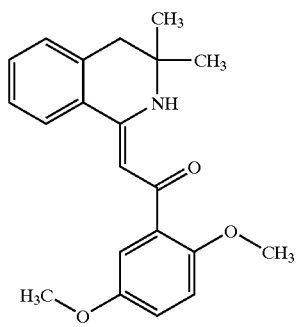

TLC: Rf 0.36 (hexane:ethyl acetate=2:1);

NMR (CDCl$_3$): δ 11.69 (br, 1H), 7.75 (d, J=7.5 Hz, 1H), 7.41 (t, J=7.5 Hz, 1H), 7.33–7.25 (m, 2H), 7.20 (d, J=7.5 Hz, 1H), 6.92–6.91 (m, 2H), 6.37 (s, 1H), 3.88 (s, 3H), 3.81 (s, 3H), 2.90 (s, 2H), 1.36 (s, 6H).

EXAMPLE 11(56)

(Z)-2-(3,3-dimethyl-3,4-dihydro-(2H)-isoquinolin-1-ylidene)-1-(2,4-dimethoxyphenyl)ethan-1-one

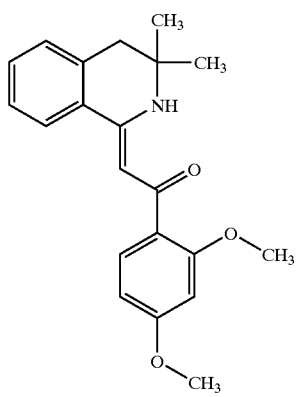

TLC: Rf 0.31 (hexane:ethyl acetate=2:1);

NMR (CDCl$_3$): δ 11.67 (br, 1H), 7.78–7.75 (m, 2H), 7.39 (t, J=7.5 Hz, 1H), 7.33–7.25 (m, 1H), 7.19 (d, J=7.5 Hz, 1H), 6.55 (dd, J=8.5, 2.5 Hz, 1H), 6.50 (d, J=2.5 Hz, 1H), 6.40 (s, 1H), 3.91 (s, 3H), 3.85 (s, 3H), 2.88 (s, 2H), 1.34 (s, 6H).

EXAMPLE 11(57)

(Z)-2-(7-methoxy-3,3-dimethyl-3,4-dihydro-(2H)-isoquinolin-1-ylidene)-1-(naphthalen-1-yl)ethan-1-one

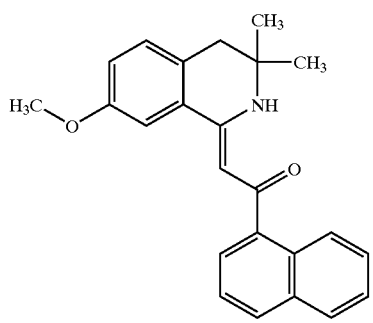

TLC: Rf 0.22 (ethyl acetate:hexane=1:5);

NMR (CDCl$_3$): δ 11.78 (br., 1H), 8.48 (m, 1H), 7.90–7.80 (m, 2H), 7.69 (dd, J=7.0, 1.0 Hz, 1H), 7.55–7.45 (m, 3H), 7.22 (d, J=2.5 Hz, 1H), 7.14 (d, J=8.5 Hz, 1H), 6.98 (dd, J=8.0, 2.5 Hz, 1H), 6.04 (s, 1H), 3.80 (s, 3H), 2.88 (s, 2H), 1.40 (s, 6H).

EXAMPLE 11(58)

(Z)-2-(3,3-dimethyl-3,4-dihydro-(2H)-isoquinolin-1-ylidene)-1-(thiazol-2-yl)ethan-1-one

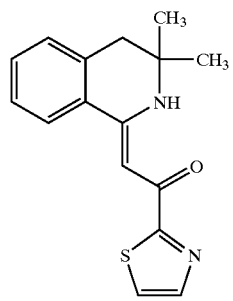

TLC: Rf 0.40 (hexane:ethyl acetate=2:1);

NMR (CDCl$_3$): δ 11.63 (br, 1H), 7.97–7.92 (m, 2H), 7.52 (d, J=3.0 Hz, 1H), 7.45 (dt, J=1.0, 7.5 Hz, 1H), 7.35 (t, J=7.5 Hz, 1H), 7.21 (d, J=7.5 Hz, 1H), 6.80 (s, 1H), 2.92 (s, 2H), 1.38 (s, 6H).

EXAMPLE 11(59)

(Z)-2-(3,3-dimethyl-3,4-dihydro-(2H)-isoquinolin-1-ylidene)-1-(pyrrol-2-yl)ethan-1-one

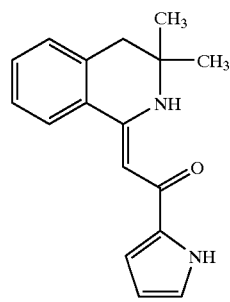

TLC: Rf 0.19 (hexane:ethyl acetate=3:1);

NMR (CDCl$_3$): δ 11.14 (br, 1H), 9.42 (br, 1H), 7.80 (dd, J=7.5, 1.0 Hz, 1H), 7.41 (dt, J=1.0, 7.5 Hz, 1H), 7.33 (dt, J=1.0, 7.5 Hz, 1H), 7.20 (dd, J=7.5, 1.0 Hz, 1H), 6.94 (m, 1H), 6.80 (m, 1H), 6.27 (m, 1H), 6.14 (s, 1H), 2.88 (s, 2H), 1.34 (s, 6H).

EXAMPLE 11(60)

(Z)-2-(3,3-dimethyl-3,4-dihydro-(2H)-isoquinolin-1-ylidene)-1-(anthracen-9-yl)ethan-1-one

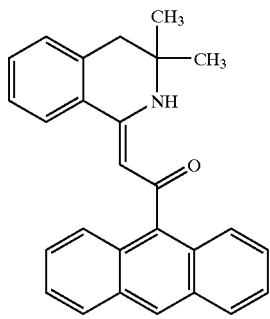

TLC: Rf 0.28 (hexane:ethyl acetate=3:1);

NMR (CDCl$_3$): δ 11.93 (br, 1H), 8.44 (s, 1H), 8.26–8.22 (m, 2H), 8.03–7.98 (m, 2H), 7.59 (d, J=7.5 Hz, 1H), 7.48–7.37 (m, 5H), 7.26–7.17 (m, 2H), 6.03 (s, 1H), 3.01 (s, 2H), 1.49 (s, 6H).

EXAMPLE 11(61)

(Z)-2-(3,3-dimethyl-3,4-dihydro-(2H)-isoquinolin-1-ylidene)-1-(pyrazin-2-yl)ethan-1-one

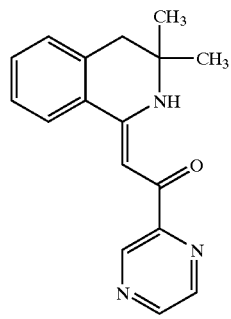

TLC: Rf 0.13 (hexane:ethyl acetate=3:1);

NMR (CDCl$_3$): δ 11.96 (br, 1H), 9.35 (d, J=1.5 Hz, 1H), 8.63 (d, J=2.5 Hz, 1H), 8.59 (dd, J=2.5, 1.5 Hz, 1H), 7.96 (d, J=7.5 Hz, 1H), 7.46 (t, J=7.5 Hz, 1H), 7.36 (t, J=7.5 Hz, 1H), 7.22 (d, J=7.5 Hz, 1H), 7.02 (s, 1H), 2.93 (s, 2H), 1.40 (s, 6H).

EXAMPLE 11(62)

(Z)-2-(3,3-dimethyl-4-oxa-3,4-dihydro-(2H)-isoquinolin-1-ylidene)-1-(adamantan-1-yl)ethan-1-one

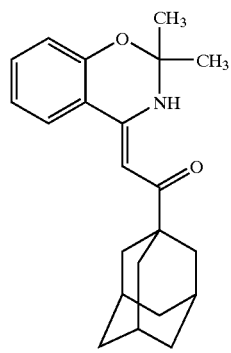

TLC: Rf 0.60 (hexane:ethyl acetate=3:1);

NMR (CDCl$_3$): δ 11.34 (br, 1H), 7.64 (dd, J=8.0, 1.5 Hz, 1H), 7.37 (ddd, J=8.0, 7.5, 1.5 Hz, 1H), 7.02 (ddd, J=8.0, 7.5, 1.0 Hz, 1H), 6.91 (dd, J=8.0, 1.0 Hz, 1H), 5.80 (s, 1H), 2.06 (br, 3H), 1.90–1.89 (m, 6H), 1.74 (br, 6H), 1.60 (s, 6H).

EXAMPLE 11(63)

(Z)-2-(3,3,7-trimethyl-3,4-dihydro-(2H)-isoquinolin-1-ylidene)-1-(adamantan-1-yl)ethan-1-one

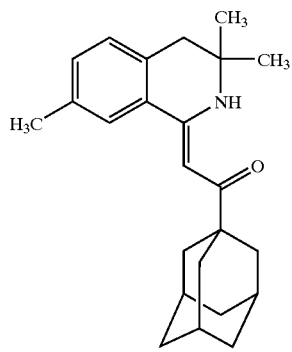

TLC: Rf 0.61 (hexane:ethyl acetate=3:1);

NMR (CDCl$_3$): δ 11.51 (br, 1H), 7.51 (s, 1H), 7.20 (d, J=7.5 Hz, 1H), 7.05 (d, J=7.5 Hz, 1H), 5.76 (s, 1H), 2.79 (s, 2H), 2.40 (s, 3H), 2.06 (br, 3H), 1.93 (br, 6H), 1.75 (br, 6H), 1.28 (s, 6H).

EXAMPLE 11(64)

(Z)-2-(7-methoxy-3,3-dimethyl-3,4-dihydro-(2H)-isoquinolin-1-ylidene)-1-(adamantan-1-yl)ethan-1-one

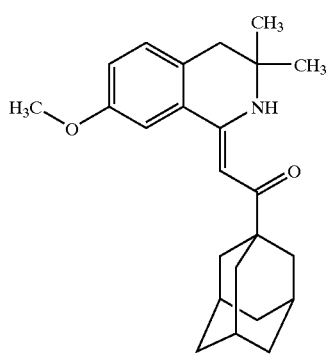

TLC: Rf 0.50 (hexane:ethyl acetate=3:1);

NMR (CDCl$_3$): δ 11.47 (br, 1H), 7.25 (d, J=2.5 Hz, 1H), 7.09 (d, J=8.0 Hz, 1H), 6.94 (dd, J=8.0, 2.5 Hz, 1H), 5.73 (s, 1H), 3.87 (s, 3H), 2.77 (s, 2H), 2.05 (br, 3H), 1.91 (br, 6H), 1.74 (br, 6H), 1.28 (s, 6H).

EXAMPLE 11(65)

(Z)-2-(3,3-dimethyl-3,4-dihydro-(2H)-isoquinolin-1-ylidene)-1-(thiophen-3-yl)ethan-1-one

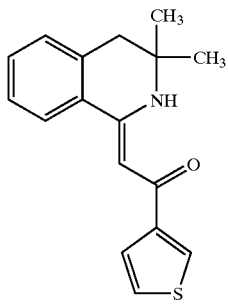

TLC: Rf 0.47 (hexane:ethyl acetate=2:1);

NMR (CDCl$_3$): δ 11.67 (br, 1H), 7.93 (dd, J=3.0, 1.0 Hz, 1H), 7.80 (d, J=7.5 Hz, 1H), 7.56 (dd, J=5.0, 1.0 Hz, 1H), 7.43 (t, J=7.5 Hz, 1H), 7.37–7.29 (m, 2H), 7.21 (d, J=7.5 Hz, 1H), 6.18 (s, 1H), 2.89 (s, 2H), 1.35 (s, 6H).

EXAMPLE 11(66)

(Z)-2-(3,3-dimethyl-3,4-dihydro-(2H)-isoquinolin-1-ylidene)-1-(5-methylfuran-2-yl)ethan-1-one

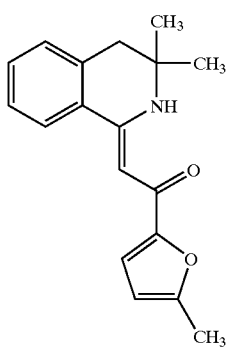

TLC: Rf 0.39 (hexane:ethyl acetate=2:1);

NMR (CDCl$_3$): δ 11.54 (br, 1H), 7.84 (dd, J=7.5, 1.0 Hz, 1H), 7.42 (dt, J=1.0, 7.5 Hz, 1H), 7.34 (dt, J=1.0, 7.5 Hz, 1H), 7.20 (dd, J=7.5, 1.0 Hz, 1H), 6.95 (d, J=3.5 Hz, 1H), 6.23 (s, 1H), 6.10 (d, J=3.5 Hz, 1H), 2.88 (s, 2H), 2.39 (s, 3H), 1.34 (s, 6H).

EXAMPLE 11(67)

(Z)-2-(7-fluoro-3,3-dimethyl-4-oxa-3,4-dihydro-(2H)-isoquinolin-1-ylidene)-1-(adamantan-1-yl)ethan-1-one

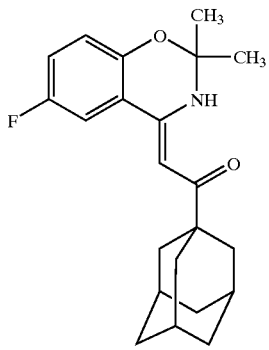

TLC: Rf 0.61 (hexane:ethyl acetate=3:1);

NMR (CDCl$_3$): δ 11.24 (br, 1H), 7.32 (dd, J=9.5, 3.0 Hz, 1H), 7.09 (ddd, J=9.5, 9.0, 3.0 Hz, 1H), 6.88 (dd, J=9.0, 4.5 Hz, 1H), 5.72 (s, 1H), 2.07 (br, 3H), 1.89 (br, 6H), 1.75 (br, 6H), 1.59 (s, 6H).

EXAMPLE 11(68)

(Z)-2-(7-chloro-3,3-dimethyl-4-oxa-3,4-dihydro-(2H)-isoquinolin-1-ylidene)-1-(adamantan-1-yl)ethan-1-one

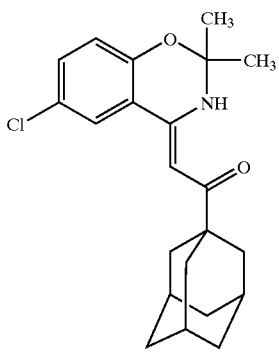

TLC: Rf 0.61 (hexane:ethyl acetate=3:1);

NMR (CDCl$_3$): δ 11.25 (br, 1H), 7.58 (d, J=2.5 Hz, 1H), 7.32 (dd, J=9.0, 2.5 Hz, 1H), 6.87 (d, J=9.0 Hz, 1H), 5.74 (s, 1H), 2.07 (br, 3H), 1.89 (br, 6H), 1.75 (br, 6H), 1.59 (s, 6H).

EXAMPLE 11(69)

(Z)-2-(7-methoxy-3,3-dimethyl-4-oxa-3,4-dihydro-(2H)-isoquinolin-1-ylidene)-1-(adamantan-1-yl)ethan-1-one

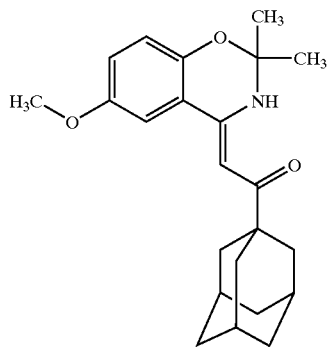

TLC: Rf 0.56 (hexane:ethyl acetate=3:1);

NMR (CDCl$_3$): δ 11.32 (br, 1H), 7.11 (d, J=3.0 Hz, 1H), 6.97 (dd, J=9.0, 3.0 Hz, 1H), 6.85 (d, J=9.0 Hz, 1H), 5.73 (s, 1H), 3.84 (s, 3H), 2.06 (br, 3H), 1.89 (br, 6H), 1.74 (br, 6H), 1.58 (s, 6H).

EXAMPLE 11(70)

(Z)-2-(7-bromo-3,3-dimethyl-3,4-dihydro-(2H)-isoquinolin-1-ylidene)-1-(naphthalen-1-yl)ethan-1-one

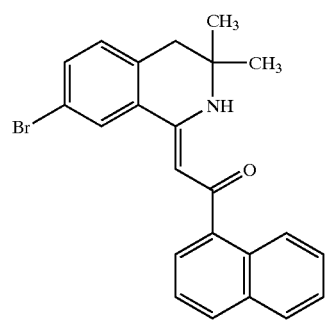

TLC: Rf 0.20 (ethyl acetate:hexane=1:5);

NMR (CDCl$_3$): δ 11.70 (br., 1H), 8.46 (m, 1H), 7.90–7.85 (m, 2H), 7.83 (d, J=2.0 Hz, 1H), 7.70 (dd, J=7.0, 1.5 Hz, 1H), 7.55–7.45 (m, 4H), 7.11 (d, J=8.0 Hz, 1H), 6.03 (s, 1H), 2.89 (s, 2H), 1.41 (s, 6H).

EXAMPLE 11(71)

(Z)-2-(3,3,7-trimethyl-4-oxa-3,4-dihydro-(2H)-isoquinolin-1-ylidene)-1-(adamantan-1-yl)ethan-1-one

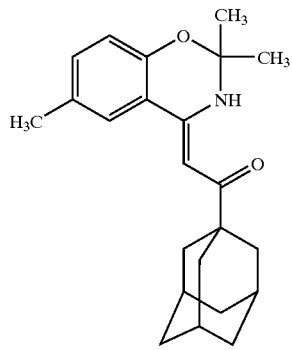

TLC: Rf 0.61 (hexane:ethyl acetate=3:1);

NMR (CDCl$_3$): δ 11.35 (br, 1H), 7.40 (d, J=2.0 Hz, 1H), 7.18 (dd, J=8.5, 2.0 Hz, 1H), 6.81 (d, J=8.5 Hz, 1H), 5.77 (s, 1H), 2.35 (s, 3H), 2.07 (br, 3H), 1.90 (br, 6H), 1.75 (br, 6H), 1.58 (s, 6H).

EXAMPLE 11(72)

(Z)-2-(6-chloro-3,3-dimethyl-3,4-dihydro-(2H)-isoquinolin-1-ylidene)-1-(4-cyanophenyl)ethan-1-one

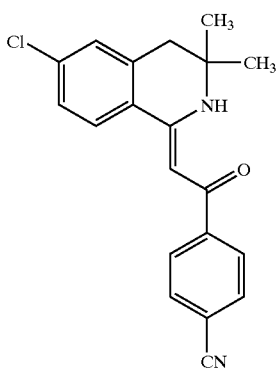

TLC: Rf 0.49 (hexane:ethyl acetate=2:1);

NMR (CDCl$_3$): δ 11.90 (br, 1H), 8.00 (d, J=8.5 Hz, 2H), 7.76–7.71 (m, 3H), 7.34 (dd, J=8.5, 2.5 Hz, 1H), 7.24 (d, J=2.5 Hz, 1H), 6.22 (s, 1H), 2.90 (s, 2H), 1.38 (s, 6H).

EXAMPLE 11(73)

(Z)-2-(8-chloro-3,3-dimethyl-3,4-dihydro-(2H)-isoquinolin-1-ylidene)-1-(4-cyanophenyl)ethan-1-one

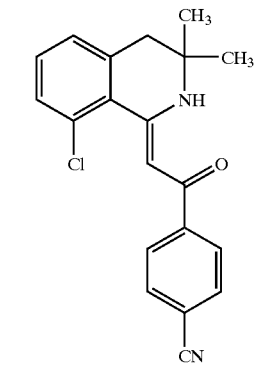

TLC: Rf 0.34 (hexane:ethyl acetate=2:1);

NMR (CDCl$_3$): δ 12.18 (br, 1H), 7.99 (d, J=8.5 Hz, 2H), 7.72 (d, J=8.5 Hz, 2H), 7.45 (d, J=7.5 Hz, 1H), 7.33 (t, J=7.5 Hz, 1H), 7.15 (d, J=7.5 Hz, 1H), 6.81 (s, 1H), 2.87 (s, 2H), 1.34 (s, 6H).

EXAMPLE 11(74)

(Z)-2-(8-chloro-3,3-dimethyl-3,4-dihydro-(2H)-isoquinolin-1-ylidene)-1-cyclohexylethan-1-one

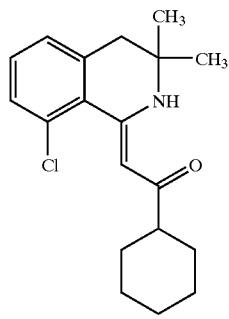

TLC: Rf 0.49 (hexane:ethyl acetate=3:1);

NMR (CDCl$_3$): δ 11.49 (br, 1H), 7.37 (dd, J=8.0, 1.0 Hz, 1H), 7.24 (t, J=8.0 Hz, 1H), 7.08 (dd, J=8.0, 1.0 Hz, 1H), 6.11 (s, 1H), 2.79 (s, 2H), 2.27 (tt, J=11.5, 3.5 Hz, 1H), 1.91–1.87 (m, 2H), 1.82–1.78 (m, 2H), 1.67 (m, 1H), 1.53–1.25 (m, 11H).

EXAMPLE 11(75)

(Z)-2-(3,3-dimethyl-3,4-dihydro-(2H)-isoquinolin-1-ylidene)-1-(5-methylthiophen-2-yl)ethan-1-one

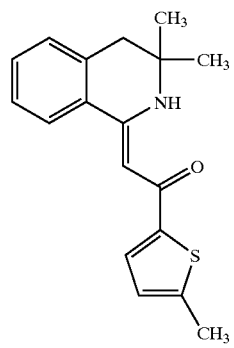

TLC: Rf 0.41 (hexane:ethyl acetate=3:1);

NMR (CDCl$_3$): δ 11.40 (br, 1H), 7.79 (dd, J=7.5, 1.5 Hz, 1H), 7.46–7.39 (m, 2H), 7.33 (dt, J=1.5, 7.5 Hz, 1H), 7.20 (dd, J=7.5, 1.5 Hz, 1H), 6.76 (dq, J=4.0, 1.0 Hz, 1H), 6.15 (s, 1H), 2.88 (s, 2H), 2.53 (d, J=1.0 Hz, 3H), 1.33 (s, 6H).

EXAMPLE 11(76)

(Z)-2-(3,3-dimethyl-3,4-dihydro-(2H)-isoquinolin-1-ylidene)-1-(2,5-dimethylfuran-3-yl)ethan-1-one

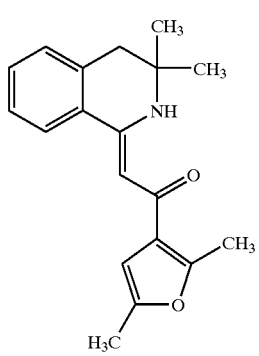

TLC: Rf 0.45 (hexane:ethyl acetate=3:1);

NMR (CDCl$_3$): δ 11.50 (br, 1H), 7.74 (dd, J=7.5, 1.5 Hz, 1H), 7.40 (dt, J=1.5, 7.5 Hz, 1H), 7.31 (dt, J=1.5, 7.5 Hz, 1H), 7.19 (dd, J=7.5, 1.5 Hz, 1H), 6.23 (d, J=1.0 Hz, 1H), 5.92 (s, 1H), 2.87 (s, 2H), 2.61 (s, 3H), 2.26 (d, J=1.0 Hz, 3H), 1.33 (s, 6H).

EXAMPLE 11(77)

(Z)-2-(6-chloro-3,3-dimethyl-4-oxa-3,4-dihydro-(2H)-isoquinolin-1-ylidene)-1-(4-cyanophenyl)ethan-1-one

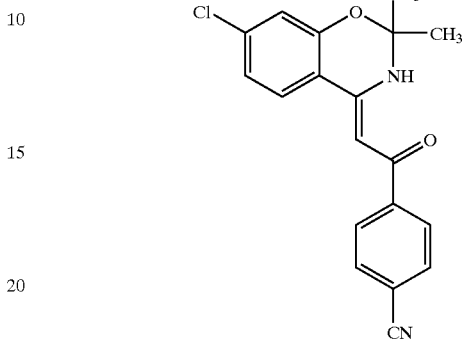

TLC: Rf 0.21 (ethyl acetate:hexane=1:5);

NMR (CDCl$_3$): δ 11.69 (br., 1H), 7.99 (d, J=9.0 Hz, 2H), 7.74 (d, J=9.0 Hz, 2H), 7.65 (d, J=8.5 Hz, 1H), 7.07 (dd, J=8.5, 2.0 Hz, 1H), 7.01 (d, J=2.0 Hz, 1H), 6.22 (s, 1H), 1.68 (s, 6H).

EXAMPLE 11(78)

(Z)-2-(7-fluoro-3,3-dimethyl-3,4-dihydro-(2H)-isoquinolin-1-ylidene)-1-(adamantan-1-yl)ethan-1-one

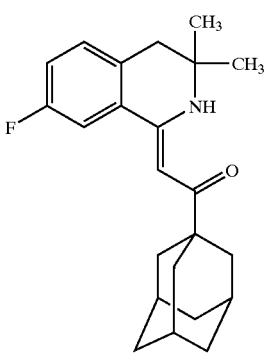

TLC: Rf 0.53 (hexane:ethyl acetate=3:1);

NMR (CDCl$_3$): δ 11.41 (br, 1H), 7.41 (dd, J=10.0, 2.5 Hz, 1H), 7.17–7.05 (m, 2H), 5.71 (s, 1H), 2.80 (s, 2H), 2.06 (br, 3H), 1.91 (br, 6H), 1.75 (br, 6H), 1.29 (s, 6H).

EXAMPLE 11(79)

(Z)-2-(7-chloro-3,3-dimethyl-3,4-dihydro-(2H)-isoquinolin-1-ylidene)-1-(adamantan-1-yl)ethan-1-one

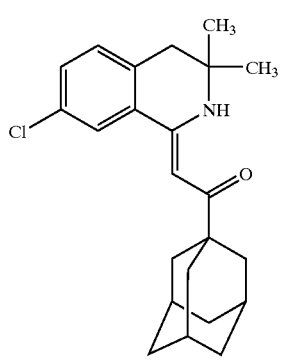

TLC: Rf 0.53 (hexane:ethyl acetate=3:1);

NMR (CDCl$_3$): δ 11.42 (br, 1H), 7.67 (d, J=2.0 Hz, 1H), 7.35 (dd, J=8.0, 2.0 Hz, 1H), 7.12 (d, J=8.0 Hz, 1H), 5.72 (s, 1H), 2.80 (s, 2H), 2.07 (br, 3H), 1.91 (br, 6H), 1.75 (br, 6H), 1.29 (s, 6H).

EXAMPLE 11(80)

(Z)-2-(6-chloro-3,3-dimethyl-3,4-dihydro-(2H)-isoquinolin-1-ylidene)-1-(adamantan-1-yl)ethan-1-one

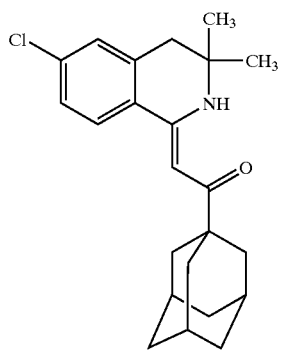

TLC: Rf 0.57 (hexane:ethyl acetate=3:1);

NMR (CDCl$_3$): δ 11.43 (br, 1H), 7.65 (d, J=8.0 Hz, 1H), 7.27 (dd, J=8.0, 2.0 Hz, 1H), 7.17 (d, J=2.0 Hz, 1H), 5.74 (s, 1H), 2.81 (s, 2H), 2.05 (br, 3H), 1.90 (br, 6H), 1.74 (br, 6H), 1.29 (s, 6H).

EXAMPLE 11(81)

(Z)-2-(3,3-dimethyl-3,4-dihydro-(2H)-isoquinolin-1-ylidene)-1-(4-bromophenyl)ethan-1-one

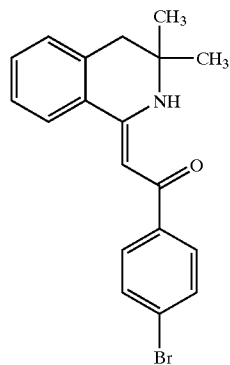

TLC: Rf 0.45 (hexane:ethyl acetate=3:1);

NMR (CDCl$_3$): δ 11.84 (br, 1H), 7.84–7.80 (m, 3H), 7.56 (d, J=8.5 Hz, 2H), 7.44 (t, J=7.5 Hz, 1H), 7.35 (t, J=7.5 Hz, 1H), 7.22 (d, J=7.5 Hz, 1H), 6.27 (s, 1H), 2.91 (s, 2H), 1.37 (s, 6H).

EXAMPLE 11(82)

(Z)-2-(3,3-dimethyl-3,4-dihydro-(2H)-isoquinolin-1-ylidene)-1-(5-cyanothiophen-2-yl)ethan-1-one

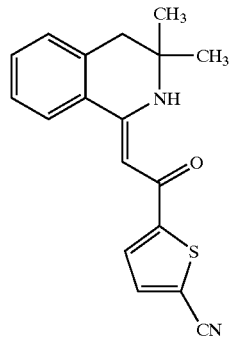

TLC: Rf 0.29 (hexane:ethyl acetate=3:1);

NMR (CDCl$_3$): δ 11.63 (br, 1H), 7.78 (d, J=7.5 Hz, 1H), 7.58 (d, J=4.0 Hz, 1H), 7.53 (d, J=4.0 Hz, 1H), 7.48 (t, J=7.5 Hz, 1H), 7.37 (t, J=7.5 Hz, 1H), 7.24 (d, J=7.5 Hz, 1H), 6.15 (s, 1H), 2.92 (s, 2H), 1.36 (s, 6H).

EXAMPLE 11(83)

(Z)-2-(3,3-dimethyl-3,4-dihydro-(2H)-isoquinolin-1-ylidene)-1-(4-methylthiophenyl)ethan-1-one

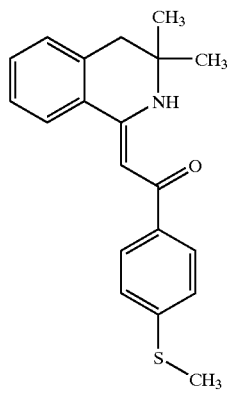

TLC: Rf 0.31 (hexane:ethyl acetate=3:1);

NMR (CDCl$_3$): δ 11.81 (br, 1H), 7.89 (d, J=8.5 Hz, 2H), 7.83 (d, J=7.5 Hz, 1H), 7.43 (t, J=7.5 Hz, 1H), 7.34 (t, J=7.5 Hz, 1H), 7.28 (d, J=8.5 Hz, 2H), 7.21 (d, J=7.5 Hz, 1H), 6.31 (s, 1H), 2.90 (s, 2H), 2.53 (s, 3H), 1.36 (s, 6H).

EXAMPLE 11(84)

(Z)-2-(6-chloro-3,3-dimethyl-4-oxa-3,4-dihydro-(2H)-isoquinolin-1-ylidene)-1-phenylethan-1-one

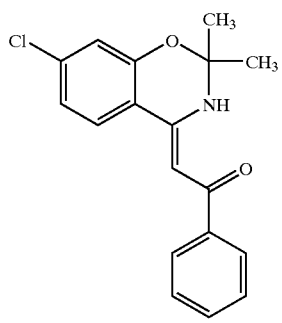

TLC: Rf 0.36 (ethyl acetate:hexane=1:5);

NMR (CDCl$_3$): δ 11.59 (br., 1H), 7.93 (m, 2H), 7.66 (d, J=8.5 Hz, 1H), 7.50–7.40 (m, 3H), 7.04 (dd, J=8.5, 2.0 Hz, 1H), 6.98 (d, J=2.0 Hz, 1H), 6.29 (s, 1H), 1.66 (s, 6H).

EXAMPLE 11(85)

(Z)-2-(6-chloro-3,3-dimethyl-4-oxa-3,4-dihydro-(2H)-isoquinolin-1-ylidene)-1-cyclohexylethan-1-one

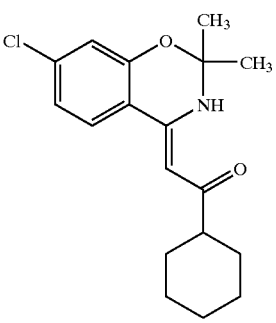

TLC: Rf 0.44 (ethyl acetate:hexane=1:5);

NMR (CDCl$_3$): δ 11.11 (br., 1H), 7.53 (d, J=8.5 Hz, 1H), 6.98 (dd, J=8.5, 2.0 Hz, 1H), 6.94 (d, J=2.0 Hz, 1H), 5.60 (s, 1H), 2.30 (m, 1H), 1.90–1.20 (m, 10H), 1.66 (s, 6H).

EXAMPLE 11(86)

(Z)-2-(6-chloro-3,3-dimethyl-4-oxa-3,4-dihydro-(2H)-isoquinolin-1-ylidene)-1-cycloheptylethan-1-one

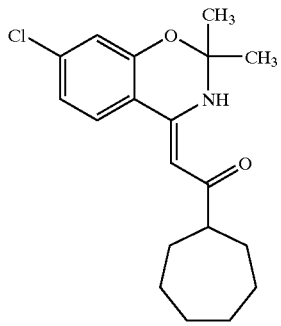

TLC: Rf 0.60 (ethyl acetate:hexane=1:3);

NMR (CDCl$_3$): δ 11.02 (br., 1H), 7.53 (d, J=8.5 Hz, 1H), 6.98 (dd, J=8.5, 2.0 Hz, 1H), 6.93 (d, J=2.0 Hz, 1H), 5.56 (s, 1H), 2.47 (m, 1H), 1.95–1.40 (m, 12H), 1.59 (s, 6H).

EXAMPLE 11(87)

(Z)-2-(3,3-dimethyl-3,4-dihydro-(2H)-isoquinolin-1-ylidene)-1-(4-dimethylaminophenyl)ethan-1-one

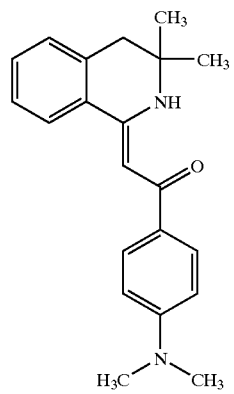

TLC: Rf 0.19 (hexane:ethyl acetate=3:1);

NMR (CDCl$_3$): δ 11.65 (br, 1H), 7.91 (d, J=9.0 Hz, 2H), 7.83 (d, J=7.5 Hz, 1H), 7.40 (t, J=7.5 Hz, 1H), 7.33 (t, J=7.5 Hz, 1H), 7.19 (d, J=7.5 Hz, 1H), 6.71 (d, J=9.0 Hz, 2H), 6.32 (s, 1H), 3.04 (s, 6H), 2.88 (s, 2H), 1.34 (s, 6H).

EXAMPLE 11(88)

(Z)-2-(3,3-dimethyl-3,4-dihydro-(2H)-isoquinolin-1-ylidene)-1-(4-mesylphenyl)ethan-1-one

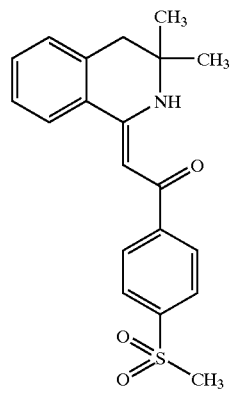

TLC: Rf 0.32 (hexane:ethyl acetate=1:1);

NMR (CDCl$_3$): δ 11.97 (br, 1H), 8.10 (d, J=9.0 Hz, 2H), 8.00 (d, J=9.0 Hz, 2H), 7.83 (d, J=7.5 Hz, 1H), 7.47 (t, J=7.5 Hz, 1H), 7.37 (t, J=7.5 Hz, 1H), 7.24 (d, J=7.5 Hz, 1H), 6.30 (s, 1H), 3.09 (s, 3H), 2.93 (s, 2H), 1.39 (s, 6H).

EXAMPLE 11(89)

(Z)-2-(8-chloro-3,3-dimethyl-3,4-dihydro-(2H)-isoquinolin-1-ylidene)-1-phenylethan-1-one

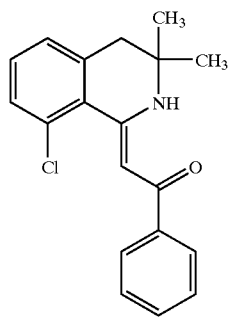

TLC: Rf 0.39 (hexane:ethyl acetate=3:1);

NMR (CDCl$_3$): δ 12.03 (br, 1H), 7.95–7.91 (m, 2H), 7.44–7.41 (m, 4H), 7.29 (m, 1H), 7.13 (dd, J=7.5, 1.5 Hz, 1H), 6.85 (s, 1H), 2.86 (s, 2H), 1.33 (s, 6H).

EXAMPLE 11(90)

(Z)-2-(6-chloro-3,3-dimethyl-4-oxa-3,4-dihydro-(2H)-isoquinolin-1-ylidene)-1-(adamantan-1-yl)ethan-1-one

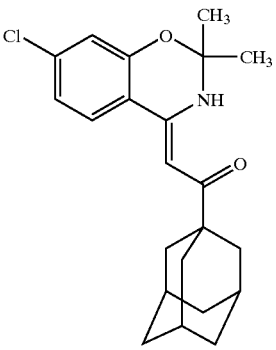

TLC: Rf 0.28 (ethyl acetate:hexane=1:10);

NMR (CDCl$_3$): δ 11.28 (br., 1H), 7.56 (d, J=8.5 Hz, 1H), 6.99 (dd, J=8.5, 2.0 Hz, 1H), 6.93 (d, J=2.0 Hz, 1H), 5.76 (s, 1H), 2.06 (m, 3H), 1.88 (m, 6H), 1.74 (m, 6H), 1.59 (s, 6H).

EXAMPLE 11(91)

(Z)-2-(6-chloro-3,3-dimethyl-3,4-dihydro-(2H)-isoquinolin-1-ylidene)-1-(tetrahydropyran-4-yl)ethan-1-one

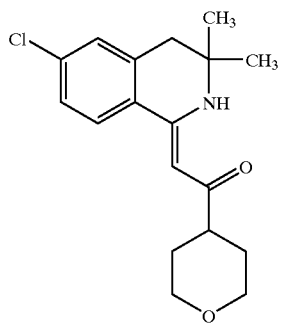

TLC: Rf 0.38 (ethyl acetate:hexane=1:1);

NMR (CDCl$_3$): δ 11.27 (br., 1H), 7.63 (d, J=8.5 Hz, 1H), 7.27 (dd, J=8.5, 2.0 Hz, 1H), 7.19 (d, J=2.0 Hz, 1H), 5.59 (s, 1H), 4.05 (m, 2H), 3.45 (dt, J=3.0, 11.5 Hz, 2H), 2.82 (s, 2H), 2.51 (m, 1H), 1.90–1.70 (m, 4H), 1.30 (s, 6H).

EXAMPLE 11(92)

(Z)-2-(7-chloro-3,3-dimethyl-3,4-dihydro-(2H)-isoquinolin-1-ylidene)-1-(tetrahydropyran-4-yl)ethan-1-one

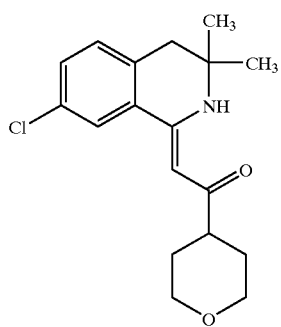

TLC: Rf 0.39 (ethyl acetate:hexane=1:1);

NMR (CDCl$_3$): δ 11.24 (br., 1H), 7.66 (d, J=2.0 Hz, 1H), 7.37 (dd, J=8.0, 2.0 Hz, 1H), 7.13 (d, J=8.0 Hz, 1H), 5.58 (s, 1H), 4.05 (m, 2H), 3.46 (dt, J=3.0, 11.5 Hz, 2H), 2.81 (s, 2H), 2.54 (m, 1H), 1.90–1.70 (m, 4H), 1.30 (s, 6H).

EXAMPLE 11(93)

(Z)-2-(7-fluoro-3,3-dimethyl-3,4-dihydro-(2H)-isoquinolin-1-ylidene)-1-(tetrahydropyran-4-yl)ethan-1-one

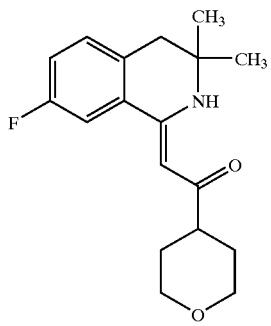

TLC: Rf 0.38 (ethyl acetate:hexane=1:1);

NMR (CDCl$_3$): δ 11.25 (br., 1H), 7.38 (dd, J=9.5, 2.5 Hz, 1H), 7.20–7.05 (m, 2H), 5.56 (s, 1H), 4.05 (m, 2H), 3.46 (dt, J=3.0, 11.5 Hz, 2H), 2.82 (s, 2H), 2.53 (m, 1H), 1.90–1.70 (m, 4H), 1.30 (s, 6H).

EXAMPLE 11(94)

(Z)-2-(3,3-dimethyl-3,4-dihydro-(2H)-isoquinolin-1-ylidene)-1-(2,4-dichlorophenyl)ethan-1-one

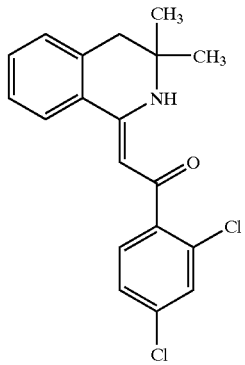

TLC: Rf 0.29 (hexane:ethyl acetate=5:1);

NMR (CDCl$_3$): δ 11.56 (br, 1H), 7.71 (d, J=7.5 Hz, 1H), 7.50 (d, J=8.0 Hz, 1H), 7.46–7.41 (m, 2H), 7.34–7.26 (m, 2H), 7.21 (d, J=7.5 Hz, 1H), 5.94 (s, 1H), 2.92 (s, 2H), 1.38 (s, 6H).

EXAMPLE 11(95)

(Z)-2-(3,3-dimethyl-3,4-dihydro-(2H)-isoquinolin-1-ylidene)-1-(2,5-dichlorothiophen-3-yl)ethan-1-one

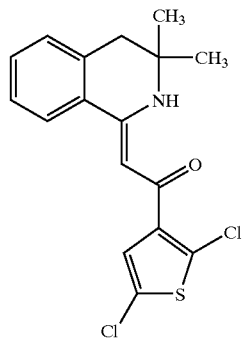

TLC: Rf 0.36 (hexane:ethyl acetate=5:1);

NMR (CDCl$_3$): δ 11.61 (br, 1H), 7.76 (d, J=7.5 Hz, 1H), 7.44 (t, J=7.5 Hz, 1H), 7.34 (t, J=7.5 Hz, 1H), 7.21 (d, J=7.5 Hz, 1H), 7.16 (s, 1H), 6.17 (s, 1H), 2.90 (s, 2H), 1.36 (s, 6H).

EXAMPLE 11(96)

(Z)-2-(6-fluoro-3,3-dimethyl-3,4-dihydro-(2H)-isoquinolin-1-ylidene)-1-(adamantan-1-yl)ethan-1-one

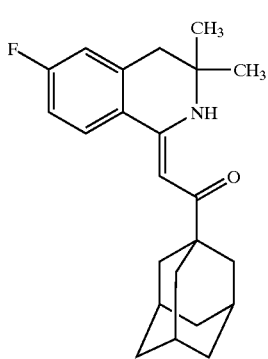

TLC: Rf 0.35 (ethyl acetate:hexane=1:5);

NMR (CDCl$_3$): δ 11.48 (br., 1H), 7.72 (dd, J=8.5, 5.5 Hz, 1H), 6.99 (ddd, J=8.5, 8.5, 2.5 Hz, 1H), 6.88 (dd, J=8.5, 2.5 Hz, 1H), 5.72 (s, 1H), 2.82 (s, 2H), 2.05 (m, 3H), 1.91 (m, 6H), 1.74 (m, 6H), 1.30 (s, 6H).

EXAMPLE 11(97)

(Z)-2-(6-fluoro-3,3-dimethyl-3,4-dihydro-(2H)-isoquinolin-1-ylidene)-1-(4-cyanophenyl)ethan-1-one

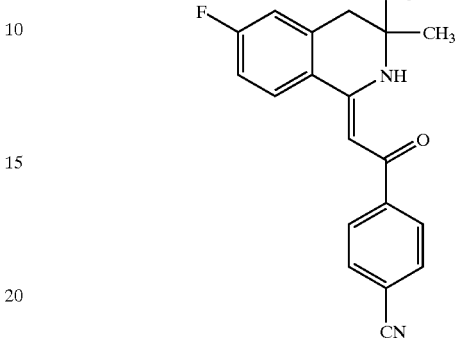

TLC: Rf 0.13 (ethyl acetate:hexane=1:5);

NMR (CDCl$_3$): δ 11.94 (br., 1H), 8.00 (d, J=8.5 Hz, 2H), 7.82 (dd, J=8.5, 5.5 Hz, 1H), 7.72 (d, J=8.5 Hz, 2H), 7.05 (ddd, J=8.5, 8.5, 2.5 Hz, 1H), 6.95 (dd, J=8.5, 2.5 Hz, 1H), 6.21 (s, 1H), 2.91 (s, 2H), 1.38 (s, 6H).

EXAMPLE 11(98)

(Z)-2-(3,3-dimethyl-3,4-dihydro-(2H)-isoquinolin-1-ylidene)-1-(4-methylnaphthalen-1-yl)ethan-1-one

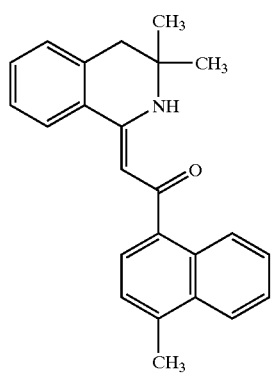

TLC: Rf 0.45 (hexane:ethyl acetate=3:1);

NMR (CDCl$_3$): δ 11.76 (br, 1H), 8.54 (m, 1H), 8.03 (m, 1H), 7.71 (d, J=7.5 Hz, 1H), 7.61 (d, J=7.0 Hz, 1H), 7.56–7.50 (m, 2H), 7.41 (t, J=7.5 Hz, 1H), 7.35–7.25 (m, 2H), 7.22 (d, J=7.5 Hz, 1H), 6.08 (s, 1H), 2.94 (s, 2H), 2.73 (s, 3H), 1.41 (s, 6H).

EXAMPLE 11(99)

(Z)-2-(3,3-dimethyl-3,4-dihydro-(2H)-isoquinolin-1-ylidene)-1-(4-fluoronaphthalen-1-yl)ethan-1-one

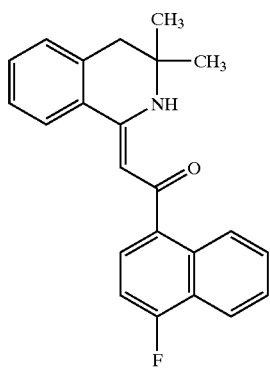

TLC: Rf 0.46 (hexane:ethyl acetate=3:1);

NMR (CDCl$_3$): δ 11.76 (br, 1H), 8.55 (m, 1H), 8.14 (m, 1H), 7.72 (d, J=7.5 Hz, 1H), 7.67 (dd, J=8.0, 5.5 Hz, 1H), 7.60–7.53 (m, 2H), 7.43 (t, J=7.5 Hz, 1H), 7.29 (t, J=7.5 Hz, 1H), 7.23 (d, J=7.5 Hz, 1H), 7.14 (dd, J=10.5, 8.0 Hz, 1H), 6.06 (s, 1H), 2.95 (s, 2H), 1.41 (s, 6H).

EXAMPLE 11(100)

(Z)-2-(7-nitro-3,3-dimethyl-3,4-dihydro-(2H)-isoquinolin-1-ylidene)-1-phenylethan-1-one

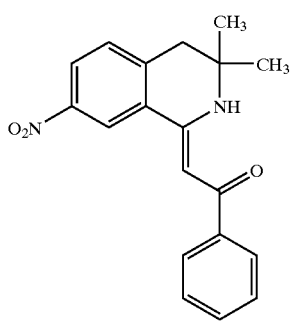

TLC: Rf 0.53 (hexane:ethyl acetate=1:1);

NMR (CDCl$_3$): δ 11.78 (brs, 1H), 8.69 (d, J=2.4 Hz, 1H), 8.29 (dd, J=8.4, 2.4 Hz, 1H), 8.00–7.95 (m, 2H), 7.52–7.44 (m, 3H), 7.42 (d, J=8.4 Hz, 1H), 6.40 (s, 1H), 3.01 (s, 2H), 1.39 (s, 6H).

EXAMPLE 11(101)

(Z)-2-(spiro[6-chloro-3,4-dihydro-(2H)-isoquinolin-3,4'-3,4,5,6-tetrahydropyran]-1-ylidene)-1-phenylethan-1-one

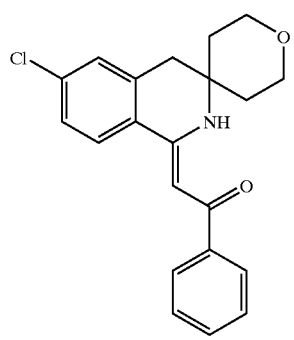

TLC: Rf 0.43 (ethyl acetate:hexane=1:1);

NMR (CDCl$_3$): δ 12.35 (br., 1H), 7.94 (m, 2H), 8.76 (d, J=8.5 Hz, 1H), 7.50–7.40 (m, 3H), 7.32 (dd, J=8.5, 2.0 Hz, 1H), 7.25 (d, J=2.0 Hz, 1H), 6.34 (s, 1H), 3.86 (m, 4H), 2.93 (s, 2H), 1.74 (m, 4H).

EXAMPLE 11(102)

(Z)-2-(spiro[6-chloro-3,4-dihydro-(2H)-isoquinolin-3,4'-3,4,5,6-tetrahydropyran]-1-ylidene)-1-(4-cyanophenyl)ethan-1-one

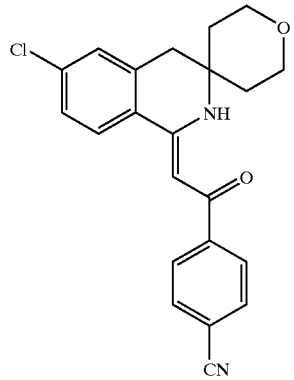

TLC: Rf 0.35 (ethyl acetate:hexane=1:1);

NMR (CDCl$_3$): δ 12.48 (br., 1H), 8.02 (d, J=8.5 Hz, 2H), 7.74 (d, J=8.5 Hz, 2H), 7.74 (d, J=8.5 Hz, 1H), 7.34 (dd, J=8.5, 2.0 Hz, 1H), 7.28 (d, J=2.0 Hz, 1H), 6.28 (s, 1H), 3.86 (m, 4H), 2.95 (s, 2H), 1.76 (m, 4H).

EXAMPLE 11(103)

(Z)-2-(spiro[6-chloro-3,4-dihydro-(2H)-isoquinolin-3,4'-3,4,5,6-tetrahydropyran]-1-ylidene)-1-(adamantan-1-yl)ethan-1-one

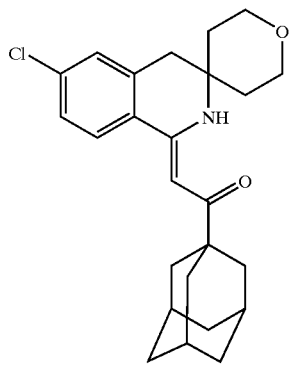

TLC: Rf 0.56 (ethyl acetate:hexane=1:1);

NMR (CDCl$_3$): δ 11.92 (br., 1H), 7.64 (d, J=8.5 Hz, 1H), 7.28 (dd, J=8.5, 2.0 Hz, 1H), 7.20 (d, J=2.0 Hz, 1H), 5.79 (s, 1H), 3.80 (m, 4H), 2.86 (s, 2H), 2.06 (m, 3H), 1.91 (m, 6H), 1.80–1.60 (m, 10H).

EXAMPLE 11(104)

(Z)-2-(3,3-dimethyl-3,4-dihydro-(2H)-isoquinolin-1-ylidene)-1-(noradamantan-1-yl)ethan-1-one

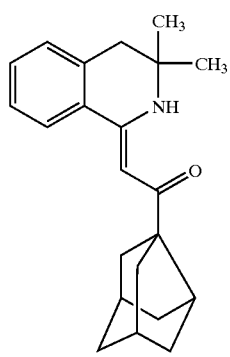

TLC: Rf 0.47 (hexane:ethyl acetate=3:1);

NMR (CDCl$_3$): δ 11.35 (br, 1H), 7.70.(dd, J=7.5, 1.0 Hz, 1H), 7.38 (dt, J=1.0, 7.5 Hz, 1H), 7.29 (dt, J=1.0, 7.5 Hz, 1H), 7.17 (dd, J=7.5, 1.0 Hz, 1H), 5.74 (s, 1H), 2.85 (s, 2H), 2.72 (t, J=6.5 Hz, 1H), 2.32 (br, 2H), 2.12–2.07 (m, 2H), 1.89–1.81 (m, 4H), 1.67–1.63 (m, 4H), 1.30 (s, 6H).

EXAMPLE 11(105)

(Z)-2-(6-chloro-3,3-dimethyl-3,4-dihydro-(2H)-isoquinolin-1-ylidene)-1-(noradamantan-1-yl)ethan-1-one

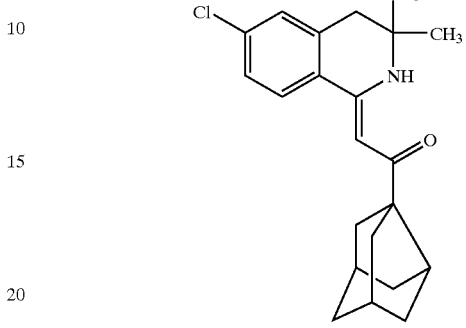

TLC: Rf 0.50 (hexane:ethyl acetate=3:1);

NMR (CDCl$_3$): δ 11.30 (br, 1H), 7.63 (d, J=8.5 Hz, 1H), 7.26 (dd, J=8.5, 2.0 Hz, 1H), 7.18 (d, J=2.0 Hz, 1H), 5.69 (s, 1H), 2.82 (s, 2H), 2.71 (t, J=6.5 Hz, 1H), 2.32 (br, 2H), 2.10–2.05 (m, 2H), 1.88–1.80 (m, 4H), 1.69–1.63 (m, 4H), 1.30 (s, 6H).

EXAMPLE 11(106)

(Z)-2-(6-methoxy-3,3-dimethyl-4-oxa-3,4-dihydro-(2H)-isoquinolin-1-ylidene)-1-(4-cyanophenyl)ethan-1-one

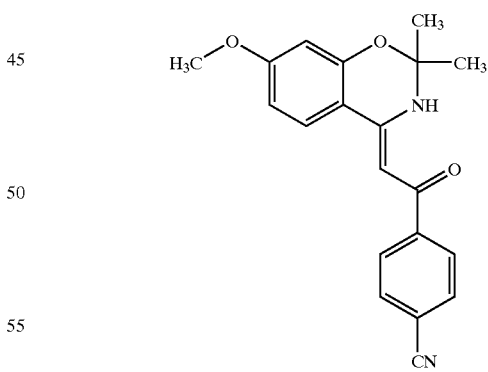

TLC: Rf 0.26 (hexane:ethyl acetate=3:1);

NMR (CDCl$_3$): δ 11.75 (br, 1H), 7.99 (d, J=8.5 Hz, 2H), 7.73 (d, J=8.5 Hz, 2H), 7.63 (d, J=9.0 Hz, 1H), 6.64 (dd, J=9.0, 2.5 Hz, 1H), 6.48 (d, J=2.5 Hz, 1H), 6.17 (s, 1H), 3.85 (s, 3H), 1.69 (s, 6H).

EXAMPLE 11(107)

(Z)-2-(6-methoxy-3,3-dimethyl-4-oxa-3,4-dihydro-(2H)-isoquinolin-1-ylidene)-1-phenylethan-1-one

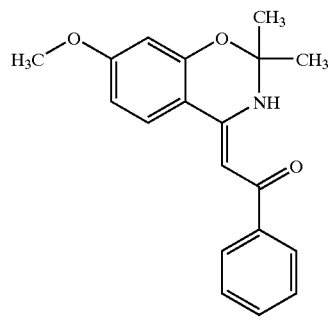

TLC: Rf 0.34 (hexane:ethyl acetate=3:1);

NMR (CDCl$_3$): δ 11.66 (br, 1H), 7.95–7.92 (m, 2H), 7.65 (d, J=8.5 Hz, 1H), 7.49–7.40 (m, 3H), 6.63 (dd, J=8.5, 2.5 Hz, 1H), 6.46 (d, J=2.5 Hz, 1H), 6.24 (s, 1H), 3.84 (s, 3H), 1.67 (s, 6H).

EXAMPLE 11(108)

(Z)-2-(6-methoxy-3,3-dimethyl-4-oxa-3,4-dihydro-(2H)-isoquinolin-1-ylidene)-1-(adamantan-1-yl)ethan-1-one

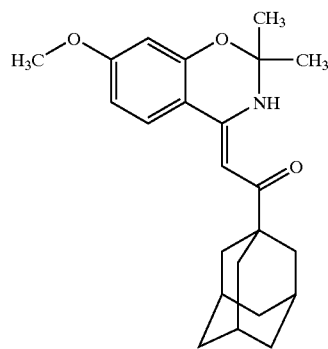

TLC: Rf 0.49 (hexane:ethyl acetate=3:1);

NMR (CDCl$_3$): δ 11.37 (br, 1H), 7.55 (d, J=9.0 Hz, 1H), 6.58 (dd, J=9.0, 2.5 Hz, 1H), 6.42 (d, J=2.5 Hz, 1H), 5.70 (s, 1H), 3.82 (s, 3H), 2.05 (br, 3H), 1.89 (br, 6H), 1.74 (br, 6H), 1.60 (s, 6H).

EXAMPLE 11(109)

(Z)-2-(3,3,6-trimethyl-4-oxa-3,4-dihydro-(2H)-isoquinolin-1-ylidene)-1-phenylethan-1-one TLC: Rf 0.51 (ethyl acetate:hexane=1:3);

NMR (CDCl$_3$): δ 11.63 (br., 1H), 7.94 (m, 2H), 7.62 (d, J=8.0 Hz, 1H), 7.50–7.40 (m, 3H), 6.87 (m, 1H), 6.77 (s, 1H), 6.30 (s, 1H), 2.37 (s, 3H), 1.66 (s, 6H).

EXAMPLE 11(110)

(Z)-2-(3,3,6-trimethyl-4-oxa-3,4-dihydro-(2H)-isoquinolin-1-ylidene)-1-(4-cyanophenyl)ethan-1-one

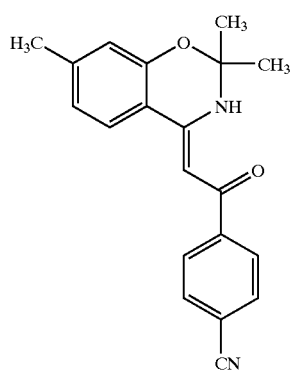

TLC: Rf 0.39 (ethyl acetate:hexane=1:3);

NMR (CDCl$_3$): δ 11.73 (br., 1H), 8.00 (d, J=8.0 Hz, 2H), 7.73 (d, J=8.0 Hz, 2H), 7.59 (d, J=8.0 Hz, 1H), 6.89 (m, 1H), 6.79 (s, 1H), 6.23 (s, 1H), 2.38 (s, 3H), 1.67 (s, 6H).

EXAMPLE 11(111)

(Z)-2-(3,3,6-trimethyl-4-oxa-3,4-dihydro-(2H)-isoquinolin-1-ylidene)-1-(adamantan-1-yl)ethan-1-one

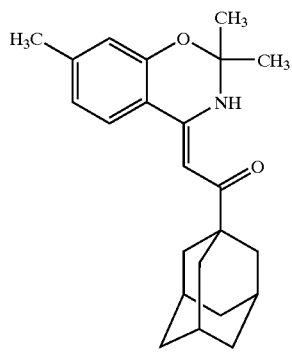

TLC: Rf 0.70 (ethyl acetate:hexane=1:3);

NMR (CDCl$_3$): δ 11.34 (br., 1H), 7.51 (d, J=8.0 Hz, 1H), 6.82 (m, 1H), 6.73 (s, 1H), 5.76 (s, 1H), 2.35 (s, 3H), 2.05 (m, 3H), 1.90 (m, 6H), 1.74 (m, 6H), 1.59 (s, 6H).

EXAMPLE 11(112)

(Z)-2-(3,3-dimethyl-4-oxa-3,4-dihydro-(2H)-isoquinolin-1-ylidene)-1-(tetrahydropyran-4-yl)ethan-1-one

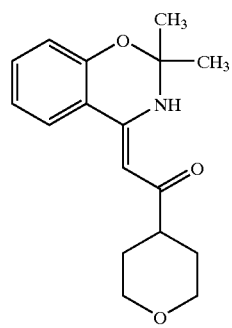

TLC: Rf 0.17 (ethyl acetate:hexane=1:3);

NMR (CDCl$_3$): δ 11.17 (br., 1H), 7.60 (dd, J=8.0, 1.5 Hz, 1H), 7.39 (ddd, J=8.0, 8.0, 1.5 Hz, 1H), 7.02 (ddd, J=8.0, 8.0, 1.0 Hz, 1H), 6.92 (dd, J=8.0, 1.0 Hz, 1H), 5.64 (s, 1H), 4.05 (m, 2H), 3.46 (m, 2H), 2.54 (m, 1H), 1.90–1.70 (m, 4H), 1.61 (s, 6H).

EXAMPLE 11(113)

(Z)-2-(3,3-dimethyl-3,4-dihydro-(2H)-isoquinolin-1-ylidene)-1-(2-chloro-4-mesylphenyl)ethan-1-one

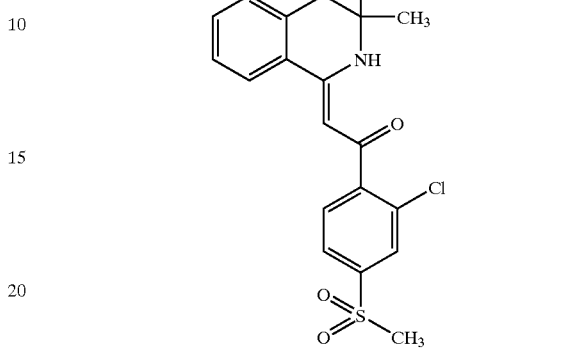

TLC: Rf 0.09 (hexane:ethyl acetate=2:1);

NMR (CDCl$_3$): δ 11.58 (br, 1H), 8.00 (d, J=1.5 Hz, 1H), 7.86 (dd, J=8.0, 1.5 Hz, 1H), 7.72–7.70 (m, 2H), 7.46 (t, J=7.5 Hz, 1H), 7.32 (t, J=7.5 Hz, 1H), 7.23 (d, J=7.5 Hz, 1H), 5.89 (s, 1H), 3.09 (s, 3H), 2.94 (s, 2H), 1.40 (s, 6H).

EXAMPLE 11(114)

(Z)-2-(6,6-dimethyl-4,5,6,7-tetrahydrothiopheno[3,2-c]pyridin-4-ylidene)-1-phenylethan-1-one

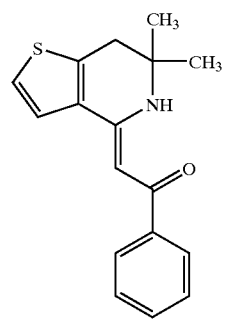

TLC: Rf 0.44 (hexane:ethyl acetate=3:1);

NMR (CDCl$_3$): δ 11.08 (br, 1H), 7.94–7.91 (m, 2H), 7.46–7.40 (m, 3H), 7.32 (d, J=5.0 Hz, 1H), 7.17 (d, J=5.0 Hz, 1H), 6.14 (s, 1H), 3.00 (s, 2H), 1.43 (s, 6H).

EXAMPLE 11(115)

(Z)-2-(6,6-dimethyl-4,5,6,7-tetrahydrothiopheno[3,2-c]pyridin-4-ylidene)-1-(adamantan-1-yl)ethan-1-one

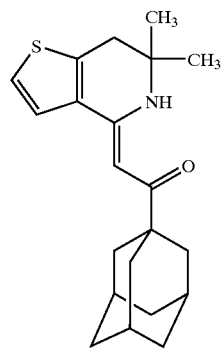

TLC: Rf 0.58 (hexane:ethyl acetate=3:1);

NMR (CDCl$_3$): δ 10.74 (br, 1H), 7.23 (d, J=5.5 Hz, 1H), 7.12 (d, J=5.5 Hz, 1H), 5.59 (s, 1H), 2.93 (s, 2H), 2.05 (br, 3H), 1.89 (br, 6H), 1.73 (br, 6H), 1.36 (s, 6H).

EXAMPLE 11(116)

(Z)-2-(6,6-dimethyl-4,5,6,7-tetrahydro-thiopheno[3,2-c]pyridin-4-ylidene)-1-(4-cyanophenyl)ethan-1-one

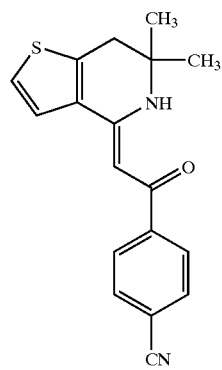

TLC: Rf 0.26 (hexane:ethyl acetate=3:1);

NMR (CDCl$_3$): δ 11.21 (br, 1H), 7.99 (d, J=8.0 Hz, 2H), 7.72 (d, J=8.0 Hz, 2H), 7.31 (d, J=5.0 Hz, 1H), 7.20 (d, J=5.0 Hz, 1H), 6.07 (s, 1H), 3.02 (s, 2H), 1.45 (s, 6H).

EXAMPLE 11(117)

(Z)-2-(6-methoxy-3,3-dimethyl-3,4-dihydro-(2H)-isoquinolin-1-ylidene)-1-(adamantan-1-yl)ethan-1-one

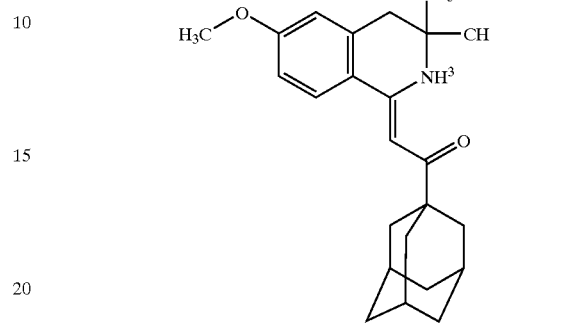

TLC: Rf 0.40 (hexane:ethyl acetate=3:1);

NMR (CDCl$_3$): δ 11.51 (br, 1H), 7.67 (d, J=8.5 Hz, 1H), 6.81 (dd, J=8.5, 2.5 Hz, 1H), 6.68 (d, J=2.5 Hz, 1H), 5.70 (s, 1H), 3.85 (s, 3H), 2.80 (s, 2H), 2.05 (br, 3H), 1.91 (br, 6H), 1.74 (br, 6H), 1.29 (s, 6H).

EXAMPLE 11(118)

(Z)-2-(6-methoxy-3,3-dimethyl-3,4-dihydro-(2H)-isoquinolin-1-ylidene)-1-(4-cyanophenyl)ethan-1-one

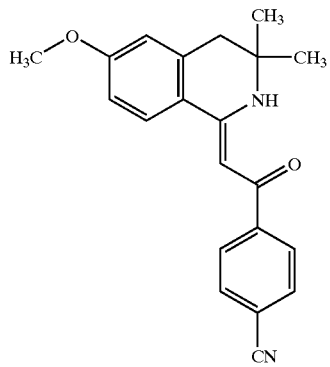

TLC: Rf 0.18 (hexane:ethyl acetate=3:1);

NMR (CDCl$_3$): δ 11.96 (br, 1H), 8.01 (d, J=8.5 Hz, 2H), 7.77–7.70 (m, 3H), 6.87 (dd, J=8.5, 2.5 Hz, 1H), 6.74 (d, J=2.5 Hz, 1H), 6.20 (s, 1H), 3.88 (s, 3H), 2.88 (s, 2H), 1.38 (s, 6H).

EXAMPLE 11(119)

(Z)-2-(7-bromo-6-chloro-3,3-dimethyl-3,4-dihydro-(2H)-isoquinolin-1-ylidene)-1-(adamantan-1-yl)ethan-1-one

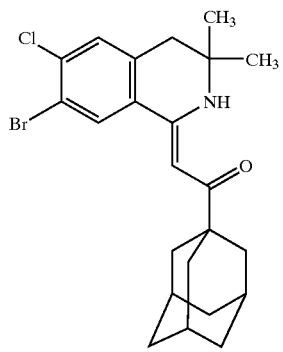

TLC: Rf 0.36 (ethyl acetate:hexane=1:5);

NMR (CDCl$_3$): δ 11.39 (br., 1H), 7.91 (s, 1H), 7.28 (s, 1H), 5.69 (s, 1H), 2.76 (s, 2H), 2.07 (m, 3H), 1.91 (m, 6H), 1.75 (m, 6H), 1.29 (s, 6H).

EXAMPLE 11(120)

(Z)-2-(2-chloro-6,6-dimethyl-4,5,6,7-tetrahydrothiopheno[3,2-c]pyridin-4-ylidene)-1-phenylethan-1-one

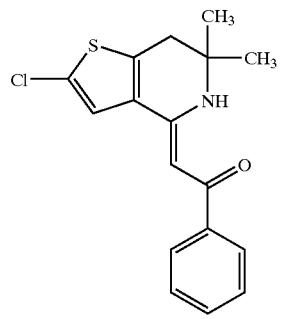

TLC: Rf 0.44 (hexane:ethyl acetate=3:1);

NMR (CDCl$_3$): δ 10.96 (br, 1H), 7.92–7.89 (m, 2H), 7.46–7.40 (m, 3H), 7.14 (s, 1H), 6.02 (s, 1H), 2.90 (s, 2H), 1.43 (s, 6H).

EXAMPLE 11(121)

(Z)-2-(2-chloro-6,6-dimethyl-4,5,6,7-tetrahydrothiopheno[3,2-c]pyridin-4-ylidene)-1-(adamantan-1-yl)ethan-1-one

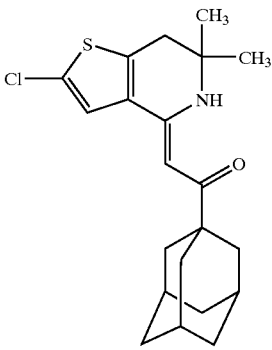

TLC: Rf 0.56 (hexane:ethyl acetate=3:1);

NMR (CDCl$_3$): δ 10.62 (br, 1H), 7.05 (s, 1H), 5.47 (s, 1H), 2.82 (s, 2H), 2.05 (br, 3H), 1.87 (br, 6H), 1.73 (br, 6H), 1.36 (s, 6H).

EXAMPLE 11(122)

(Z)-2-(2-chloro-6,6-dimethyl-4,5,6,7-tetrahydrothiopheno[3,2-c]pyridin-4-ylidene)-1-(4-cyanophenyl)ethan-1-one

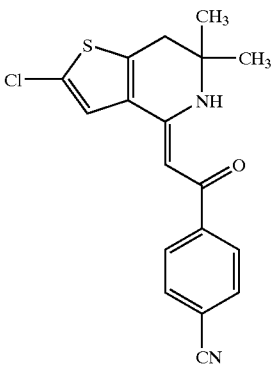

TLC: Rf 0.29 (hexane:ethyl acetate=3:1);

NMR (CDCl$_3$): δ 11.09 (br, 1H), 7.97 (d, J=8.5 Hz, 2H), 7.72 (d, J=8.5 Hz, 2H), 7.13 (s, 1H), 5.95 (s, 1H), 2.92 (s, 2H), 1.45 (s, 6H).

EXAMPLE 11(123)

(Z)-2-(5-methoxy-3,3-dimethyl-3,4-dihydro-(2H)-isoquinolin-1-ylidene)-1-phenylethan-1-one

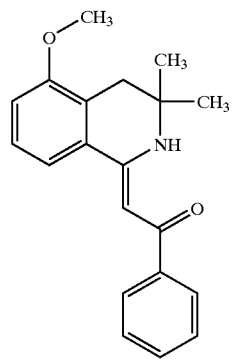

TLC: Rf 0.49 (hexane:ethyl acetate=2:1);

NMR (CDCl$_3$): δ 11.84 (brs, 1H), 7.97–7.91 (m, 2H), 7.48–7.40 (m, 4H), 7.30 (t, J=8.1 Hz, 1H), 7.00 (d, J=8.1 Hz, 1H), 6.33 (s, 1H), 3.87 (s, 3H), 2.90 (s, 2H), 1.37 (s, 6H).

EXAMPLE 11(124)

(Z)-2-(3,3,6-trimethyl-3,4-dihydro-(2H)-isoquinolin-1-ylidene)-1-(adamantan-1-yl)ethan-1-one

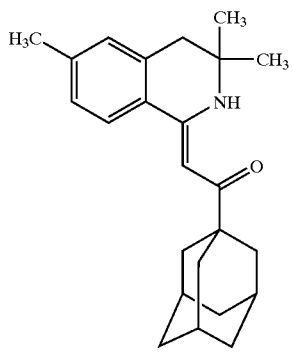

TLC: Rf 0.41 (hexane:ethyl acetate=4:1);

NMR (CDCl$_3$): δ 11.48 (brs, 1H), 7.61 (d, J=8.1 Hz, 1H), 7.09 (brd, J=8.1 Hz, 1H), 6.97 (brs, 1H), 5.75 (s, 1H), 2.79 (s, 2H), 2.37 (s, 3H), 2.05 (brs, 3H), 1.91 (d, J=3.0 Hz, 6H), 1.74 (d, J=3.0 Hz, 6H), 1.29 (s, 6H).

EXAMPLE 11(125)

(Z)-2-(3,3,6-trimethyl-3,4-dihydro-(2H)-isoquinolin-1-ylidene)-1-(4-cyanophenyl)ethan-1-one

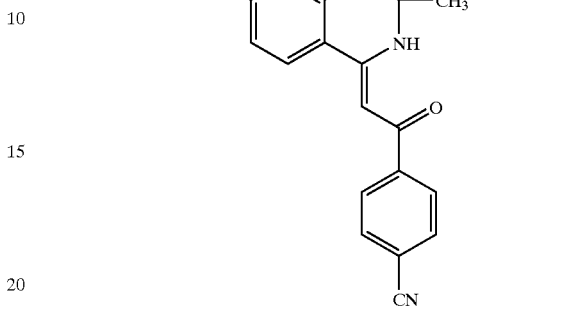

TLC: Rf 0.13 (hexane:ethyl acetate=4:1);

NMR (CDCl$_3$): δ 11.94 (brs, 1H), 8.01 (d, J=8.4 Hz, 2H), 7.72 (d, J=8.4 Hz, 2H), 7.70 (d, J=8.4 Hz, 1H), 7.16 (brd, J=8.4 Hz, 1H), 7.04 (brs, 1H), 6.25 (s, 1H), 2.87 (s, 2H), 2.41 (s, 3H), 1.37 (s, 6H).

EXAMPLE 11(126)

(Z)-2-(7-nitro-3,3-dimethyl-3,4-dihydro-(2H)-isoquinolin-1-ylidene)-1-(4-cyanophenyl)ethan-1-one

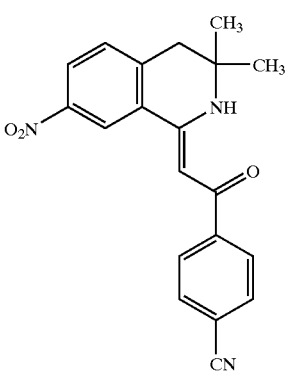

TLC: Rf 0.14 (ethyl acetate:hexane=1:1);

NMR (CDCl$_3$): δ 11.91 (br., 1H), 8.67 (d, J=2.0 Hz, 1H), 8.32 (dd, J=8.0, 2.0 Hz, 1H), 8.05 (d, J=8.5 Hz, 2H), 7.77 (d, J=8.5 Hz, 2H), 7.45 (d, J=8.0 Hz, 1H), 6.34 (s, 1H), 6.04 (s, 2H), 1.41 (s, 6H).

EXAMPLE 11(127)

(Z)-2-(6-chloro-7-nitro-3,3-dimethyl-3,4-dihydro-(2H)-isoquinolin-1-ylidene)-1-cyclohexylethan-1-one

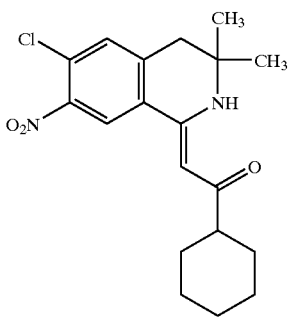

TLC: Rf 0.29 (ethyl acetate:hexane=1:3);

NMR (CDCl$_3$): δ 11.15 (br., 1H), 8.23 (s, 1H), 7.38 (s, 1H), 5.61 (s, 1H), 2.88 (s, 2H), 2.33 (m, 1H), 1.90–1.65 (m, 5H), 1.55–1.20 (m, 5H), 1.31 (s, 6H).

EXAMPLE 11(128)

(Z)-2-(6-chloro-7-nitro-3,3-dimethyl-3,4-dihydro-(2H)-isoquinolin-1-ylidene)-1-cycloheptylethan-1-one

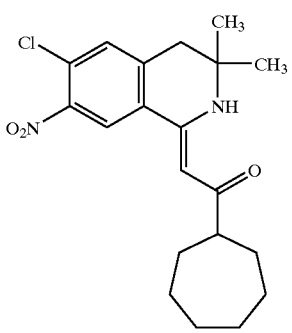

TLC: Rf 0.30 (ethyl acetate:hexane=1:3);

NMR (CDCl$_3$): δ 11.08 (br., 1H), 8.23 (s, 1H), 7.39 (s, 1H), 5.58 (s, 1H), 2.88 (s, 2H), 2.51 (m, 1H), 1.95–1.20 (m, 12H), 1.31 (s, 6H).

EXAMPLE 11(129)

(Z)-2-(6-chloro-7-nitro-3,3-dimethyl-3,4-dihydro-(2H)-isoquinolin-1-ylidene)-1-(4-cyanophenyl)ethan-1-one

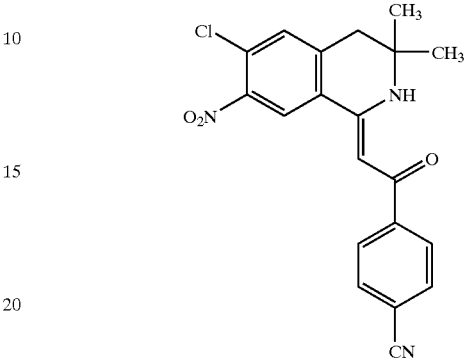

TLC: Rf 0.13 (ethyl acetate:hexane=1:3);

NMR (CDCl$_3$): δ 11.83 (br., 1H), 8.34 (s, 1H), 8.01 (d, J=8.5 Hz, 2H), 7.76 (d, J=8.5 Hz, 2H), 7.46 (s, 1H), 6.24 (s, 1H), 2.97 (s, 2H), 1.41 (s, 6H).

EXAMPLE 11(130)

(Z)-2-(6-chloro-7-nitro-3,3-dimethyl-3,4-dihydro-(2H)-isoquinolin-1-ylidene)-1-(adamantan-1-yl)ethan-1-one

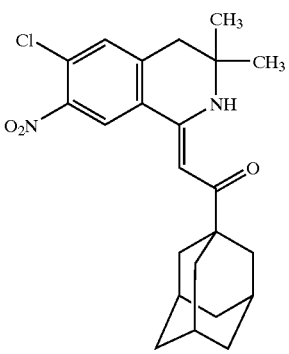

TLC: Rf 0.35 (ethyl acetate:hexane=1:3);

NMR (CDCl$_3$): δ 11.36 (br., 1H), 8.22 (s, 1H), 7.39 (s, 1H), 5.75 (s, 1H), 2.88 (s, 2H), 2.07 (m, 3H), 1.90 (m, 6H), 1.75 (m, 6H), 1.32 (s, 6H).

EXAMPLE 11(131)

(Z)-2-(7-dimethylaminomethyl-3,3-dimethyl-3,4-dihydro-(2H)-isoquinolin-1-ylidene)-1-(4-cyanophenyl)ethan-1-one

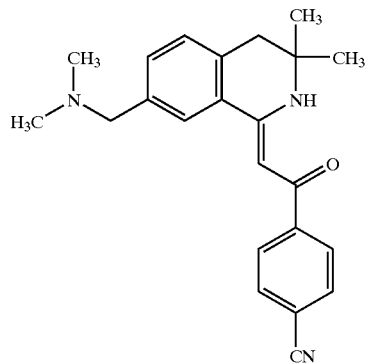

TLC: Rf 0.41 (water: methanol:chloroform=1:10:100);

NMR (CDCl$_3$): δ 12.01 (br., 1H), 8.03 (d, J=8.0 Hz, 2H), 7.74 (s, 1H), 7.73 (d, J=8.0 Hz, 2H), 7.41 (d, J=7.5 Hz, 1H), 7.19 (d, J=7.5 Hz, 1H), 6.29 (s, 1H), 3.48 (s, 2H), 2.90 (s, 2H), 2.28 (s, 6H), 1.37 (s, 6H).

EXAMPLE 11(132)

(Z)-2-(7-dimethylaminomethyl-3,3-dimethyl-3,4-dihydro-(2H)-isoquinolin-1-ylidene)-1-(adamantan-1-yl)ethan-1-one

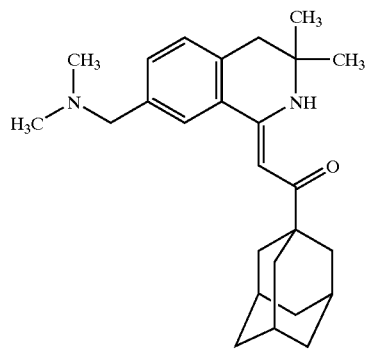

TLC: Rf 0.39 (water:methanol:chloroform=1:10:100);

NMR (CDCl$_3$): δ 11.55 (br., 1H), 7.66 (s, 1H), 7.40 (d, J=7.5 Hz, 1H), 7.15 (d, J=7.5 Hz, 1H), 5.80 (s, 1H), 3.55 (br., 2H), 2.82 (s, 2H), 2.33 (s, 6H), 2.06 (m, 3H), 1.92 (m, 6H), 1.75 (m, 6H), 1.29 (s, 6H).

EXAMPLE 11(133)

(Z)-2-(7-amino-6-methoxy-3,3-dimethyl-3,4-dihydro-(2H)-isoquinolin-1-ylidene)-1-(4-cyanophenyl)ethan-1-one

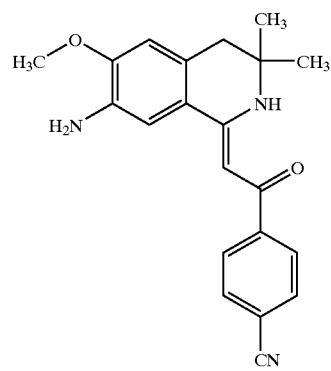

TLC: Rf 0.35 (hexane:ethyl acetate=1:1);

NMR (CDCl$_3$): δ 11.91 (br, 1H), 8.00 (d, J=8.5 Hz, 2H), 7.71 (d, J=8.5 Hz, 2H), 7.13 (s, 1H), 6.59 (s, 1H), 6.12 (s, 1H), 3.92 (s, 3H), 3.88 (br, 2H), 2.80 (s, 2H), 1.37 (s, 6H).

EXAMPLE 11(134)

(Z)-2-(7-amino-6-methoxy-3,3-dimethyl-3,4-dihydro-(2H)-isoquinolin-1-ylidene)-1-(adamantan-1-yl)ethan-1-one

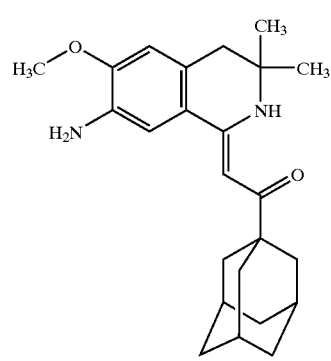

TLC: Rf 0.56 (hexane:ethyl acetate=1:1);

NMR (CDCl$_3$): δ 11.46 (br, 1H), 7.07 (s, 1H), 6.54 (s, 1H), 5.62 (s, 1H), 3.89 (s, 3H), 3.82 (br, 2H), 2.72 (s, 2H), 2.05 (br, 3H), 1.91 (br, 6H), 1.74 (br, 6H), 1.28 (s, 6H).

EXAMPLE 11(135)

(Z)-2-(6-chloro-7-dimethylamino-3,3-dimethyl-3,4-dihydro-(2H)-isoquinolin-1-ylidene)-1-cyclohexylethan-1-one

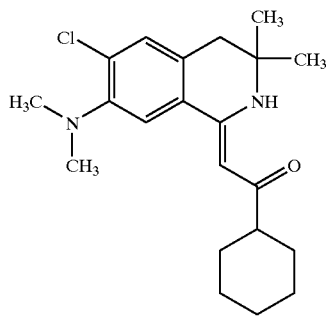

TLC: Rf 0.32 (ethyl acetate:hexane=1:5);

NMR (CDCl$_3$): δ 11.33 (br., 1H), 7.36 (s, 1H), 7.17 (s, 1H), 5.54 (s, 1H), 2.86 (s, 6H), 2.74 (s, 2H), 2.32 (m, 1H), 1.95–1.20 (m, 10H), 1.28 (s, 6H).

EXAMPLE 11(136)

(Z)-2-(6-chloro-7-dimethylamino-3,3-dimethyl-3,4-dihydro-(2H)-isoquinolin-1-ylidene)-1-cycloheptylethan-1-one

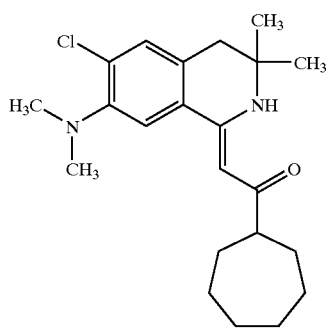

TLC: Rf 0.34 (ethyl acetate:hexane=1:5);

NMR (CDCl$_3$): δ 11.25 (br., 1H), 7.35 (s, 1H), 7.17 (s, 1H), 5.51 (s, 1H), 2.86 (s, 6H), 2.74 (s, 2H), 2.48 (m, 1H), 1.95–1.40 (m, 12H), 1.28 (s, 6H).

EXAMPLE 11(137)

(Z)-2-(6-chloro-7-dimethylamino-3,3-dimethyl-3,4-dihydro-(2H)-isoquinolin-1-ylidene)-1-(4-cyanophenyl)ethan-1-one

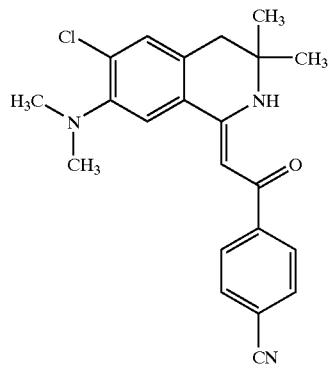

TLC: Rf 0.24 (ethyl acetate:hexane=1:5);

NMR (CDCl$_3$): δ 11.95 (br., 1H), 8.00 (d, J=8.5 Hz, 2H), 7.73 (d, J=8.5 Hz, 2H), 7.43 (s, 1H), 7.24 (s, 1H), 6.17 (s, 1H), 2.89 (s, 6H), 2.82 (s, 2H), 1.37 (s, 6H).

EXAMPLE 11(138)

(Z)-2-(6-chloro-7-dimethylamino-3,3-dimethyl-3,4-dihydro-(2H)-isoquinolin-1-ylidene)-1-(adamantan-1-yl)ethan-1-one

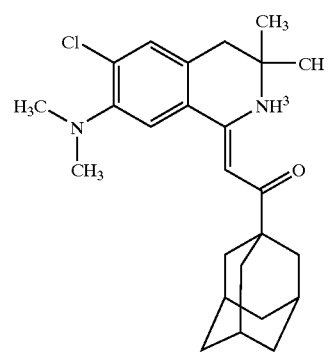

TLC: Rf 0.36 (ethyl acetate:hexane=1:5);

NMR (CDCl$_3$): δ 11.51 (br., 1H), 7.36 (s, 1H), 7.16 (s, 1H), 5.69 (s, 1H), 2.86 (s, 6H), 2.73 (s, 2H), 2.06 (m, 3H), 1.91 (m, 6H), 1.74 (m, 6H), 1.28 (s, 6H).

EXAMPLE 11(139)

(Z)-2-(7-dimethylamino-3,3,6-trimethyl-3,4-dihydro-(2H)-isoquinolin-1-ylidene)-1-(4-cyanophenyl)ethan-1-one

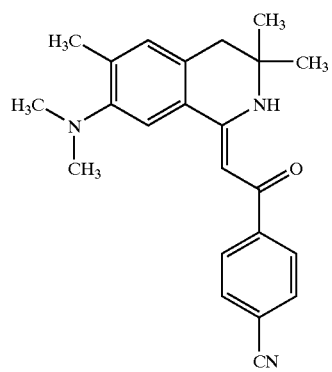

TLC: Rf 0.16 (hexane:ethyl acetate=4:1);

NMR (CDCl$_3$): δ 11.98 (brs, 1H), 8.01 (d, J=8.4 Hz, 2H), 7.73 (d, J=8.4 Hz, 2H), 7.40 (s, 1H), 7.01 (s, 1H), 6.19 (s, 1H), 2.81 (s, 2H), 2.76 (s, 6H), 2.37 (s, 3H), 1.37 (s, 6H).

EXAMPLE 11(140)

(Z)-2-(7-dimethylamino-3,3,6-trimethyl-3,4-dihydro-(2H)-isoquinolin-1-ylidene)-1-(adamantan-1-yl)ethan-1-one

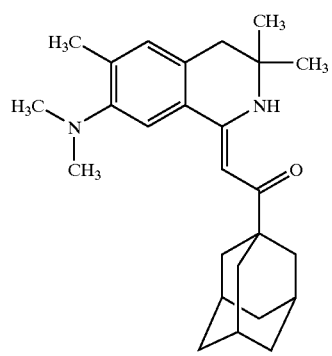

TLC: Rf 0.36 (hexane:ethyl acetate=4:1);

NMR (CDCl$_3$): δ 11.55 (brs, 1H), 7.33 (s, 1H), 6.95 (s, 1H), 5.71 (s, 1H), 2.74 (s, 6H), 2.73 (s, 2H), 2.34 (s, 3H), 2.09–2.03 (m, 3H), 1.94–1.90 (m, 6H), 1.77–1.73 (m, 6H), 1.28 (s, 6H).

EXAMPLE 11(141)

(Z)-2-(7-dimethylamino-3,3,6-trimethyl-3,4-dihydro-(2H)-isoquinolin-1-ylidene)-1-cyclohexylethan-1-one

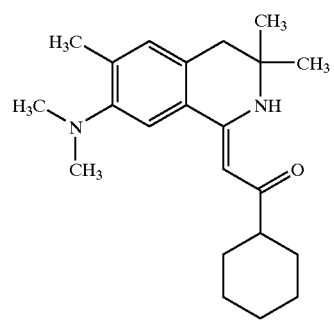

TLC: Rf 0.39 (hexane:ethyl acetate=4:1);

NMR (CDCl$_3$): δ 11.36 (brs, 1H), 7.32 (s, 1H), 6.95 (s, 1H), 5.56 (s, 1H), 2.74 (s, 8H), 2.34 (s, 3H), 2.31 (m, 1H), 1.92–1.20 (m, 10H), 1.28 (s, 6H).

EXAMPLE 11(142)

(Z)-2-(7-dimethylamino-3,3,6-trimethyl-3,4-dihydro-(2H)-isoquinolin-1-ylidene)-1-cycloheptylethan-1-one

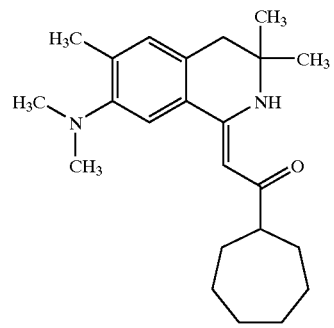

TLC: Rf 0.41 (hexane:ethyl acetate=4:1);

NMR (CDCl$_3$): δ 11.29 (brs, 1H), 7.32 (s, 1H), 5.52 (s, 1H), 2.74 (s, 6H), 2.73 (s, 2H), 2.47 (m, 1H), 2.34 (s, 3H), 1.97–1.43 (m, 12H), 1.27 (s, 6H).

EXAMPLE 11(143)

(Z)-2-(7-dimethylaminomethyl-3,3-dimethyl-3,4-dihydro-(2H)-isoquinolin-1-ylidene)-1-cyclohexylethan-1-one

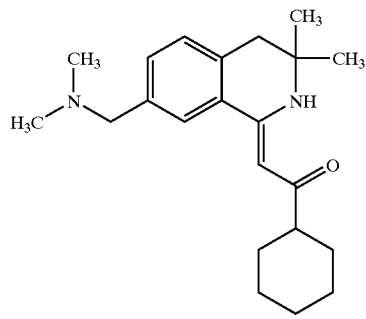

TLC: Rf 0.44 (water:methanol:chloroform=1:10:100);

NMR (CDCl$_3$): δ 11.34 (br., 1H), 7.63 (d, J=1.5 Hz, 1H), 7.34 (dd, J=8.0, 1.5 Hz, 1H), 7.12 (d, J=8.0 Hz, 1H), 5.66 (s, 1H), 3.46 (s, 2H), 2.82 (s, 2H), 2.32 (m, 1H), 2.28 (s, 6H), 1.90–1.20 (m, 10H), 1.28 (s, 6H).

EXAMPLE 11(144)

(Z)-2-(7-dimethylaminomethyl-3,3-dimethyl-3,4-dihydro-(2H)-isoquinolin-1-ylidene)-1-cycloheptylethan-1-one

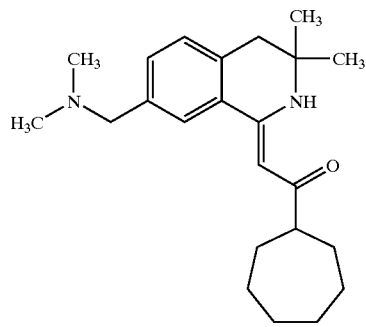

TLC: Rf 0.46 (water:methanol:chloroform=1:10:100);

NMR (CDCl$_3$): δ 11.27 (br., 1H), 7.63 (s, 1H), 7.33 (d, J=7.5 Hz, 1H), 7.12 (d, J=7.5 Hz, 1H), 5.62 (s, 1H), 3.45 (s, 2H), 2.82 (s, 2H), 2.48 (m, 1H), 2.27 (s, 6H), 1.95–1.40 (m, 12H), 1.28 (s, 6H).

EXAMPLE 11(145)

(Z)-2-(6-methoxy-7-methylamino-3,3-dimethyl-3,4-dihydro-(2H)-isoquinolin-1-ylidene)-1-(4-cyanophenyl)ethan-1-one

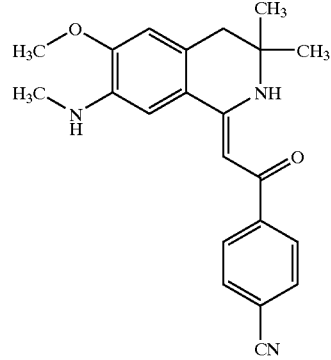

TLC: Rf 0.13 (hexane:ethyl acetate=3:1);

NMR (CDCl$_3$): δ 11.97 (br, 1H), 8.00 (d, J=8.5 Hz, 2H), 7.72 (d, J=8.5 Hz, 2H), 6.89 (s, 1H), 6.56 (s, 1H), 6.17 (s, 1H), 4.33 (br, 1H), 3.92 (s, 3H), 2.95 (s, 3H), 2.81 (s, 2H), 1.37 (s, 6H).

EXAMPLE 11(146)

(Z)-2-(6-methoxy-7-methylamino-3,3-dimethyl-3,4-dihydro-(2H)-isoquinolin-1-ylidene)-1-(adamantan-1-yl)ethan-1-one

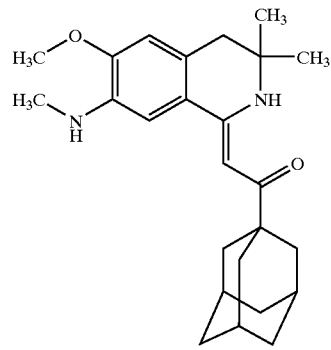

TLC: Rf 0.34 (hexane:ethyl acetate=3:1);

NMR (CDCl$_3$): δ 11.57 (br, 1H), 6.85 (s, 1H), 6.50 (s, 1H), 5.68 (s, 1H), 4.23 (br, 1H), 3.88 (s, 3H), 2.94 (s, 3H), 2.72 (s, 2H), 2.05 (br, 3H), 1.92 (br, 6H), 1.74 (br, 6H), 1.29 (s, 6H).

EXAMPLE 11(147)

(Z)-2-(7-dimethylamino-6-methoxy-3,3-dimethyl-3,4-dihydro-(2H)-isoquinolin-1-ylidene)-1-cyclohexylethan-1-one

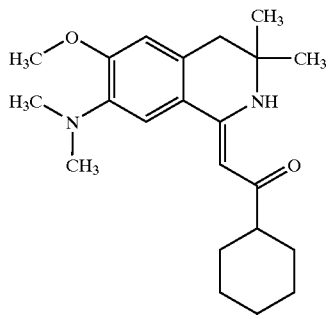

TLC: Rf 0.20 (hexane:ethyl acetate=3:1);

NMR (CDCl$_3$): δ 11.37 (br, 1H), 7.23 (s, 1H), 6.60 (s, 1H), 5.51 (s, 1H), 3.93 (s, 3H), 2.82 (s, 6H), 2.76 (s, 2H), 2.30 (tt, J=11.5, 3.5 Hz, 1H), 1.89–1.79 (m, 4H), 1.69 (m, 1H), 1.56–1.20 (m, 11H).

EXAMPLE 11(148)

(Z)-2-(7-dimethylamino-6-methoxy-3,3-dimethyl-3,4-dihydro-(2H)-isoquinolin-1-ylidene)-1-cycloheptylethan-1-one

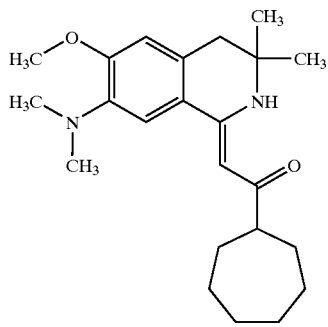

TLC: Rf 0.20 (hexane:ethyl acetate=3:1);

NMR (CDCl$_3$): δ 11.30 (br, 1H), 7.23 (s, 1H), 6.60 (s, 1H), 5.48 (s, 1H), 3.93 (s, 3H), 2.82 (s, 6H), 2.76 (s, 2H), 2.46 (m, 1H), 1.95–1.88 (m, 2H), 1.83–1.45 (m, 10H), 1.29 (s, 6H).

EXAMPLE 11(149)

(Z)-2-(7-dimethylamino-3,3-dimethyl-3,4-dihydro-(2H)-isoquinolin-1-ylidene)-1-(4-cyanophenyl)ethan-1-one

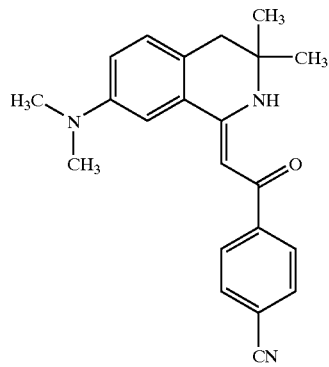

TLC: Rf 0.14 (hexane:ethyl acetate=4:1);

NMR (CDCl$_3$): δ 12.02 (brs, 1H), 8.00 (d, J=8.7 Hz, 2H), 7.72 (d, J=8.7 Hz, 2H), 7.09 (d, J=8.7 Hz, 1H), 7.08 (d, J=2.4 Hz, 1H), 6.86 (dd, J=8.7, 2.4 Hz, 1H), 6.21 (s, 1H), 3.02 (s, 6H), 2.81 (s, 2H), 1.36 (s, 6H).

EXAMPLE 11(150)

(Z)-2-(7-dimethylamino-3,3-dimethyl-3,4-dihydro-(2H)-isoquinolin-1-ylidene)-1-(adamantan-1-yl)ethan-1-one

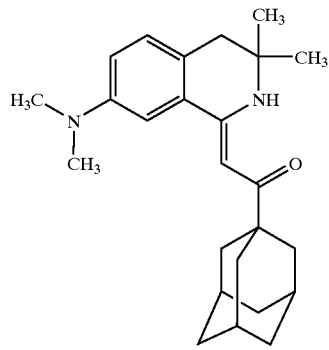

TLC: Rf 0.35 (hexane:ethyl acetate=4:1);

NMR (CDCl$_3$): δ 11.57 (brs, 1H), 7.05 (d, J=2.4 Hz, 1H), 7.03 (d, J=8.4 Hz, 1H), 6.80 (dd, J=8.4, 2.4 Hz, 1H), 5.73 (s, 1H), 2.99 (s, 6H), 2.73 (s, 2H), 2.08–2.02 (m, 3H), 1.94–1.90 (m, 6H), 1.76–1.72 (m, 6H), 1.28 (s, 6H).

EXAMPLE 11(151)

(Z)-2-(7-amino-6-methoxy-3,3-dimethyl-3,4-dihydro-(2H)-isoquinolin-1-ylidene)-1-cyclohexylethan-1-one

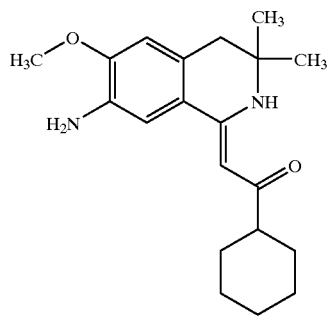

TLC: Rf 0.26 (hexane:ethyl acetate=2:1);

NMR (CDCl$_3$): δ 11.28 (br, 1H), 7.05 (s, 1H), 6.54 (s, 1H), 5.48 (s, 1H), 3.89 (s, 3H), 3.80 (br, 2H), 2.72 (s, 2H), 2.26 (tt, J=11.5, 3.5 Hz, 1H), 1.89–1.79 (m, 4H), 1.68 (m, 1H), 1.56–1.22 (m, 11H).

EXAMPLE 11(152)

(Z)-2-(7-amino-6-methoxy-3,3-dimethyl-3,4-dihydro-(2H)-isoquinolin-1-ylidene)-1-cycloheptylethan-1-one

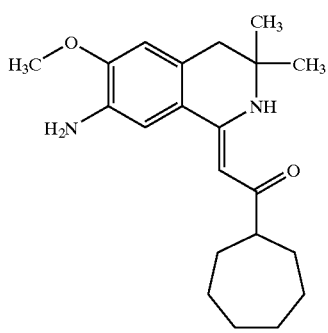

TLC: Rf 0.31 (hexane:ethyl acetate=2:1);

NMR (CDCl$_3$): δ 11.19 (br, 1H), 6.53 (s, 1H), 5.44 (s, 1H), 3.89 (s, 3H), 3.80 (br, 2H), 2.72 (s, 2H), 2.42 (m, 1H), 1.95–1.87 (m, 2H), 1.82–1.46 (m, 10H), 1.28 (s, 6H).

EXAMPLE 11(153)

(Z)-2-(7-bromo-6-chloro-3,3-dimethyl-3,4-dihydro-(2H)-isoquinolin-1-ylidene)-1-cyclohexylethan-1-one

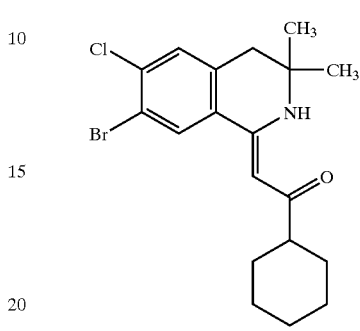

TLC: Rf 0.25 (ethyl acetate:hexane=1:5);

NMR (CDCl$_3$): δ 11.19 (br., 1H), 7.91 (s, 1H), 7.28 (s, 1H), 5.54 (s, 1H), 2.76 (s, 2H), 2.31 (m, 1H), 1.90–1.20 (m, 10H), 1.29 (s, 6H).

EXAMPLE 11(154)

(Z)-2-(7-bromo-6-chloro-3,3-dimethyl-3,4-dihydro-(2H)-isoquinolin-1-ylidene)-1-cycloheptylethan-1-one

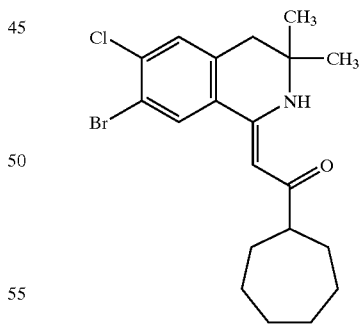

TLC: Rf 0.24 (ethyl acetate:hexane=1:5);

NMR (CDCl$_3$): δ 11.11 (br., 1H), 7.91 (s, 1H), 7.28 (s, 1H), 5.51 (s, 1H), 2.76 (s, 2H), 2.48 (m, 1H), 1.95–1.40 (m, 12H), 1.28 (s, 6H).

EXAMPLE 11(155)

(Z)-2-(7-nitro-3,3-dimethyl-3,4-dihydro-(2H)-isoquinolin-1-ylidene)-1-cyclohexylethan-1-one

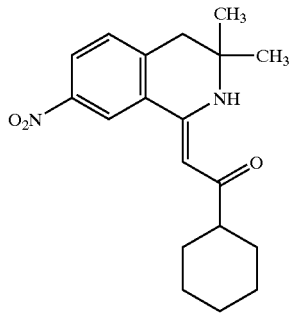

TLC: Rf 0.67 (ethyl acetate:hexane=2:3);

NMR (CDCl$_3$): δ 11.23 (br., 1H), 8.56 (d, J=2.5 Hz, 1H), 8.24 (dd, J=8.0, 2.5 Hz, 1H), 7.37 (d, J=8.0 Hz, 1H), 5.71 (s, 1H), 2.95 (s, 2H), 2.37 (m, 1H), 1.95–1.20 (m, 10H), 1.31 (s, 6H).

EXAMPLE 11(156)

(Z)-2-(7-bromo-6-methoxy-3,3-dimethyl-3,4-dihydro-(2H)-isoquinolin-1-ylidene)-1-(adamantan-1-yl)ethan-1-one

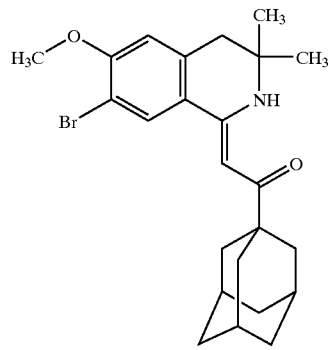

TLC: Rf 0.28 (hexane:ethyl acetate=3:1);

NMR (CDCl$_3$): δ 11.45 br, 1H), 7.86 (s, 1H), 6.67 (s, 1H), 5.65 (s, 1H), 0.94 (s, 3H), 2.78 (s, 2H), 2.06 (br, 3H), 1.91 (br, 6H), 1.75 (br, 6H), 1.29 (s, 6H).

EXAMPLE 11(157)

(Z)-2-(7-nitro-3,3-dimethyl-3,4-dihydro-(2H)-isoquinolin-1-ylidene)-1-(adamantan-1-yl)ethan-1-one

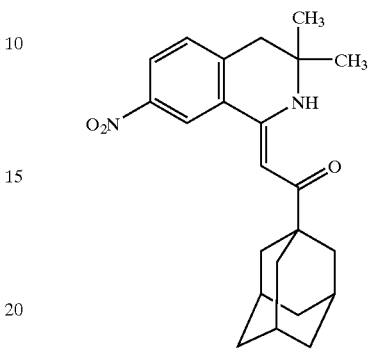

TLC: Rf 0.63 (hexane:ethyl acetate=1:1);

NMR (CDCl$_3$): δ 11.45 (brs, 1H), 8.56 (d, J=2.1 Hz, 1H), 8.24 (dd, J=8.1, 2.1 Hz, 1H), 7.37 (d, J=8.1 Hz, 1H), 5.85 (s, 1H), 2.94 (s, 2H), 2.12–2.06 (m, 3H), 1.94–1.90 (m, 6H), 1.78–1.74 (m, 6H), 1.31 (s, 6H).

EXAMPLE 11(158)

(Z)-2-(7-dimethylamino-3,3-dimethyl-3,4-dihydro-(2H)-isoquinolin-1-ylidene)-1-cyclohexylethan-1-one

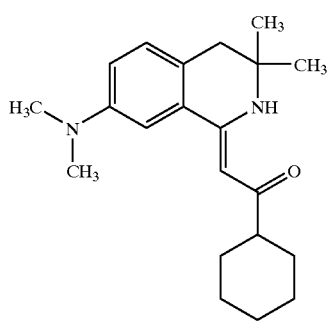

TLC: Rf 0.24 (hexane:ethyl acetate=4:1);

NMR (CDCl$_3$): δ 11.40 (brs. 1H), 7.03 (d., J=8.4 Hz, 1H). 7.03 (d. J=2.4 Hz, 1H), 6.80 (dd, J=8.4, 2.4 Hz, 1H), 5.57 (s, 1H), 2.99 (s, 6H), 2.73 (s, 2H), 2.31 (m, 1H), 1.93–1.10 (m, 10H), 1.28 (s, 6H).

EXAMPLE 11(159)

(Z)-2-(7-dimethylamino-3,3-dimethyl-3,4-dihydro-(2H)-isoquinolin-1-ylidene)-1-cycloheptylethan-1-one

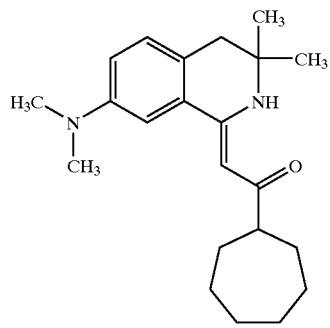

TLC: Rf 0.26 (hexane:ethyl acetate=4:1);

NMR (CDCl$_3$): δ 11.32 (brs, 1H), 7.03 (d, J=8.4 Hz, 1H), 7.02 (d, J=2.4 Hz, 1H), 6.80 (dd, J=8.4, 2.4 Hz, 1H), 5.54 (s, 1H), 2.99 (s, 6H), 2.73 (s, 2H), 2.47 (m, 1H), 1.97–1.40 (m, 12H), 1.28 (s, 6H).

EXAMPLE 11(160)

(Z)-2-(7-methylamino-3,3-dimethyl-3,4-dihydro-(2H)-isoquinolin-1-ylidene)-1-cyclohexylethan-1-one

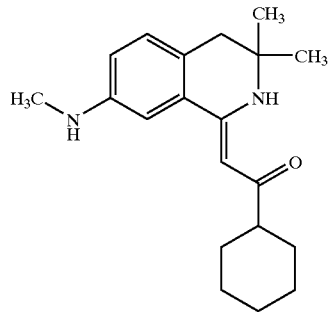

TLC: Rf 0.55 (hexane:ethyl acetate=2:1);

NMR (CDCl$_3$): δ 11.34 (brs. 1H), 6.98 (d, J=8.1 Hz, 1H), 6.91 (d, J=2.4 Hz, 1H), 6.66 (dd, J=8.1, 2.4 Hz, 1H), 5.56 (s, 1H), 3.76 (brs, 1H), 2.89 (s, 3H), 2.72 (s, 2H), 2.29 (m, 1H), 1.93–1.10 (m, 10H), 1.27 (s, 6H).

EXAMPLE 11(161)

(Z)-2-(7-methylamino-3,3-dimethyl-3,4-dihydro-(2H)-isoquinolin-1-ylidene)-1-cycloheptylethan-1-one

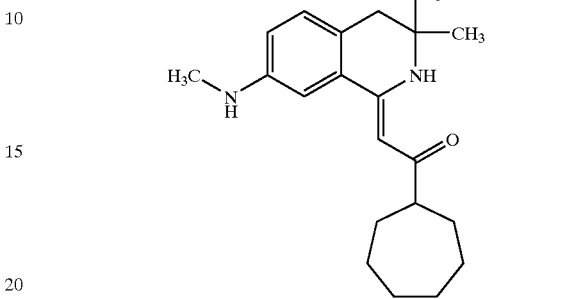

TLC: Rf 0.59 (hexane:ethyl acetate=2:1);

NMR (CDCl$_3$): δ 11.26 (brs, 1H), 6.98 (d, J=8.4 Hz, 1H), 6.91 (d, J=2.4 Hz, 1H), 6.66 (dd, J=8.4, 2.4 Hz, 1H), 5.53 (s, 1H), 3.77 (brs, 1H), 2.89 (s, 3H), 2.71 (s, 2H), 2.45 (m, 1H), 1.97–1.42 (m, 12H), 1.27 (s, 6H).

EXAMPLE 11(162)

(Z)-2-(7-methylamino-3,3-dimethyl-3,4-dihydro-(2H)-isoquinolin-1-ylidene)-1-(4-cyanophenyl)ethan-1-one

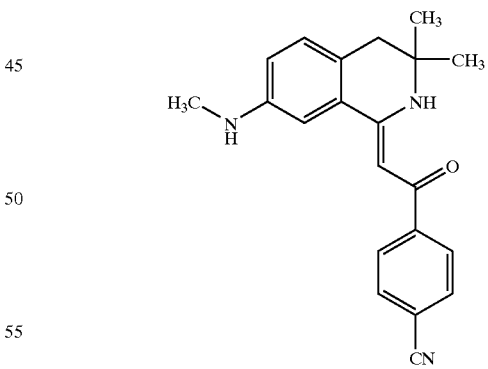

TLC: Rf 0.19 (hexane:ethyl acetate=3:1);

NMR (CDCl$_3$): δ 11.97 (br, 1H), 8.00 (d, J=8.7 Hz, 2H), 7.72 (d, J=8.7 Hz, 2H), 7.05 (d, J=8.1 Hz, 1H), 6.99 (d, J=2.4 Hz, 1H), 6.73 (dd, J=8.1, 2.4 Hz, 1H), 6.19 (s, 1H), 3.90 (br, 1H), 2.91 (s, 3H), 2.80 (s, 2H), 1.36 (s, 6H).

EXAMPLE 11(163)

(Z)-2-(7-cyano-6-methoxy-3,3-dimethyl-3,4-dihydro-(2H)-isoquinolin-1-ylidene)-1-(4-cyanophenyl)ethan-1-one

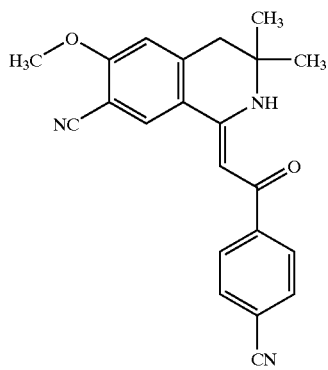

TLC: Rf 0.23 (hexane:ethyl acetate=1:1);

NMR (CDCl$_3$): δ 11.88 (br, 1H), 8.03–8.00 (m, 3H), 7.75 (d, J=8.5 Hz, 2H), 6.82 (s, 1H), 6.16 (s, 1H), 4.02 (s, 3H), 2.95 (s, 2H), 1.39 (s, 6H).

EXAMPLE 11(164)

(Z)-2-(7-methylamino-3,3-dimethyl-3,4-dihydro-(2H)-isoquinolin-1-ylidene)-1-(adamantan-1-yl)ethan-1-one

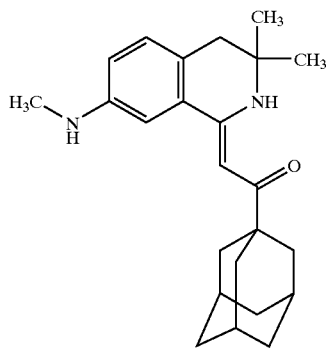

TLC: Rf 0.55 (hexane:ethyl acetate=3:1);

NMR (CDCl$_3$): δ 11.51 (br, 1H), 6.99 (d, J=8.1 Hz, 1H), 6.94 (d, J=2.4 Hz, 1H), 6.66 (dd, J=8.1, 2.4 Hz, 1H), 5.70 (s, 1H), 3.78 (br, 1H), 2.89 (s, 3H), 2.72 (s, 2H), 2.05 (s, 3H), 1.91 (br, 6H), 1.74 (br, 6H), 1.27 (s, 6H).

EXAMPLE 11(165)

(Z)-2-(7-cyano-6-methoxy-3,3-dimethyl-3,4-dihydro-(2H)-isoquinolin-1-ylidene)-1-(adamantan-1-yl)ethan-1-one

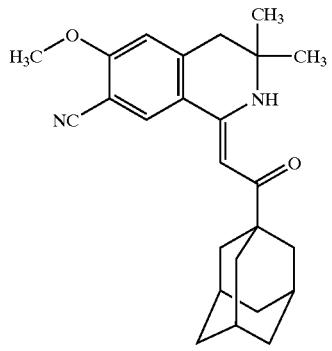

TLC: Rf 0.23 (hexane:ethyl acetate=2:1);

NMR (CDCl$_3$): δ 11.41 (br, 1H), 7.93 (s, 1H), 6.76 (s, 1H), 5.67 (s, 1H), 3.99 (s, 3H), 2.86 (s, 2H), 2.07 (br, 3H), 1.90 (br, 6H), 1.75 (br, 6H), 1.30 (s, 6H).

EXAMPLE 11(166)

(Z)-2-(7-cyano-6-methoxy-3,3-dimethyl-3,4-dihydro-(2H)-isoquinolin-1-ylidene)-1-cyclohexylethan-1-one

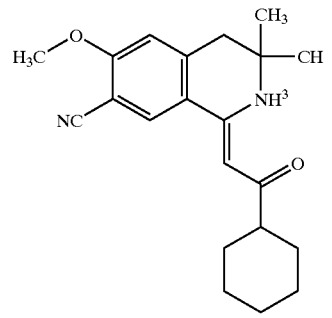

TLC: Rf 0.22 (hexane:ethyl acetate=2:1);

NMR (CDCl$_3$): δ 11.25 (br. 1H), 7.91 (s, 1H), 6.76 (s, 1H), 5.53 (s, 1H), 3.98 (s, 3H), 2.87 (s, 2H), 2.30 (m, 1H), 1.89–1.80 (m, 4H), 1.70 (m, 1H), 1.57–1.16 (m, 11H).

EXAMPLE 11(167)

(Z)-2-(7-cyano-6-methoxy-3,3-dimethyl-3,4-dihydro-(2H)-isoquinolin-1-ylidene)-1-cycloheptylethan-1-one

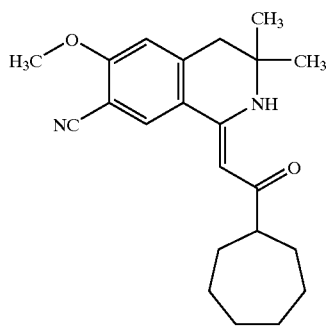

TLC: Rf 0.26 (hexane:ethyl acetate=2:1);

NMR (CDCl$_3$): δ 11.16 (br, 1H), 7.91 (s, 1H), 6.75 (s, 1H), 5.49 (s, 1H), 3.98 (s, 3H), 2.86 (s, 2H), 2.46 (m, 1H), 1.95–1.87 (m, 2H), 1.82–1.47 (m, 10H), 1.30 (s, 6H).

EXAMPLE 11(168)

(Z)-2-(7-bromo-3,3-dimethyl-3,4-dihydro-(2H)-isoquinolin-1-ylidene)-1-(adamantan-1-yl)ethan-1-one

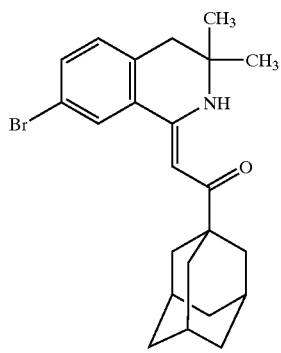

TLC: Rf 0.36 (hexane:ethyl acetate=4:1);

NMR (CDCl$_3$): δ 11.42 (brs, 1H), 7.82 (d, J=10 Hz, 1H), 7.50 (dd, J=7.8, 1.8 Hz, 1H), 7.06 (d, J=7.8 Hz, 1H), 5.71 (s, 1H), 2.78 (s, 2H), 2.10–2.04 (m, 3H), 1.93–1.89 (m, 6H), 1.78–1.73 (m, 6H), 1.31 (s, 6H).

EXAMPLE 11(169)

(Z)-2-(7-dimethylaminomethyl-6-methoxy-3,3-dimethyl-3,4-dihydro-(2H)-isoquinolin-1-ylidene)-1-cycloheptylethan-1-one

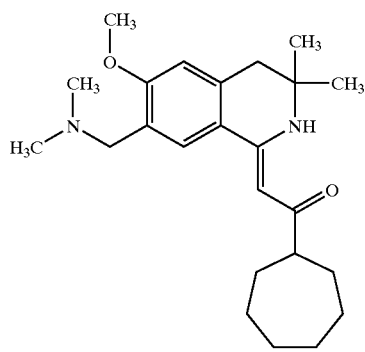

TLC: Rf 0.42 (chloroform:methanol=10:1);

NMR (CDCl$_3$): δ 11.28 (br, 1H), 7.59 (s, 1H), 6.62 (s, 1H), 5.55 (s, 1H), 3.87 (s, 3H), 3.45 (s, 2H), 2.80 (s, 2H), 2.46 (m, 1H), 2.29 (s, 6H), 1.95–1.87 (m, 2H), 1.82–1.47 (m, 10H), 1.29 (s, 6H).

EXAMPLE 11(170)

(Z)-2-(7-bromo-6-methoxy-3,3-dimethyl-3,4-dihydro-(2H)-isoquinolin-1-ylidene)-1-cyclohexylethan-1-one

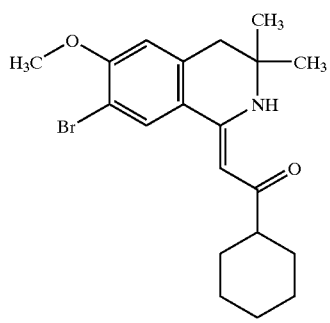

TLC: Rf 0.27 (hexane:ethyl acetate=3:1);

NMR (CDCl$_3$): δ 11.24 (br. 1H), 7.86 (s, 1H), 6.67 (s. 1H), 5.51 (s, 1H), 3.94 (s, 3H), 2.79 (s, 2H), 2.29 (tt, J=11.5, 3.5 Hz, 1H), 1.89–1.79 (m, 4H), 1.71–1.20 (m, 12H).

EXAMPLE 11(171)

(Z)-2-(7-dimethylaminomethyl-6-methoxy-3,3-dimethyl-3,4-dihydro-(2H)-isoquinolin-1-ylidene)-1-cyclohexylethan-1-one

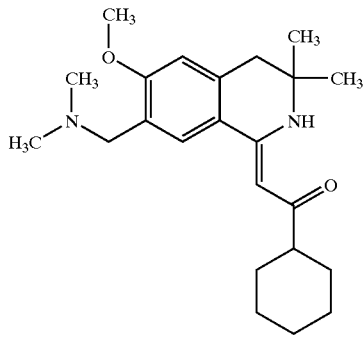

TLC: Rf 0.42 (chloroform:methanol=10:1);

NMR (CDCl$_3$): δ 11.35 (br, 1H), 7.60 (s, 1H), 6.63 (s, 1H), 5.58 (s, 1H), 3.87 (s, 3H), 3.45 (s, 2H), 2.81 (s, 2H), 2.37–2.25 (m, 7H), 1.88–1.79 (m, 4H), 1.71–1.20 (m, 12H).

EXAMPLE 11(172)

(Z)-2-(7-nitro-3,3,6-trimethyl-3,4-dihydro-(2H)-isoquinolin-1-ylidene)-1-(adamantan-1-yl)ethan-1-one

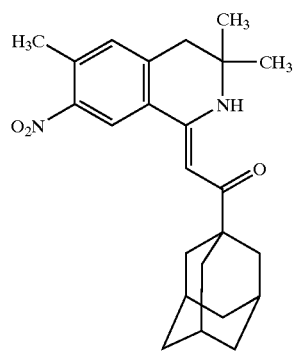

TLC: Rf 0.33 (hexane:ethyl acetate=5:1);

NMR (CDCl$_3$): δ 11.42 (br, 1H), 8.33 (s, 1H), 7.16 (s, 1H), 5.79 (s, 1H), 2.86 (s, 2H), 2.64 (s, 3H), 2.07 (br, 3H), 1.91–1.90 (br, 6H), 1.76–1.75 (br, 6H), 1.31 (s, 6H).

EXAMPLE 11(173)

(Z)-2-(6-methoxy-7-methylaminomethyl-3,3-dimethyl-3,4-dihydro-(2H)-isoquinolin-1-ylidene)-1-cyclohexylethan-1-one

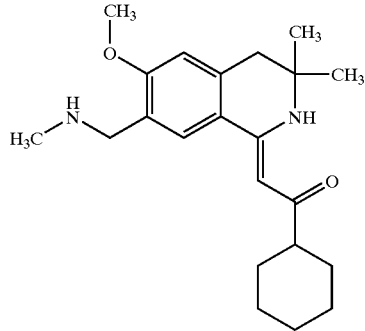

TLC: Rf 0.28 (chloroform:methanol=10:1);

NMR (CDCl$_3$): δ 11.31 (br, 1H), 7.57 (s, 1H), 6.62 (s, 1H), 5.58 (s, 1H), 3.88 (s, 3H), 3.75 (s, 2H), 2.80 (s, 2H), 2.47 (s, 3H), 2.29 (tt, J=11.5, 3.5 Hz, 1H), 1.89–1.79 (m, 4H), 1.71–1.20 (m, 12H).

EXAMPLE 11(174)

(Z)-2-(7-dimethylaminomethyl-6-methoxy-3,3-dimethyl-3,4-dihydro-(2H)-isoquinolin-1-ylidene)-1-(4-cyanophenyl)ethan-1-one

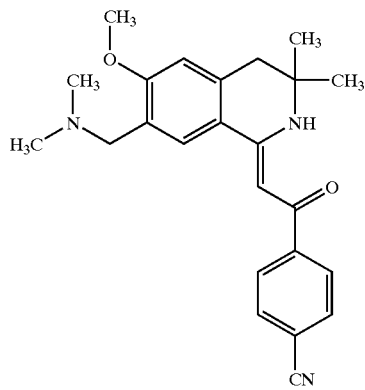

TLC: Rf 0.47 (chloroform:methanol=10:1);

NMR (CDCl$_3$): δ 11.99 (br, 1H), 8.02 (d, J=8.5 Hz, 2H), 7.74–7.71 (m, 3H), 6.69 (s, 1H), 6.22 (s, 1H), 3.91 (s, 3H), 3.49 (s, 2H), 2.89 (s, 2H), 2.31 (s, 6H), 1.38 (s, 6H).

EXAMPLE 11(175)

(Z)-2-(7-nitro-3,3,6-trimethyl-3,4-dihydro-(2H)-isoquinolin-1-ylidene)-1-(4-cyanophenyl)ethan-1-one

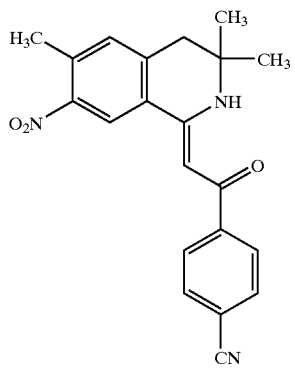

TLC: Rf 0.89 (chloroform:methanol=50:1);

NMR (CDCl$_3$): δ 11.88 (br, 1H), 8.44 (s, 1H), 8.03 (d, J=8.7 Hz, 2H), 7.76 (d, J=8.7 Hz, 2H), 7.24 (s, 1H), 6.28 (s, 1H), 2.95 (s, 2H), 2.68 (s, 3H), 1.40 (s, 6H).

EXAMPLE 11(176)

(Z)-2-(7-nitro-3,3,6-trimethyl-3,4-dihydro-(2H)-isoquinolin-1-ylidene)-1-cyclohexylethan-1-one

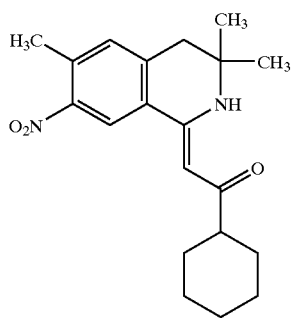

TLC: Rf 0.25 (hexane:ethyl acetate=4:1);

NMR (CDCl$_3$): δ 11.25 (brs, 1H), 8.34 (s, 1H), 7.16 (s, 1H), 5.65 (S, 1H), 2.87 (s, 2H), 2.65 (s, 3H), 2.34 (tt, J=11.4, 3.3 Hz, 1H), 1.93–1.65 (m, 5H), 1.58–1.18 (m, 11H).

EXAMPLE 11(177)

(Z)-2-(7-nitro-3,3,6-trimethyl-3,4-dihydro-(2H)-isoquinolin-1-ylidene)-1-cycloheptylethan-1-one

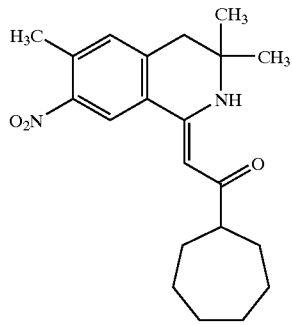

TLC: Rf 0.27 (hexane:ethyl acetate=4:1);

NMR (CDCl$_3$): δ 11.17 (brs, 1H), 8.34 (s, 1H), 7.16 (s, 1H), 5.62 (s, 1H), 2.86 (s, 2H), 2.65 (s, 3H), 2.51 (tt, J=9.9, 3.9 Hz, 1H), 1.97–1.44 (m, 12H), 1.30 (s, 6H).

EXAMPLE 11(178)

(Z)-2-(7-methylamino-3,3,6-trimethyl-3,4-dihydro-(2H)-isoquinolin-1-ylidene)-1-cyclohexylethan-1-one

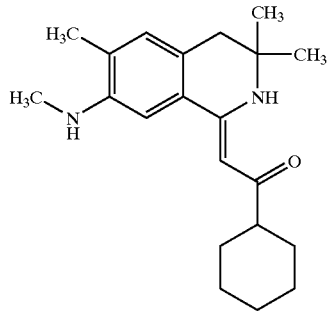

TLC: Rf 0.55 (hexane:ethyl acetate=2:1);

NMR (CDCl$_3$): δ 11.37 (brs, 1H), 6.86 (s, 1H), 6.84 (s, 1H), 5.58 (s, 1H), 3.58 (brs, 1H), 2.97 (s, 3H), 2.70 (s, 2H), 2.31 (tt, J=12.0, 3.3 Hz, 1H), 2.15 (s, 3H), 1.92–1.18 (m, 16H).

EXAMPLE 11(179)

(Z)-2-(7-methylamino-3,3,6-trimethyl-3,4-dihydro-(2H)-isoquinolin-1-ylidene)-1-cycloheptylethan-1-one

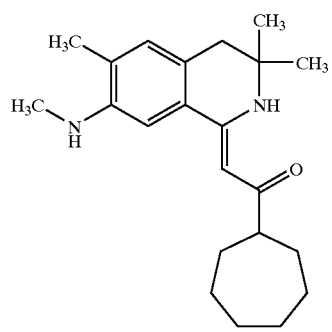

TLC: Rf 0.59 (hexane:ethyl acetate=2:1);

NMR (CDCl$_3$): δ 11.29 (brs, 1H), 6.86 (s, 1H), 6.84 (s, 1H), 5.55 (s, 1H), 3.58 (brs, 1H), 2.97 (s, 3H), 2.70 (s, 2H), 2.47 (tt, J=9.9, 3.9 Hz, 1H), 2.15 (s, 3H), 1.97–1.43 (m, 12H), 1.28 (s, 6H).

EXAMPLE 11(180)

(Z)-2-(7-methylamino-3,3,6-trimethyl-3,4-dihydro-(2H)-isoquinolin-1-ylidene)-1-(adamantan-1-yl)ethan-1-one

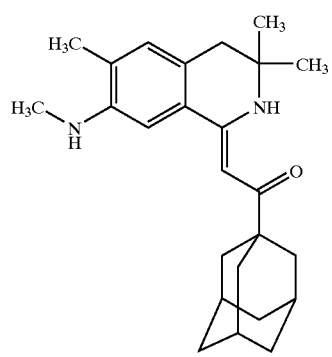

TLC: Rf 0.61 (hexane:ethyl acetate=2:1);

NMR (CDCl$_3$): δ 11.55 (brs, 1H), 6.88 (s, 1H), 6.84 (s, 1H), 5.74 (s, 1H), 3.58 (brs, 1H), 2.97 (s, 3H), 2.70 (s, 2H), 2.16 (s, 3H), 2.08–2.02 (m, 3H), 1.94–1.90 (m, 6H), 1.76–1.72 (m, 6H), 1.28 (s, 6H).

EXAMPLE 11(181)

(Z)-2-(7-bromo-6-methoxy-3,3-dimethyl-3,4-dihydro-(2H)-isoquinolin-1-ylidene)-1-cycloheptylethan-1-one

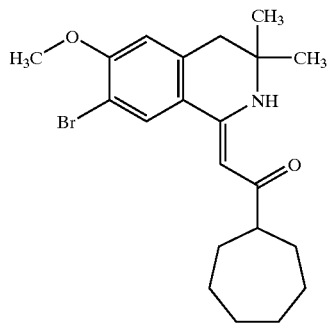

TLC: Rf 0.39 (hexane:ethyl acetate=2:1);

NMR (CDCl$_3$): δ 11.16 (br, 1H), 7.86 (s, 1H), 6.67 (s, 1H), 5.48 (s, 1H), 3.94 (s, 3H), 2.78 (s, 2H), 2.46 (m, 1H), 1.94–1.50 (m, 12H), 1.29 (s, 6H).

EXAMPLE 11(182)

(Z)-2-(6,7-dicyano-3,3-dimethyl-3,4-dihydro-(2H)-isoquinolin-1-ylidene)-1-cyclohexylethan-1-one

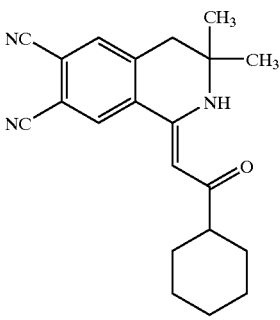

TLC: Rf 0.35 (hexane:ethyl acetate=2:1);

NMR (CDCl$_3$): δ 11.07 (brs, 1H), 8.09 (s, 1H), 7.63 (s, 1H), 5.64 (s, 1H), 2.94 (s, 2H), 2.35 (m, 1H), 1.93–1.75 (m, 5H), 1.56–1.20 (m, 11H).

EXAMPLE 11(183)

(Z)-2-(6,7-dicyano-3,3-dimethyl-3,4-dihydro-(2H)-isoquinolin-1-ylidene)-1-(adamantan-1-yl)ethan-1-one

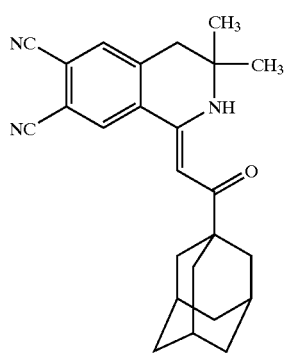

TLC: Rf 0.37 (hexane:ethyl acetate=2:1);

NMR (CDCl$_3$): δ 11.22 (brs, 1H), 8.10 (s, 1H), 7.63 (s, 1H), 5.78 (s, 1H), 2.94 (s, 2H), 2.12–2.05 (m, 3H), 1.91–1.87 (m, 6H), 1.83–1.69 (m, 6H), 1.31 (s, 6H).

EXAMPLE 11(184)

(Z)-2-(7-bromo-3,3,6-trimethyl-3,4-dihydro-(2H)-isoquinolin-1-ylidene)-1-(adamantan-1-yl)ethan-1-one

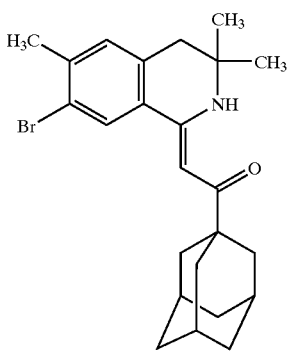

TLC: Rf 0.33 (hexane:ethyl acetate=9:1);

NMR (CDCl$_3$): δ 11.40 (br, 1H), 7.83 (s, 1H), 7.04 (s, 1H), 5.69 (s, 1H), 2.74 (s, 2H), 2.42 (s, 3H), 2.06 (br, 3H), 1.91–1.90 (br, 6H), 1.76–1.75 (br, 6H), 1.28 (s, 6H).

EXAMPLE 11(185)

(Z)-2-(6,7-dicyano-3,3-dimethyl-3,4-dihydro-(2H)-isoquinolin-1-ylidene)-1-cycloheptylethan-1-one

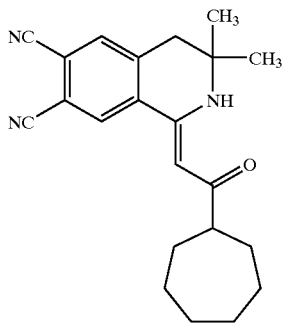

TLC: Rf 0.30 (hexane:ethyl acetate=2:1);

NMR (CDCl$_3$): δ 10.98 (brs, 1H), 8.09 (s, 1H), 7.63 (s, 1H), 5.60 (s, 1H), 2.94 (s, 2H), 2.52 (m, 1H), 1.96–1.44 (m, 12H), 1.31 (s, 6H).

EXAMPLE 11(186)

(Z)-2-(6,7-dicyano-3,3-dimethyl-3,4-dihydro-(2H)-isoquinolin-1-ylidene)-1-(4-cyanophenyl)ethan-1-one

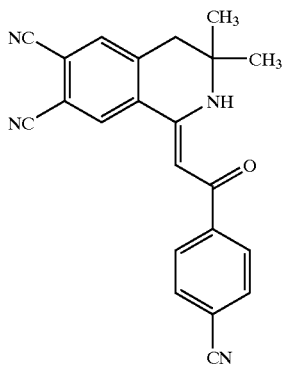

TLC: Rf 0.68 (chloroform:methanol=9:1);

NMR (DMSO-d$_6$): δ 11.77 (brs, 1H), 9.01 (s, 1H), 8.25 (d, J=8.4 Hz, 2H), 8.17 (s, 1H), 7.97 (d, J=8.4 Hz, 2H), 6.75 (s, 1H), 3.09 (s, 2H), 1.30 (s, 6H).

EXAMPLE 11(187)

(Z)-2-(7-methylamino-3,3,6-trimethyl-3,4-dihydro-(2H)-isoquinolin-1-ylidene)-1-(4-cyanophenyl)ethan-1-one

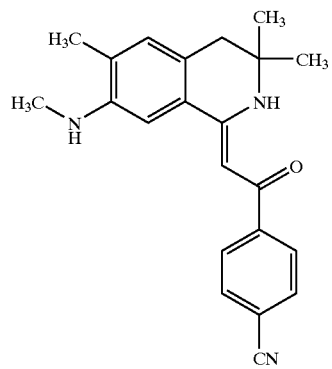

TLC: Rf 0.50 (hexane:ethyl acetate=1:1);

NMR (CDCl$_3$): δ 11.98 (brs, 1H), 8.01 (d, J=8.7 Hz, 2H), 7.72 (d, J=8.7 Hz, 2H), 6.92 (s, 1H), 6.91 (s, 1H), 6.22 (s, 1H), 3.66 (brs, 1H), 2.99 (s, 3H), 2.78 (s, 2H), 2.19 (s, 3H), 1.36 (s, 6H).

EXAMPLE 11(188)

(Z)-2-(7-bromo-3,3-dimethyl-3,4-dihydro-(2H)-isoquinolin-1-ylidene)-1-cyclohexylethan-1-one

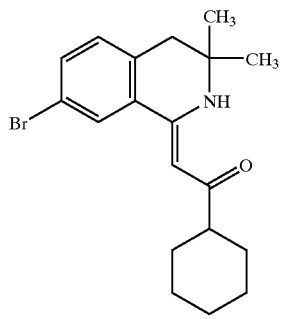

TLC: Rf 0.41 (hexane:ethyl acetate=4:1);

NMR (CDCl$_3$): δ 11.23 (brs. 1H), 7.81 (d, J=2.1 Hz, 1H), 7.50 (dd, J=8.1, 2.1 Hz, 1H), 7.05 (d, J=8.1 Hz, 1H), 5.57 (s, 1H), 2.78 (s, 2H), 2.31 (tt, J=11.4, 3.3 Hz, 1H), 1.92–1.65 (m, 5H), 1.58–1.18 (m, 11H).

EXAMPLE 11(189)

(Z)-2-(7-bromo-3,3,6-trimethyl-3,4-dihydro-(2H)-isoquinolin-1-ylidene)-1-cyclohexylethan-1-one

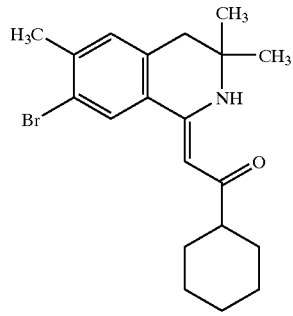

TLC: Rf 0.41 hexane:ethyl acetate=4:1);

NMR (CDCl$_3$): δ 11.22 (br, 1H), 7.83 (s, 1H), 7.04 (s, 1H), 5.55 (s, 1H), 2.74 (s, 2H), 2.41 (s, 3H), 2.30 (m, 1H), 1.92–1.20 (m, 16H).

EXAMPLE 11(190)

(Z)-2-(6-chloro-7-methylamino-3,3-dimethyl-3,4-dihydro-(2H)-isoquinolin-1-ylidene)-1-cyclohexylethan-1-one

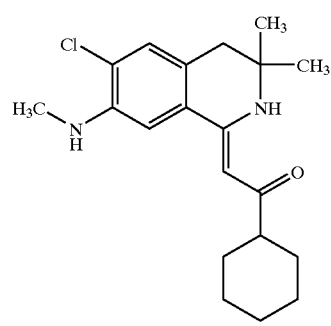

TLC: Rf 0.34 (ethyl acetate:hexane=1:5);

NMR (CDCl$_3$): δ 11.34 (br., 1H). 7.07 (s, 1H), 6.90 (s, 1H), 5.55 (s. 1H), 4.33 (br., 1H), 2.98 (d, J=4.5 Hz, 3H), 2.69 (s, 2H), 2.31 (m, 1H), 1.90–1.20 (m, 10H), 1.27 (s, 6H).

EXAMPLE 11(191)

(Z)-2-(6-chloro-7-methylamino-3,3-dimethyl-3,4-dihydro-(2H)-isoquinolin-1-ylidene)-1-cycloheptylethan-1-one

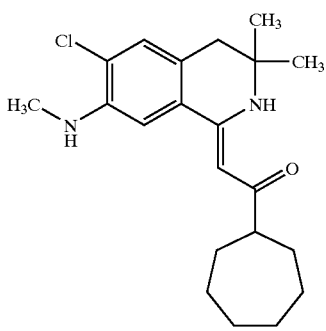

TLC: Rf 0.38 (ethyl acetate:hexane=1:5);

NMR (CDCl$_3$): δ 11.27 (br., 1H), 7.07 (s, 1H), 6.90 (s, 1H), 5.52 (s, 1H), 4.33 (br., 1H), 2.98 (d, J=3.5 Hz, 3H), 2.70 (s, 2H), 2.48 (m, 1H), 1.95–1.40 (m, 12H), 1.27 (s, 6H).

EXAMPLE 11(192)

(Z)-2-(6-chloro-7-methylamino-3,3-dimethyl-3,4-dihydro-(2H)-isoquinolin-1-ylidene)-1-(adamantan-1-yl)ethan-1-one

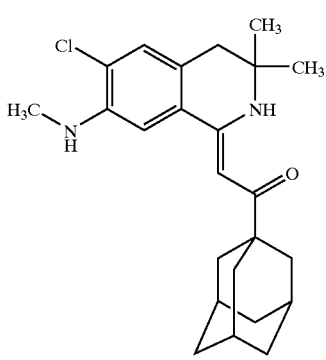

TLC: Rf 0.41 (ethyl acetate:hexane=1:5);

NMR (CDCl$_3$): δ 11.53 (br., 1H), 7.07 (s, 1H), 6.92 (s, 1H), 5.71 (s, 1H), 4.33 (br., 1H), 2.99 (s, 3H), 2.70 (s, 2H), 2.06 (m, 3H), 1.92 (m, 6H), 1.75 (m, 6H), 1.28 (s, 6H).

EXAMPLE 11(193)

(Z)-2-(7-bromo-3,3-dimethyl-3,4-dihydro-(2H)-isoquinolin-1-ylidene)-1-cycloheptylethan-1-one

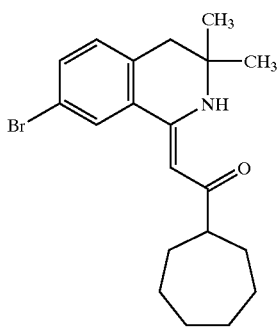

TLC: Rf 0.39 (hexane:ethyl acetate=4:1);

NMR (CDCl$_3$): δ 11.14 (brs, 1H), 7.81 (d, J=1.8 Hz, 1H), 7.50 (dd, J=7.8, 1.8 Hz, 1H), 7.05 (d, J=7.8 Hz, 1H), 5.54 (s, 1H), 2.78 (s, 2H), 2.48 (tt, J=9.9, 3.9 Hz, 1H), 1.97–1.43 (m, 12H), 1.28 (s, 6H).

EXAMPLE 11(194)

(Z)-2-(7-bromo-3,3,6-trimethyl-3,4-dihydro-(2H)-isoquinolin-1-ylidene)-1-cycloheptylethan-1-one

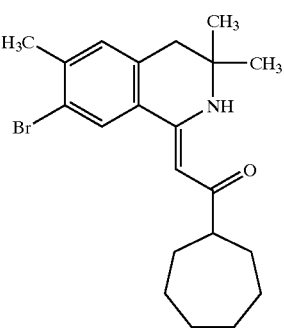

TLC: Rf 0.60 (hexane:ethyl acetate=5:1);

NMR (CDCl$_3$): δ 11.15 (br, 1H), 7.83 (s, 1H), 7.04 (s, 1H), 5.52 (s, 1H), 2.74 (s, 2H), 2.41 (s, 3H), 2.46 (m, 1H), 1.96–1.46 (m, 12H), 1.28 (s, 6H).

EXAMPLE 11(195)

(Z)-2-(7-nitro-3,3-dimethyl-3,4-dihydro-(2H)-isoquinolin-1-ylidene)-1-cycloheptylethan-1-one

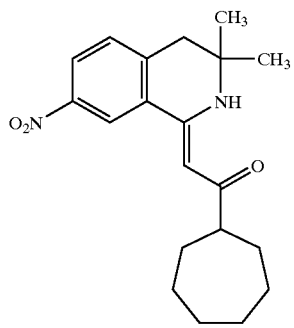

TLC: Rf 0.57 (hexane:ethyl acetate=1:1);

NMR (CDCl$_3$): δ 11.15 (brs, 1H), 8.56 (d, J=2.1 Hz, 1H), 8.24 (dd, J=8.7, 2.1 Hz, 1H), 7.37 (d, J=8.7 Hz, 1H), 5.68 (s, 1H), 2.94 (s, 2H), 2.53 (ft, J=9.9, 3.9 Hz, 1H), 1.98–1.46 (m, 12H), 1.31 (s, 6H).

EXAMPLE 11(196)

(Z)-2-(7-dimethylsulfamoyl-3,3-dimethyl-3,4-dihydro-(2H)-isoquinolin-1-ylidene)-1-(adamantan-1-yl)ethan-1-one

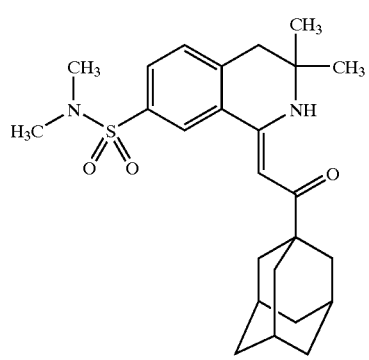

TLC: Rf 0.53 (hexane:ethyl acetate=1:1);

NMR (CDCl$_3$): δ 11.51 (brs, 1H), 8.08 (d, J=1.8 Hz, 1H), 7.77 (dd, J=7.8, 1.8 Hz, 1H), 7.36 (d, J=1.8 Hz, 1H), 5.79 (s, 1H), 2.92 (s, 2H), 2.77 (s, 6H), 2.10–2.03 (m, 3H), 1.92–1.88 (m, 6H), 1.77–1.72 (m, 6H), 1.31 (s, 6H).

EXAMPLE 11(197)

(Z)-2-(7-butoxycarbonyl-6-chloro-3,3-dimethyl-3,4-dihydro-(2H)-isoquinolin-1-ylidene)-1-(adamantan-1-yl)ethan-1-one

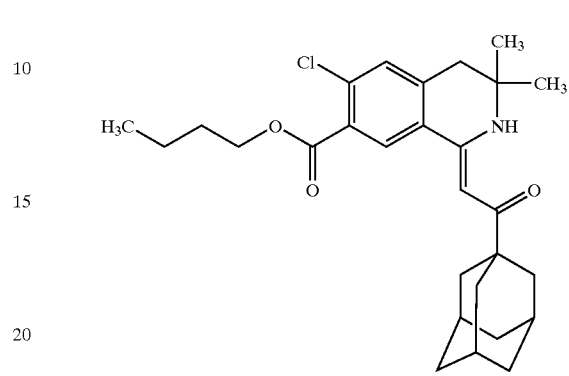

TLC: Rf 0.40 (hexane:ethyl acetate=4:1);

NMR (CDCl$_3$): δ 11.38 (brs, 1H), 8.18 (s, 1H), 7.28 (s, 1H), 5.78 (s, 1H), 4.39 (t, J=6.6 Hz, 2H), 2.83 (s, 2H), 2.10–2.02 (m, 3H), 1.93–1.88 (m, 6H), 1.84–1.72 (m, 8H), 1.61–1.48 (m, 8H), 1.01 (t, J=7.2 Hz, 3H).

EXAMPLE 11(198)

(Z)-2-(7-butoxycarbonyl-6-chloro-3,3-dimethyl-3,4-dihydro-(2H)-isoquinolin-1-ylidene)-1-cycloheptylethan-1-one

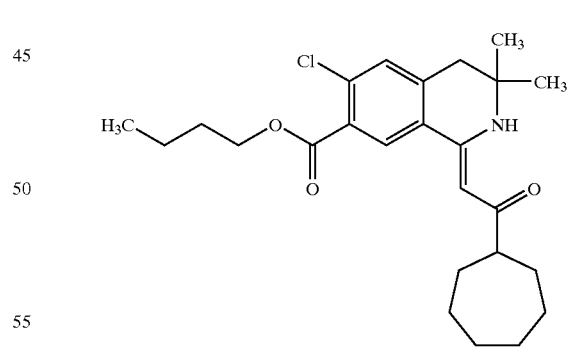

TLC: Rf 0.38 (hexane:ethyl acetate=4:1);

NMR (CDCl$_3$): δ 11.12 (brs, 1H), 8.15 (s, 1H), 7.8 (s, 1H), 5.59 (s, 1H), 4.39 (t, J=6.6 Hz, 2H), 2.83 (s, 2H), 2.48 (tt, J=9.9, 3.9 Hz, 1H), 1.96–1.43 (m, 16H), 1.29 (s, 6H), 1.01 (t, J=7.2 Hz, 3H).

EXAMPLE 11(199)

(Z)-2-(7-methylsulfamoyl-3,3-dimethyl-3,4-dihydro-(2H)-isoquinolin-1-ylidene)-1-(adamantan-1-yl)ethan-1-one

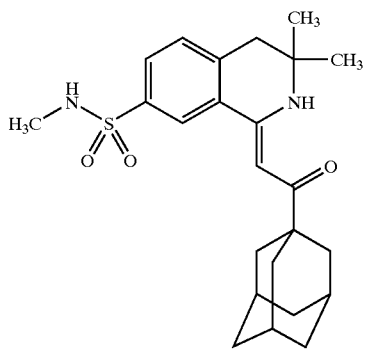

TLC: Rf 0.39 (hexane:ethyl acetate=1:1);

NMR (CDCl$_3$): δ 11.50 (brs, 1H), 8.17 (d, J=1.8 Hz, 1H), 7.86 (dd, J=7.8, 1.8 Hz, 1H), 7.35 (d, J=7.8 Hz, 1H), 5.81 (s, 1H), 4.41 (q, J=5.4 Hz, 1H), 2.91 (s, 2H), 2.72 (d, J=5.4 Hz, 3H), 2.10–2.03 (m, 3H), 1.92–1.87 (m, 6H), 1.77–1.73 (m, 6H), 1.31 (s, 6H).

EXAMPLE 11(200)

(Z)-2-(6-chloro-7-methoxy-3,3-dimethyl-3,4-dihydro-(2H)-isoquinolin-1-ylidene)-1-(adamantan-1-yl)ethan-1-one

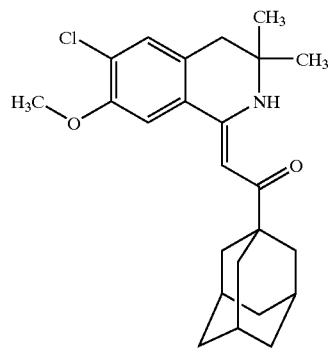

TLC: Rf 0.33 (ethyl acetate:hexane=5:1);

NMR (CDCl$_3$): δ 11.53 (br., 1H), 7.21 (s, 1H), 7.19 (s, 1H), 5.68 (s, 1H), 3.99 (s, 3H), 2.74 (s, 2H), 2.06 (m, 3H), 1.91 (m, 6H), 1.75 (m, 6H), 1.28 (s, 6H).

EXAMPLE 11(201)

(Z)-2-(7-methoxy-3,3,6-trimethyl-3,4-dihydro-(2H)-isoquinolin-1-ylidene)-1-(adamantan-1-yl)ethan-1-one

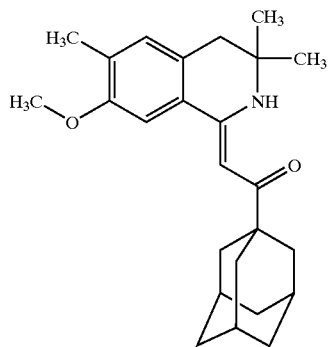

TLC: Rf 0.39 (hexane:ethyl acetate=6:1);

NMR (CDCl$_3$): δ 11.54 (br, 1H), 7.10 (s, 1H), 6.93 (s, 1H), 5.69 (s, 1H), 3.91 (s, 3H), 2.73 (s, 2H), 2.24 (s, 3H), 2.06 (br, 3H), 1.92–1.91 (br, 6H), 1.75 (br, 6H), 1.28 (s, 6H).

EXAMPLE 11(202)

(Z)-2-(7-methoxy-3,3,6-trimethyl-3,4-dihydro-(2H)-isoquinolin-1-ylidene)-1-cyclohexylethan-1-one

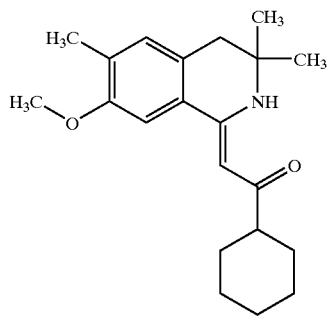

TLC: Rf 0.35 (hexane:ethyl acetate=6:1);

NMR (CDCl$_3$): δ 11.34 (br, 1H), 7.09 (S, 1H), 6.92 (s, 1H), 5.54 (s, 1H), 3.90 (s, 3H), 2.73 (s, 2H), 2.31 (m, 1H), 2.24 (s, 3H), 1.92–1.18 (m, 16H).

EXAMPLE 11(203)

(Z)-2-(7-methoxy-3,3,6-trimethyl-3,4-dihydro-(2H)-isoquinolin-1-ylidene)-1-cycloheptylethan-1-one

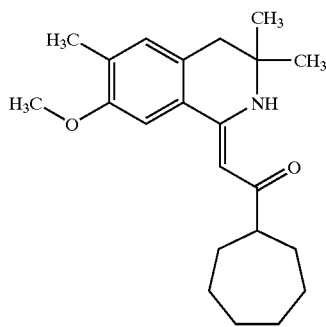

TLC: Rf 0.31 (hexane:ethyl acetate=6:1);

NMR (CDCl$_3$): δ 11.27 (br, 1H), 7.08 (s, 1H), 6.92 (s, 1H), 5.51 (s, 1H), 3.90 (s, 3H), 2.73 (s, 2H), 2.46 (m, 1H), 2.24 (s, 3H), 1.96–1.42 (m, 12H), 1.27 (s, 6H).

EXAMPLE 12~EXAMPLE 12(31)

By the same procedure as described in example 1 using the compound prepared in reference example 1 or a corresponding nitrile derivative and 2-methyl-1-phenylpropan-2-ol or an alcohol derivative, the following compounds of the present invention were given. And the compounds of example 12 (20) and example 12 (24) were given by conversion to hydrochloride additionally.

EXAMPLE 12

(Z)-2-(6-bromo-3,3-dimethyl-3,4-dihydro-(2H)-isoquinolin-1-ylidene)-1-phenylethan-1-one

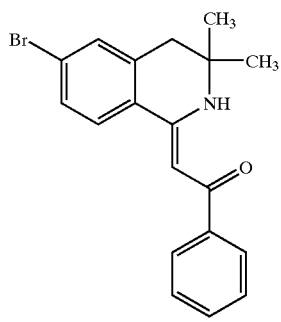

TLC: Rf 0.35 (hexane:ethyl acetate=5:1);

NMR (CDCl$_3$): δ 11.78 (br, 1H), 7.95–7.92 (m, 2H), 7.69 (d, J=8.5 Hz, 1H), 7.49–7.38 (m, 5H), 6.28 (br, 1H), 2.87 (s, 2H), 1.37 (s, 6H).

EXAMPLE 12(1)

(Z)-2-(3,3-dimethyl-3,4-dihydro-(2H)-isoquinolin-1-ylidene)-1-(tetrahydropyran-4-yl)ethan-1-one

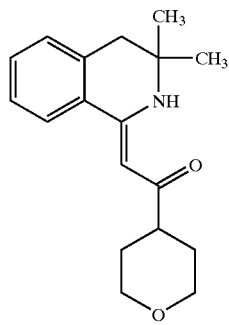

TLC: Rf 0.54 (ethyl acetate:hexane=1:1);

NMR (CDCl$_3$): δ 11.35 (br., 1H), 7.70 (m, 1H), 7.41 (m, 1H), 7.30 (m, 1H), 7.19 (m, 1H), 5.63 (br., 1H), 4.05 (m, 2H), 3.46 (dt, J=11.5, 3.5 Hz, 2H), 2.86 (s, 2H), 2.54 (m, 1H), 1.90–1.70 (m, 4H), 1.31 (s, 6H).

EXAMPLE 12(2)

(Z)-2-(6-fluoro-3,3-dimethyl-3,4-dihydro-(2H)-isoquinolin-1-ylidene)-1-cyclohexylethan-1-one

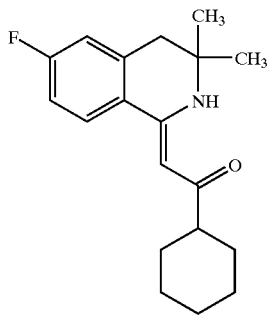

TLC: Rf 0.35 (ethyl acetate:hexane=1:5);

NMR (CDCl$_3$): δ 11.31 (br., 1H), 7.70 (dd, J=9.0, 5.5 Hz, 1H), 6.98 (ddd, J=9.0, 9.0, 2.5 Hz, 1H), 6.88 (dd, J=9.0, 2.5 Hz, 1H), 5.57 (s, 1H), 2.82 (s, 2H), 2.28 (m, 1H), 1.95–1.20 (m, 10H), 1.29 (s, 6H).

EXAMPLE 12(3)

(Z)-2-(6-chloro-3,3-dimethyl-3,4-dihydro-(2H)-isoquinolin-1-ylidene)-1-cyclohexylethan-1-one

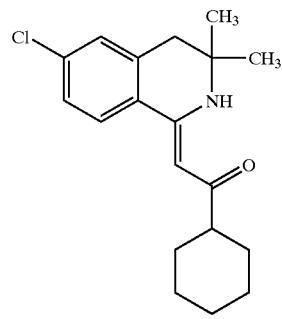

TLC: Rf 0.40 (ethyl acetate:hexane=1:5);

NMR (CDCl$_3$): δ 11.26 (br., 1H), 7.63 (d, J=9.0 Hz, 1H), 7.26 (dd, J=9.0, 2.5 Hz, 1H), 7.17 (d, J=2.5 Hz, 1H), 5.58 (s, 1H), 2.81 (s, 2H), 2.29 (m, 1H), 1.95–1.20 (m, 10H), 1.29 (s, 6H).

EXAMPLE 12(4)

(Z)-2-(6-fluoro-3,3-dimethyl-3,4-dihydro-(2H)-isoquinolin-1-ylidene)-1-cycloheptylethan-1-one

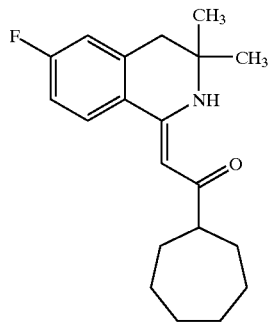

TLC: Rf 0.37 (ethyl acetate:hexane=1:5);

NMR (CDCl$_3$): δ 11.22 (br., 1H), 7.70 (dd, J=9.0, 5.5 Hz, 1H), 6.97 (ddd, J=9.0, 9.0, 2.5 Hz, 1H), 6.87 (dd, J=9.0, 2.5 Hz, 1H), 5.53 (s, 1H), 2.82 (s, 2H), 2.45 (m, 1H), 2.00–1.40 (m, 12H), 1.29 (s, 6H).

EXAMPLE 12(5)

(Z)-2-(6-chloro-3,3-dimethyl-3,4-dihydro-(2H)-isoquinolin-1-ylidene)-1-cycloheptylethan-1-one

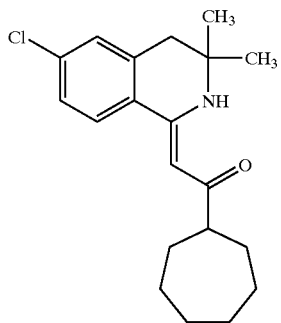

TLC: Rf 0.42 (ethyl acetate:hexane=1:5);

NMR (CDCl$_3$): δ 11.17 (br., 1H), 7.63 (d, J=8.5 Hz, 1H), 7.25 (dd, J=8.5, 2.0 Hz, 1H), 7.17 (d, J=2.0 Hz, 1H), 5.55 (s, 1H), 2.80 (s, 2H), 2.45 (m, 1H), 2.00–1.40 (m, 12H), 1.29 (s, 6H).

EXAMPLE 12(6)

(Z)-2-(8-methoxy-3,3-dimethyl-3,4-dihydro-(2H)-isoquinolin-1-ylidene)-1-cyclohexylethan-1-one

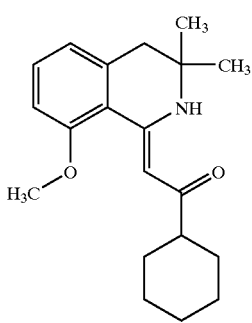

TLC: Rf 0.42 (ethyl acetate:hexane=1:3);

NMR (CDCl$_3$): δ 11.77 (br., 1H), 7.30 (dd, J=7.5, 7.5 Hz. 1H), 6.87 (d. J=7.5 Hz, 1H), 6.77 (d, J=7.5 Hz, 1H), 6.20 (s, 1H), 3.92 (s, 3H), 2.79 (s, 2H), 2.26 (m, 1H), 1.95–1.10 (m, 10H), 1.26 (s, 6H).

EXAMPLE 12(7)

(Z)-2-(6-methoxy-3,3-dimethyl-3,4-dihydro-(2H)-isoquinolin-1-ylidene)-1-cyclohexylethan-1-one

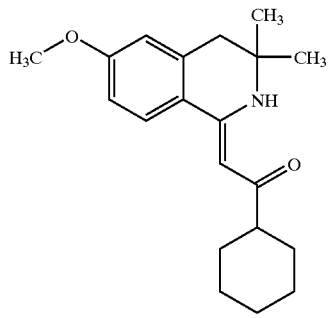

TLC: Rf 0.32 (ethyl acetate:hexane=1:3);

NMR (CDCl$_3$): δ 11.33 (br., 1H), 7.65 (d, J=8.5 Hz, 1H), 6.80 (dd, J=8.5, 2.5 Hz, 1H), 6.67 (d, J=2.5 Hz, 1H), 5.55 (s, 1H), 3.85 (s, 3H), 2.80 (s, 2H), 2.27 (m, 1H), 1.95–1.10 (m, 10H), 1.29 (s, 6H).

EXAMPLE 12(8)

(Z)-2-(8-methoxy-3,3-dimethyl-3,4-dihydro-(2H)-isoquinolin-1-ylidene)-1-cycloheptylethan-1-one

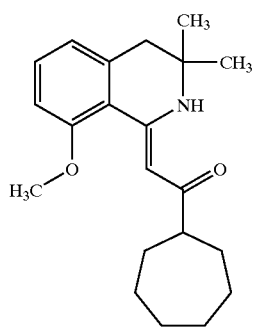

TLC: Rf 0.46 (ethyl acetate:hexane=1:3);

NMR (CDCl$_3$): δ 11.67 (br. 1H), 7.29 (dd, J=7.5, 7.5 Hz, 1H), 6.87 (d, J=7.5 Hz, 1H), 6.76 (d, J=7.5 Hz, 1H), 6.17 (s, 1H), 3.91 (s, 3H), 2.78 (s, 2H), 2.42 (m, 1H), 2.00–1.40 (m, 12H), 1.26 (s, 6H).

EXAMPLE 12(9)

(Z)-2-(6-methoxy-3,3-dimethyl-3,4-dihydro-(2H)-isoquinolin-1-ylidene)-1-cycloheptylethan-1-one

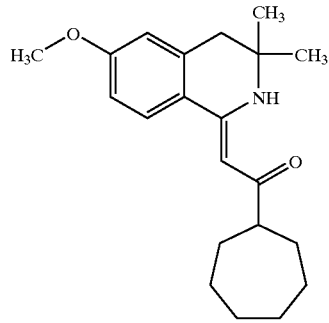

TLC: Rf 0.37 (ethyl acetate:hexane=1:3);

NMR (CDCl$_3$): δ 11.25 (br., 1H), 7.65 (d, J=8.5 Hz, 1H), 6.80 (dd, J=8.5, 3.0 Hz, 1H), 6.67 (d, J=3.0 Hz, 1H), 5.52 (s, 1H), 3.85 (s, 3H), 2.80 (s, 2H), 2.43 (m, 1H), 2.00–1.40 (m, 12H), 1.29 (s, 6H).

EXAMPLE 12(10)

(Z)-2-(3,3,4,4-tetramethyl-3,4-dihydro-(2H)-isoquinolin-1-ylidene)-1-(2-methoxyphenyl)ethan-1-one

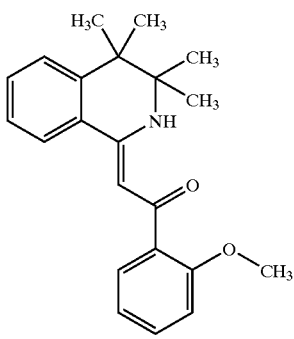

TLC: Rf 0.30 (hexane:ethyl acetate=3:1);

NMR (CDCl$_3$): δ 11.63 (br, 1H), 7.74–7.68 (m, 2H), 7.49–7.25 (m, 4H), 7.03–6.95 (m, 2H), 6.26 (s, 1H), 3.92 (s, 3H), 1.31 (br, 12H).

EXAMPLE 12(11)

(Z)-2-(3,3,4,4-tetramethyl-3,4-dihydro-(2H)-isoquinolin-1-ylidene)-1-cyclohexylethan-1-one

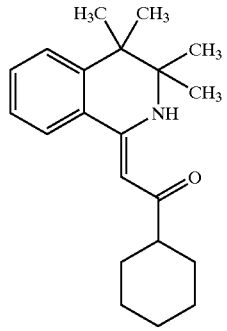

TLC: Rf 0.58 (hexane:ethyl acetate=3:1);

NMR (CDCl$_3$): δ 11.25 (br, 1H), 7.69 (dd, J=7.5, 1.0 Hz, 1H), 7.47–7.37 (m, 2H), 7.29–7.24 (m, 1H), 5.59 (s, 1H), 2.35–2.24 (m, 1H), 1.91–1.79 (m, 4H), 1.69–1.64 (m, 1H), 1.55–1.19 (m, 17H).

EXAMPLE 12(12)

(Z)-2-(3,3,4,4-tetramethyl-3,4-dihydro-(2H)-isoquinolin-1-ylidene)-1-cycloheptylethan-1-one

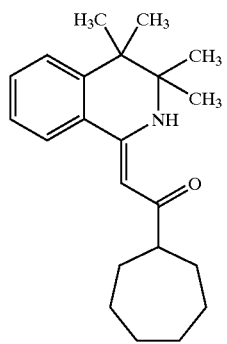

TLC: Rf 0.57 (hexane:ethyl acetate=3:1);

NMR (CDCl$_3$): δ 11.16 (br, 1H), 7.68 (dd, J=8.0, 1.0 Hz, 1H), 7.47–7.37 (m, 2H), 7.29–7.24 (m, 1H), 5.56 (s, 1H), 2.50–2.41 (m, 1H), 1.96–1.90 (m, 2H), 1.83–1.43 (m, 10H), 1.26 (br, 12H).

EXAMPLE 12(13)

(Z)-2-(3,3-dimethyl-3,4-dihydro-(2H)-isoquinolin-1-ylidene)-1-(isoquinolin-1-yl)ethan-1-one

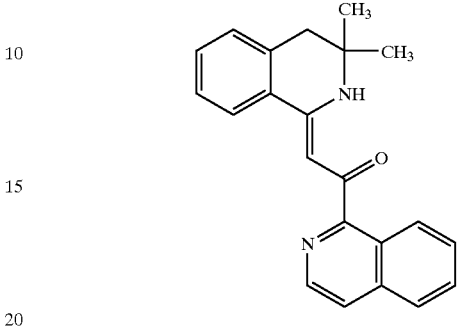

TLC: Rf 0.30 (hexane:ethyl acetate=2:1);

NMR (CDCl$_3$): δ 11.79 (br, 1H), 8.86 (d, J=8.0 Hz, 1H), 8.55 (d, J=5.5 Hz, 1H), 7.88–7.84 (m, 2H), 7.72–7.59 (m, 3H), 7.42 (dt, J=1.0, 7.0 Hz, 1H), 7.33–7.27 (m, 1H), 7.21 (d, J=7.5 Hz, 1H), 6.54 (s, 1H), 2.94 (s, 2H), 1.42 (s, 6H).

EXAMPLE 12(14)

(Z)-2-(3,3-dimethyl-3,4-dihydro-(2H)-isoquinolin-1-ylidene)-1-(quinolin-4-yl)ethan-1-one

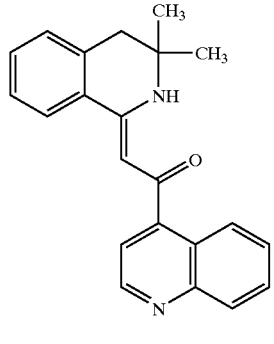

TLC: Rf 0.11 (hexane:ethyl acetate=2:1);

NMR (CDCl$_3$): δ 11.84 (br, 1H), 8.96 (d, J=4.5 Hz, 1H), 8.42 (d, J=7.5 Hz, 1H), 8.14 (d, J=8.0 Hz, 1H), 7.75–7.69 (m, 2H), 7.57 (t, J=8.0 Hz, 1H), 7.51 (d, J=4.5 Hz, 1H), 7.45 (t, J=7.5 Hz, 1H), 7.33–7.23 (m, 2H), 6.02 (s, 1H), 2.97 (s, 2H), 1.43 (s, 6H).

EXAMPLE 2(15)

(Z)-2-(6-chloro-3,3-dimethyl-3,4-dihydro-(2H)-isoquinolin-1-ylidene)-1-(2-methoxyphenyl)ethan-1-one

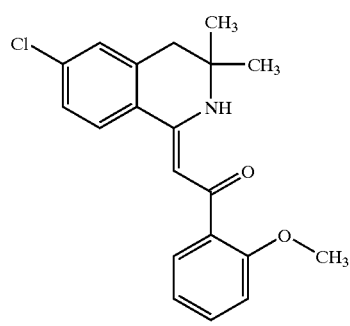

TLC: Rf 0.44 (hexane:ethyl acetate=2:1);

NMR (CDCl$_3$): δ 11.63 (br, 1H), 7.68–7.65 (m, 2H), 7.37 (ddd, J=8.0, 7.5, 2.0 Hz, 1H), 7.29–7.26 (m, 1H), 7.20 (d, J=2.0 Hz, 1H), 7.03–6.95 (m, 2H), 6.23 (s, 1H), 3.91 (s, 3H), 2.86 (s, 2H), 1.36 (s, 6H).

EXAMPLE 12(16)

(Z)-2-(6-chloro-3,3-dimethyl-3,4-dihydro-(2H)-isoquinolin-1-ylidene)-1-(2-chlorophenyl)ethan-1-one

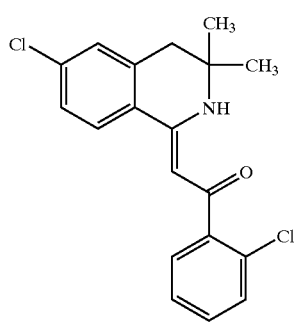

TLC: Rf 0.38 (hexane:ethyl acetate=3:1);

NMR (CDCl$_3$): δ 11.49 (br, 1H), 7.65 (d, J=8.5 Hz, 1H), 7.54–7.51 (m 1H), 7.42–7.39 (m, 1H), 7.32–7.27 (m, 3H), 7.21 (d, J=2.0 Hz, 1H), 5.93 (s, 1H), 2.89 (s, 2H), 1.38 (s, 6H).

EXAMPLE 12(17)

(Z)-2-(3,3-dimethyl-3,4-dihydro-(2H)-isoquinolin-1-ylidene)-1-(quinolin-8-yl)ethan-1-one

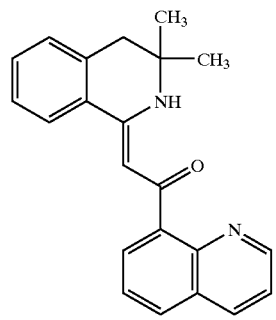

TLC: Rf 0.17 (hexane:ethyl acetate=1:1);

NMR (CDCl$_3$): δ 11.80 (br, 1H), 9.05 (dd, J=4.0, 2.0 Hz, 1H), 8.19 (dd, J=8.0, 2.0 Hz, 1H), 7.98 (dd, J=7.5, 1.5 Hz, 1H), 7.85 (dd, J=8.0, 1.5 Hz, 1H), 7.74 (d, J=7.5 Hz, 1H), 7.58 (dd, J=8.0, 7.5 Hz, 1H), 7.44–7.37 (m, 2H), 7.29–7.24 (m, 1H), 7.20 (d, J=7.5 Hz, 1H), 6.35 (s, 1H), 2.92 (s, 2H), 1.40 (s, 6H).

EXAMPLE 12(18)

(Z)-2-(6,8-dichloro-3,3-dimethyl-3,4-dihydro-(2H)-isoquinolin-1-ylidene)-1-phenylethan-1-one

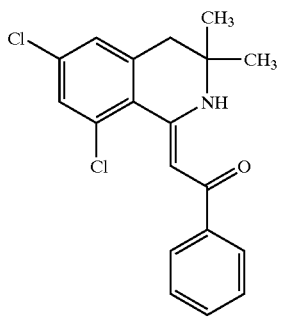

TLC: Rf 0.52 (hexane:ethyl acetate=2:1);

NMR (CDCl$_3$): δ 11.98 (brs, 1H); 7.93–7.89 (m 2H), 7.47–7.41 (m, 4H), 7.14 (m, 1H), 6.79 (s, 1H), 2.83 (s, 2H), 1.33 (s, 6H).

EXAMPLE 12(19)

(Z)-2-(3,3-dimethyl-3,4-dihydro-(2H)-isoquinolin-1-ylidene)-1-(2-ethoxyphenyl)ethan-1-one

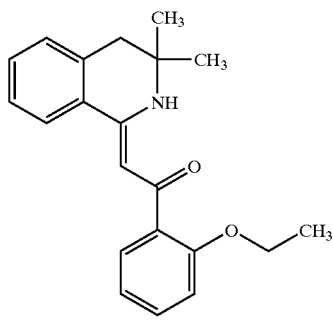

TLC: Rf 0.31 (hexane:ethyl acetate=3:1);

NMR (CDCl$_3$): δ 11.70 (br, 1H), 7.81 (dd, J=7.5, 2.0 Hz, 1H), 7.77 (d, J=7.5 Hz, 1H), 7.43–7.27 (m, 3H), 7.20 (d, J=7.5 Hz, 1H), 7.01 (dt, J=1.0, 7.5 Hz, 1H), 6.95 (dd, J=7.5, 1.0 Hz, 1H), 6.55 (s, 1H), 4.15 (q, J=7.0 Hz, 2H), 2.90 (s, 2H), 1.49 (t, J=7.0 Hz, 3H), 1.36 (s, 6H).

EXAMPLE 12(20)

2-(3,3-dimethyl-3,4-dihydroisoquinolin-1-yl)-1-(adamantan-1-yl)propan-1-one hydrochloride

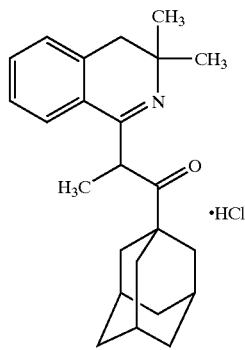

TLC: Rf 0.40 (ethyl acetate:hexane=1:5);

NMR (CDCl$_3$): δ 7.92 (d, J=7.5 Hz, 1H), 7.67 (dd, J=7.5, 7.5 Hz, 1H), 7.42 (dd, J=7.5, 7.5 Hz, 1H), 7.34 (d, J=7.5 Hz, 1H), 5.80 (q, J=7.0 Hz, 1H), 3.03 (s, 2H), 2.02 (m, 3H), 1.87 (m, 6H), 1.80–1.55 (m, 15H).

EXAMPLE 12(21)

(Z)-2-(3,3-dimethyl-3,4-dihydro-(2H)-isoquinolin-1-ylidene)-1-(4-chloro-2-methoxyphenyl)ethan-1-one

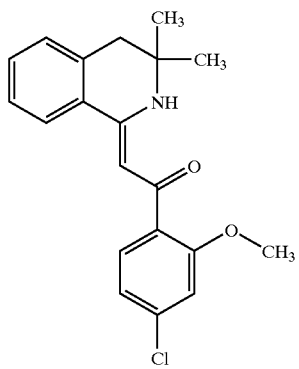

TLC: Rf 0.40 (hexane:ethyl acetate=3:1);

NMR (CDCl$_3$): δ 11.70 (br, 1H), 7.73 (d, J=7.5 Hz, 1H), 7.64 (d, J=8.0 Hz, 1H), 7.41 (t, J=7.5 Hz, 1H), 7.31 (t, J=7.5 Hz, 1H), 7.20 (d, J=7.5 Hz, 1H), 6.99 (dd, J=8.0, 2.0 Hz, 1H), 6.94 (d, J=2.0 Hz, 1H), 6.25 (s, 1H), 3.91 (s, 3H), 2.89 (s, 2H), 1.35 (s, 6H).

EXAMPLE 12(22)

(Z)-2-(3,3-dimethyl-3,4-dihydro-(2H)-isoquinolin-1-ylidene)-1-(2-methoxy-4-methylthiophenyl)ethan-1-one

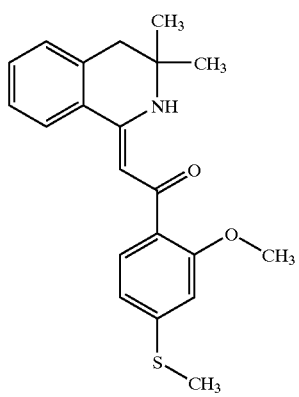

TLC: Rf 0.20 (hexane:ethyl acetate=3:1);

NMR (CDCl$_3$): δ 11.70 (br, 1H), 7.74 (d, J=7.5 Hz, 1H), 7.69 (d, J=8.0 Hz, 1H), 7.40 (t, J=7.5 Hz, 1H), 7.30 (t, J=7.5 Hz, 1H), 7.19 (d, J=7.5 Hz, 1H), 6.87 (dd, J=8.0, 2.0 Hz, 1H), 6.83 (d, J=2.0 Hz, 1H), 6.34 (s, 1H), 3.92 (s, 3H), 2.89 (s, 2H), 2.52 (s, 3H), 1.35 (s, 6H).

EXAMPLE 12(23)

(Z)-2-(3,3-dimethyl-3,4-dihydro-(2H)-isoquinolin-1-ylidene)-1-(2-methoxy-4-mesylphenyl)ethan-1-one

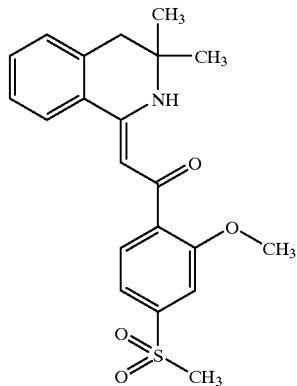

TLC: Rf 0.15 (hexane:ethyl acetate=1:1);

NMR (CDCl$_3$): δ 11.73 (br, 1H), 7.79 (d, J=8.0 Hz, 1H), 7.72 (d, J=7.5 Hz, 1H), 7.57 (dd, J=8.0, 1.5 Hz, 1H), 7.50 (d, J=1.5 Hz, 1H), 7.44 (t, J=7.5 Hz, 1H), 7.32 (t, J=7.5 Hz, 1H), 7.22 (d, J=7.5 Hz, 1H), 6.14 (s, 1H), 3.98 (s, 3H), 3.08 (s, 3H), 2.92 (s, 2H), 1.38 (s, 6H).

EXAMPLE 12(24)

2-(6-fluoro-3,3-dimethyl-3,4-dihydroisoquinolin-1-yl)-1-phenylpropan-1-one hydrochloride

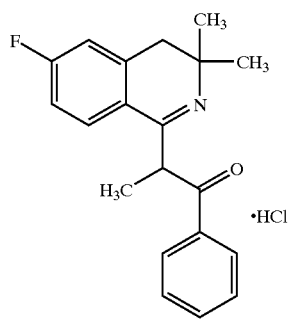

TLC: Rf 0.35 (ethyl acetate:hexane=1:3);

NMR (CDCl$_3$): δ 8.14 (d, J=8.0 Hz, 2H), 7.86 (dd, J=8.5, 5.0 Hz, 1H), 7.54 (m, 1H), 7.46 (m, 2H), 7.05 (ddd, J=8.5, 8.5, 2.5 Hz, 1H), 6.96 (dd, J=8.5, 2.5 Hz, 1H), 6.34 (q, J=6.5 Hz, 1H), 3.04 (d, J=17.0 Hz, 1H), 2.85 (d, J=17.0 Hz, 1H), 1.79 (d, J=6.5 Hz, 3H), 1.71 (s, 3H), 1.46 (s, 3H).

EXAMPLE 12(25)

(Z)-2-(6,7-dichloro-3,3-dimethyl-3,4-dihydro-(2H)-isoquinolin-1-ylidene)-1-phenylethan-1-one

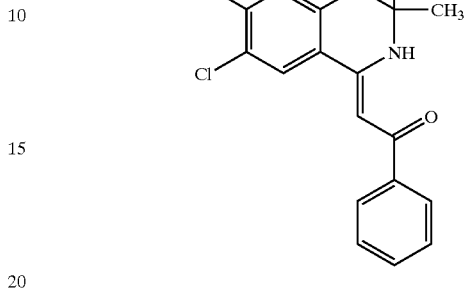

TLC: Rf 0.23 (hexane:ethyl acetate=5:1),

NMR (CDCl$_3$): δ 11.72 (br, 1H), 7.96–7.93 (m, 2H), 7.88 (s, 1H), 7.48–7.43 (m, 3H), 7.33 (s, 1H), 6.24 (s, 1H), 2.85 (s, 2H), 1.36 (s, 6H).

EXAMPLE 12(26)

(Z)-2-(3,3-dimethyl-3,4-dihydro-(2H)-isoquinolin-1-ylidene)-1-(4-bromo-2-methoxyphenyl)ethane-1-one

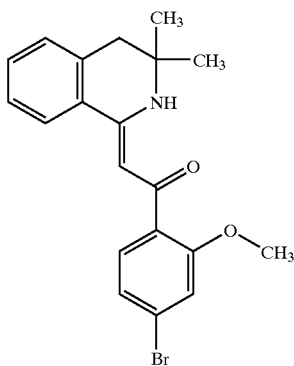

TLC: Rf 0.29 (hexane:ethyl acetate=3:1);

NMR (CDCl$_3$): δ 11.70 (br, 1H), 7.72 (d, J=7.5 Hz, 1H), 7.57 (d, J=8.0 Hz, 1H), 7.41 (t, J=7.5 Hz, 1H), 7.31 (t, J=7.5 Hz, 1H), 7.20 (d, J=7.5 Hz, 1H), 7.15 (dd, J=8.0, 2.0 Hz, 1H), 7.10 (d, J=2.0 Hz, 1H), 6.24 (s, 1H), 3.91 (s, 3H), 2.89 (s, 2H), 1.35 (s, 6H).

EXAMPLE 12(27)

(Z)-2-(3,3-dimethyl-3,4-dihydro-(2H)-isoquinolin-1-ylidene)-1-(4-bromo-2-chlorophenyl)ethan-1-one

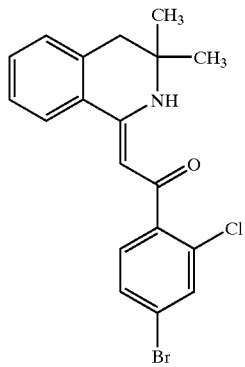

TLC: Rf 0.40 (hexane:ethyl acetate=3:1);

NMR (CDCl$_3$): δ 11.56 (br, 1H), 7.71 (d, J=7.5 Hz, 1H), 7.58 (m, 1H), 7.46–7.41 (m, 3H), 7.31 (t, J=7.5 Hz, 1H), 7.21 (d, J=7.5 Hz, 1H), 5.93 (s, 1H), 2.91 (s, 2H), 1.37 (s, 6H).

EXAMPLE 12(28)

(Z)-2-(6-bromo-3,3-dimethyl-3,4-dihydro-(2H)-isoquinolin-1-ylidene)-1-cyclohexylethan-1-one

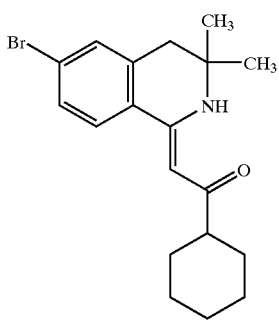

TLC: Rf 0.42 (hexane:ethyl acetate=5:1);

NMR (CDCl$_3$): δ 11.25 (br, 1H), 7.56 (d, J=8.5 Hz, 1H), 7.42 (dd, J=8.5, 2.0 Hz, 1H), 7.33 (d, J=2.0 Hz, 1H), 5.59 (s, 1H), 2.81 (s, 2H), 2.29 (m, 1H), 1.89–1.79 (m, 4H), 1.69 (m, 1H), 1.55–1.24 (m, 11H).

EXAMPLE 12(29)

(Z)-2-(6-bromo-3,3-dimethyl-3,4-dihydro-(2H)-isoquinolin-1-ylidene)-1-cycloheptylethan-1-one

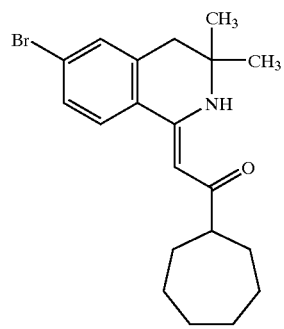

TLC: Rf 0.42 (hexane:ethyl acetate=5:1);

NMR (CDCl$_3$): δ 11.16 (br, 1H), 7.56 (d, J=8.5 Hz, 1H), 7.42 (dd, J=8.5, 2.0 Hz, 1H), 7.33 (d, J=2.0 Hz, 1H), 5.55 (s, 1H), 2.81 (s, 2H), 2.45 (m, 1H), 1.95–1.85 (m, 2H), 1.82–1.45 (m, 10H), 1.29 (s, 6H).

EXAMPLE 12(30)

(Z)-2-(6-bromo-3,3-dimethyl-3,4-dihydro-(2H)-isoquinolin-1-ylidene)-1-(adamantan-1-yl)ethan-1-one

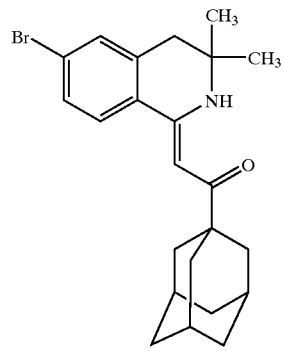

TLC: Rf 0.41 (hexane:ethyl acetate=5:1);

NMR (CDCl$_3$): δ 11.42 (br, 1H), 7.58 (d, J=8.5 Hz, 1H), 7.42 (dd, J=8.5, 2.0 Hz, 1H), 7.33 (d, J=2.0 Hz, 1H), 5.74 (s, 1H), 2.81 (s, 2H), 2.05 (br, 3H), 1.90 (br, 6H), 1.74 (br, 6H), 1.29 (s, 6H).

EXAMPLE 12(31)

(Z)-2-(6-bromo-3,3-dimethyl-3,4-dihydro-(2H)-isoquinolin-1-ylidene)-1-(pyridin-3-yl)ethan-1-one

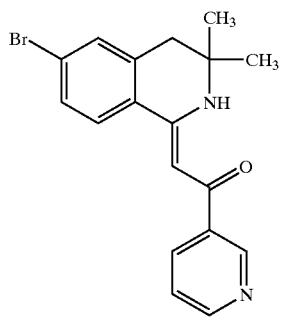

TLC: Rf 0.25 (hexane:ethyl acetate=1:1);

NMR (CDCl$_3$): δ 11.82 (br, 1H), 9.13 (dd, J=2.0, 1.0 Hz, 1H), 8.67 (dd, J=5.0, 2.0 Hz, 1H), 8.20 (ddd, J=8.0, 2.0, 2.0 Hz, 1H), 7.69 (d, J=8.5 Hz, 1H), 7.50 (dd, J=8.5, 2.0 Hz, 1H), 7.40–7.35 (m, 2H), 6.24 (s, 1H), 2.89 (s, 2H), 1.38 (s, 6H).

EXAMPLE 13

(Z)-2-(6-formyl-3,3-dimethyl-3,4-dihydro-(2H)-isoquinolin-1-ylidene)-1-phenylethan-1-one

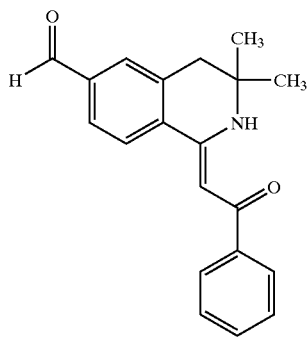

To a solution of the compound prepared in example 12 (356 mg) in ether (10 ml) was added n-butyl lithium (1.4 ml; 1.6M hexane solution) dropwise and 10 minutes later the mixture was warmed to 0° C. and the mixture was stirred for 30 minutes. To the reaction mixture was added dimethylformamide (0.20 ml) dropwise at −78° C. and the mixture was stirred for 30 minutes at 0° C. To the reaction mixture was added a saturated aqueous solution of ammonium chloride and was extracted with ethyl acetate. The residue was purified by column chromatography on silica gel (hexane:ethyl acetate=20:1→5:1) to give the compound of the present invention (165 mg) having the following physical data.

TLC: Rf 0.34 (hexane:ethyl acetate=3:1);

NMR (CDCl$_3$): δ 11.75 (br, 1H), 10.07 (s, 1H), 8.01–7.94 (m, 3H), 7.85 (d, J=8.0 Hz, 1H), 7.74 (s, 1H), 7.48–7.42 (m, 3H), 6.38 (s, 1H), 2.99 (s, 2H), 1.38 (s, 6H).

EXAMPLE 13–EXAMPLE 13(16)

By the same procedure as described in example 13, using the compound prepared in Example 11(7), Example 11(70), Example 11(81), Example 12(26), Example 11(119), Example 11(153), Example 11(154), Example 11(156), Example 11(168), Example 11(170), Example 11(181), Example 11(184), Example 11(188), Example 11(189), Example 11(193), or Example 11(194) in place of the compound prepared in Example 12, the compounds having the following physical data were given.

EXAMPLE 13(1)

(Z)-2-(7-formyl-3,3-dimethyl-3,4-dihydro-(2H)-isoquinolin-1-ylidene)-1-phenylethan-1-one

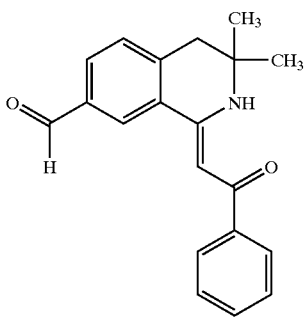

TLC: Rf 0.24 (hexane:ethyl acetate=3:1);

NMR (CDCl$_3$): δ 11.82 (br, 1H), 10.08 (s, 1H), 8.34 (d, J=1.5 Hz, 1H), 7.99–7.93 (m, 3H), 7.49–7.40 (m, 4H), 6.42 (s, 1H), 2.99 (s, 2H), 1.38 (s, 6H).

EXAMPLE 13(2)

(Z)-2-(7-formyl-3,3-dimethyl-3,4-dihydro-(2H)-isoquinolin-1-ylidene)-1-(naphthalen-1-yl)ethan-1-one

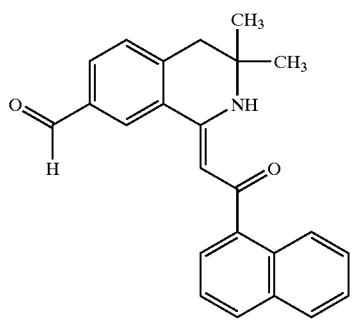

TLC: Rf 0.31 (ethyl acetate:hexane=1:3);

NMR (CDCl$_3$): δ 11.76 (br., 1H), 10.00 (s, 1H), 8.48 (m, 1H), 8.22 (d, J=1.5 Hz, 1H), 7.95–7.85 (m, 3H), 7.72 (dd, J=7.0, 1.5 Hz, 1H), 7.55–7.45 (m, 3H), 7.42 (d, J=8.0 Hz, 1H), 6.19 (s, 1H), 3.04 (s, 2H), 1.44 (s, 6H).

EXAMPLE 13(3)

(Z)-2-(3,3-dimethyl-3,4-dihydro-(2H)-isoquinolin-1-ylidene)-1-(4-formylphenyl)ethan-1-one

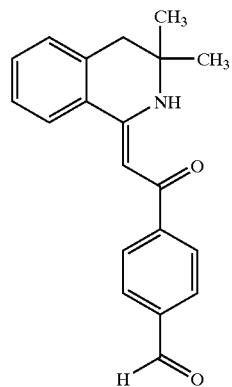

TLC: Rf 0.26 (hexane:ethyl acetate=3:1);

NMR (CDCl$_3$): δ 11.99 (br, 1H), 10.08 (s, 1H), 8.08 (d, J=8.5 Hz, 2H), 7.95 (d, J=8.5 Hz, 2H), 7.84 (d, J=7.5 Hz, 1H), 7.46 (t, J=7.5 Hz, 1H), 7.37 (t, J=7.5 Hz, 1H), 7.24 (d, J=7.5 Hz, 1H), 6.34 (s, 1H), 2.93 (s, 2H), 1.39 (s, 6H).

EXAMPLE 13(4)

(Z)-2-(3,3-dimethyl-3,4-dihydro-(2H)-isoquinolin-1-ylidene)-1-(4-formyl-2-methoxyphenyl)ethan-1-one

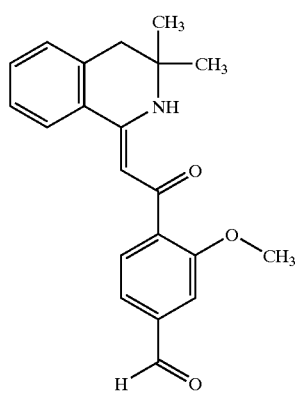

TLC: Rf 0.26 (hexane:ethyl acetate=2:1);

NMR (CDCl$_3$): δ 11.76 (br, 1H), 10.02 (s, 1H), 7.79 (d, J=7.5 Hz, 1H), 7.73 (d, J=7.5 Hz, 1H), 7.51 (dd, J=7.5, 1.0 Hz, 1H), 7.48 (d, J=1.0 Hz, 1H), 7.43 (t, J=7.5 Hz, 1H), 7.31 (t, J=7.5 Hz, 1H), 7.21 (d, J=7.5 Hz, 1H), 6.20 (s, 1H), 3.89 (s, 3H), 2.91 (s, 2H), 1.37 (s, 6H).

EXAMPLE 13(5)

(Z)-2-(6-chloro-7-formyl-3,3-dimethyl-3,4-dihydro-(2H)-isoquinolin-1-ylidene)-1-(adamantan-1-yl)ethan-1-one

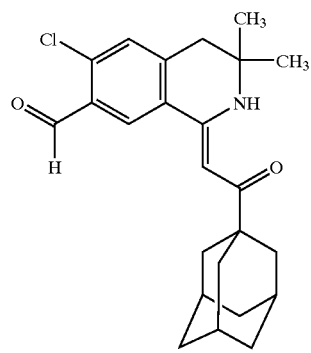

TLC: Rf 0.28 (ethyl acetate:hexane=1:5);

NMR (CDCl$_3$): δ 11.43 (br., 1H), 10.47 (s, 1H), 8.25 (s, 1H), 7.30 (s, 1H), 5.83 (s, 1H), 2.87 (s, 2H), 2.06 (m, 3H), 1.90 (m, 6H), 1.76 (m, 6H), 1.30 (s, 6H).

EXAMPLE 13(6)

(Z)-2-(6-chloro-7-formyl-3,3-dimethyl-3,4-dihydro-(2H)-isoquinolin-1-ylidene)-1-cyclohexylethan-1-one

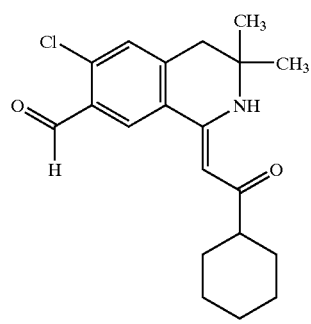

TLC: Rf 0.36 (ethyl acetate:hexane=1:3);

NMR (CDCl$_3$): δ 11.19 (br., 1H), 10.46 (s, 1H), 8.25 (s, 1H), 7.29 (s, 1H), 5.70 (s, 1H), 2.87 (s, 2H), 2.35 (m, 1H), 1.90–1.20 (m, 10H), 1.30 (s, 6H).

EXAMPLE 13(7)

(Z)-2-(6-chloro-7-formyl-3,3-dimethyl-3,4-dihydro-(2H)-isoquinolin-1-ylidene)-1-cycloheptylethan-1-one

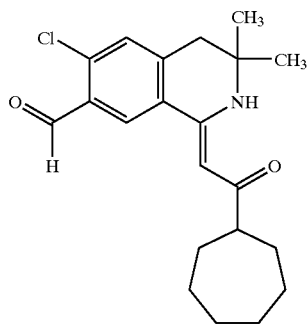

TLC: Rf 0.38 (ethyl acetate:hexane=1:3);

NMR (CDCl₃): δ 11.11 (br., 1H), 10.45 (s, 1H), 8.24 (s, 1H), 7.29 (s, 1H), 5.66 (s, 1H), 2.86 (s, 2H), 2.48 (m, 1H), 1.95–1.40 (m, 12H), 1.28 (s, 6H).

EXAMPLE 13(8)

(Z)-2-(7-formyl-6-methoxy-3,3-dimethyl-3,4-dihydro-(2H)-isoquinolin-1-ylidene)-1-(adamantan-1-yl)ethan-1-one

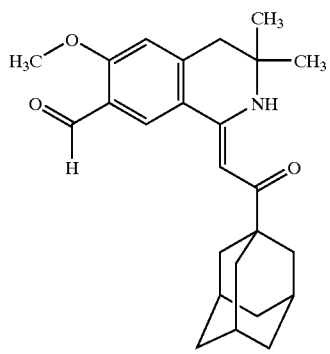

TLC: Rf 0.22 (hexane:ethyl acetate=2:1);

NMR (CDCl₃): δ 11.52 (br, 1H), 10.45 (s, 1H), 8.20 (s, 1H), 6.78 (s, 1H), 5.80 (s, 1H), 3.99 (s, 3H), 2.87 (s, 2H), 2.05 (br, 3H), 1.91 (br, 6H), 1.75 (br, 6H), 1.30 (s, 6H).

EXAMPLE 13(9)

(Z)-2-(7-formyl-3,3-dimethyl-3,4-dihydro-(2H)-isoquinolin-1-ylidene)-1-(adamantan-1-yl)ethan-1-one

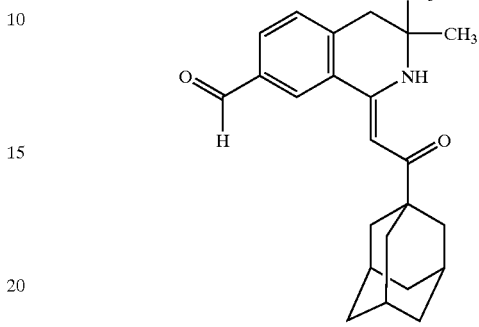

TLC: Rf 0.64 (hexane:ethyl acetate=1:1);

NMR (CDCl₃): δ 11.49 (brs, 1H), 10.06 (s, 1H), 8.22 (d, J=1.5 Hz, 1H), 7.90 (dd, J=7.8, 1.5 Hz, 1H), 7.36 (d, J=7.8 Hz, 1H), 5.87 (s, 1H), 2.93 (s, 2H), 2.11–2.04 (m, 3H), 1.94–1.90 (m, 6H), 1.78–1.73 (m, 6H), 1.31 (s, 6H).

EXAMPLE 13(10)

(Z)-2-(7-formyl-6-methoxy-3,3-dimethyl-3,4-dihydro-(2H)-isoquinolin-1-ylidene)-1-cyclohexylethan-1-one

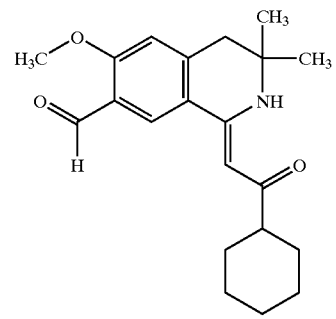

TLC: Rf 0.10 (hexane:ethyl acetate=3:1);

NMR (CDCl₃): δ 11.27 (br, 1H), 10.44 (s, 1H), 8.19 (s, 1H), 6.77 (s, 1H), 5.67 (s, 1H), 3.99 (s, 3H), 2.87 (s, 2H), 2.31 (m, 1H), 1.90–1.79 (m, 4H), 1.70 (m, 1H), 1.56–1.20 (m, 11H).

EXAMPLE 13(11)

(Z)-2-(7-formyl-6-methoxy-3,3-dimethyl-3,4-dihydro-(2H)-isoquinolin-1-ylidene)-1-cycloheptylethan-1-one

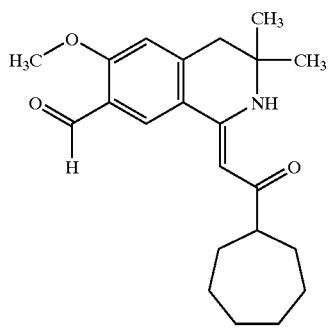

TLC: Rf 0.21 (hexane:ethyl acetate=2:1);

NMR (CDCl$_3$): δ 11.20 (br, 1H), 10.44 (s, 1H), 8.19 (s, 1H), 6.77 (s, 1H), 5.64 (s, 1H), 3.99 (s, 3H), 2.87 (s, 2H), 2.47 (m, 1H), 1.94–1.45 (m, 12H), 1.30 (s, 6H).

EXAMPLE 13(12)

(Z)-2-(7-formyl-3,3,6-trimethyl-3,4-dihydro-(2H)-isoquinolin-1-ylidene)-1-(adamantan-1-yl)ethan-1-one

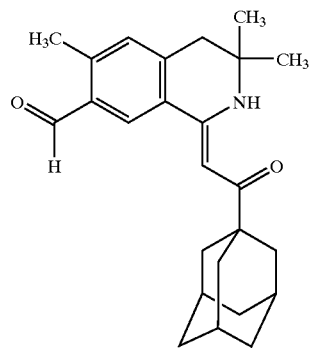

TLC: Rf 0.20 (hexane:ethyl acetate=6:1);

NMR (CDCl$_3$): δ 11.48 (br, 1H), 10.31 (s, 1H), 8.13 (s, 1H), 7.09 (s, 1H), 5.84 (s, 1H), 2.86 (s, 2H), 2.70 (s, 3H), 2.07–2.06 (br, 3H), 1.93–1.92 (br, 6H), 1.75 (br, 6H), 1.30 (s, 6H).

EXAMPLE 13(13)

(Z)-2-(7-formyl-3,3-dimethyl-3,4-dihydro-(2H)-isoquinolin-1-ylidene)-1-cyclohexylethan-1-one

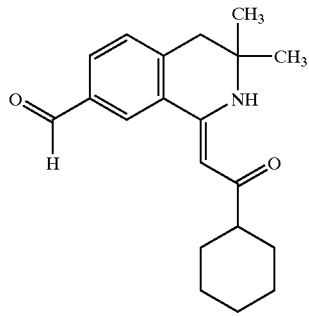

TLC: Rf 0.19 (hexane:ethyl acetate=4:1);

NMR (CDCl$_3$): δ 11.27 (brs, 1H), 10.04 (s, 1H), 8.22 (d, J=1.5 Hz, 1H), 7.90 (dd, J=7.5, 1.5 Hz, 1H), 7.36 (d, J=7.5 Hz, 1H), 5.73 (s, 1H), 2.93 (s, 2H), 2.34 (tt, J=11.7, 3.3 Hz, 1H), 1.94–1.66 (m, 5H), 1.58–1.24 (m, 11H).

EXAMPLE 13(14)

(Z)-2-(7-formyl-3,3,6-trimethyl-3,4-dihydro-(2H)-isoquinolin-1-ylidene)-1-cyclohexylethan-1-one

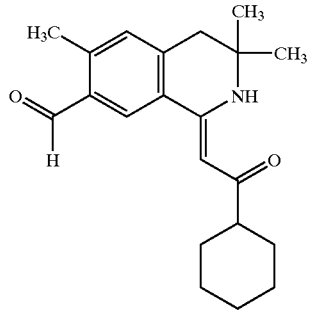

TLC: Rf 0.27 (hexane:ethyl acetate=5:1);

NMR (CDCl$_3$): δ 11.26 (br, 1H), 10.29 (s, 1H), 8.13 (s, 1H), 7.09 (s, 1H), 5.71 (s, 1H), 2.86 (s, 2H), 2.70 (s, 3H), 2.33 (m, 1H), 1.90–1.27 (m, 16H).

EXAMPLE 13(15)

(Z)-2-(7-formyl-3,3-dimethyl-3,4-dihydro-(2H)-isoquinolin-1-ylidene)-1-cycloheptylethan-1-one

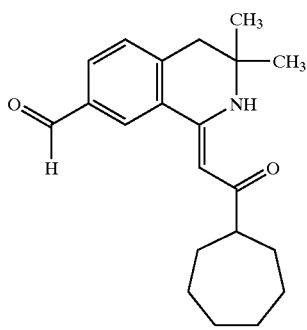

TLC: Rf 0.41 (hexane:ethyl acetate=2:1);

NMR (CDCl$_3$): δ 11.19 (brs, 1H), 10.05 (s, 1H), 8.21 (d, J=1.5 Hz, 1H), 7.89 (dd, J=7.5, 1.5 Hz, 1H), 7.36 (d, J=7.5 Hz, 1H), 5.70 (s, 1H), 2.93 (s, 2H), 2.51 (tt, J=9.9, 3.9 Hz, 1H), 1.98–1.46 (m, 12H), 1.31 (s, 6H).

EXAMPLE 13(16)

(Z)-2-(7-formyl-3,3,6-trimethyl-3,4-dihydro-(2H)-isoquinolin-1-ylidene)-1-cycloheptylethan-1-one

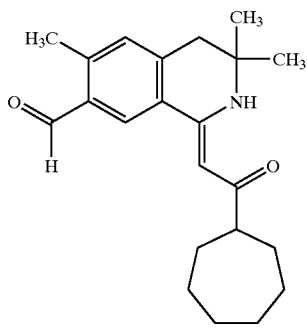

TLC: Rf 0.26 (hexane:ethyl acetate=5:1);

NMR (CDCl$_3$): δ 11.18 (br, 1H), 10.29 (s, 1H), 8.13 (s, 1H), 7.08 (s, 1H), 5.67 (s, 1H), 2.86 (s, 2H), 2.70 (s, 3H), 2.50 (m, 1H), 1.98–1.54 (m, 12H), 1.30 (s, 6H).

EXAMPLE 14

(Z)-2-(3,3-dimethyl-3,4-dihydro-(2H)-isoquinolin-1-ylidene)-1-(4-aminophenyl)ethan-1-one

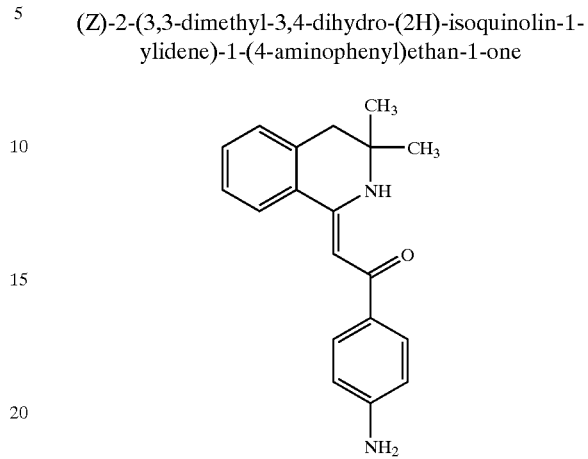

To a suspension of the compound prepared in example 11 (54) (312 mg) in acetic acid (10 ml) was added steel powder (1.35 g) at room temperature and the mixture was stirred for 40 minutes at 70° C. The reaction mixture was allowed to cool and thereto was added ice and 1N hydrochloric acid, and the mixture was filtered over celite. The filtrate was separated. The organic layer was extracted with 2N hydrochloric acid. The combined aqueous layer was alkalified by 5N aqueous solution of sodium hydroxide and was extracted with t-butyl methyl ether. The extract was washed with water and a saturated aqueous solution of sodium chloride and dried over anhydrous magnesium sulfate and was concentrated to give the compound of the present invention (229 mg) having the following physical data.

TLC: Rf 0.15 (hexane:ethyl acetate=2:1);

NMR (CDCl$_3$): δ 11.67 (br, 1H), 7.86–7.81 (m, 3H), 7.41 (t, J=7.5 Hz, 1H), 7.33 (t, J=7.5 Hz, 1H), 7.20 (d, J=7.5 Hz, 1H), 6.71–6.67 (m, 2H), 6.29 (s, 1H), 4.02–3.84 (br, 2H), 2.88 (s, 2H), 1.34 (s, 6H).

EXAMPLE 14(1)~EXAMPLE 14(15)

By the same procedure as described in example 14, using the compound prepared in Example 11(52), Example 11(53), Example 11(100), Example 11(126)~11(130), Example 11(150), Example 11(157), Example 11(195), Example 11(172), or Example 11(175)~11(177) in place of the compound prepared in Example 11(54), the following compounds of the present invention were given.

EXAMPLE 14(1)

(Z)-2-(3,3-dimethyl-3,4-dihydro-(2H)-isoquinolin-1-ylidene)-1-(2-aminophenyl)ethan-1-one

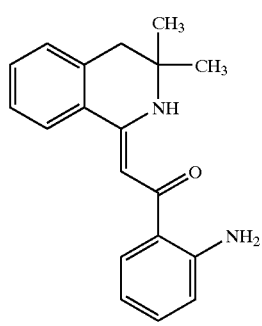

TLC: Rf 0.14 (chloroform:methanol=10:1);

NMR (CDCl$_3$): δ 8.43 (dd, J=8.0, 1.5 Hz, 1H), 7.62–7.56 (m, 2H), 7.48–7.32 (m, 5H), 6.35 (s, 1H), 2.82 (br, 2H), 1.43 (s, 6H).

EXAMPLE 14(2)

(Z)-2-(3,3-dimethyl-3,4-dihydro-(2H)-isoquinolin-1-ylidene)-1-(3-aminophenyl)ethan-1-one

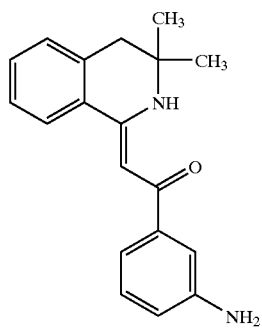

TLC: Rf 0.26 (hexane:ethyl acetate=1:1);

NMR (CDCl$_3$): δ 11.80 (br, 1H), 7.82 (d, J=7.5 Hz, 1H), 7.43 (t, J=7.5 Hz, 1H), 7.36–7.27 (m, 3H), 7.24–7.19 (m, 2H), 6.78 (ddd, J=8.0, 2.5, 1.0 Hz, 1H), 6.29 (s, 1H), 3.79 (br, 2H), 2.90 (s, 2H), 1.36 (s, 6H).

EXAMPLE 14(3)

(Z)-2-(7-amino-3,3-dimethyl-3,4-dihydro-(2H)-isoquinolin-1-ylidene)-1-phenylethan-1-one

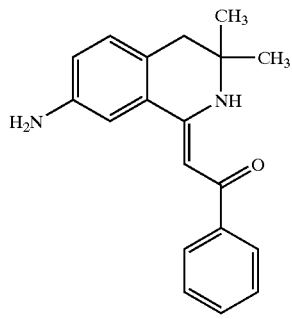

TLC: Rf 0.36 (hexane:ethyl acetate=1:1);

NMR (CDCl$_3$): δ 11.81 (brs, 1H), 7.97–7.92 (m, 2H), 7.46–7.41 (m, 3H), 7.14 (d, J=2.7 Hz, 1H), 7.00 (d, J=7.8 Hz, 1H), 6.77 (dd, J=7.8, 2.7 Hz, 1H), 6.24 (s, 1H), 3.74 (brs, 2H), 2.78 (s, 2H), 1.35 (s, 6H).

EXAMPLE 14(4)

(Z)-2-(7-amino-3,3-dimethyl-3,4-dihydro-(2H)-isoquinolin-1-ylidene)-1-(4-cyanophenyl)ethan-1-one

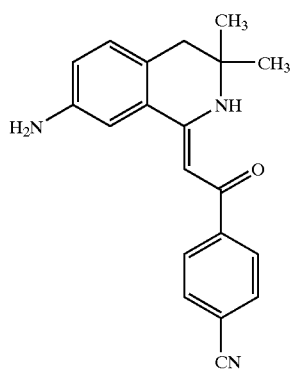

TLC: Rf 0.44 (ethyl acetate:hexane=1:1);

NMR (CDCl$_3$): δ 11.93 (br., 1H), 8.01 (d, J=8.5 Hz, 2H), 7.71 (d, J=8.5 Hz, 2H), 7.11 (d, J=2.5 Hz, 1H), 7.02 (d, J=8.0 Hz, 1H), 6.80 (dd, J=8.0, 2.5 Hz, 1H), 6.18 (s, 1H), 3.77 (br., 2H), 2.79 (s, 2H), 1.36 (s, 6H).

EXAMPLE 14(5)

(Z)-2-(7-amino-6-chloro-3,3-dimethyl-3,4-dihydro-(2H)-isoquinolin-1-ylidene)-1-cyclohexylethan-1-one

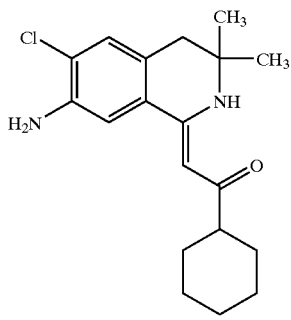

TLC: Rf 0.58 (ethyl acetate:hexane=1:2);

NMR (CDCl$_3$): δ 11.26 (br., 1H), 7.11 (s, 1H), 7.06 (s, 1H), 5.51 (s, 1H), 4.06 (br., 2H), 2.69 (s, 2H), 2.27 (m, 1H), 1.95–1.20 (m, 10H), 1.27 (s, 6H).

EXAMPLE 14(6)

(Z)-2-(7-amino-6-chloro-3,3-dimethyl-3,4-dihydro-(2H)-isoquinolin-1-ylidene)-1-cycloheptylethan-1-one

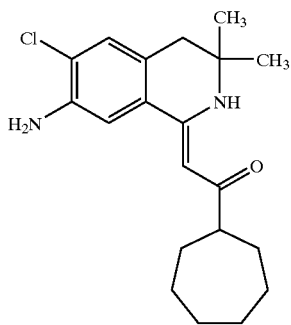

TLC: Rf 0.63 (ethyl acetate:hexane=1:2);

NMR (CDCl$_3$): δ 11.17 (br., 1H), 7.10 (s, 1H), 7.06 (s, 1H), 5.47 (s, 1H), 4.06 (br., 2H), 2.69 (s, 2H), 2.44 (m, 1H), 2.00–1.40 (m, 12H), 1.27 (s, 6H).

EXAMPLE 14(7)

(Z)-2-(7-amino-6-chloro-3,3-dimethyl-3,4-dihydro-(2H)-isoquinolin-1-ylidene)-1-(4-cyanophenyl)ethan-1-one

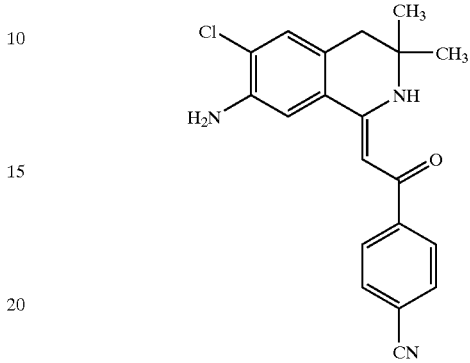

TLC: Rf 0.40 (ethyl acetate:hexane=1:2);

NMR (CDCl$_3$): δ 11.90 (br., 1H), 8.00 (d, J=8.5 Hz, 2H), 7.72 (d, J=8.5 Hz, 2H), 7.19 (s, 1H), 7.13 (s, 1H), 6.14 (s, 1H), 4.14 (br., 2H), 2.78 (s, 2H), 1.36 (s, 6H).

EXAMPLE 14(8)

(Z)-2-(7-amino-6-chloro-3,3-dimethyl-3,4-dihydro-(2H)-isoquinolin-1-ylidene)-1-(adamantan-1-yl)ethan-1-one

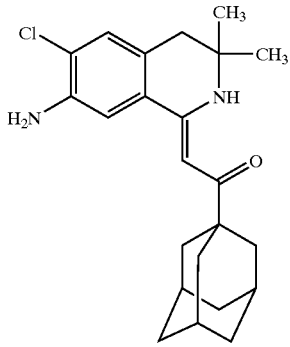

TLC: Rf 0.68 (ethyl acetate:hexane=1:2);

NMR (CDCl$_3$): δ 11.43 (br., 1H), 7.12 (s, 1H), 7.07 (s, 1H), 5.65 (s, 1H), 4.08 (br., 2H), 2.69 (s, 2H), 2.05 (m, 3H), 1.90 (m, 6H), 1.74 (m, 6H), 1.27 (s, 6H).

EXAMPLE 14(9)

(Z)-2-(7-amino-3,3-dimethyl-3,4-dihydro-(2H)-isoquinolin-1-ylidene)-1-cyclohexylethan-1-one

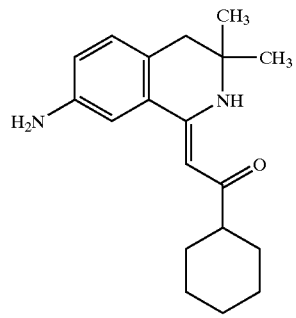

TLC: Rf 0.15 (ethyl acetate:hexane=1:3);

NMR (CDCl$_3$): δ 11.29 (br., 1H), 7.02 (d, J=2.5 Hz, 1H), 6.95 (d, J=8.0 Hz, 1H), 6.73 (dd, J=8.0, 2.5 Hz, 1H), 5.54 (s, 1H), 3.69 (br., 2H), 2.71 (s, 2H), 2.28 (m, 1H), 1.95–1.20 (m, 10H), 1.27 (s, 6H).

EXAMPLE 14(10)

(Z)-2-(7-amino-3,3-dimethyl-3,4-dihydro-(2H)-isoquinolin-1-ylidene)-1-(adamantan-1-yl)ethan-1-one

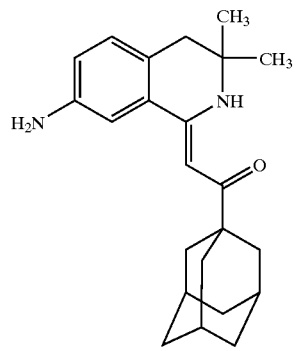

TLC: Rf 0.57 (hexane:ethyl acetate=1:1);

NMR (CDCl$_3$): δ 11.46 (brs, 1H), 7.04 (d, J=2.4 Hz, 1H), 6.95 (d, J=8.4 Hz, 1H), 6.73 (dd, J=8.4, 2.4 Hz, 1H), 5.69 (s, 1H), 3.72 (brs, 2H), 2.71 (s, 2H), 2.05 (brs, 3H), 1.93–1.89 (m, 6H), 1.77–1.72 (m, 6H), 1.27 (s, 6H).

EXAMPLE 14(11)

(Z)-2-(7-amino-3,3-dimethyl-3,4-dihydro-(2H)-isoquinolin-1-ylidene)-1-cycloheptylethan-1-one

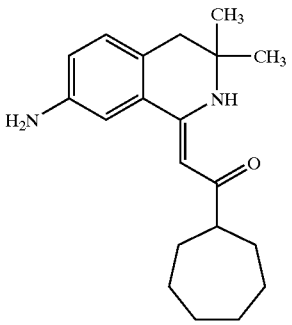

TLC: Rf 0.57 (hexane:ethyl acetate=1:1);

NMR (CDCl$_3$): δ 11.20 (brs, 1H), 7.02 (d, J=2.4 Hz, 1H), 6.95 (d, J=7.8 Hz, 1H), 6.73 (dd, J=7.8, 2.4 Hz, 1H), 5.51 (s, 1H), 3.69 (brs, 2H), 2.71 (s, 2H), 2.44 (m, 1H), 1.97–1.42 (m, 12H), 1.27 (s, 6H).

EXAMPLE 14(12)

(Z)-2-(7-amino-3,3,6-trimethyl-3,4-dihydro-(2H)-isoquinolin-1-ylidene)-1-(adamantan-1-yl)ethan-1-one

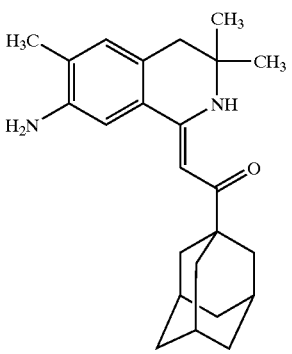

TLC: Rf 0.21 (ethyl acetate:hexane=1:4);

NMR (CDCl$_3$): δ 11.45 (br, 1H), 7.02 (s, 1H), 6.84 (s, 1H), 5.67 (s, 1H), 3.66 (br, 2H), 2.69 (s, 2H), 2.19 (s, 3H), 2.05 (br, 3H), 1.92–1.91 (br, 6H), 1.75–1.74 (br, 6H), 1.27 (s, 6H).

EXAMPLE 14(13)

(Z)-2-(7-amino-3,3,6-trimethyl-3,4-dihydro-(2H)-isoquinolin-1-ylidene)-1-(4-cyanophenyl)ethan-1-one

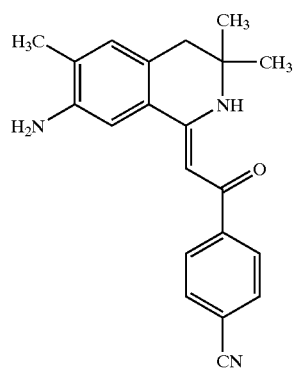

TLC: Rf 0.31 (hexane:ethyl acetate=3:2);

NMR (CDCl$_3$): δ 11.91 (br, 1H), 8.01 (d, J=8.7 Hz, 2H), 7.72 (d, J=8.7 Hz, 2H), 7.09 (s, 1H), 6.91 (s, 1H), 6.17 (s, 1H), 3.71 (br, 2H), 2.78 (s, 2H), 2.22 (s, 3H), 1.36 (s, 6H).

EXAMPLE 14(14)

(Z)-2-(7-amino-3,3,6-trimethyl-3,4-dihydro-(2H)-isoquinolin-1-ylidene)-1-cyclohexylethan-1-one

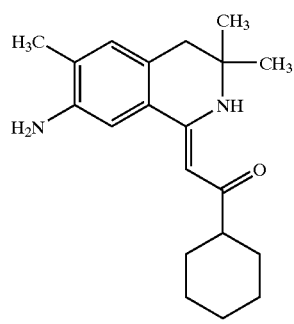

TLC: Rf 0.37 (hexane:ethyl acetate=2:1);

NMR (CDCl$_3$): δ 11.28 (brs, 1H), 7.01 (s, 1H), 6.84 (s, 1H), 5.53 (s, 1H), 3.62 (brs, 2H), 2.69 (s, 2H), 2.27 (tt, J=12.0, 3.3 Hz, 1H), 2.19 (s, 3H), 1.92–1.18 (m, 16H).

EXAMPLE 14(15)

(Z)-2-(7-amino-3,3,6-trimethyl-3,4-dihydro-(2H)-isoquinolin-1-ylidene)-1-cycloheptylethan-1-one

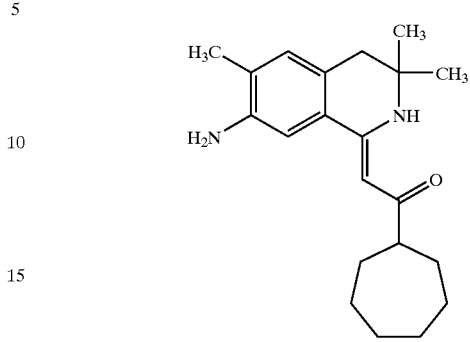

TLC: Rf 0.40 (hexane:ethyl acetate=2:1);

NMR (CDCl$_3$): δ 11.19 (brs, 1H), 7.00 (s, 1H), 6.84 (s, 1H), 5.49 (s, 1H), 3.62 (brs, 2H), 2.69 (s, 2H), 2.43 (tt, J=9.9, 3.6 Hz, 1H), 2.19 (s, 3H), 1.96–1.42 (m, 12H), 1.27 (s, 6H).

EXAMPLE 15

(Z)-2-(6-carboxy-3,3-dimethyl-3,4-dihydro-(2H)-isoquinolin-1-ylidene)-1-phenylethan-1-one

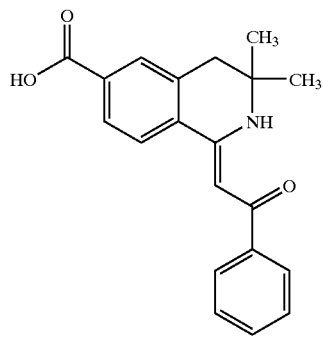

To a solution of the compound prepared in example 12 (356 mg) in ether (10 ml (was added t-butyl lithium (2.2 ml; 1.5M pentane solution) at −78° C. and 5 minutes later the mixture was bubbled with carbon dioxide gas. The reaction mixture was allowed to warm to room temperature and to the mixture was added water and ethyl acetate and the mixture was separated. The organic layer was extracted with water. The combined aqueous layer was azeotroped with ethanol. To the given solid was added ethanol and was filtered and the filtrate was concentrated. The residue was purified by column chromatography on silica gel (hexane:ethyl acetate= 1:1) to give the compound of the present invention (19 mg) having the following physical data.

TLC: Rf 0.25 (hexane:ethyl acetate=1:1);

NMR (CDCl$_3$): δ 11.76 (br, 1H), 8.06 (dd, J=8.0, 1.5 Hz, 1H), 7.97–7.92 (m, 4H), 7.49–7.42 (m, 3H), 6.38 (s, 1H), 2.98 (s, 2H), 1.39 (s, 6H).

EXAMPLE 15(1)–EXAMPLE 15(14)

By the same procedure as described in example 15 using the compound prepared in example 11(7), Example 11(168), Example 12(28), Example 12(29), Example 11(188), Example 11(193), Example 11(181), Example 11(156), Example 11(189), Example 11(170), Example 11(184), Example 111(194), Example 12(30) or Example 12(31) in place of the compound prepared in example 12, the following compounds of the present invention were given.

EXAMPLE 15(1)

(Z)-2-(7-carboxy-3,3-dimethyl-3,4-dihydro-(2H)-isoquinolin-1-ylidene)-1-phenylethan-1-one

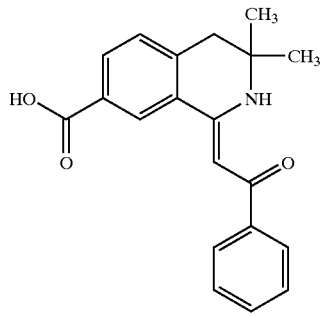

TLC: Rf 0.13 (hexane:ethyl acetate=1:1);

NMR (CDCl$_3$): δ 11.84 (br, 1H), 8.57 (d, J=2.0 Hz, 1H), 8.16 (dd, J=8.0, 2.0 Hz, 1H), 8.00–7.96 (m, 2H), 7.48–7.44 (m, 3H), 7.35 (d, J=8.0 Hz, 1H), 6.43 (s, 1H), 2.99 (s, 2H), 1.39 (s, 6H).

EXAMPLE 15(2)

(Z)-2-(7-carboxy-3,3-dimethyl-3,4-dihydro-(2H)-isoquinolin-1-ylidene)-1-(adamantan-1-yl)ethan-1-one

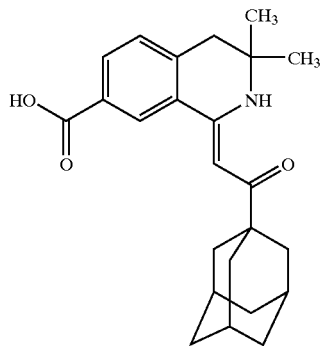

TLC: Rf 0.27 (chloroform:methanol=10:1);

NMR (CDCl$_3$): δ 11.52 (br, 1H), 8.45 (d, J=1.5 Hz, 1H), 8.12 (dd, J=8.0, 1.5 Hz, 1H), 7.31 (d, J=8.0 Hz, 1H), 5.87 (s, 1H), 2.92 (s, 2H), 2.08 (br, 3H), 1.93 (br, 6H), 1.77 (br, 6H), 1.31 (s, 6H).

EXAMPLE 15(3)

(Z)-2-(6-carboxy-3,3-dimethyl-3,4-dihydro-(2H)-isoquinolin-1-ylidene)-1-cyclohexylethan-1-one

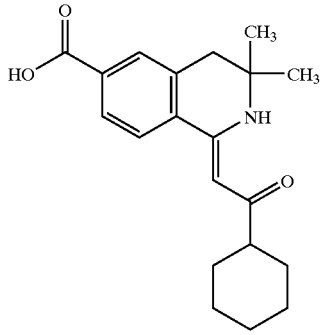

TLC: Rf 0.36 (chloroform:methanol=10:1);

NMR (CDCl$_3$): δ 11.25 (br, 1H), 8.01 (dd, J=8.0, 1.5 Hz, 1H), 7.92 (d, J=1.5 Hz, 1H), 7.81 (d, J=8.0 Hz, 1H), 5.69 (s, 1H), 2.91 (s, 2H), 2.33 (m, 1H), 1.91–1.80 (m, 4H), 1.72 (m, 1H), 1.50–1.20 (m, 11H).

EXAMPLE 15(4)

(Z)-2-(6-carboxy-3,3-dimethyl-3,4-dihydro-(2H)-isoquinolin-1-ylidene)-1-cycloheptylethan-1-one

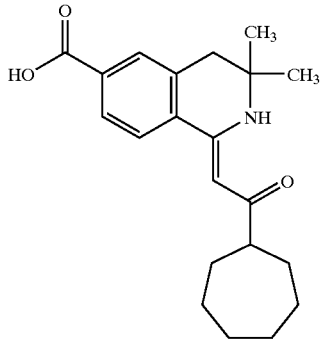

TLC: Rf 0.39 (chloroform:methanol=10:1);

NMR (CDCl$_3$): δ 11.16 (br, 1H), 8.02 (dd, J=8.5, 1.5 Hz, 1H), 7.92 (d, J=1.5 Hz, 1H), 7.81 (d, J=8.5 Hz, 1H), 5.66 (s, 1H), 2.91 (s, 2H), 2.50 (m, 1H), 1.97–1.90 (m, 2H), 1.84–1.45 (m, 10H), 1.31 (s, 6H).

EXAMPLE 15(5)

(Z)-2-(7-carboxy-3,3-dimethyl-3,4-dihydro-(2H)-isoquinolin-1-ylidene)-1-cyclohexylethan-1-one

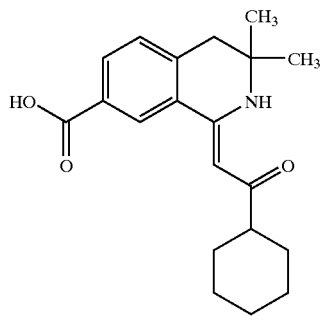

TLC: Rf 0.24 (hexane:ethyl acetate=1:1);

NMR (CDCl$_3$): δ 11.29 (brs, 1H), 8.45 (d, J=1.8 Hz, 1H), 8.11 (dd, J=7.8, 1.8 Hz, 1H), 7.30 (d, J=7.8 Hz, 1H), 5.73 (s, 1H), 2.92 (s, 2H), 2.35 (m, 1H), 1.95–1.65 (m, 5H), 1.54–1.20 (m, 11H).

EXAMPLE 15(6)

(Z)-2-(7-carboxy-3,3-dimethyl-3,4-dihydro-(2H)-isoquinolin-1-ylidene)-1-cycloheptylethan-1-one

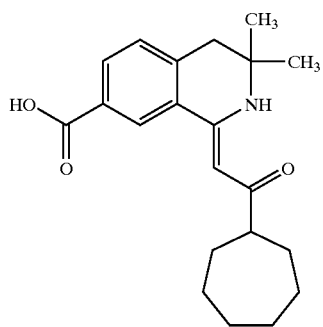

TLC: Rf 0.30 (hexane:ethyl acetate=1:1);

NMR (CDCl$_3$): δ 11.22 (brs, 1H), 8.45 (d, J=1.8 Hz, 1H), 8.12 (dd, J=7.8, 1.8 Hz, 1H), 7.30 (d, J=7.8 Hz, 1H), 5.71 (s, 1H), 2.92 (s, 2H), 2.52 (tt, J=9.9, 3.6 Hz, 1H), 1.99–1.45 (m, 12H), 1.31 (s, 6H).

EXAMPLE 15(7)

(Z)-2-(7-carboxy-6-methoxy-3,3-dimethyl-3,4-dihydro-(2H)-isoquinolin-1-ylidene)-1-cycloheptylethan-1-one

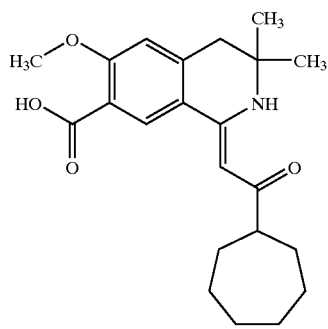

TLC: Rf 0.09 (hexane:ethyl acetate=1:1);

NMR (CDCl$_3$): δ 11.17 (br, 1H), 10.40 (br, 1H), 8.54 (s, 1H), 6.85 (s, 1H), 5.67 (s, 1H), 4.13 (s, 3H), 2.89 (s, 2H), 2.49 (tt, J=10.0, 4.0 Hz, 1H), 1.94–1.87 (m, 2H), 1.83–1.48 (m, 10H), 1.30 (s, 6H).

EXAMPLE 15(8)

(Z)-2-(7-carboxy-6-methoxy-3,3-dimethyl-3,4-dihydro-(2H)-isoquinolin-1-ylidene)-1-(adamantan-1-yl)ethan-1-one

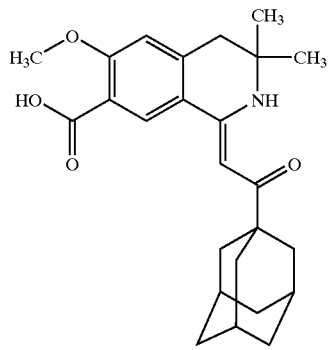

TLC: Rf 0.10 (hexane:ethyl acetate=1:1);

NMR (CDCl$_3$): δ 11.50 (br, 1H), 10.40 (br, 1H), 8.55 (s, 1H), 6.85 (s, 1H), 5.83 (s, 1H), 4.14 (s, 3H), 2.89 (s, 2H), 2.06 (br, 3H), 1.91 (br, 6H), 1.75 (br, 6H), 1.31 (s, 6H).

EXAMPLE 15(9)

(Z)-2-(7-carboxy-3,3,6-trimethyl-3,4-dihydro-(2H)-isoquinolin-1-ylidene)-1-cyclohexylethan-1-one

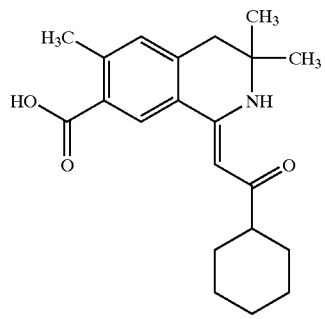

TLC: Rf 0.16 (hexane:ethyl acetate=3:1);

NMR (CDCl$_3$): δ 11.29 (br, 1H), 8.41 (s, 1H), 7.10 (s, 1H), 5.69 (s, 1H), 2.85 (s, 2H), 2.68 (s, 3H), 2.34 (m, 1H), 1.91–1.20 (m, 16H).

EXAMPLE 15(10)

(Z)-2-(7-carboxy-6-methoxy-3,3-dimethyl-3,4-dihydro-(2H)-isoquinolin-1-ylidene)-1-cyclohexylethan-1-one

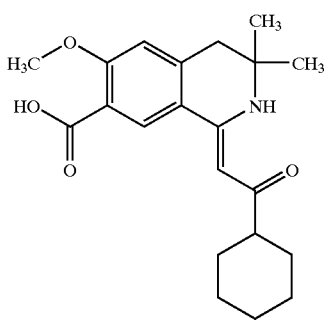

TLC: Rf 0.07 (hexane:ethyl acetate=1:1);

NMR (CDCl$_3$): δ 11.23 (br, 1H), 10.40 (br, 1H), 8.54 (s, 1H), 6.85 (s, 1H), 5.71 (s, 1H), 4.13 (s, 3H), 2.89 (s, 2H), 2.32 (tt, J=11.5, 3.5 Hz, 1H), 1.89–1.79 (m, 4H), 1.70 (m, 1H), 1.56–1.21 (m, 11H).

EXAMPLE 15(11)

(Z)-2-(7-carboxy-3,3,6-trimethyl-3,4-dihydro-(2H)-isoquinolin-1-ylidene)-1-(adamantan-1-yl)ethan-1-one

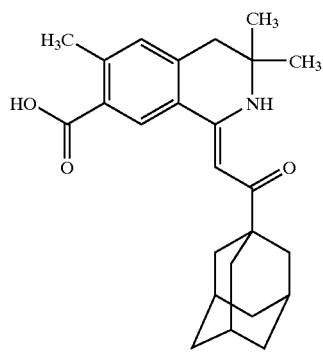

TLC: Rf 0.25 (hexane:ethyl acetate=2:1);

NMR (CDCl$_3$): δ 11.51 (br, 1H), 8.41 (s, 1H), 7.10 (s, 1H), 5.83 (s, 1H), 2.85 (s, 2H), 2.69 (s, 3H), 2.07–2.05 (br, 3H), 1.93–1.92 (br, 6H), 1.76–1.75 (br, 6H), 1.31 (s, 6H).

EXAMPLE 15(12)

(Z)-2-(7-carboxy-3,3,6-trimethyl-3,4-dihydro-(2H)-isoquinolin-1-ylidene)-1-cycloheptylethan-1-one

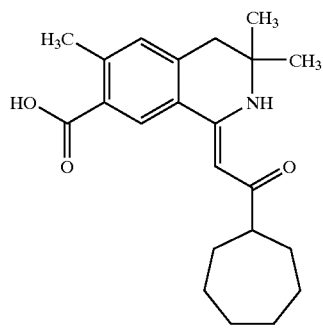

TLC: Rf 0.13 (hexane:ethyl acetate=3:1);

NMR (CDCl$_3$): δ 11.22 (br, 1H), 8.42 (s, 1H), 7.10 (s, 1H), 5.66 (s, 1H), 2.85 (s, 2H), 2.69 (s, 3H), 2.50 (m, 1H), 1.98–1.64 (m, 12H), 1.31 (s, 6H).

EXAMPLE 15(13)

(Z)-2-(6-carboxy-3,3-dimethyl-3,4-dihydro-(2H)-isoquinolin-1-ylidene)-1-(adamantan-1-yl)ethan-1-one

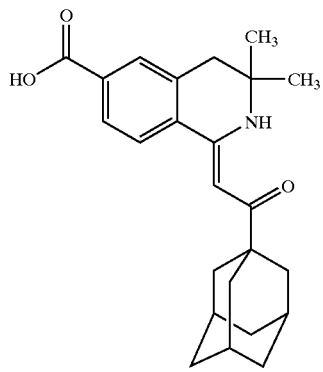

TLC: Rf 0.08 (hexane:ethyl acetate=2:1);

NMR (CDCl₃): δ 11.39 (br, 1H), 7.99 (br, 1H), 7.88 (s, 1H), 7.78 (br, 1H), 5.82 (s, 1H), 2.86 (s, 2H), 2.06 (br, 3H), 1.91 (br, 6H), 1.74 (br, 6H), 1.28 (s, 6H).

EXAMPLE 15(14)

(Z)-2-(6-carboxy-3,3-dimethyl-3,4-dihydro-(2H)-isoquinolin-1-ylidene)-1-(pyridin-3-yl)ethan-1-one

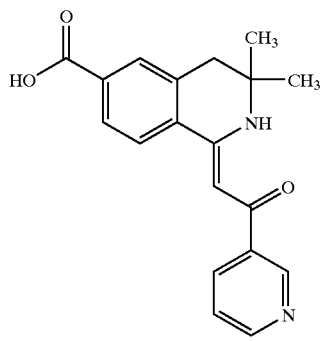

TLC: Rf 0.31 (methylene chloride:methanol=10:1);

NMR (CDCl₃ + a few drops of CD₃OD): δ 9.17 (d, J=1.5 Hz, 1H), 8.67 (dd, J=4.5, 1.5 Hz, 1H), 8.27 (ddd, J=8.5, 1.5, 1.5 Hz, 1H), 8.06 (dd, J=8.5, 2.0 Hz, 1H), 7.94–7.91 (m, 2H), 7.44 (dd, J=8.5, 4.5 Hz, 1H), 6.35 (s, 1H), 2.98 (s, 2H), 1.39 (s, 6H).

EXAMPLE 16~EXAMPLE 16(6)

By the same procedure as described in example 5 using the compound prepared in example 12(10), example 11(57), example 11(2), example 11(123), example 11(200), example 11(64) or example 11(32) in place of the compound prepared in example 1(18), the following compounds of the present invention were given.

EXAMPLE 16

(Z)-2-(3,3,4,4-tetramethyl-3,4-dihydro-(2H)-isoquinolin-1-ylidene)-1-(2-hydroxyphenyl)ethan-1-one

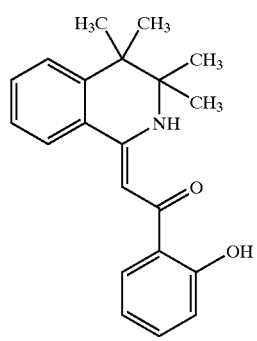

TLC: Rf 0.60 (hexane:ethyl acetate=3:1);

NMR (CDCl₃): δ 13.65 (s, 1H), 11.29 (br, 1H), 7.81 (d, J=7.5 Hz, 1H), 7.76 (dd, J=8.0, 1.5 Hz, 1H), 7.54–7.49 (m, 1H), 7.44 (dd, J=8.0, 1.5 Hz, 1H), 7.38–7.30 (m, 2H), 6.94 (dd, J=7.0, 1.5 Hz, 1H), 6.83 (dt, J=1.5, 7.5 Hz, 1H), 6.30 (s, 1H), 1.31 (br, 12H).

EXAMPLE 16(1)

(Z)-2-(7-hydroxy-3,3-dimethyl-3,4-dihydro-(2H)-isoquinolin-1-ylidene)-1-(naphthalen-1-yl)ethan-1-one

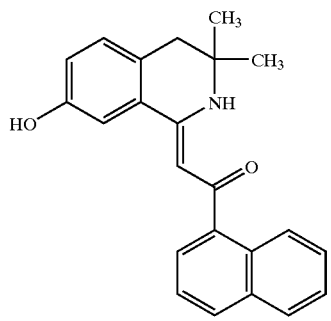

TLC: Rf 0.44 (ethyl acetate:hexane=1:2);

NMR (CDCl₃): δ 11.70 (br., 1H), 8.45 (m, 1H), 7.90–7.80 (m, 2H), 7.62 (dd, J=7.0, 1.0 Hz, 1H), 7.50–7.40 (m, 2H), 7.38 (dd, J=8.0, 7.0 Hz, 1H), 7.10 (d, J=2.5 Hz, 1H), 7.00 (d, J=8.5 Hz, 1H), 6.85 (dd, J=8.5, 2.5 Hz, 1H), 6.04 (br., 1H), 5.94 (br., 1H), 2.79 (s, 2H), 1.34 (s, 6H).

EXAMPLE 16(2)

(Z)-2-(7-hydroxy-3,3-dimethyl-3,4-dihydro-(2H)-isoquinolin-1-ylidene)-1-phenylethan-1-one

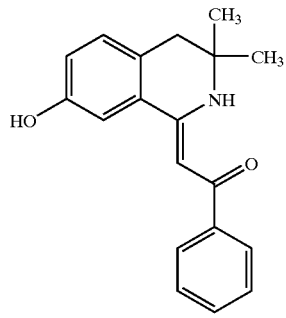

TLC: Rf 0.14 (ethyl acetate:hexane=1:5);

NMR (CDCl$_3$): δ 11.76 (br., 1H), 7.91 (m, 2H), 7.50–7.35 (m, 3H), 7.26 (d, J=2.5 Hz, 1H), 7.05 (d, J=8.5 Hz, 1H), 6.93 (dd, J=8.5, 2.5 Hz, 1H), 6.24 (s, 1H), 5.95 (s, 1H), 2.78 (s, 2H), 1.30 (s, 6H).

EXAMPLE 16(3)

(Z)-2-(5-hydroxy-3,3-dimethyl-3,4-dihydro-(2H)-isoquinolin-1-ylidene)-1-phenylethan-1-one

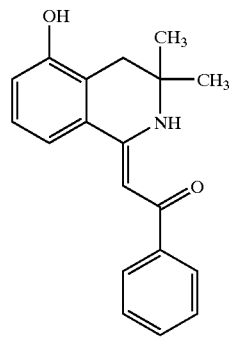

TLC: Rf 0.25 (hexane:ethyl acetate=2:1);

NMR (DMSO-d$_6$): δ 11.87 (brs, 1H), 9.80 (s, 1H), 7.98–7.93 (m, 2H), 7.52 (d, J=8.4 Hz, 1H), 7.48–7.40 (m, 3H), 7.18 (t, J=8.4 Hz, 1H), 7.01 (d, J=8.4 Hz, 1H), 6.39 (s, 1H), 2.81 (s, 2H), 1.28 (s, 6H).

EXAMPLE 16(4)

(Z)-2-(6-chloro-7-hydroxy-3,3-dimethyl-3,4-dihydro-(2H)-isoquinolin-1-ylidene)-1-(adamantan-1-yl)ethan-1-one

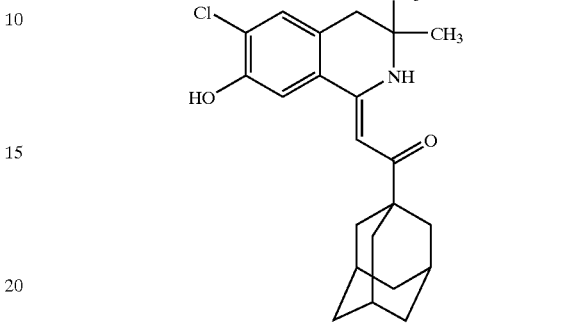

TLC: Rf 0.28 (ethyl acetate:hexane=5:1);

NMR (CDCl$_3$): δ 11.38 (br., 1H), 7.39 (s, 1H), 7.14 (s, 1H), 5.70 (s, 1H), 5.60 (br., 1H), 2.73 (s, 2H), 2.04 (m, 3H), 1.89 (m, 6H), 1.73 (m, 6H), 1.28 (s, 6H).

EXAMPLE 16(5)

(Z)-2-(7-hydroxy-3,3-dimethyl-3,4-dihydro-(2H)-isoquinolin-1-ylidene)-1-(adamantan-1-yl)ethan-1-one

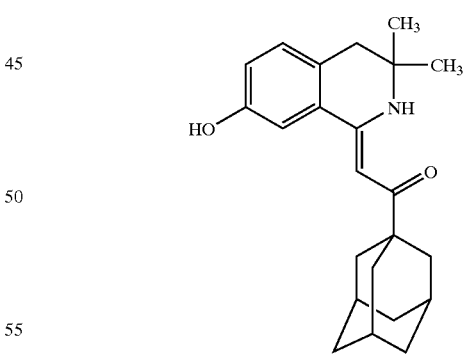

TLC: Rf 0.18 (ethyl acetate:hexane=1:4);

NMR (CDCl$_3$): δ 11.42 (br, 1H), 7.21 (d, J=2.4 Hz, 1H), 7.04 (d, J=8.1 Hz, 1H), 6.88 (dd, J=2.4, 8.1 Hz, 1H), 5.71 (s, 1H), 5.16 (br, 1H), 2.75 (s, 2H), 2.05 (br, 3H), 1.91–1.90 (br, 6H), 1.73 (br, 6H), 1.27 (s, 6H).

EXAMPLE 16(6)

(Z)-2-(7-hydroxy-3,3-dimethyl-3,4-dihydro-(2H)-isoquinolin-1-ylidene)-1-cyclohexylethan-1-one

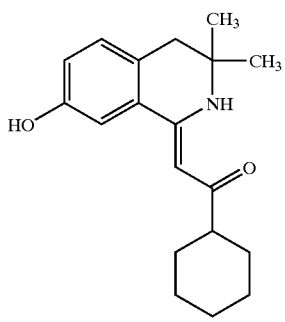

TLC: Rf 0.13 (ethyl acetate:hexane=1:4);

NMR (CDCl$_3$): δ 11.27 (br, 1H), 7.19 (d, J=2.4 Hz, 1H), 7.03 (d, J=8.1 Hz, 1H), 6.89 (dd, J=2.4, 8.1 Hz, 1H), 5.57 (s, 1H), 2.75 (s, 2H), 2.28 (m, 1H), 1.92–1.18 (m, 16H).

EXAMPLE 17~EXAMPLE 17(1)

By the same procedure as described in example 9 using the compound prepared in example 11 (7) in place of the compound prepared in example 1 (68) and benzeneboronic acid or pyridin-3-ylboronic acid in its place, the compounds of the present invention were given.

EXAMPLE 17

(Z)-2-(7-phenyl-3,3-dimethyl-3,4-dihydro-(2H)-isoquinolin-1-ylidene)-1-phenylethan-1-one

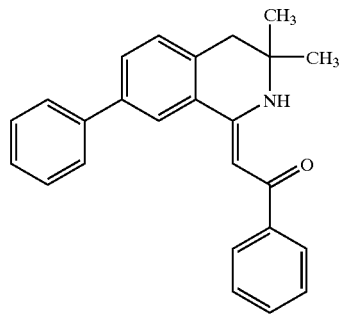

TLC: Rf 0.44 (hexane:ethyl acetate=3:1);

NMR (CDCl$_3$): δ 11.88 (br, 1H), 8.01 (d, J=2.0 Hz, 1H), 7.97–7.94 (m, 2H), 7.66–7.62 (m, 3H), 7.52–7.40 (m, 6H), 7.30 (d, J=8.0 Hz, 1H), 6.39 (s, 1H), 2.95 (s, 2H), 1.40 (s, 6H).

EXAMPLE 17(1)

(Z)-2-(7-(pyridin-3-yl)-3,3-dimethyl-3,4-dihydro-(2H)-isoquinolin-1-ylidene)-1-phenylethan-1-one

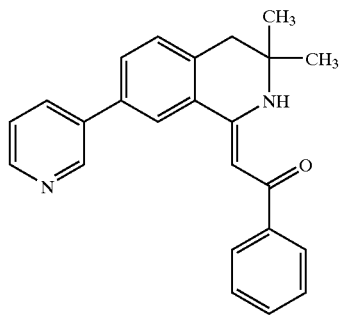

TLC: Rf 0.32 (hexane:ethyl acetate=1:1);

NMR (CDCl$_3$): δ 11.87 (br, 1H), 8.90 (d, J=1.5 Hz, 1H), 8.65 (dd, J=5.0, 1.5 Hz, 1H), 8.00–7.91 (m, 4H), 7.64 (dd, J=8.0, 1.5 Hz, 1H), 7.46–7.41 (m, 4H), 7.35 (d, J=7.5 Hz, 1H), 6.38 (s, 1H), 2.96 (s, 2H), 1.41 (s, 6H).

EXAMPLE 18

(Z)-2-(6-(morpholin-4-yl)-3,3-dimethyl-3,4-dihydro-(2H)-isoquinolin-1-ylidene)-1-phenylethan-1-one

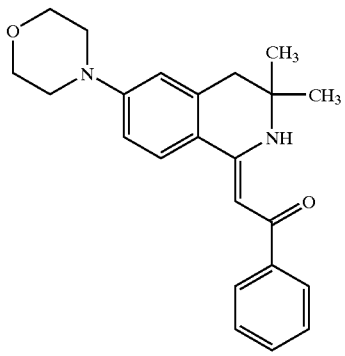

To a solution of the compound prepared in example 12 (180 mg) in toluene (5 ml) were added morpholine (0.060 ml) and sodium t-butylate (70.5 mg) and the mixture was degassed. Thereto was added dichlorobis(tri-O-tolylphosphine)palladium (II) (12 mg) and the mixture was stirred for 8 hours at 100° C. To the reaction mixture was added dichlorobis(tri-O-tolylphosphine)palladium (II) (12 mg) and the mixture was stirred for 2 hours. The reaction mixture was allowed to cool and was concentrated. The residue was purified by column chromatography on silica gel (hexane:ethyl acetate=4:1) to give the compound of the present invention (65 mg) having the following physical data.

TLC: Rf 0.30 (hexane:ethyl acetate=1:1);

NMR (CDCl$_3$): δ 11.81 (brs, 1H), 7.98–7.90 (m, 2H), 7.73 (d, J=8.7 Hz, 1H), 7.45–7.39 (m, 3H), 6.81 (dd, J=8.7, 2.7 Hz, 1H), 6.65 (d, J=2.7 Hz, 1H), 6.24 (s, 1H), 3.88 (t, J=4.8 Hz, 4H), 3.29 (t, J=4.8 Hz, 4H), 2.83 (s, 2H), 1.36 (s, 6H).

EXAMPLE 18(1)

(Z)-2-(7-(morpholin-4-yl)-3,3-dimethyl-3,4-dihydro-(2H)-isoquinolin-1-ylidene)-1-phenylethan-1-one

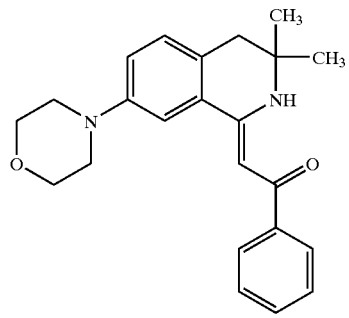

By the same procedure as described in example 18 using the compound prepared in example 11(7) in place of the compound prepared in example 12, the compound of the present invention having the following physical data was given.

TLC: Rf 0.44 (hexane:ethyl acetate=1:1);

NMR (CDCl$_3$): δ 11.87 (brs, 1H), 7.97–7.90 (m, 2H), 7.48–7.41 (m, 3H), 7.32 (d, J=2.4 Hz, 1H), 7.12 (d, J=8.1 Hz, 1H), 7.00 (dd, J=8.1, 2.4 Hz, 1H), 6.25 (s, 1H), 3.91 (t, J=4.8 Hz, 4H), 3.21 (t, J=4.8 Hz, 4H), 2.82 (s, 2H), 1.35 (s, 6H).

EXAMPLE 19

(Z)-2-(6-chloro-7-propoxycarbonyl-3,3-dimethyl-3,4-dihydro-(2H)-isoquinolin-1-ylidene)-1-cyclohexylethan-1-one

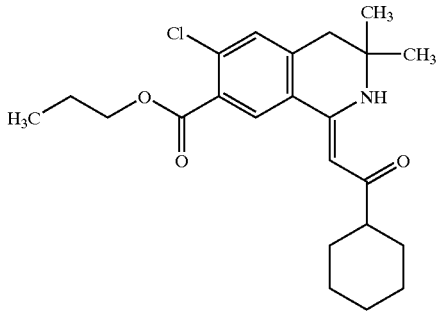

To n-propanol (5 ml) were added the compound prepared in example 11(153) (198 mg), dichlorobis(triphenylphosphine)palladium (II) (35 mg) and triethylamine (0.14 ml) and under atmosphere of carbon monoxide the mixture was stirred overnight at 100° C. To the reaction mixture were added dichlorobis(triphenylphosphine) palladium (II) (315 mg) and triethylamine (0.84 ml) and the mixture was stirred overnight at 100° C. The reaction mixture was filtered over Celite. The filtrate was added to water and the mixture was extracted with ethyl acetate. The extract was washed with a saturated aqueous solution of sodium chloride and was dried over anhydrous magnesium sulfate and was concentrated. The residue was purified by column chromatography on silica gel (hexane:chloroform=3:2→2:3) to give the compound of the present invention (140 mg) having the following physical data.

TLC: Rf 0.31 (ethyl acetate:hexane=1:5);

NMR (CDCl$_3$): δ 11.22 (br, 1H), 8.16 (s, 1H), 7.28 (s, 1H), 5.63 (s, 1H), 4.35 (t, J=6.5 Hz, 2H), 2.83 (s, 2H), 2.32 (m, 1H), 1.90–1.20 (m, 12H), 1.29 (s, 6H), 1.07 (t, J=7.5 Hz, 3H).

EXAMPLE 20

(Z)-2-(3,3-dimethyl-3,4-dihydro-(2H)-isoquinolin-1-ylidene)-1-(4-methylsulfynylphenyl)ethan-1-one

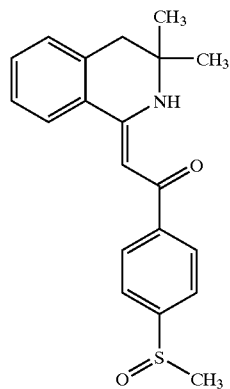

To a solution of the compound prepared in example 11(83) (296 mg) in acetone (4 ml) was added a suspension of oxone (844 mg, a brand name) in water/a saturated aqueous solution of sodium bicarbonate/acetone (2 ml/2 ml/2 ml) and the mixture was stirred for 45 minutes at 0° C. To the reaction mixture was added water and the mixture was extracted with ethyl acetate. The extract was washed with water and a saturated aqueous solution of sodium chloride, and was dried over anhydrous magnesium sulfate and was concentrated. The residue was purified roughly by column chromatography on silica gel (hexane:ethyl acetate=3:1→1:2). The product was further roughly purified by column chromatography on silica gel (chloroform:methanol=100:0→100:1). The product was washed with a mixture of t-butyl methyl ether/hexane to give the compound of the present invention (20 mg) having the following physical data.

TLC: Rf 0.07 (hexane:ethyl acetate=1:2);

NMR (CDCl$_3$): δ 11.91 (br, 1H), 8.09 (d, J=8.5 Hz, 2H), 7.84 (d, J=7.5 Hz, 1H), 7.71 (d, J=8.5 Hz, 2H), 7.46 (t, J=7.5 Hz, 1H), 7.36 (t, J=7.5 Hz, 1H), 7.23 (d, J=7.5 Hz, 1H), 6.31 (s, 1H), 2.92 (s, 2H), 2.76 (s, 3H), 1.38 (s, 6H).

EXAMPLE 21

(Z)-2-(6-cyano-3,3-dimethyl-3,4-dihydro-(2H)-isoquinolin-1-ylidene)-1-phenylethan-1-one

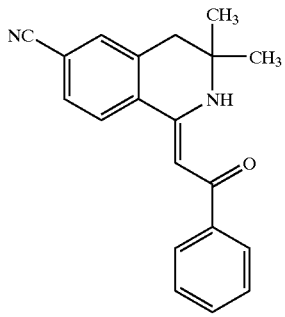

To a solution of the compound prepared in example 1(68) (312 mg) in N-methylpyrrolidone (3 ml) was added cuprous cyanide (448 mg) at room temperature and the mixture was stirred for 19 hours at 180–190° C. The reaction mixture was allowed to cool and thereto was added a saturated aqueous solution of sodium bicarbonate and was extracted with ethyl acetate. The extract was washed with water and a saturated aqueous solution of sodium chloride successively, dried over anhydrous magnesium sulfate and was concentrated. The residue was purified by column chromatography on silica gel (hexane:ethyl acetate=20:1→15:1) to give the compound of the present invention (450 mg) having the following physical data.

TLC: Rf 0.43 (hexane:ethyl acetate=3:1);

NMR (CDCl$_3$): δ 11.75 (br, 1H), 7.95–7.91 (m, 3H), 7.64 (d, J=8.0 Hz, 1H), 7.53 (s, 1H), 7.49–7.41 (m, 3H), 6.33 (br, 1H), 2.94 (s, 2H), 1.38 (s, 6H).

EXAMPLE 22

(Z)-2-(7-(1-hydroxy-1-methylethyl)-3,3-dimethyl-3,4-dihydro-(2H)-isoquinolin-1-ylidene)-1-phenylethan-1-one

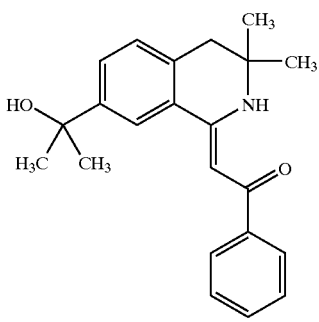

To a solution of the compound prepared in example 11(7) (186 mg) in ether (4 ml) was added n-butyl lithium (1.4 ml, 1.5 M solution in hexane) dropwise and the mixture was stirred for 90 minutes at 0° C. To the mixture was added acetone (0.23 ml) dropwise and the mixture was stirred for 45 minutes at 0° C. To the reaction mixture was added water and extracted with ethyl acetate. The extract was washed with water and a saturated aqueous solution of sodium chloride successively and dried over anhydrous magnesium sulfate and concentrated. The residue was roughly purified by column chromatography on silica gel (hexane:ethyl acetate=4:1→25:1) and then washed with ethyl acetate to give the compound of the present invention (91 mg) having the following physical data.

TLC: Rf 0.16 (hexane:ethyl acetate=3:1);

NMR (CDCl$_3$): δ 11.89 (br, 1H), 7.98–7.94 (m, 3H), 7.53 (dd, J=8.0, 2.0 Hz, 1H), 7.47–7.42 (m, 3H), 7.19 (d, J=8.0 Hz, 1H), 6.35 (s, 1H), 2.88 (s, 2H), 1.80 (br, 1H), 1.64 (s, 6H), 1.36 (s, 6H).

EXAMPLE 22(1)–EXAMPLE 22(2)

By the same procedure as described in example 22 using the compound prepared in example 11(188) or example 11(168), the following compounds having the following physical data were given.

EXAMPLE 22(1)

(Z)-2-(7-(1-hydroxy-1-methylethyl)-3,3-dimethyl-3,4-dihydro-(2H)-isoquinolin-1-ylidene)-1-cyclohexylethan-1-one

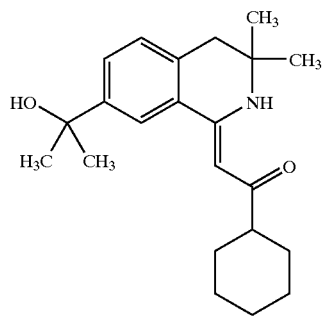

TLC: Rf 0.26 (hexane:ethyl acetate=3:1);

NMR (CDCl$_3$): δ 11.36 (br, 1H), 7.86 (d, J=2.0 Hz, 1H), 7.48 (dd, J=8.0, 2.0 Hz, 1H), 7.14 (d, J=8.0 Hz, 1H), 5.66 (s, 1H), 2.82 (s, 2H), 2.32 (tt, J=11.5, 3.5 Hz, 1H), 1.90–1.76 (m, 5H), 1.71–1.20 (m, 18H).

EXAMPLE 22(2)

(Z)-2-(7-(1-hydroxy-1-methylethyl)-3,3-dimethyl-3,4-dihydro-(2H)-isoquinolin-1-ylidene)-1-(adamantan-1-yl)ethan-1-one

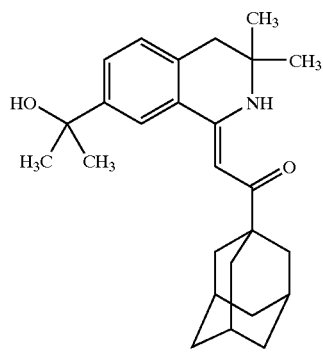

TLC: Rf 0.31 (hexane:ethyl acetate=3:1);

NMR (CDCl$_3$): δ 11.59 (br, 1H), 7.87 (d, J=2.0 Hz, 1H), 7.47 (dd, J=8.0, 2.0 Hz, 1H), 7.14 (d, J=8.0 Hz, 1H), 5.80 (s, 1H), 2.81 (s, 2H), 2.06 (br, 3H), 1.92 (br, 6H), 1.80 (s, 1H), 1.75 (br, 6H), 1.63 (s, 6H), 1.29 (s, 6H).

EXAMPLE 23

(Z)-2-(6-acetyl-3,3-dimethyl-3,4-dihydro-(2H)-isoquinolin-1-ylidene)-1-phenylethan-1-one

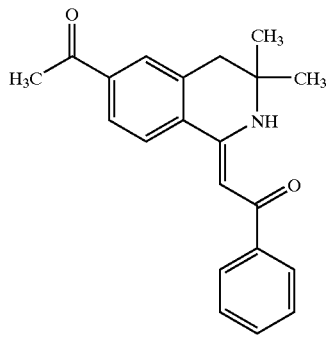

To a solution of the compound prepared in example 12 (356 mg) in ether (10 ml) was added n-butyl lithium (1.8 ml; 1.6M solution in hexane) dropwise and the mixture was stirred for 30 minutes at 0° C. and then it was bubbled with carbon dioxide. The reaction mixture was stirred for 20 minutes at 0° C. and thereto was added methyl magnesium bromide (3.00 ml, 0.9 M solution in tetrahydrofuran) dropwise and the mixture was stirred for 2 hours at 0° C. To the reaction mixture was added tetrahydrofuran, water and ethyl acetate and was extracted with ethyl acetate. The combined organic layer was washed with water and a saturated aqueous solution of sodium chloride successively, dried over anhydrous magnesium sulfate and was concentrated. The residue was purified by column chromatography on silica gel (hexane:ethyl acetate=10:1→3:1) to give the compound of the present invention (84 mg) having the following physical data.

TLC: Rf 0.27 (hexane:ethyl acetate=3:1);

NMR (CDCl$_3$): δ 11.74 (br, 1H), 7.97–7.93 (m, 2H), 7.91–7.88 (m, 2H), 7.80 (s, 1H), 7.48–7.42 (m, 3H), 6.37 (s, 1H), 2.97 (s, 2H), 2.65 (s, 3H), 1.37 (s, 6H).

EXAMPLE 24

(Z)-2-(7-hydroxyiminomethyl-3,3-dimethyl-3,4-dihydro-(2H)-isoquinolin-1-ylidene)-1-phenylethan-1-one

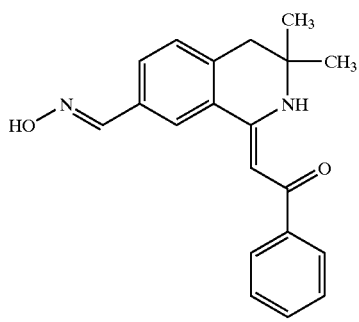

The compound prepared in example 13(1) (209 mg) was dissolved in formic acid (4 ml) and thereto was added hydroxyamine hydrochloride (62 mg) and the mixture was stirred for 1 hour at 100° C. The reaction mixture was allowed to cool, added to ice-cooled 2N aqueous solution of sodium hydroxide, and then extracted with ethyl acetate. The extract was washed with water and a saturated aqueous solution of sodium chloride, dried over anhydrous magnesium sulfate, and concentrated. The residue was purified by column chromatography on silica gel (hexane:ethyl acetate=3:1) to give the compound of the present invention (84 mg) having the following physical data.

TLC: Rf 0.49 (hexane:ethyl acetate=1:1);

NMR (CDCl$_3$): δ 11.83 (brs, 1H), 8.20 (s, 1H), 8.03 (d, J=1.5 Hz, 1H), 7.98–7.93 (m, 2H), 7.64 (dd, J=8.1, 1.5 Hz, 1H), 7.48–7.43 (m, 3H), 7.41 (brs, 1H), 7.25 (d, J=8.1 Hz, 1H), 6.35 (s, 1H), 2.92 (s, 2H), 1.37 (s, 6H).

EXAMPLE 24(1)~EXAMPLE 24(10)

By the same procedure as described in example 24 using the compound prepared in Example 13, Example 13(8), Example 13(10), Example 13(9), Example 13(11), Example 13(13), Example 13(12), Example 13(15), Example 13(14), or Example 13(16) in place of the compound prepared in example 13(1).

EXAMPLE 24(1)

(Z)-2-(6-hydroxyiminomethyl-3,3-dimethyl-3,4-dihydro-(2H)-isoquinolin-1-ylidene)-1-phenylethan-1-one

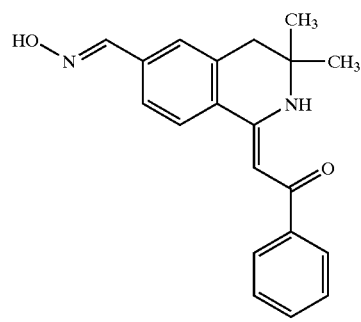

TLC: Rf 0.51 (hexane:ethyl acetate=1:1);

NMR (CDCl$_3$): δ 11.78 (brs, 1H), 8.15 (s, 1H), 7.97–7.92 (m, 2H), 7.84 (d, J=8.1 Hz, 1H), 7.53 (dd, J=8.1, 1.5 Hz, 1H), 7.50–7.40 (m, 4H), 6.34 (s, 1H), 2.92 (s, 2H), 1.37 (s, 6H).

EXAMPLE 24(2)

(Z)-2-(7-hydroxyiminomethyl-6-methoxy-3,3-dimethyl-3,4-dihydro-(2H)-isoquinolin-1-ylidene)-1-(adamantan-1-yl)ethan-1-one

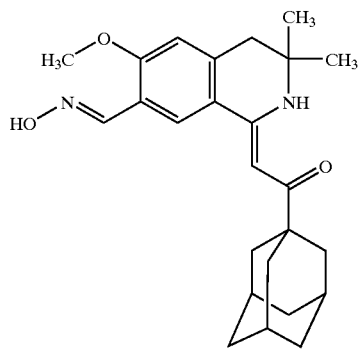

TLC: Rf 0.30 (hexane:ethyl acetate=2:1);

NMR (CDCl$_3$): δ 11.54 (br, 1H), 8.49 (s, 1H), 8.08 (s, 1H), 7.55 (br, 1H), 6.68 (s, 1H), 5.75 (s, 1H), 3.91 (s, 3H), 2.82 (s, 2H), 2.05 (br, 3H), 1.91 (br, 6H), 1.74 (br, 6H), 1.30 (s, 6H).

EXAMPLE 24(3)

(Z)-2-(7-hydroxyiminomethyl-6-methoxy-3,3-dimethyl-3,4-dihydro-(2H)-isoquinolin-1-ylidene)-1-cyclohexylethan-1-one

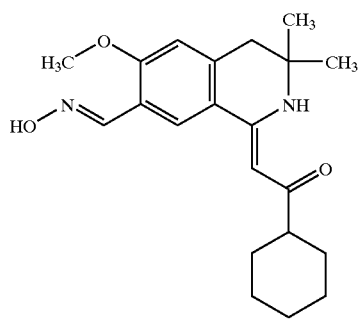

TLC: Rf 0.45 (hexane:ethyl acetate=1:1);

NMR (CDCl$_3$): δ 11.31 (br, 1H), 8.49 (s, 1H), 8.08 (s, 1H), 7.38 (br, 1H), 6.68 (s, 1H), 5.61 (s, 1H), 3.91 (s, 3H), 2.83 (s, 2H), 2.29 (m, 1H), 1.88–1.79 (m, 4H), 1.70–1.20 (m, 12H).

EXAMPLE 24(4)

(Z)-2-(7-hydroxyiminomethyl-3,3-dimethyl-3,4-dihydro-(2H)-isoquinolin-1-ylidene)-1-(adamantan-1-yl)ethan-1-one

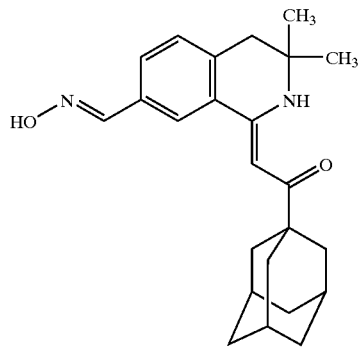

TLC: Rf 0.16 (hexane:ethyl acetate=4:1).

EXAMPLE 24(5)

(Z)-2-(7-hydroxyiminomethyl-6-methoxy-3,3-dimethyl-3,4-dihydro-(2H)-isoquinolin-1-ylidene)-1-cycloheptylethan-1-one

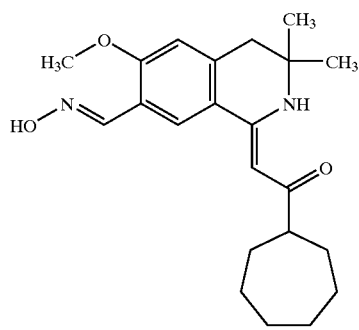

TLC: Rf 0.57 (hexane:ethyl acetate=1:1).

EXAMPLE 24(6)

(Z)-2-(7-hydroxyiminomethyl-3,3-dimethyl-3,4-dihydro-(2H)-isoquinolin-1-ylidene)-1-cyclohexylethan-1-one

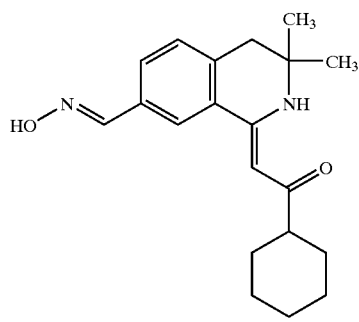

TLC: Rf 0.34 (hexane:ethyl acetate=2:1).

EXAMPLE 24(7)

(Z)-2-(7-hydroxyiminomethyl-3,3,6-trimethyl-3,4-dihydro-(2H)-isoquinolin-1-ylidene)-1-(adamantan-1-yl)ethan-1-one

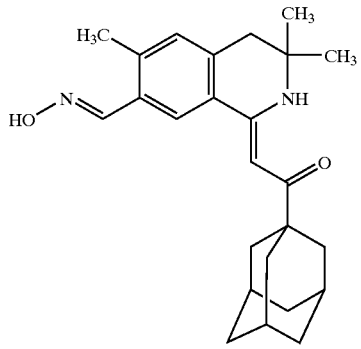

TLC: Rf 0.56 (hexane:ethyl acetate=3:1).

EXAMPLE 24(8)

(Z)-2-(7-hydroxyiminomethyl-3,3-dimethyl-3,4-dihydro-(2H)-isoquinolin-1-ylidene)-1-cycloheptylethan-1-one

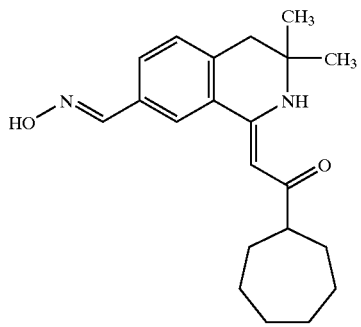

TLC: Rf 0.31 (hexane:ethyl acetate=2:1).

EXAMPLE 24(9)

(Z)-2-(7-hydroxyiminomethyl-3,3,6-trimethyl-3,4-dihydro-(2H)-isoquinolin-1-ylidene)-1-cyclohexylethan-1-one

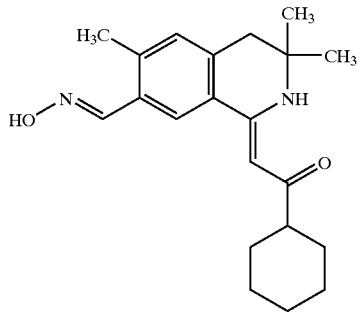

TLC: Rf 0.47 (hexane:ethyl acetate=3:1).

EXAMPLE 24(10)

(Z)-2-(7-hydroxyiminomethyl-3,3,6-trimethyl-3,4-dihydro-(2H)-isoquinolin-1-ylidene)-1-cycloheptylethan-1-one

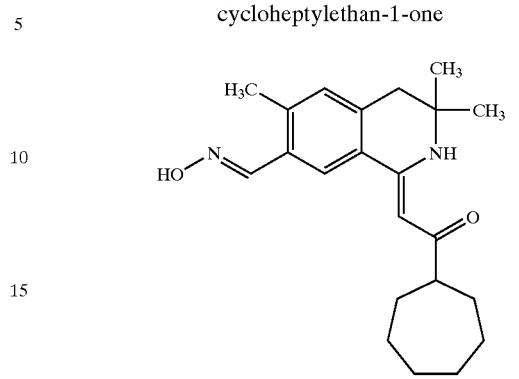

TLC: Rf 0.39 (hexane:ethyl acetate=3:1);

NMR (CDCl$_3$): δ 11.22 (br, 1H), 8.41 (s, 1H), 8.01 (s, 1H), 7.00 (s, 1H), 5.62 (s, 1H), 2.80 (s, 2H), 2.50–2.44 (m, 4H), 1.96–1.42 (m, 12H), 1.28 (s, 6H).

EXAMPLE 25

(Z)-2-(6-aminomethyl-3,3-dimethyl-3,4-dihydro-(2H)-isoquinolin-1-ylidene)-1-phenylethan-1-one

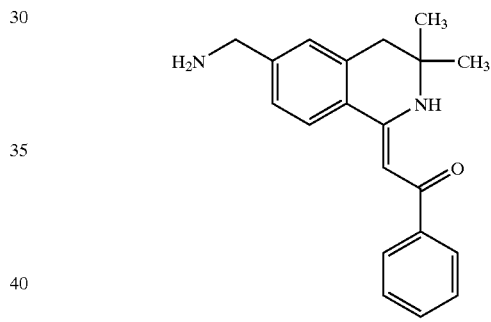

To the compound prepared in example 24(1) (360 mg) were added ethanol (16 ml) and a 50% aqueous solution of acetic acid (4 ml), and to the mixture was added 10% palladium carbon (30 mg), and under atmosphere of hydrogen the mixture was stirred vigorously for 7 hours. The reaction mixture was filtered over celite. The filtrate was concentrated and was azetroped with ethanol. The residue was purified by column chromatography on silica gel (chloroform:methanol=19:1→4:1) to give the compound of the present invention (240 mg) having the following physical data.

TLC: Rf 0.22 (chloroform:methanol=4:1);

NMR (CDCl$_3$): δ 11.82 (brs, 1H), 7.97–7.91 (m, 2H), 7.79 (d, J=7.8 Hz, 1H), 7.46–7.40 (m, 3H), 7.28 (brd, J=7.8 Hz, 1H), 7.18 (brs, 1H), 6.32 (s, 1H), 3.93 (s, 2H), 2.89 (s, 2H), 1.36 (s, 6H).

EXAMPLE 25(1)~EXAMPLE 25(10)

By the same procedure as described in example 25 using the compound prepared in Example 24, Example 24(2) ~Example 24(5), Example 24(7), Example 24(6), or Example 24(8)→Example 24(10) in place of the compound prepared in example 24(1), the following compounds of the present invention were given.

EXAMPLE 25(1)

(Z)-2-(7-aminomethyl-3,3-dimethyl-3,4-dihydro-(2H)-isoquinolin-1-ylidene)-1-phenylethan-1-one

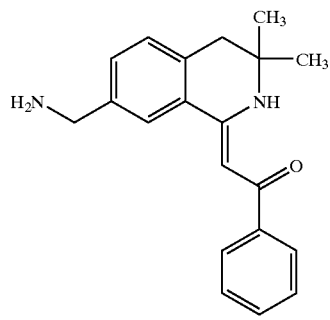

TLC: Rf 0.15 (hexane:ethyl acetate:isopropylamine=10:2:1);

NMR (CDCl$_3$): δ 11.86 (br, 1H), 7.98–7.94 (m, 2H), 7.77 (s, 1H), 7.46–7.38 (m, 4H), 7.19 (d, J=7.5 Hz, 1H), 6.35 (s, 1H), 3.95 (s, 2H), 2.89 (s, 2H), 1.36 (s, 6H).

EXAMPLE 25(2)

(Z)-2-(7-aminomethyl-6-methoxy-3,3-dimethyl-3,4-dihydro-(2H)-isoquinolin-1-ylidene)-1-(adamantan-1-yl)ethan-1-one

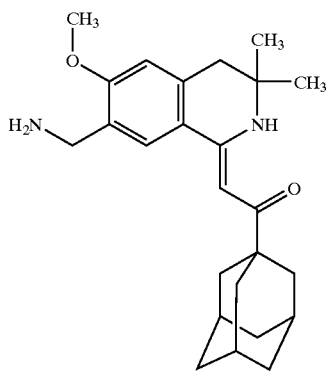

TLC: Rf 0.16 (chloroform:methanol=10:1);

NMR (CDCl$_3$): δ 11.52 (br, 1H), 7.56 (s, 1H), 6.63 (s, 1H), 5.71 (s, 1H), 3.90 (s, 3H), 3.85 (s, 2H), 2.80 (s, 2H), 2.06 (br, 3H), 1.92 (br, 6H), 1.75 (br, 6H), 1.29 (s, 6H).

EXAMPLE 25(3)

(Z)-2-(7-aminomethyl-6-methoxy-3,3-dimethyl-3,4-dihydro-(2H)-isoquinolin-1-ylidene)-1-cyclohexylethan-1-one

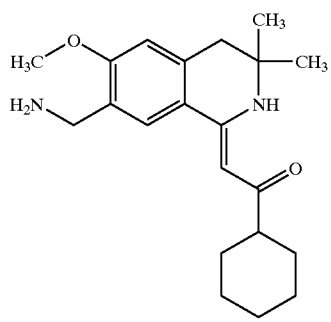

TLC: Rf 0.10 (chloroform:methanol=10:1);

NMR (CDCl$_3$): δ 11.31 (br, 1H), 7.57 (s, 1H), 6.62 (s, 1H), 5.58 (s, 1H), 3.89 (s, 3H), 3.84 (s, 2H), 2.81 (s, 2H), 2.29 (tt, J=11.5, 3.5 Hz, 1H), 1.90–1.79 (m, 4H), 1.70–1.16 (m, 12H).

EXAMPLE 25(4)

(Z)-2-(7-aminomethyl-3,3-dimethyl-3,4-dihydro-(2H)-isoquinolin-1-ylidene)-1-(adamantan-1-yl)ethan-1-one

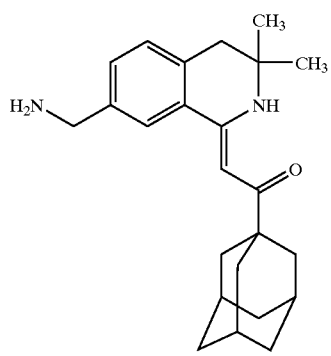

TLC: Rf 0.27 (chloroform:methanol=9:1);

NMR (CDCl$_3$): δ 11.53 (brs, 1H), 7.64 (s, 1H), 7.35 (brd, J=7.8 Hz, 1H), 7.14 (d, J=7.8 Hz, 1H), 5.79 (s, 1H), 3.92 (s, 2H), 2.82 (s, 2H), 2.09–2.02 (m, 3H), 1.94–1.90 (m, 6H), 1.77–1.72 (m, 6H), 1.29 (s, 6H).

EXAMPLE 25(5)

(Z)-2-(7-aminomethyl-6-methoxy-3,3-dimethyl-3,4-dihydro-(2H)-isoquinolin-1-ylidene)-1-cycloheptylethan-1-one

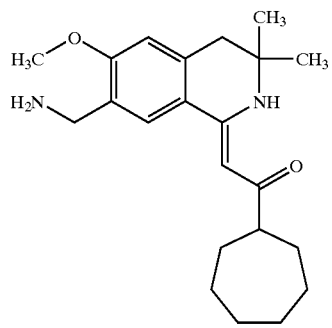

TLC: Rf 0.25 (chloroform:methanol=10:1);

NMR (CDCl$_3$): δ 11.23 (br, 1H), 7.57 (s, 1H), 6.62 (s, 1H), 5.55 (s, 1H), 3.89 (s, 3H), 3.84 (s, 2H), 2.80 (s, 2H), 2.45 (tt, J=10.0, 4.0 Hz, 1H), 1.95–1.88 (m, 2H), 1.83–1.46 (m, 10H), 1.29 (s, 6H).

EXAMPLE 25(6)

(Z)-2-(7-aminomethyl-3,3,6-trimethyl-3,4-dihydro-(2H)-isoquinolin-1-ylidene)-1-(adamantan-1-yl)ethan-1-one

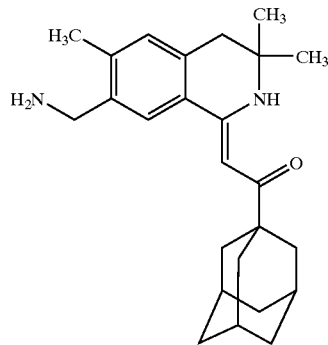

TLC: Rf 0.28 (hexane:ethyl acetate:isopropylamine=10:1:0.5);

NMR (CDCl$_3$): δ 11.52 (br, 1H), 7.63 (s, 1H), 6.96 (s, 1H), 5.78 (s, 1H), 3.90 (s, 2H), 2.78 (s, 2H), 2.37 (s, 3H), 2.06 (br, 3H), 1.93–1.92 (br, 6H), 1.76–1.75 (br, 6H), 1.28 (s, 6H).

EXAMPLE 25(7)

(Z)-2-(7-aminomethyl-3,3-dimethyl-3,4-dihydro-(2H)-isoquinolin-1-ylidene)-1-cyclohexylethan-1-one

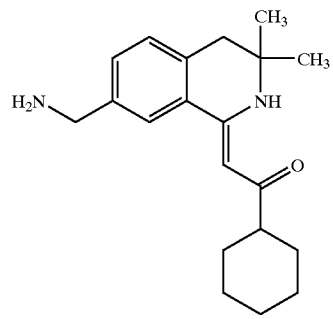

TLC: Rf 0.23 (chloroform:methanol=9:1);

NMR (CDCl$_3$): δ 11.32 (brs, 1H), 7.66 (brs, 1H), 7.34 (dd, J=7.8, 1.8 Hz, 1H), 7.14 (d, J=7.8 Hz, 1H), 5.65 (s, 1H), 3.92 (s, 2H), 2.82 (s, 2H), 2.31 (tt, J=12.0, 3.3 Hz, 1H), 1.93–1.18 (m, 16H).

EXAMPLE 25(8)

(Z)-2-(7-aminomethyl-3,3-dimethyl-3,4-dihydro-(2H)-isoquinolin-1-ylidene)-1-cycloheptylethan-1-one

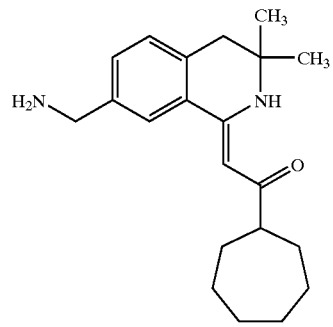

TLC: Rf 0.28 (chloroform:methanol=9:1);

NMR (CDCl$_3$): δ 11.24 (brs, 1H), 7.66 (d, J=1.8 Hz, 1H), 7.34 (dd, J=7.8, 1.8 Hz, 1H), 7.14 (d, J=7.8 Hz, 1H), 5.62 (s, 1H), 3.92 (s, 2H), 2.82 (s, 2H), 2.48 (tt, J=9.9, 3.3 Hz, 1H), 1.97–1.43 (m, 12H), 1.28 (s, 6H).

EXAMPLE 25(9)

(Z)-2-(7-aminomethyl-3,3,6-trimethyl-3,4-dihydro-(2H)-isoquinolin-1-ylidene)-1-cyclohexylethan-1-one

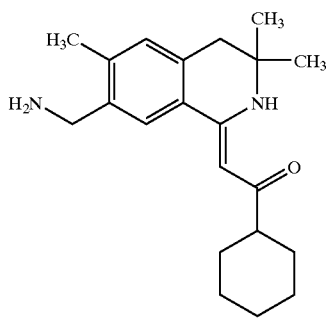

TLC: Rf 0.17 (hexane:ethyl acetate:isopropylamine=10:1:0.5);

NMR (CDCl$_3$): δ 11.31 (br, 1H), 7.65 (s, 1H), 6.96 (s, 1H), 5.65 (s, 1H), 3.89 (s, 2H), 2.78 (s, 2H), 2.36 (s, 3H), 2.30 (m, 1H), 1.86 (m, 4H), 1.68 (m, 1H), 1.50–1.28 (m, 11H).

EXAMPLE 25(10)

(Z)-2-(7-aminomethyl-3,3,6-trimethyl-3,4-dihydro-(2H)-isoquinolin-1-ylidene)-1-cycloheptylethan-1-one

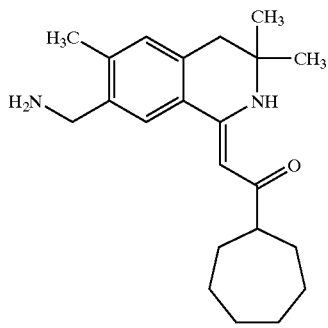

TLC: Rf 0.49 (hexane:ethyl acetate:isopropylamine=10:1:1);

NMR (CDCl$_3$): δ 11.23 (br, 1H), 7.64 (s, 1H), 6.96 (s, 1H), 5.61 (s, 1H), 3.89 (s, 2H), 2.78 (s, 2H), 2.46 (m, 1H), 2.36 (s, 3H), 1.96–1.46 (m, 12H), 1.28 (s, 6H).

EXAMPLE 26

(Z)-2-(7-cyano-3,3-dimethyl-3,4-dihydro-(2H)-isoquinolin-1-ylidene)-1-(adamantan-1-yl)ethan-1-one

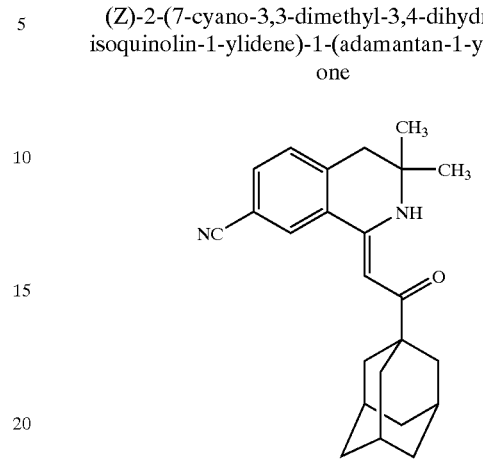

The compound prepared in example 24(4) (214 mg) in methylene chloride (6 ml) and the mixture was cooled to −78° C. and to the mixture were added anhydrous trifluoromethanesulfonic acid (0.11 ml) and triethylamine (0.11 ml), and the mixture was stirred for 3 hours at room temperature. To the reaction mixture was added a saturated aqueous solution of sodium bicarbonate and was extracted with ethyl acetate. The extract was washed with a saturated aqueous solution of sodium chloride, dried over anhydrous magnesium sulfate, and concentrated. The residue was roughly purified by column chromatography on silica gel (hexane:ethyl acetate=4:1). The product was dissolved in a mixture of ethanol (6 ml) and tetrahydrofuran (3 ml) and to the mixture was added sodium borohydride (75 mg) and the mixture was stirred overnight. To the reaction mixture was added water and was extracted with methylene chloride. The extract was dried over anhydrous magnesium sulfate and concentrated. The extract was dried over anhydrous magnesium sulfate and was concentrated. The residue was purified by column chromatography on silica gel (hexane:ethyl acetate=4:;1) to give the compound of the present invention (52 mg) having the following physical data.

TLC: Rf 0.23 (hexane:ethyl acetate=4:1);

NMR (CDCl$_3$): δ 11.36 (brs, 1H), 8.00 (s, 1H), 7.65 (dd, J=7.8, 1.5 Hz, 1H), 7.30 (d, J=7.8 Hz, 1H), 5.76 (s, 1H), 2.90 (s, 2H), 2.12–2.04 (m, 3H), 1.93–1.88 (m, 6H), 1.78–1.73 (m, 6H), 1.30 (s, 6H).

EXAMPLE 26(1)~EXAMPLE 26(2)

By the same procedure as described in example 26 using the compound prepared in example 24(6) or example 24(8) in place of the compound prepared in example 24(4), the following compounds were given.

EXAMPLE 26(1)

(Z)-2-(7-cyano-3,3-dimethyl-3,4-dihydro-(2H)-isoquinolin-1-ylidene)-1-cyclohexylethan-1-one

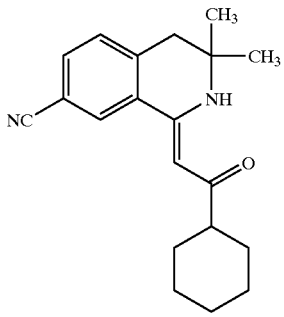

TLC: Rf 0.36 (hexane:ethyl acetate=2:1);

NMR (CDCl$_3$): δ 11.21 (brs, 1H), 7.99 (d, J=1.5 Hz, 1H), 7.65 (dd, J=7.5, 1.5 Hz, 1H), 7.31 (d, J=7.5 Hz, 1H), 5.62 (s, 1H), 2.90 (s, 2H), 2.33 (tt, J=11.4, 3.6 Hz, 1H), 1.94–1.66 (m, 5H), 1.52–1.18 (m, 11H).

EXAMPLE 26(2)

(Z)-2-(7-cyano-3,3-dimethyl-3,4-dihydro-(2H)-isoquinolin-1-ylidene)-1-cycloheptylethan-1-one

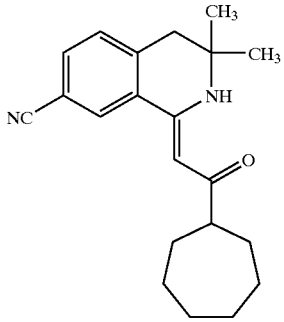

TLC: Rf 0.42 (hexane:ethyl acetate=2:1);

NMR (CDCl$_3$): δ 11.12 (brs, 1H), 7.98 (d, J=1.8 Hz, 1H), 7.65 (dd, J=8.1, 1.8 Hz, 1H), 7.30 (d, J=8.1 Hz, 1H), 5.58 (s, 1H), 2.90 (s, 2H), 2.50 (tt, J=9.9, 3.9 Hz, 1H), 1.97–1.43 (m, 12H), 1.30 (s, 6H).

EXAMPLE 27

(Z)-2-(7-(morpholin-4-yl)methyl-3,3-dimethyl-3,4-dihydro-(2H)-isoquinolin-1-ylidene)-1-(naphthalen-1-yl)ethan-1-one

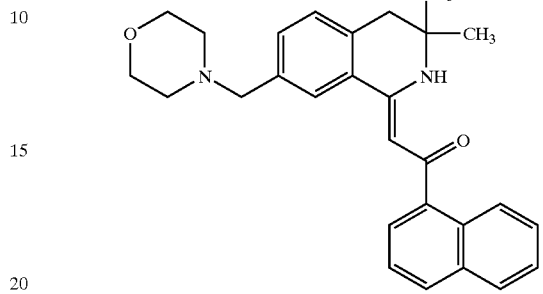

To tetrahydrofuran (5 ml) was added the compound prepared in example 13(2) (206 mg), and to the mixture was added morpholine at room temperature (0.065 ml) dropwise and the mixture was stirred for 2 hours at room temperature. To the reaction mixture was added sodium triacetoxyborohydride (167 mg) and the mixture was stirred for 3 hours. To the reaction mixture was added sodium triacetoxyborohydride (30 mg) and the mixture was stirred for 1 hour. The reaction mixture was added to a cool saturated aqueous solution of sodium bicarbonate, and was extracted with ethyl acetate. The extract was washed with water and a saturated aqueous solution of sodium chloride successively, dried over magnesium sulfate and concentrated. The residue was purified by column chromatography on silica gel (hexane:ethyl acetate=1:1→2:3) to give the compound of the present invention (205 mg) having the following physical data.

TLC: Rf 0.17 (ethyl acetate:hexane=1:1);

NMR (CDCl$_3$): δ 11.80 (br., 1H), 8.47 (m, 1H), 7.90–7.85 (m, 2H), 7.70 (dd, J=7.0, 1.0 Hz, 1H), 7.64 (s, 1H), 7.55–7.45 (m, 3H), 7.40 (dd, J=8.0, 1.5 Hz, 1H), 7.17 (d, J=8.0 Hz, 1H), 6.08 (s, 1H), 3.68 (t, J=7.5 Hz, 4H), 3.47 (s, 2H), 2.92 (s, 2H), 2.41 (t, J=7.5 Hz, 4H), 1.41 (s, 6H).

EXAMPLE 27(1)~EXAMPLE 27(27)

By the same procedure as described in example 27, using the compound prepared in Example 13(1), Example 13, Example 13(1), Example 13(8), Example 13(9), Example 13(11), Example 11(119), Example 13(12), Example 13(5), Example 13(13), Example 13(7), Example 13(14), Example 13(15), Example 13(14), Example 13(6), or Example 13(16) in place of the compound prepared in Example 13(2), and morpholine or a corresponding amine derivative thereto, the following compounds were given.

EXAMPLE 27(1)

(Z)-2-(7-(morpholin-4-yl)methyl-3,3-dimethyl-3,4-dihydro-(2H)-isoquinolin-1-ylidene)-1-phenylethan-1-one

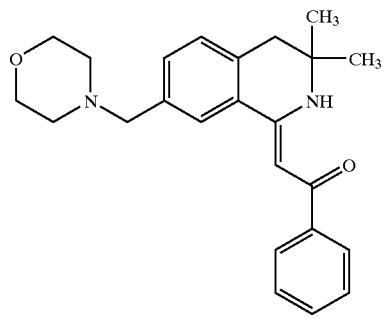

TLC: Rf 0.32 (hexane:ethyl acetate=1:4);

NMR (CDCl$_3$): δ 11.87 (brs, 1H), 7.99–7.93 (m, 2H), 7.75 (brs, 1H), 7.48–7.39 (m, 4H), 7.17 (d, J=7.8 Hz, 1H), 6.33 (s, 1H), 3.74 (t, J=4.8 Hz, 4H), 3.55 (s, 2H), 2.88 (s, 2H), 2.48 (t, J=4.8 Hz, 4H), 1.36 (s, 6H).

EXAMPLE 27(2)

(Z)-2-(7-(piperidin-1-yl)methyl-3,3-dimethyl-3,4-dihydro-(2H)-isoquinolin-1-ylidene)-1-phenylethan-1-one

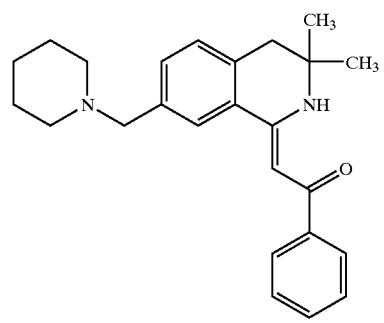

TLC: Rf 0.49 (chloroform:methanol=9:1);

NMR (CDCl$_3$): δ 11.87 (brs, 1H), 7.99–7.93 (m, 2H), 7.74 (brs, 1H), 7.48–7.39 (m, 4H), 7.16 (d, J=7.8 Hz, 1H), 6.34 (s, 1H), 3.52 (s, 2H), 2.88 (s, 2H), 2.41 (brs, 4H), 1.60 (quintet, J=5.4 Hz, 4H), 1.46 (m, 2H), 1.36 (s, 6H).

EXAMPLE 27(3)

(Z)-2-(7-(N-methyl-N-(2-dimethylaminoethyl)aminomethyl)-3,3-dimethyl-3,4-dihydro-(2H)-isoquinolin-1-ylidene)-1-phenylethan-1-one

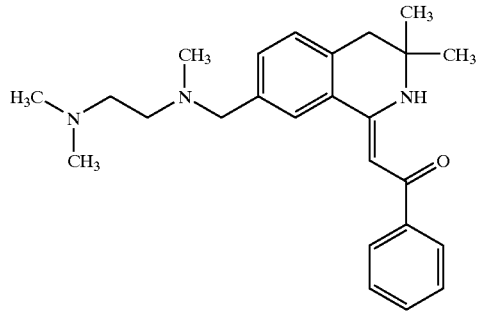

TLC: Rf 0.13 (chloroform:methanol=9:1);

NMR (CDCl$_3$): δ 11.87 (brs, 1H), 7.99–7.93 (m, 2H), 7.76 (brs, 1H), 7.47–7.38 (m, 4H), 7.16 (d, J=7.8 Hz, 1H), 6.34 (s, 1H), 3.57 (s, 2H), 2.88 (s, 2H), 2.55–2.44 (m, 4H), 2.28 (s, 3H), 2.23 (s, 6H), 1.36 (s, 6H).

EXAMPLE 27(4)

(Z)-2-(7-(N-(2-hydroxyethyl)-N-methylaminomethyl)-3,3-dimethyl-3,4-dihydro-(2H)-isoquinolin-1-ylidene)-1-phenylethan-1-one

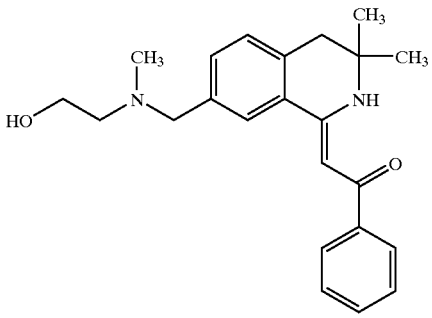

TLC: Rf 0.40 (chloroform:methanol=9:1);

NMR (CDCl$_3$): δ 11.86 (brs, 1H), 7.99–7.93 (m, 2H), 7.71 (brs, 1H), 7.47–7.38 (m, 4H), 7.18 (d, J=7.8 Hz, 1H), 6.32 (s, 1H), 3.67 (t, J=5.4 Hz, 2H), 3.63 (s, 2H), 2.89 (s, 2H), 2.64 (t, J=5.4 Hz, 2H), 2.42 (m, 1H), 2.28 (s, 3H), 1.36 (s, 6H).

EXAMPLE 27(5)

(Z)-2-(7-(N-cyclohexylaminomethyl)-3,3-dimethyl-3,4-dihydro-(2H)-isoquinolin-1-ylidene)-1-phenylethan-1-one

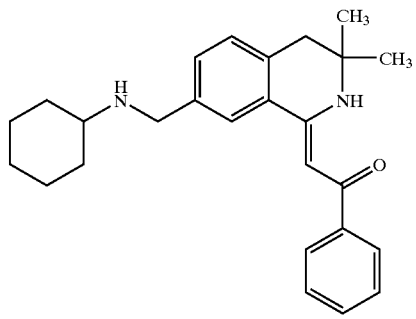

TLC: Rf 0.36 (chloroform:methanol=9:1);

NMR (CDCl$_3$): δ 11.85 (brs, 1H), 7.99–7.93 (m, 2H), 7.76 (brs, 1H), 7.47–7.38 (m, 4H), 7.17 (d, J=7.8 Hz, 1H), 6.34 (s, 1H), 3.87 (s, 2H), 2.88 (s, 2H), 2.53 (m, 1H), 2.01–1.91 (m, 2H), 1.82–1.71 (m, 2H), 1.62 (m, 1H), 1.38–1.08 (m, 6H), 1.36 (s, 6H).

EXAMPLE 27(6)

(Z)-2-(6-(morpholin-4-yl)methyl-3,3-dimethyl-3,4-dihydro-(2H)-isoquinolin-1-ylidene)-1-phenylethan-1-one

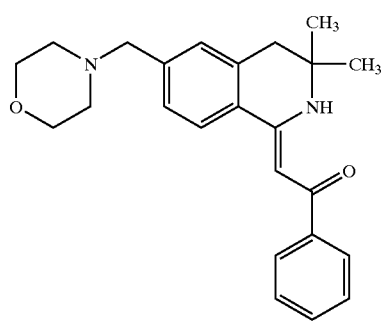

TLC: Rf 0.28 (hexane:ethyl acetate=1:4);

NMR (CDCl$_3$): δ 11.82 (brs, 1H), 7.97–7.92 (m, 2H), 7.78 (d, J=8.4 Hz, 1H), 7.47–7.40 (m, 3H), 7.30 (brd, J=8.4 Hz, 1H), 7.19 (brs, 1H), 6.32 (s, 1H), 3.74 (t, J=4.8 Hz, 4H), 3.53 (s, 2H), 2.89 (s, 2H), 2.48 (t, J=4.8 Hz, 4H), 1.36 (s, 6H).

EXAMPLE 27(7)

(Z)-2-(6-dimethylaminomethyl-3,3-dimethyl-3,4-dihydro-(2H)-isoquinolin-1-ylidene)-1-phenylethan-1-one

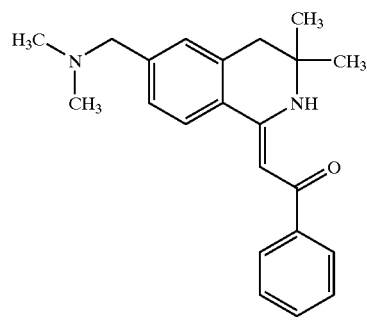

TLC: Rf 0.31 (chloroform:methanol=9:1);

NMR (CDCl$_3$): δ 11.82 (brs, 1H), 7.98–7.92 (m, 2H), 7.78 (d, J=8.4 Hz, 1H), 7.47–7.40 (m, 3H), 7.27 (m, 1H), 7.19 (brs, 1H), 6.32 (s, 1H), 3.46 (s, 2H), 2.89 (s, 2H), 2.28 (s, 6H), 1.36 (s, 6H).

EXAMPLE 27(8)

(Z)-2-(6-methylaminomethyl-3,3-dimethyl-3,4-dihydro-(2H)-isoquinolin-1-ylidene)-1-phenylethan-1-one

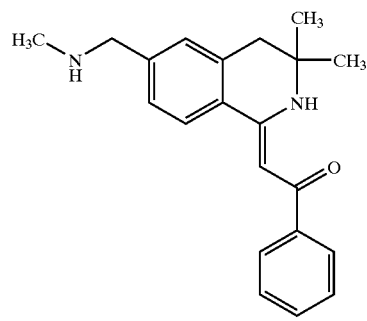

TLC: Rf 0.23 (chloroform:methanol=4:1);

NMR (CDCl$_3$): δ 11.82 (brs, 1H), 7.98–7.91 (m, 2H), 7.79 (d, J=8.4 Hz, 1H), 7.47–7.40 (m, 3H), 7.28 (m, 1H), 7.20 (brs, 1H), 6.32 (s, 1H), 3.80 (s, 2H), 2.89 (s, 2H), 2.50 (s, 3H), 1.36 (s, 6H).

EXAMPLE 27(9)

(Z)-2-(7-dimethylaminomethyl-3,3-dimethyl-3,4-dihydro-(2H)-isoquinolin-1-ylidene)-1-phenylethan-1-one

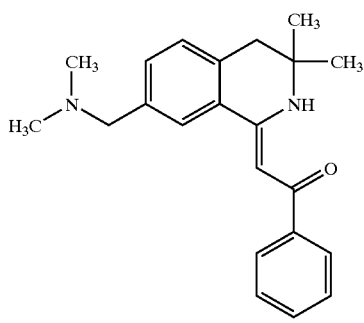

TLC: Rf 0.53 (hexane:ethyl acetate:isopropylamine= 10:2:1);

NMR (CDCl$_3$): δ 11.88 (br, 1H), 7.98–7.95 (m, 2H), 7.74 (d, J=1.5 Hz, 1H), 7.46–7.42 (m, 3H), 7.39 (dd, J=8.0, 1.5 Hz, 1H), 7.17 (d, J=8.0 Hz, 1H), 6.34 (s, 1H), 3.47 (s, 2H), 2.89 (s, 2H), 2.28 (s, 6H), 1.36 (s, 6H).

EXAMPLE 27(10)

(Z)-2-(7-dimethylaminomethyl-6-methoxy-3,3-dimethyl-3,4-dihydro-(2H)-isoquinolin-1-ylidene)-1-(adamantan-1-yl)ethan-1-one

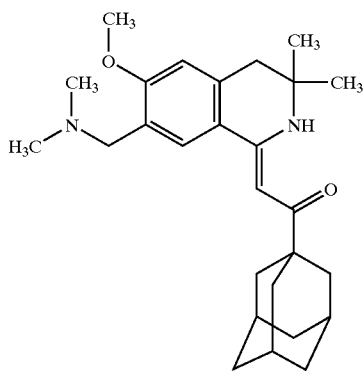

TLC: Rf 0.22 (chloroform:methanol=10:1);

NMR (CDCl$_3$): δ 11.58 (br, 1H), 7.58 (s, 1H), 6.63 (s, 1H), 5.71 (s, 1H), 3.88 (s, 3H), 3.46 (s, 2H), 2.80 (s, 2H), 2.30 (s, 6H), 2.06 (br, 3H), 1.92 (br, 6H), 1.74 (br, 6H), 1.29 (s, 6H).

EXAMPLE 27(11)

(Z)-2-(6-methoxy-7-methylaminomethyl-3,3-dimethyl-3,4-dihydro-(2H)-isoquinolin-1-ylidene)-1-(adamantan-1-yl)ethan-1-one

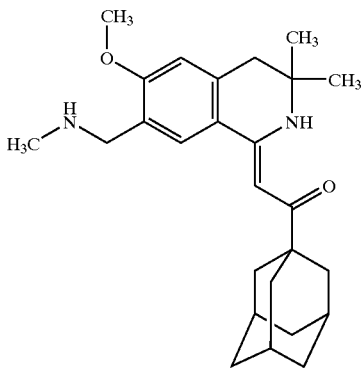

TLC: Rf 0.35 (hexane:ethyl acetate:isopropylamine= 10:1:1);

NMR (CDCl$_3$): δ 11.53 (br, 1H), 7.56 (s, 1H), 6.63 (s, 1H), 5.71 (s, 1H), 3.88 (s, 3H), 3.76 (s, 2H), 2.80 (s, 2H), 2.48 (s, 3H), 2.06 (br, 3H), 1.92 (br, 6H), 1.75 (br, 6H), 1.29 (s, 6H).

EXAMPLE 27(12)

(Z)-2-(7-methylaminomethyl-3,3-dimethyl-3,4-dihydro-(2H)-isoquinolin-1-ylidene)-1-(adamantan-1-yl)ethan-1-one

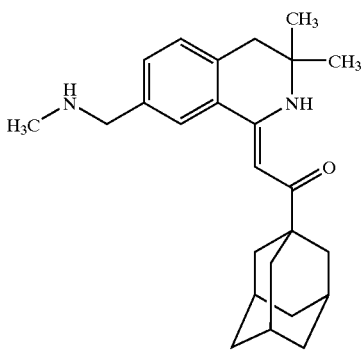

TLC: Rf 0.28 (chloroform:methanol=9:1);

NMR (CDCl$_3$): δ 11.54 (brs, 1H), 7.64 (d, J=1.5 Hz, 1H), 7.36 (dd, J=7.5, 1.5 Hz, 1H), 7.13 (d, J=7.5 Hz, 1H), 5.79 (s, 1H), 3.79 (s, 2H), 2.82 (s, 2H), 2.50 (s, 3H), 2.09–2.03 (m, 3H), 1.94–1.90 (m, 6H), 1.77–1.72 (m, 6H), 1.28 (s, 6H).

EXAMPLE 27(13)

(Z)-2-(6-methoxy-7-methylaminomethyl-3,3-dimethyl-3,4-dihydro-(2H)-isoquinolin-1-ylidene)-1-cycloheptylethan-1-one

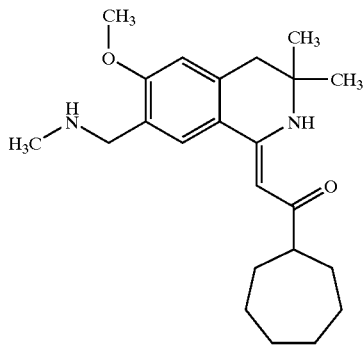

TLC: Rf 0.24 (chloroform:methanol=10:1);

NMR (CDCl$_3$): δ 11.24 (br, 1H), 7.57 (s, 1H), 6.62 (s, 1H), 5.54 (s, 1H), 3.88 (s, 3H), 3.75 (s, 2H), 2.80 (s, 2H), 2.49–2.40 (m, 4H), 1.95–1.87 (m, 2H), 1.82–1.46 (m, 10H), 1.29 (s, 6H).

EXAMPLE 27(14)

(Z)-2-(6-chloro-7-dimethylaminomethyl-3,3-dimethyl-3,4-dihydro-(2H)-isoquinolin-1-ylidene)-1-(adamantan-1-yl)ethan-1-one

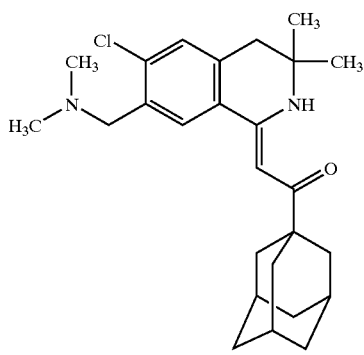

TLC: Rf 0.16 (ethyl acetate:hexane=1:5);

NMR (CDCl$_3$): δ 11.52 (br., 1H), 7.73 (s, 1H), 7.18 (s, 1H), 5.76 (s, 1H), 3.57 (s, 2H), 2.78 (s, 2H), 2.34 (s, 6H), 2.05 (m, 3H), 1.91 (m, 6H), 1.74 (m, 6H), 1.28 (s, 6H).

EXAMPLE 27(15)

(Z)-2-(7-methylaminomethyl-3,3,6-trimethyl-3,4-dihydro-(2H)-isoquinolin-1-ylidene)-1-(adamantan-1-yl)ethan-1-one

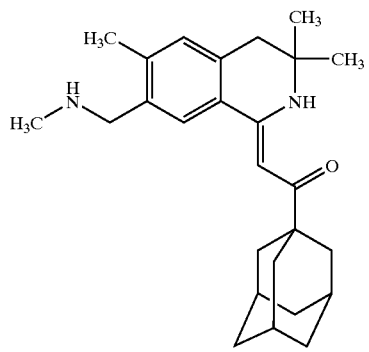

TLC: Rf 0.18 (chloroform:methanol=50:1);

NMR (CDCl$_3$): δ 11.53 (br, 1H), 7.59 (s, 1H), 6.96 (s, 1H), 5.77 (s, 1H), 3.75 (s, 2H), 2.77 (s, 2H), 2.55 (s, 3H), 2.38 (s, 3H), 2.06 (br, 3H), 1.93–1.92 (br, 6H), 1.76–1.75 (br, 6H), 1.28 (s, 6H).

EXAMPLE 27(16)

(Z)-2-(7-dimethylaminomethyl-3,3,6-trimethyl-3,4-dihydro-(2H)-isoquinolin-1-ylidene)-1-(adamantan-1-yl)ethan-1-one

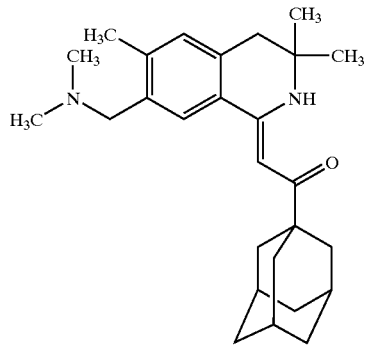

TLC: Rf 0.21 (hexane:ethyl acetate=3:1);

NMR (CDCl$_3$): δ 11.56 (br, 1H), 7.53 (s, 1H), 6.96 (s, 1H), 5.75 (s, 1H), 3.41 (s, 2H), 2.77 (s, 2H), 2.39 (s, 3H), 2.27 (s, 6H), 2.06 (br, 3H), 1.93–1.92 (br, 6H), 1.76–1.75 (br, 6H), 1.28 (s, 6H).

EXAMPLE 27(17)

(Z)-2-(6-chloro-7-methylaminomethyl-3,3-dimethyl-3,4-dihydro-(2H)-isoquinolin-1-ylidene)-1-(adamantan-1-yl)ethan-1-one

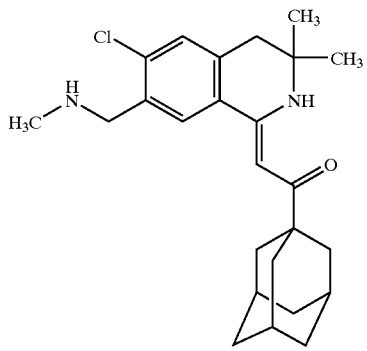

TLC: Rf 0.35 (water:methanol:chloroform=1:10:100);

NMR (CDCl$_3$): δ 11.45 (br., 1H), 7.79 (s, 1H), 7.20 (s, 1H), 5.81 (s, 1H), 3.94 (s, 2H), 2.79 (s, 2H), 2.53 (s, 3H), 2.06 (m, 3H), 1.91 (m, 6H), 1.74 (m, 6H), 1.28 (s, 6H).

EXAMPLE 27(18)

(Z)-2-(7-methylaminomethyl-3,3-dimethyl-3,4-dihydro-(2H)-isoquinolin-1-ylidene)-1-cyclohexylethan-1-one

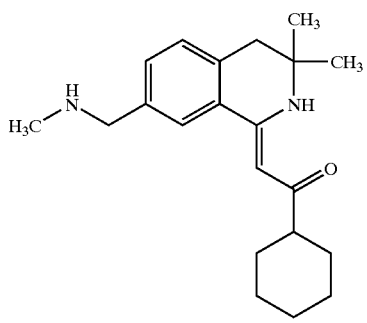

TLC: Rf 0.21 (chloroform:methanol=9:1);

NMR (CDCl$_3$): δ 11.31 (brs, 1H), 7.67 (brs, 1H), 7.36 (dd, J=7.5, 1.5 Hz, 1H), 7.13 (d, J=7.5 Hz, 1H), 5.66 (s, 1H), 3.79 (s, 2H), 2.82 (s, 2H), 2.49 (s, 3H), 2.31 (tt, J=11.4, 3.6 Hz, 1H), 1.94–1.64 (m, 5H), 1.54–1.18 (m, 11H).

EXAMPLE 27(19)

(Z)-2-(6-chloro-7-methylaminomethyl-3,3-dimethyl-3,4-dihydro-(2H)-isoquinolin-1-ylidene)-1-cycloheptylethan-1-one

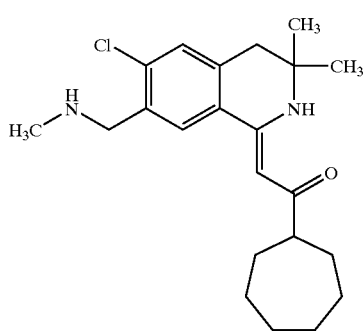

TLC: Rf 0.47 (water:methanol:chloroform=1:10:100);

NMR (CDCl$_3$): δ 11.19 (br., 1H), 7.71 (s, 1H), 7.19 (s, 1H), 5.59 (s, 1H), 3.87 (s, 2H), 2.79 (s, 2H), 2.52 (s, 3H), 2.47 (m, 1H), 1.95–1.40 (m, 12H), 1.28 (s, 6H).

EXAMPLE 27(20)

(Z)-2-(6-chloro-7-dimethylaminomethyl-3,3-dimethyl-3,4-dihydro-(2H)-isoquinolin-1-ylidene)-1-cycloheptylethan-1-one

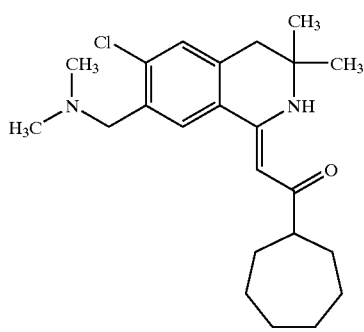

TLC: Rf 0.24 (ethyl acetate:hexane=1:3);

NMR (CDCl$_3$): δ 11.24 (br., 1H), 7.73 (s, 1H), 7.18 (s, 1H), 5.58 (s, 1H), 3.55 (s, 2H), 2.78 (s, 2H), 2.48 (m, 1H), 2.33 (s, 6H), 1.95–1.40 (m, 12H), 1.28 (s, 6H).

EXAMPLE 27(21)

(Z)-2-(7-methylaminomethyl-3,3,6-trimethyl-3,4-dihydro-(2H)-isoquinolin-1-ylidene)-1-cyclohexylethan-1-one

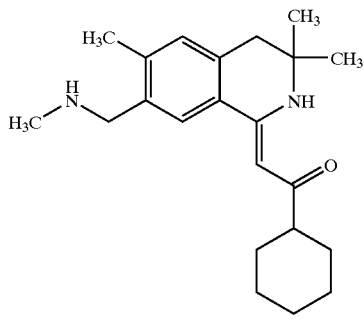

TLC: Rf 0.20 (chloroform:methanol=20:1);

NMR (CDCl$_3$): δ 11.31 (br, 1H), 7.61 (s, 1H), 6.96 (s, 1H), 5.63 (s, 1H), 3.75 (s, 2H), 2.77 (s, 2H), 2.54 (s, 3H), 2.37 (s, 3H), 2.34–2.26 (m, 1H), 1.90–1.79 (m, 4H), 1.71 (m, 1H), 1.55–1.28 (m, 11H).

EXAMPLE 27(22)

(Z)-2-(7-methylaminomethyl-3,3-dimethyl-3,4-dihydro-(2H)-isoquinolin-1-ylidene)-1-cycloheptylethan-1-one

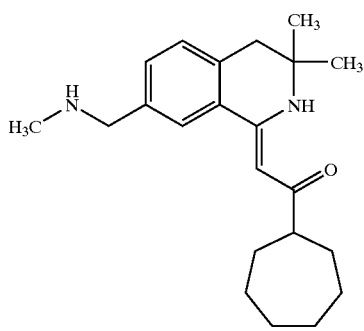

TLC: Rf 0.28 (chloroform:methanol=9:1);

NMR (CDCl$_3$): δ 11.24 (brs, 1H), 7.65 (d, J=1.8 Hz, 1H), 7.34 (dd, J=7.8, 1.8 Hz, 1H), 7.13 (d, J=7.8 Hz, 1H), 5.62 (s, 1H), 3.78 (s, 2H), 2.82 (s, 2H), 2.49 (s, 3H), 2.47 (m, 1H), 1.97–1.43 (m, 12H), 1.28 (s, 6H).

EXAMPLE 27(23)

(Z)-2-(7-dimethylaminomethyl-3,3,6-trimethyl-3,4-dihydro-(2H)-isoquinolin-1-ylidene)-1-cyclohexylethan-1-one

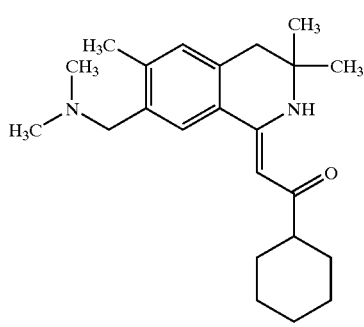

TLC: Rf 0.22 (hexane:ethyl acetate=1:2);

NMR (CDCl$_3$): δ 11.34 (br, 1H), 7.55 (s, 1H), 6.95 (s, 1H), 5.62 (s, 1H), 3.39 (s, 2H), 2.77 (s, 2H), 2.38 (s, 3H), 2.30 (m, 1H), 2.27 (s, 6H), 1.89–1.79 (m, 4H), 1.70 (m, 1H), 1.54–1.28 (m, 11H).

EXAMPLE 27(24)

(Z)-2-(6-chloro-7-methylaminomethyl-3,3-dimethyl-3,4-dihydro-(2H)-isoquinolin-1-ylidene)-1-cyclohexylethan-1-one

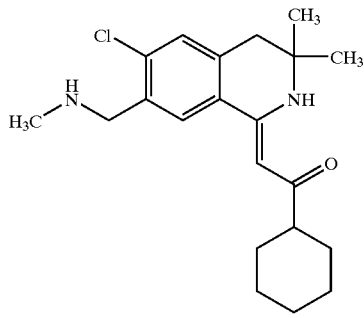

TLC: Rf 0.43 (water:methanol:chloroform=1:10:100);

NMR (CDCl$_3$): δ 11.27 (br., 1H), 7.71 (s, 1H), 7.19 (s, 1H), 5.62 (s, 1H), 3.87 (s, 2H), 2.79 (s, 2H), 2.51 (s, 3H), 2.31 (m, 1H), 1.90–1.20 (m, 10H), 1.28 (s, 6H).

EXAMPLE 27(25)

(Z)-2-(6-chloro-7-dimethylaminomethyl-3,3-dimethyl-3,4-dihydro-(2H)-isoquinolin-1-ylidene)-1-cyclohexylethan-1-one

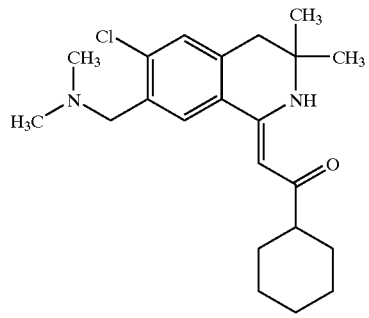

TLC: Rf 0.59 (water:methanol:chloroform=1:10:100);

NMR (CDCl$_3$): δ 11.31 (br., 1H), 7.74 (s, 1H), 7.18 (s, 1H), 5.62 (s, 1H), 3.55 (s, 2H), 2.79 (s, 2H), 2.33 (s, 6H), 2.32 (m, 1H), 1.90–1.20 (m, 10H), 1.28 (s, 6H).

EXAMPLE 27(26)

(Z)-2-(7-methylaminomethyl-3,3,6-trimethyl-3,4-dihydro-(2H)-isoquinolin-1-ylidene)-1-cycloheptylethan-1-one

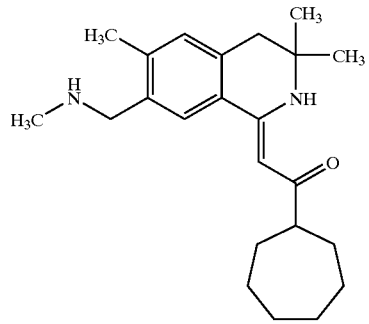

TLC: Rf 0.27 (chloroform:methanol=10:1);

NMR (CDCl$_3$): δ 11.23 (br, 1H), 7.61 (s, 1H), 6.96 (s, 1H), 5.60 (s, 1H), 3.75 (s, 2H), 2.77 (s, 2H), 2.54 (s, 3H), 2.46 (m, 1H), 2.37 (s, 3H), 1.96–1.44 (m, 12H), 1.27 (s, 6H).

EXAMPLE 27(27)

(Z)-2-(7-dimethylaminomethyl-3,3,6-trimethyl-3,4-dihydro-(2H)-isoquinolin-1-ylidene)-1-cycloheptylethan-1-one

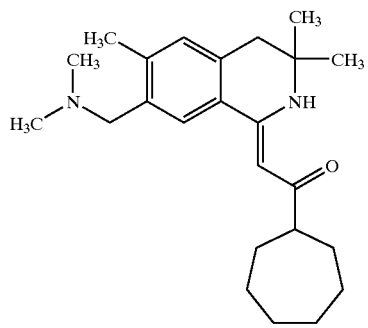

TLC: Rf 0.29 (hexane:ethyl acetate=1:2);

NMR (CDCl$_3$): δ 11.27 (br, 1H), 7.55 (s, 1H), 6.95 (s, 1H), 5.58 (s, 1H), 3.40 (s, 2H), 2.77 (s, 2H), 2.48 (m, 1H), 2.38 (s, 3H), 2.27 (s, 6H), 1.96–1.44 (m, 12H), 1.28 (s, 6H).

EXAMPLE 28

(Z)-2-(6-hydroxymethyl-3,3-dimethyl-3,4-dihydro-(2H)-isoquinolin-1-ylidene)-1-phenylethan-1-one

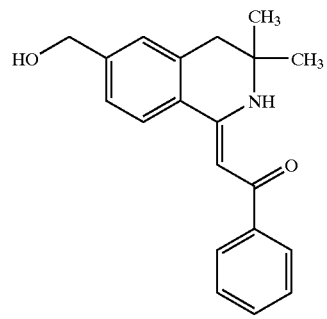

To a solution of the compound prepared in example 13 (85 mg) in methanol (4 ml) and tetrahydrofuran (1 ml) was added sodium borohydride (20 mg) at 0° C. and 10 minutes later, to the mixture was added water and the mixture was extracted with ethyl acetate. The extract was dried over anhydrous magnesium sulfate and was concentrated. The residue was purified by column chromatography in silica gel (hexane:ethyl acetate=3:1→1:1) to give the compound of the present invention (90 mg) having the following physical data.

TLC: Rf 0.34 (hexane:ethyl acetate=1:1);

NMR (CDCl$_3$): δ 11.81 (br, 1H), 7.96–7.93 (m, 2H), 7.82 (d, J=8.0 Hz, 1H), 7.46–7.41 (m, 3H), 7.32 (d, J=8.0 Hz, 1H), 7.23 (s, 1H), 6.33 (s, 1H), 4.76 (brd, 2H), 2.90 (s, 2H), 1.86 (brt, 1H), 1.36 (s, 6H).

EXAMPLE 28(1)~EXAMPLE 28(13)

By the same procedure as described in example 28 using the compound prepared in Example 13, Example 13(5)~Example 13(16) or the compound prepared in example 13, the following compounds of the present invention were given.

EXAMPLE 28(1)

(Z)-2-(7-hydroxymethyl-3,3-dimethyl-3,4-dihydro-(2H)-isoquinolin-1-ylidene)-1-phenylethan-1-one

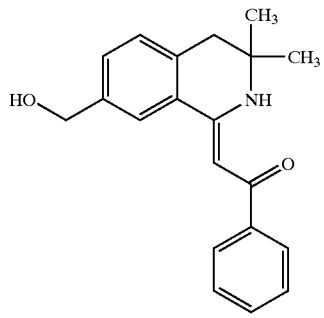

TLC: Rf 0.12 (hexane:ethyl acetate=3:1);

NMR (CDCl$_3$): δ 11.83 (br, 1H), 7.97–7.94 (m, 2H), 7.83 (s, 1H), 7.47–7.42 (m, 4H), 7.22 (d, J=7.5 Hz, 1H), 6.35 (s, 1H), 4.77 (s, 2H), 2.90 (s, 2H), 1.80 (br, 1H), 1.36 (s, 6H).

EXAMPLE 28(2)

(Z)-2-(6-chloro-7-hydroxymethyl-3,3-dimethyl-3,4-dihydro-(2H)-isoquinolin-1-ylidene)-1-(adamantan-1-yl)ethan-1-one

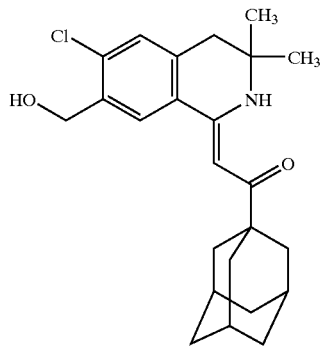

TLC: Rf 0.38 (ethyl acetate:hexane=1:3);

NMR (CDCl$_3$): δ 11.46 (br., 1H), 7.83 (s, 1H), 7.20 (s, 1H), 5.78 (s, 1H), 4.83 (s, 2H), 2.82 (s, 2H), 2.06 (m, 3H), 1.91 (m, 6H), 1.74 (m, 6H), 1.29 (s, 6H).

EXAMPLE 28(3)

(Z)-2-(6-chloro-7-hydroxymethyl-3,3-dimethyl-3,4-dihydro-(2H)-isoquinolin-1-ylidene)-1-cyclohexylethan-1-one

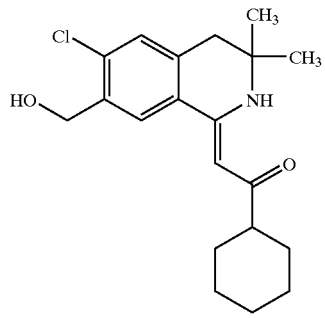

TLC: Rf 0.29 (ethyl acetate:hexane=1:3);

NMR (CDCl$_3$): δ 11.25 (br., 1H), 7.84 (s, 1H), 7.19 (s, 1H), 5.65 (s, 1H), 4.82 (d, J=6.0 Hz, 2H), 2.80 (s, 2H), 2.31 (m, 1H), 1.90–1.20 (m, 10H), 1.29 (s, 6H).

EXAMPLE 28(4)

(Z)-2-(6-chloro-7-hydroxymethyl-3,3-dimethyl-3,4-dihydro-(2H)-isoquinolin-1-ylidene)-1-cycloheptylethan-1-one

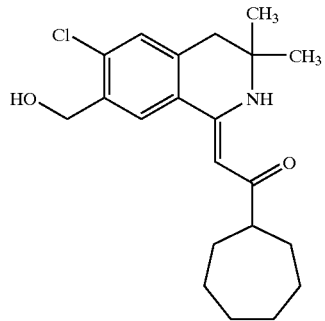

TLC: Rf 0.31 (ethyl acetate:hexane=1:3);

NMR (CDCl$_3$): δ 11.16 (br., 1H), 7.83 (s, 1H), 7.17 (s, 1H), 5.61 (s, 1H), 4.81 (s, 2H), 2.79 (s, 2H), 2.46 (m, 1H), 1.95–1.40 (m, 12H), 1.27 (s, 6H).

EXAMPLE 28(5)

(Z)-2-(7-hydroxymethyl-6-methoxy-3,3-dimethyl-3,
4-dihydro-(2H)-isoquinolin-1-ylidene)-1-
(adamantan-1-yl)ethan-1-one

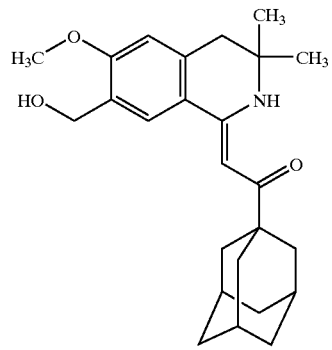

TLC: Rf 0.44 (hexane:ethyl acetate=1:1);

NMR (CDCl$_3$): δ 11.50 (br, 1H), 7.64 (s, 1H), 6.65 (s, 1H), 5.72 (s, 1H), 4.72 (d, J=6.0 Hz, 2H), 3.92 (s, 3H), 2.82 (s, 2H), 2.18 (t, J=6.0 Hz, 1H), 2.06 (br, 3H), 1.91 (br, 6H), 1.75 (br, 6H), 1.29 (s, 6H).

EXAMPLE 28(6)

(Z)-2-(7-hydroxymethyl-3,3-dimethyl-3,4-dihydro-
(2H)-isoquinolin-1-ylidene)-1-(adamantan-1-yl)
ethan-1-one

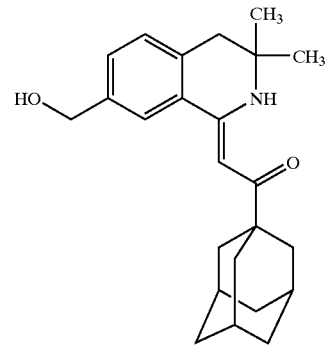

TLC: Rf 0.50 (hexane:ethyl acetate=1:1);

NMR (CDCl$_3$): δ 11.51 (brs, 1H), 7.71 (brs, 1H), 7.40 (dd, J=7.8, 1.8 Hz, 1H), 7.17 (d, J=7.8 Hz, 1H), 5.80 (s, 1H), 4.75 (d, J=5.4 Hz, 2H), 2.83 (s, 2H), 2.09–2.03 (m, 3H), 1.94–1.90 (m, 6H), 1.78–1.72 (m, 6H), 1.29 (s, 6H).

EXAMPLE 28(7)

(Z)-2-(7-hydroxymethyl-6-methoxy-3,3-dimethyl-3,
4-dihydro-(2H)-isoquinolin-1-ylidene)-1-
cyclohexylethan-1-one

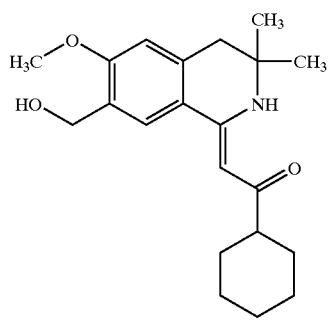

TLC: Rf 0.10 (hexane:ethyl acetate=31);

NMR (CDCl$_3$): δ 11.29 (br, 1H), 7.64 (s, 1H), 6.65 (s, 1H), 5.58 (s, 1H), 4.71 (d, J=6.0 Hz, 2H), 3.91 (s, 3H), 2.82 (s, 2H), 2.29 (tt, J=11.5, 3.5 Hz, 1H), 2.16 (t, J=6.0 Hz, 1H), 1.89–1.78 (m, 4H), 1.69 (m, 1H), 1.56–1.20 (m, 11H).

EXAMPLE 28(8)

(Z)-2-(7-hydroxymethyl-6-methoxy-3,3-dimethyl-3,
4-dihydro-(2H)-isoquinolin-1-ylidene)-1-
cycloheptylethan-1-one

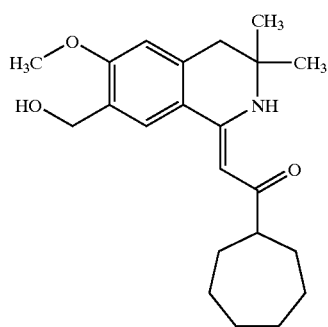

TLC: Rf 0.41 (hexane:ethyl acetate=1:1);

NMR (CDCl$_3$): δ 11.21 (br, 1H), 7.64 (s, 1H), 6.65 (s, 1H), 5.55 (s, 1H), 4.71 (d, J=6.5 Hz, 2H), 3.91 (s, 3H), 2.82 (s, 2H), 2.45 (m, 1H), 2.16 (t, J=6.5 Hz, 1H), 1.95–1.88 (m, 2H), 1.82–1.46 (m, 10H), 1.29 (s, 6H).

EXAMPLE 28(9)

(Z)-2-(7-hydroxymethyl-3,3,6-trimethyl-3,4-dihydro-(2H)-isoquinolin-1-ylidene)-1-(adamantan-1-yl)ethan-1-one

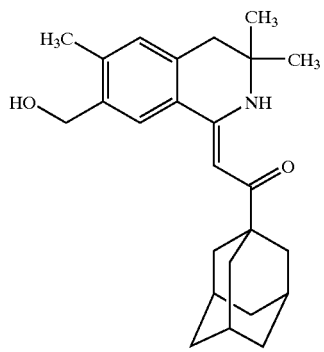

TLC: Rf 0.17 (hexane:ethyl acetate=5:1);

NMR (CDCl$_3$): δ 11.50 (br, 1H), 7.69 (s, 1H), 6.99 (s, 1H), 5.78 (s, 1H), 4.75 (d, J=5.7 Hz, 2H), 2.79 (s, 2H), 2.39 (s, 3H), 2.06 (br, 3H), 1.92–1.91 (br, 6H), 1.76–1.75 (br, 6H), 1.28 (s, 6H).

EXAMPLE 28(10)

(Z)-2-(7-hydroxymethyl-3,3-dimethyl-3,4-dihydro-(2H)-isoquinolin-1-ylidene)-1-cyclohexylethan-1-one

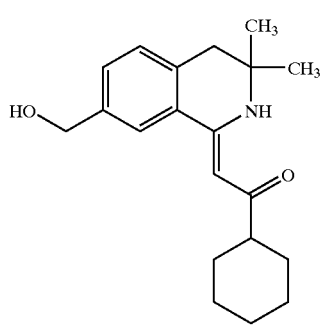

TLC: Rf 0.49 (hexane:ethyl acetate=1:1);

NMR (CDCl$_3$): δ 11.30 (brs, 1H), 7.72 (brs, 1H), 7.39 (dd, J=7.8, 1.8 Hz, 1H), 7.17 (d, J=7.8 Hz, 1H), 5.66 (s, 1H), 4.74 (s, 2H), 2.83 (s, 2H), 2.30 (tt, J=11.4, 3.6 Hz, 1H), 1.93–1.18 (m, 16H).

EXAMPLE 28(11)

(Z)-2-(7-hydroxymethyl-3,3,6-trimethyl-3,4-dihydro-(2H)-isoquinolin-1-ylidene)-1-cyclohexylethan-1-one

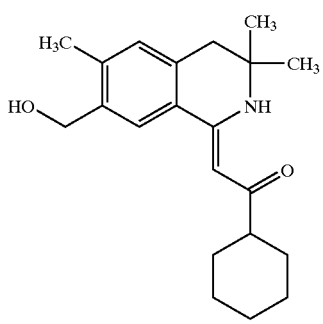

TLC: Rf 0.21 (hexane:ethyl acetate=3:1);

NMR (CDCl$_3$): δ 11.29 (br, 1H), 7.70 (s, 1H), 6.98 (s, 1H), 5.64 (s, 1H), 4.74 (d, J=5.1 Hz, 2H), 2.79 (s, 2H), 2.37 (s, 3H), 2.30 (m, 1H), 1.92–1.76 (m, 4H), 1.69 (m, 1H), 1.55–1.28 (m, 11H).

EXAMPLE 28(12)

(Z)-2-(7-hydroxymethyl-3,3-dimethyl-3,4-dihydro-(2H)-isoquinolin-1-ylidene)-1-cycloheptylethan-1-one

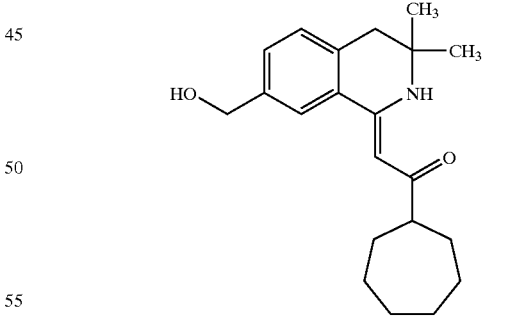

TLC: Rf 0.21 (hexane:ethyl acetate=2:1);

NMR (CDCl$_3$): δ 11.22 (brs, 1H), 7.71 (brs, 1H), 7.39 (dd, J=7.8, 1.8 Hz, 1H), 7.16 (d, J=7.8 Hz, 1H), 5.62 (s, 1H), 4.74 (s, 2H), 2.83 (s, 2H), 2.46 (tt, J=9.9, 3.3 Hz, 1H), 1.99–1.42 (m, 12H), 1.28 (s, 6H).

EXAMPLE 28(13)

(Z)-2-(7-hydroxymethyl-3,3,6-trimethyl-3,4-dihydro-(2H)-isoquinolin-1-ylidene)-1-cycloheptylethan-1-one

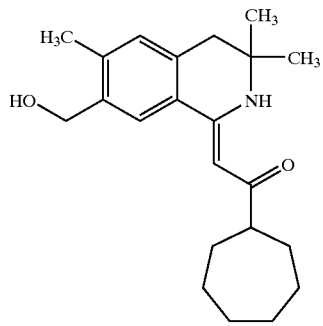

TLC: Rf 0.34 (hexane:ethyl acetate=3:1);

NMR (CDCl$_3$): δ 11.21 (br, 1H), 7.70 (s, 1H), 6.98 (s, 1H), 5.61 (s, 1H), 4.74 (d, J=4.8 Hz, 2H), 2.79 (s, 2H), 2.46 (m, 1H), 2.37 (s, 3H), 1.96–1.86 (m, 2H), 1.84–1.56 (m, 10H), 1.28 (s, 6H).

EXAMPLE 29~EXAMPLE 29(11)

By the same procedure as described in example 8 using the compound prepared in example 2(3) or the compound prepared in Example 14, Example 14(2), Example 14(3), Example 14(10), Example 14(3), or Example 14(10) and acetyl chloride or a corresponding halide derivative, the following compounds of the present invention were given.

EXAMPLE 29

(Z)-2-(3,3-dimethyl-3,4-dihydro-(2H)-isoquinolin-1-ylidene)-1-(1-phenylsulfonylpiperidin-4-yl)ethan-1-one

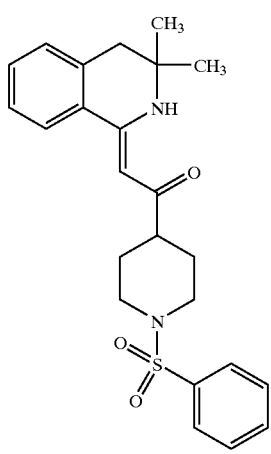

TLC: Rf 0.47 (hexane:ethyl acetate=1:1);

NMR (CDCl$_3$): δ 11.29 (br, 1H), 7.81–7.77 (m, 2H), 7.64–7.51 (m, 4H), 7.40 (t, J=7.5 Hz, 1H), 7.31–7.26 (m, 1H), 7.17 (d, J=7.5 Hz, 1H), 5.54 (s, 1H), 3.88–3.85 (m, 2H), 2.84 (s, 2H), 2.41–2.33 (m, 2H), 2.24–2.14 (m, 1H), 1.97–1.76 (m, 4H), 1.29 (s, 6H).

EXAMPLE 29(1)

(Z)-2-(3,3-dimethyl-3,4-dihydro-(2H)-isoquinolin-1-ylidene)-1-(1-ethylsulfonylpiperidin-4-yl)ethan-1-one

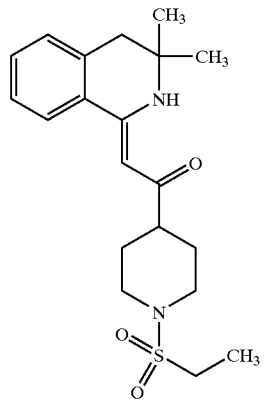

TLC: Rf 0.26 (hexane:ethyl acetate=1:1);

NMR (CDCl$_3$): δ 11.32 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.62 (s, 1H), 3.88–3.84 (m, 2H), 3.01–2.86 (m, 6H), 2.46–2.35 (m, 1H), 1.99–1.93 (m, 2H), 1.89–1.78 (m, 2H), 1.38 (t, J=7.0 Hz, 3H), 1.31 (s, 6H).

EXAMPLE 29(2)

(Z)-2-(3,3-dimethyl-3,4-dihydro-(2H)-isoquinolin-1-ylidene)-1-(1-propylsulfonylpiperidin-4-yl)ethan-1-one

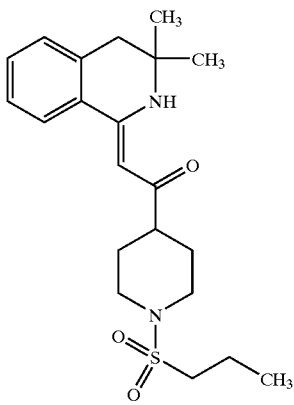

TLC: Rf 0.34 (hexane:ethyl acetate=1:1);

NMR (CDCl$_3$): δ 11.32 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.62 (s, 1H), 3.87–3.83 (m, 2H), 2.93–2.83 (m, 6H), 2.44–2.35 (m, 1H), 1.99–1.75 (m, 6H), 1.31 (s, 6H), 1.06 (t, J=7.5 Hz, 3H).

EXAMPLE 29(3)

(Z)-2-(3,3-dimethyl-3,4-dihydro-(2H)-isoquinolin-1-ylidene)-1-(1-butylsulfonylpiperidin-4-yl)ethan-1-one

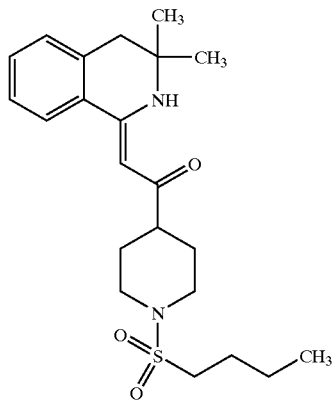

TLC: Rf 0.10 (hexane:ethyl acetate=3:1);

NMR (CDCl$_3$): δ 11.33 (br, 1H), 7.69 (dd, J=7.5, 1.0 Hz, 1H), 7.41 (dt, J=1.0, 7.5 Hz, 1H), 7.30 (dt, J=1.0, 7.5 Hz, 1H), 7.19 (dd, J=7.5, 1.0 Hz, 1H), 5.62 (s, 1H), 3.87–3.83 (m, 2H), 2.95–2.83 (m, 6H), 2.45–2.34 (m, 1H), 2.00–1.93 (m, 2H), 1.90–1.76 (m, 4H), 1.51–1.40 (m, 2H), 1.31 (s, 6H), 0.96 (t, J=7.5 Hz, 3H).

EXAMPLE 29(4)

(Z)-2-(3,3-dimethyl-3,4-dihydro-(2H)-isoquinolin-1-ylidene)-1-(1-octylsulfonylpiperidin-4-yl)ethan-1-one

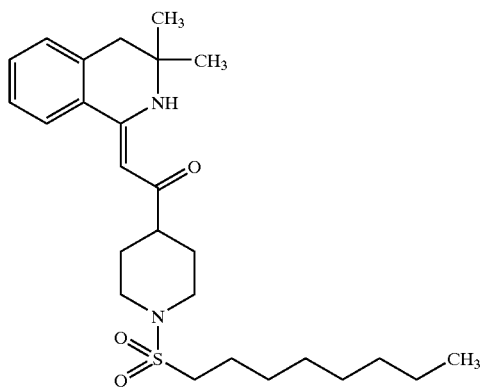

TLC: Rf 0.22 (hexane:ethyl acetate=3:1);

NMR (CDCl$_3$): δ 11.33 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.61 (s, 1H), 3.87–3.83 (m, 2H), 2.94–2.82 (m, 6H), 2.44–2.34 (m, 1H), 1.98–1.93 (m, 2H), 1.87–1.76 (m, 4H), 1.44–1.22 (m, 16H), 0.88 (brt, 3H).

EXAMPLE 29(5)

(Z)-2-(3,3-dimethyl-3,4-dihydro-(2H)-isoquinolin-1-ylidene)-1-(4-acetylaminophenyl)ethan-1-one

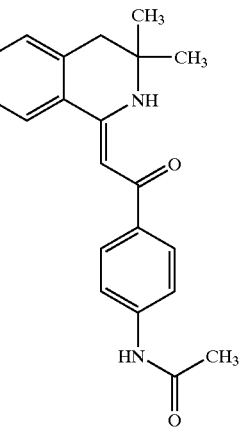

TLC: Rf 0.09 (hexane:ethyl acetate=1:1);

NMR (CDCl$_3$): δ 11.80 (br, 1H), 7.94 (d, J=8.5 Hz, 2H), 7.83 (d, J=7.5 Hz, 1H), 7.58 (d, J=8.5 Hz, 2H), 7.43 (t, J=7.5 Hz, 1H), 7.37–7.32 (m, 2H), 7.21 (d, J=7.5 Hz, 1H), 6.31 (s, 1H), 2.90 (s, 2H), 2.21 (s, 3H), 1.36 (s, 6H).

EXAMPLE 29(6)

(Z)-2-(3,3-dimethyl-3,4-dihydro-(2H)-isoquinolin-1-ylidene)-1-(3-acetylaminophenyl)ethan-1-one

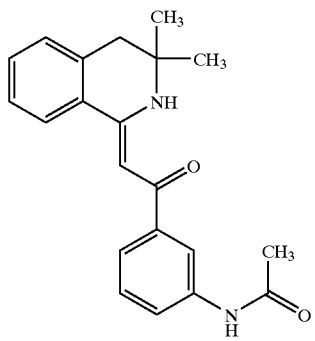

TLC: Rf 0.12 (hexane:ethyl acetate=1:1);

NMR (CDCl$_3$): δ 11.83 (br, 1H), 7.87–7.82 (m, 3H), 7.69 (d, J=8.0 Hz, 1H), 7.46–7.32 (m, 4H), 7.22 (d, J=7.5 Hz, 1H), 6.31 (s, 1H), 2.91 (s, 2H), 2.21 (s, 3H), 1.37 (s, 6H).

EXAMPLE 29(7)

(Z)-2-(3,3-dimethyl-3,4-dihydro-(2H)-isoquinolin-1-ylidene)-1-(3-mesylaminophenyl)ethan-1-one

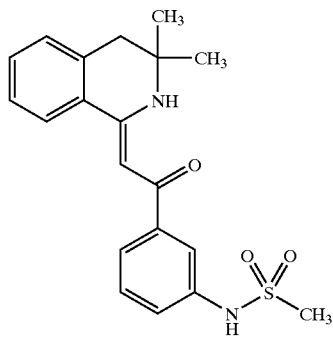

TLC: Rf 0.24 (hexane:ethyl acetate=1:1);

NMR (CDCl$_3$): δ 11.86 (br, 1H), 7.82 (d, J=7.5 Hz, 1H), 7.78–7.73 (m, 2H), 7.48–7.40 (m, 3H), 7.36 (t, J=7.5 Hz, 1H), 7.21 (d, J=7.5 Hz, 1H), 6.54 (br, 1H), 6.29 (s, 1H), 3.02 (s, 3H), 2.91 (s, 2H), 1.37 (s, 6H).

EXAMPLE 29(8)

(Z)-2-(7-acetylamino-3,3-dimethyl-3,4-dihydro-(2H)-isoquinolin-1-ylidene)-1-phenylethan-1-one

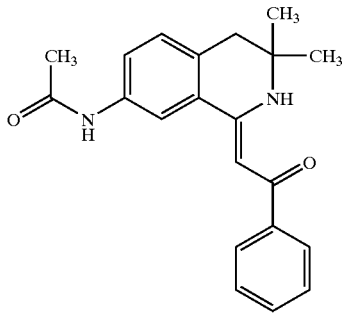

TLC: Rf 0.23 (hexane:ethyl acetate=1:1);

NMR (CDCl$_3$): δ 11.81 (br, 1H), 7.96–7.91 (m, 3H), 7.64 (dd, J=8.0, 2.0 Hz, 1H), 7.45–7.39 (m, 4H), 7.17 (d, J=8.0 Hz, 1H), 6.29 (s, 1H), 2.84 (s, 2H), 2.23 (s, 3H), 1.33 (s, 6H).

EXAMPLE 29(9)

(Z)-2-(7-acetylamino-3,3-dimethyl-3,4-dihydro-(2H)-isoquinolin-1-ylidene)-1-(adamantan-1-yl)ethan-1-one

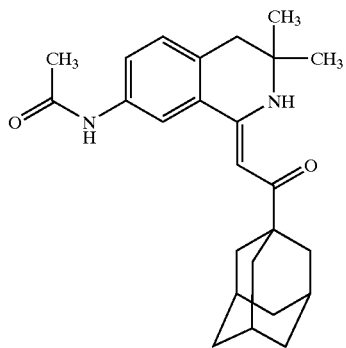

TLC: Rf 0.38 (hexane:ethyl acetate=1:1);

NMR (CDCl$_3$): δ 11.48 (br, 1H), 7.78 (d, J=2.0 Hz, 1H), 7.62 (dd, J=8.0, 2.0 Hz, 1H), 7.27 (br, 1H), 7.13 (d, J=8.0 Hz, 1H), 5.74 (s, 1H), 2.79 (s, 2H), 2.22 (s, 3H), 2.05 (br, 3H), 1.91 (br, 6H), 1.74 (br, 6H), 1.28 (s, 6H).

EXAMPLE 29(10)

(Z)-2-(7-mesylamino-3,3-dimethyl-3,4-dihydro-(2H)-isoquinolin-1-ylidene)-1-phenylethan-1-one

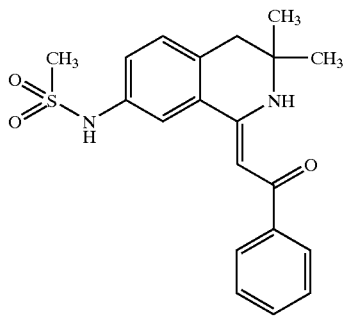

TLC: Rf 0.14 (hexane:ethyl acetate=2:1);

NMR (CDCl$_3$): δ 11.80 (br, 1H), 7.96–7.92 (m, 2H), 7.64 (d, J=2.0 Hz, 1H), 7.47–7.42 (m, 3H), 7.35 (dd, J=8.0, 2.0 Hz, 1H), 7.22 (d, J=8.0 Hz, 1H), 6.54 (br, 1H), 6.27 (s, 1H), 3.06 (s, 3H), 2.88 (s, 2H), 1.36 (s, 6H).

EXAMPLE 29(11)

(Z)-2-(7-mesylamino-3,3-dimethyl-3,4-dihydro-(2H)-isoquinolin-1-ylidene)-1-(adamantan-1-yl)ethan-1-one

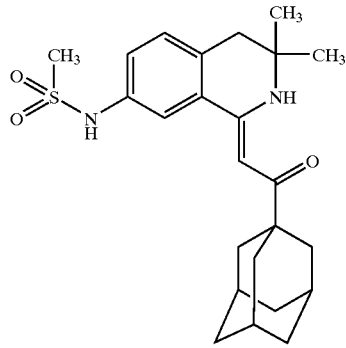

TLC: Rf 0.20 (hexane:ethyl acetate=2:1);

NMR (CDCl$_3$): δ 11.46 (br, 1H), 7.51 (d, J=2.0 Hz, 1H), 7.34 (dd, J=8.0, 2.0 Hz, 1H), 7.18 (d, J=8.0 Hz, 1H), 6.46 (br, 1H), 5.72 (s, 1H), 3.05 (s, 3H), 2.81 (s, 2H), 2.06 (br, 3H), 1.90 (br, 6H), 1.74 (br, 6H), 1.29 (s, 6H).

EXAMPLE 30

(Z)-2-(6-methylcarbamoyl-3,3-dimethyl-3,4-dihydro-(2H)-isoquinolin-1-ylidene)-1-phenylethan-1-one

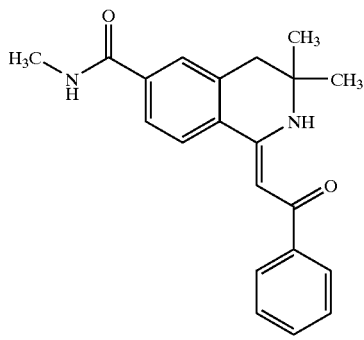

A solution of the compound prepared in example 15 (100 mg) in tetrahydrofuran (3 ml) was ice-cooled and to the mixture were added triethylamine (0.09 ml) and chloroisobutyl carbonate (0.08 ml) and the mixture was stirred for 30 minutes at room temperature. The aggregate that appeared was filtered off. To an ice-cooled solution of 40% aqueous solution of methylamine (0.120 ml) in tetrahydrofuran (2 ml) was added thus given filtrate and the mixture was stirred at room temperature overnight. The reaction mixture was concentrated. The residue was purified by column chromatography on silica gel (hexane:ethyl acetate=1:1) to give the compound of the present invention (92 mg) having the following physical data.

TLC: Rf 0.46 (ethyl acetate);

NMR (CDCl$_3$): δ 11.76 (brs, 1H), 7.97–7.92 (m, 2H), 7.87 (d, J=9.0 Hz, 1H), 7.69–7.63 (m, 2H), 7.48–7.42 (m, 3H), 6.34 (s, 1H), 6.20 (brs, 1H), 3.05 (d, J=4.8 Hz, 3H), 2.94 (s, 2H), 1.36 (s, 6H).

EXAMPLE 30(1)~EXAMPLE 30(11)

By the same procedure as described in example 30 using the compound prepared in example 15 or the compound prepared in example 15(1)~Example 15(4) or example 15(13) in its place, and methylamine or a corresponding amine derivative, the following compounds of the present invention were given.

EXAMPLE 30(1)

(Z)-2-(6-dimethylcarbamoyl-3,3-dimethyl-3,4-dihydro-(2H)-isoquinolin-1-ylidene)-1-phenylethan-1-one

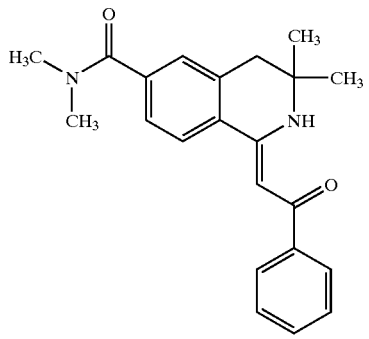

TLC: Rf 0.40 (ethyl acetate);

NMR (CDCl$_3$): δ 11.78 (brs, 1H), 7.97–7.92 (m, 2H), 7.86 (d, J=8.1 Hz, 1H), 7.48–7.41 (m, 3H), 7.37 (dd, J=8.1, 1.5 Hz, 1H), 7.29 (d, J=1.5 Hz, 1H), 6.34 (s, 1H), 3.14 (s, 3H), 3.01 (s, 3H), 2.92 (s, 2H), 1.37 (s, 6H).

EXAMPLE 30(2)

(Z)-2-(6-carbamoyl-3,3-dimethyl-3,4-dihydro-(2H)-isoquinolin-1-ylidene)-1-phenylethan-1-one

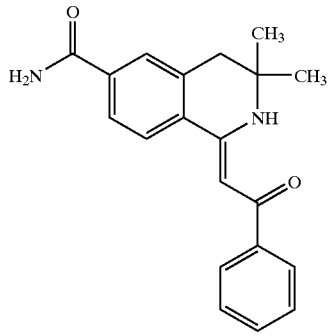

TLC: Rf 0.36 (chloroform:methanol=9:1);

NMR (CDCl$_3$): δ 11.76 (brs, 1H), 7.98–7.88 (m, 3H), 7.75–7.69 (m, 2H), 7.49–7.41 (m, 3H), 6.35 (s, 1H), 6.12 (brs, 1H), 5.71 (brs, 1H), 2.95 (s, 2H), 1.37 (s, 6H).

EXAMPLE 30(3)

(Z)-2-(7-carbamoyl-3,3-dimethyl-3,4-dihydro-(2H)-isoquinolin-1-ylidene)-1-phenylethan-1-one

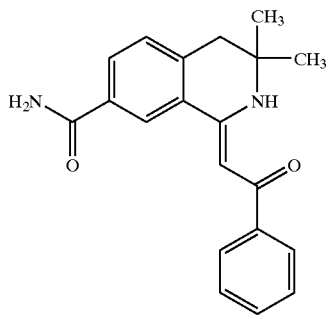

TLC: Rf 0.07 (hexane:ethyl acetate=1:1);

NMR (CDCl$_3$): δ 11.82 (br, 1H), 8.31 (d, J=1.5 Hz, 1H), 7.98–7.94 (m, 2H), 7.83 (dd, J=8.0, 1.5 Hz, 1H), 7.48–7.42 (m, 3H), 7.31 (d, J=8.0 Hz, 1H), 6.39 (s, 1H), 6.10 (br, 1H), 5.67 (br, 1H), 2.95 (s, 2H), 1.37 (s, 6H).

EXAMPLE 30(4)

(Z)-2-(7-methylcarbamoyl-3,3-dimethyl-3,4-dihydro-(2H)-isoquinolin-1-ylidene)-1-phenylethan-1-one

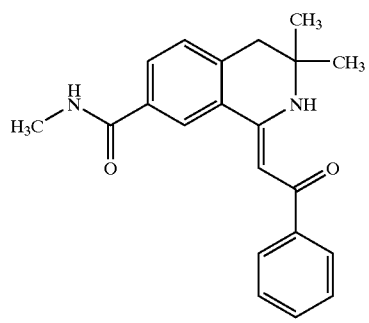

TLC: Rf 0.14 (hexane:ethyl acetate=1:1);

NMR (CDCl$_3$): δ 11.81 (br, 1H), 8.24 (d, J=2.0 Hz, 1H), 7.98–7.94 (m, 2H), 7.78 (dd, J=8.0, 2.0 Hz, 1H), 7.48–7.41 (m, 3H), 7.28 (d, J=8.0 Hz, 1H), 6.39 (s, 1H), 6.20 (br, 1H), 3.07 (d, J=5.0 Hz, 3H), 2.94 (s, 2H), 1.36 (s, 6H).

EXAMPLE 30(5)

(Z)-2-(7-dimethylcarbamoyl-3,3-dimethyl-3,4-dihydro-(2H)-isoquinolin-1-ylidene)-1-phenylethan-1-one

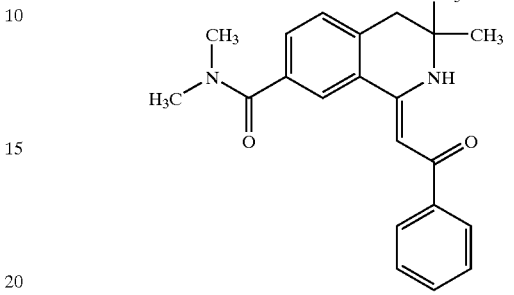

TLC: Rf 0.12 (hexane:ethyl acetate=1:1);

NMR (CDCl$_3$): δ 11.79 (br, 1H), 7.96–7.91 (m, 3H), 7.49–7.40 (m, 4H), 7.26 (m, 1H), 6.33 (s, 1H), 3.16 (br, 3H), 3.04 (br, 3H), 2.93 (s, 2H), 1.37 (s, 6H).

EXAMPLE 30(6)

(Z)-2-(7-carbamoyl-3,3-dimethyl-3,4-dihydro-(2H)-isoquinolin-1-ylidene)-1-(adamantan-1-yl)ethan-1-one

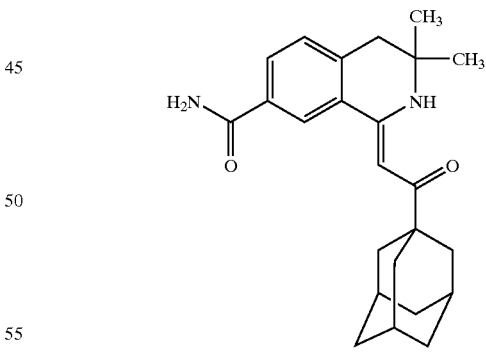

TLC: Rf 0.34 (hexane:ethyl acetate=1:1);

NMR (CDCl$_3$): δ 11.51 (br, 1H), 8.19 (d, J=1.2 Hz, 1H), 7.77 (dd, J=1.2, 7.5 Hz, 1H), 7.27 (d, J=7.5 Hz, 1H), 5.84 (s, 1H), 2.89 (s, 2H), 2.06 (br, 3H), 1.92–1.91 (br, 6H), 1.76–1.75 (br, 6H), 1.30 (s, 6H).

EXAMPLE 30(7)

(Z)-2-(7-methylcarbamoyl-3,3-dimethyl-3,4-dihydro-(2H)-isoquinolin-1-ylidene)-1-(adamantan-1-yl)ethan-1-one

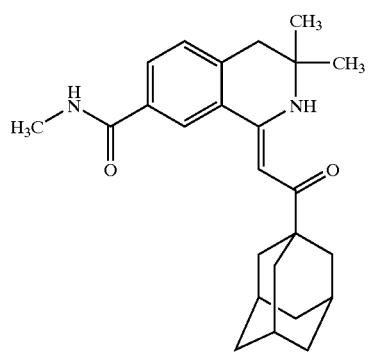

TLC: Rf 0.40 (hexane:ethyl acetate=1:1);

NMR (CDCl$_3$): δ 11.49 (br, 1H), 8.14 (d, J=1.2 Hz, 1H), 7.70 (dd, J=1.2, 7.8 Hz, 1H), 7.23 (d, J=7.8 Hz, 1H), 6.14 (br, 1H), 5.84 (s, 1H), 3.06 (d, J=7.8 Hz, 3H), 2.87 (s, 2H), 2.06 (br, 3H), 1.92–1.91 (b r, 6H), 1.75 (s, 6H), 1.29 (s, 6H).

EXAMPLE 30(8)

(Z)-2-(7-dimethylcarbamoyl-3,3-dimethyl-3,4-dihydro-(2H)-isoquinolin-1-ylidene)-1-(adamantan-1-yl)ethan-1-one

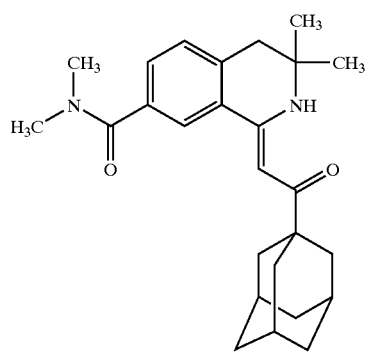

TLC: Rf 0.50 (chloroform:methanol=50:1);

NMR (CDCl$_3$): δ 11.45 (br, 1H), 7.81 (d, J=1.2 Hz, 1H), 7.41 (dd, J=1.2, 7.8 Hz, 1H), 7.20 (d, J=7.8 Hz, 1H), 5.78 (s, 1H), 3.15 (br, 3H), 3.02 (br, 3H), 2.86 (s, 2H), 2.05 (br, 3H), 1.90–1.89 (br, 6H), 1.74 (br, 6H), 1.30 (s, 6H).

EXAMPLE 30(9)

(Z)-2-(6-carbamoyl-3,3-dimethyl-3,4-dihydro-(2H)-isoquinolin-1-ylidene)-1-cyclohexylethan-1-one

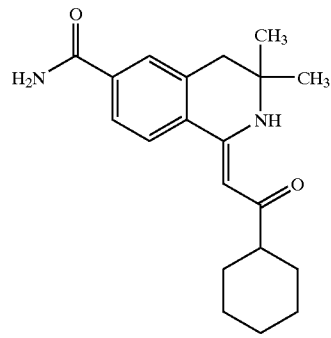

TLC: Rf 0.12 (hexane:ethyl acetate=1:1);

NMR (CDCl$_3$): δ 11.24 (br, 1H), 7.78 (d, J=8.0 Hz, 1H), 7.70–7.66 (m, 2H), 6.14 (br, 1H), 5.83 (br, 1H), 5.66 (s, 1H), 2.89 (s, 2H), 2.30 (tt, J=11.5, 3.5 Hz, 1H), 1.90–1.80 (m, 4H), 1.70 (m, 1H), 1.50–1.20 (m, 11H).

EXAMPLE 30(10)

(Z)-2-(6-carbamoyl-3,3-dimethyl-3,4-dihydro-(2H)-isoquinolin-1-ylidene)-1-cycloheptylethan-1-one

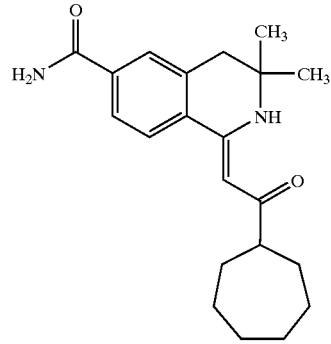

TLC: Rf 0.12 (hexane:ethyl acetate=1:1);

NMR (CDCl$_3$): δ 11.15 (br, 1H), 7.78 (d, J=8.0 Hz, 1H), 7.69–7.66 (m, 2H), 6.08 (br, 1H), 5.75 (br, 1H), 5.63 (s, 1H), 2.89 (s, 2H), 2.48 (tt, J=10.0, 4.0 Hz, 1H), 1.95–1.88 (m, 2H), 1.82–1.45 (m, 10H), 1.29 (s, 6H).

EXAMPLE 30(11)

(Z)-2-(6-carbamoyl-3,3-dimethyl-3,4-dihydro-(2H)-isoquinolin-1-ylidene)-1-(adamantan-1-yl)ethan-1-one

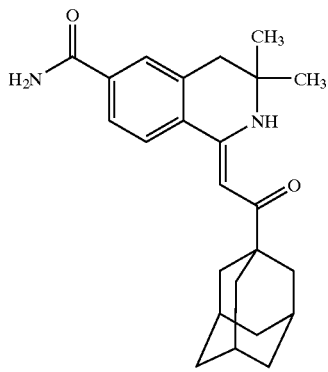

TLC: Rf 0.13 (hexane:ethyl acetate=1:1);

NMR (CDCl$_3$): δ 11.40 (br, 1H), 7.79 (d, J=8.0 Hz, 1H), 7.70–7.66 (m, 2H), 6.05 (br, 1H), 5.81 (s, 1H), 5.76 (br, 1H), 2.89 (s, 2H), 2.06 (br, 3H), 1.91 (br, 6H), 1.75 (br, 6H), 1.30 (s, 6H).

EXAMPLE 31

(Z)-2-(3,3-dimethyl-3,4-dihydro-(2H)-isoquinolin-1-ylidene)-1-(4-cyano-2-methoxyphenyl)ethan-1-one

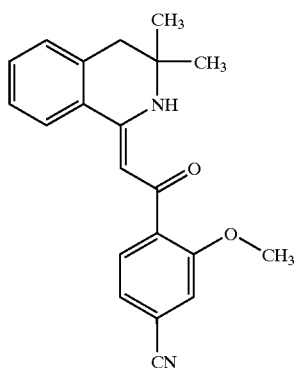

To a suspension of the compound prepared in example 13(4) (423 mg) in formic acid (10 ml) was added hydroxyamine hydrochloride (1.05 g) and the mixture was stirred for 30 minutes at 130° C. The reaction mixture was allowed to cool and to the mixture was added ice and water, and the aggregate that appeared was filtered off. The aggregate was dissolved in ethyl acetate and the mixture was washed with water and a saturated aqueous solution successively, dried over anhydrous magnesium sulfate and was concentrated. The residue was roughly purified by column chromatography on silica gel (hexane:ethyl acetate= 5:1→2:1). The product was washed with t-butyl methyl ether to give the compound of the present invention (65 mg) having the following physical data.

TLC: Rf 0.32 (hexane:ethyl acetate=2:1);

NMR (CDCl$_3$): δ 11.73 (br, 1H), 7.73–7.70 (m, 2H), 7.44 (dt, J=1.0, 7.5 Hz, 1H), 7.34–7.29 (m, 2H), 7.23–7.19 (m, 2H), 6.16 (s, 1H), 3.94 (s, 3H), 2.91 (s, 2H), 1.37 (s, 6H).

EXAMPLE 31(1)–EXAMPLE 31(3)

By the same procedure as described in example 31 using the compound prepared in example 13(1), example 13(12) or example 13(14) in place of the compound prepared in 13(4), the following compounds of the present invention were given.

EXAMPLE 31(1)

(Z)-2-(7-cyano-3,3-dimethyl-3,4-dihydro-(2H)-isoquinolin-1-ylidene)-1-phenylethan-1-one

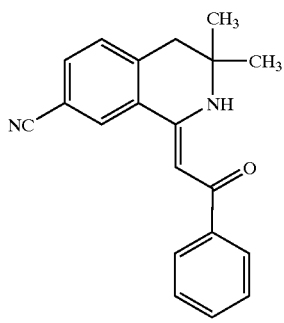

TLC: Rf 0.49 (hexane:ethyl acetate=1:1);

NMR (CDCl$_3$): δ 11.73 (brs, 1H), 8.11 (d, J=1.5 Hz, 1H), 7.99–7.93 (m, 2H), 7.70 (dd, J=8.1, 1.5 Hz, 1H), 7.51–7.44 (m, 3H), 7.35 (d, J=8.1 Hz, 1H), 6.31 (s, 1H), 2.97 (s, 2H), 1.37 (s, 6H).

EXAMPLE 31(2)

(Z)-2-(7-cyano-3,3,6-trimethyl-3,4-dihydro-(2H)-isoquinolin-1-ylidene)-1-(adamantan-1-yl)ethan-1-one

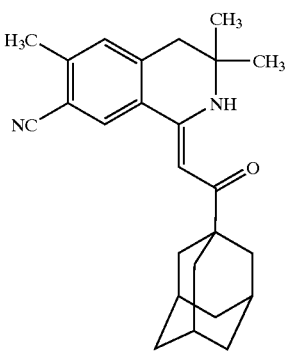

TLC: Rf 0.50 (methylene chloride);

NMR (CDCl$_3$): δ 11.37 (br, 1H), 7.94 (s, 1H), 7.14 (s, 1H), 5.73 (s, 1H), 2.84 (s, 2H), 2.57 (s, 3H), 2.07 (br, 3H), 1.91–1.90 (br, 6H), 1.76 (br, 6H), 1.29 (s, 6H).

EXAMPLE 31(3)

(Z)-2-(7-cyano-3,3,6-trimethyl-3,4-dihydro-(2H)-isoquinolin-1-ylidene)-1-cyclohexylethan-1-one

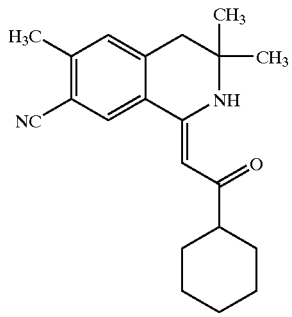

TLC: Rf 0.45 (methylene chloride);

NMR (CDCl$_3$): δ 11.21 (br, 1H), 7.92 (s, 1H), 7.14 (s, 1H), 5.58 (s, 1H), 2.84 (s, 2H), 2.57 (s, 3H), 2.36–2.28 (m, 1H), 1.92–1.29 (m, 16H).

EXAMPLE 32

(Z)-2-(6-ethynyl-3,3-dimethyl-3,4-dihydro-(2H)-isoquinolin-1-ylidene)-1-phenylethan-1-one

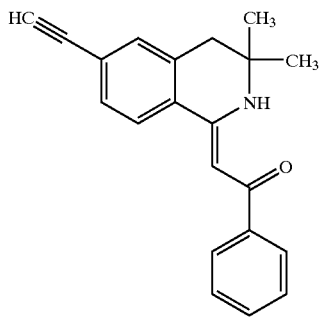

To a suspension of (bromomethyl)triphenylphosphonium bromide (371 mg) in tetrahydrofuran (3 ml) was added potassium t-butoxide (2.55 ml, 1.0M in THF) dropwise at −78° C. and the mixture was stirred for 30 minutes at 0° C. To the mixture was added the compound prepared in example 13 (200 mg) in tetrahydrofuran (5 ml) at −78° C. dropwise and the mixture was stirred for 90 minutes at 0° C. and for 60 minutes at room temperature. To the reaction mixture was added ice-water and the mixture was extracted with ethyl acetate. The extract was washed with water and a saturated aqueous solution of sodium chloride successively, and dried over anhydrous magnesium sulfate and concentrated. The residue was purified by column chromatography on silica gel (hexane:ethyl acetate= 20:1→10:1) to give the compound of the present invention (127 mg) having the following physical data.

TLC: Rf 0.46 (hexane:ethyl acetate=3:1);

NMR (CDCl$_3$): δ 11.76 (br, 1H), 7.96–7.92 (m, 2H), 7.78 (d, J=8.0 Hz, 1H), 7.47–7.41 (m, 4H), 7.35 (d, J=1.0 Hz, 1H), 6.31 (s, 1H), 3.22 (s, 1H), 2.88 (s, 2H), 1.36 (s, 6H).

EXAMPLE 32(1)–EXAMPLE 32(2)

By the same procedure as described in example 32 using the compound prepared in example 13(1) or example 13(3) in place of the compound prepared in example 13, the following compounds of the present invention were given.

EXAMPLE 32(1)

(Z)-2-(7-ethynyl-3,3-dimethyl-3,4-dihydro-(2H)-isoquinolin-1-ylidene)-1-phenylethan-1-one

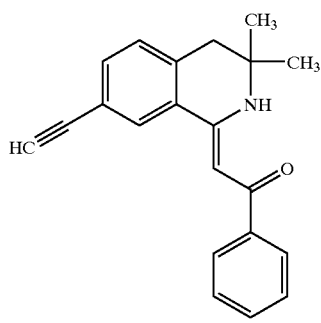

TLC: Rf 0.48 (hexane:ethyl acetate=3:1);

NMR (CDCl$_3$): δ 11.79 (br, 1H), 7.97–7.94 (m, 3H), 7.54 (dd, J=8.0, 1.5 Hz, 1H), 7.47–7.42 (m, 3H), 7.19 (d, J=8.0 Hz, 1H), 6.31 (s, 1H), 3.14 (s, 1H), 2.90 (s, 2H), 1.36 (s, 6H).

EXAMPLE 32(2)

(Z)-2-(3,3-dimethyl-3,4-dihydro-(2H)-isoquinolin-1-ylidene)-1-(4-ethynylphenyl)ethan-1-one

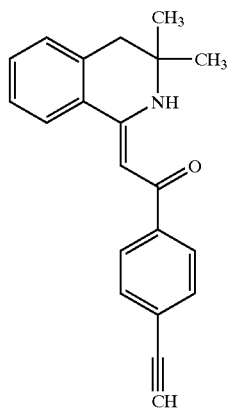

TLC: Rf 0.39 (hexane:ethyl acetate=3:1);

NMR (CDCl$_3$): δ 11.88 (br, 1H), 7.91 (d, J=8.5 Hz, 2H), 7.82 (d, J=7.5 Hz, 1H), 7.55 (d, J=8.5 Hz, 2H), 7.44 (t, J=7.5 Hz, 1H), 7.35 (t, J=7.5 Hz, 1H), 7.22 (d, J=7.5 Hz, 1H), 6.31 (s, 1H), 3.17 (s, 1H), 2.91 (s, 2H), 1.37 (s, 6H).

EXAMPLE 33

(Z)-2-(6-((E)-2-carboxyethenyl)-3,3-dimethyl-3,4-dihydro-(2H)-isoquinolin-1-ylidene)-1-phenylethan-1-one

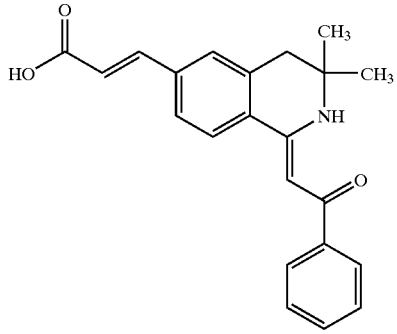

To a solution of the compound prepared in example 13 (200 mg) in pyridine (5 ml) was added piperidine (2 drops) at room temperature and to the mixture was added malonic acid (122 mg) and the mixture was stirred for 20 minutes at room temperature, for 30 minutes at 85° C., for 3.5 hours at 100° C. and overnight at 80° C. The reaction mixture was allowed to cool and was diluted with ethyl acetate. The organic layer was washed with a saturated aqueous solution of ammonium chloride, water and a saturated aqueous solution of sodium chloride successively, dried over anhydrous magnesium sulfate and concentrated. The residue was purified by column chromatography on silica gel (hexane:ethyl acetate=2:1→ethyl acetate) to give the compound of the present invention (173 mg) having the following physical data.

TLC: Rf 0.16 (hexane:ethyl acetate=1:1);

NMR (CDCl$_3$): δ 11.76 (br, 1H), 7.97–7.93 (m, 2H), 7.87 (d, J=8.0 Hz, 1H), 7.78 (d, J=16.0 Hz, 1H), 7.52 (dd, J=8.0, 1.5 Hz, 1H), 7.48–7.41 (m, 3H), 7.40 (d, J=1.5 Hz, 1H), 6.54 (d, J=16.0 Hz, 1H), 6.35 (s, 1H), 2.93 (s, 2H), 1.38 (s, 6H).

EXAMPLE 34

(Z)-2-(6-((E)-2-methoxycarbonylethenyl)-3,3-dimethyl-3,4-dihydro-(2H)-isoquinolin-1-ylidene)-1-phenylethan-1-one

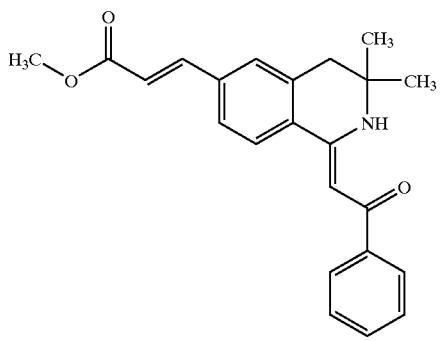

To a solution of the compound prepared in example 33 (90 mg) in dimethylformamide (2 ml) was added potassium carbonate (39 mg) and methyl iodide (0.033 ml) and the mixture was stirred overnight at room temperature. To the reaction mixture was added water and the aggregate that appeared was filtered off. The aggregate was dissolved in ethyl acetate and was washed with water and a saturated aqueous solution of sodium chloride, dried over anhydrous magnesium sulfate and concentrated to give the compound of the present invention (94 mg) having the following physical data.

TLC: Rf 0.68 (hexane:ethyl acetate=1:1);

NMR (CDCl$_3$): δ 11.76 (br, 1H), 7.96–7.93 (m, 2H), 7.85 (d, J=8.0 Hz, 1H), 7.69 (d, J=16.0 Hz, 1H), 7.51–7.41 (m, 4H), 7.36 (s, 1H), 6.52 (d, J=16.0 Hz, 1H), 6.34 (s, 1H), 3.83 (s, 3H), 2.92 (s, 2H), 1.38 (s, 6H).

EXAMPLE 34(1)–EXAMPLE 34(2)

By the same procedure as described in example 34 using the compound prepared in example 15 or example 15(1) in place of the compound prepared in example 33, the following compounds of the present invention were given.

EXAMPLE 34(1)

(Z)-2-(6-methoxycarbonyl-3,3-dimethyl-3,4-dihydro-(2H)-isoquinolin-1-ylidene)-1-phenylethan-1-one

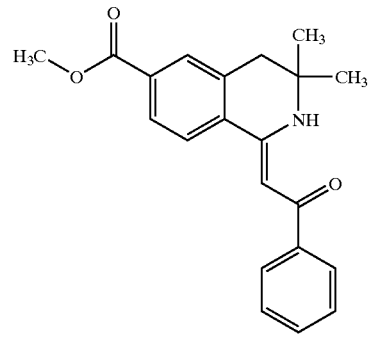

TLC: Rf 0.43 (hexane:ethyl acetate=3:1);

NMR (CDCl$_3$): δ 11.75 (br, 1H), 8.01–7.94 (m, 3H), 7.90–7.88 (m, 2H), 7.48–7.41 (m, 3H), 6.37 (s, 1H), 3.96 (s, 3H), 2.95 (s, 2H), 1.37 (s, 6H).

EXAMPLE 34(2)

(Z)-2-(7-methoxycarbonyl-3,3-dimethyl-3,4-dihydro-(2H)-isoquinolin-1-ylidene)-1-phenylethan-1-one

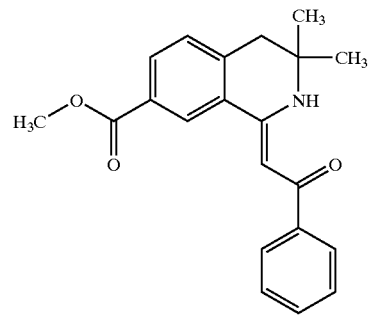

TLC: Rf 0.25 (hexane:ethyl acetate=3:1);

NMR (CDCl$_3$): δ 11.83 (br, 1H), 8.49 (d, J=2.0 Hz, 1H), 8.10 (dd, J=8.0, 2.0 Hz, 1H), 7.99–7.96 (m, 2H), 7.49–7.44 (m, 3H), 7.31 (d, J=8.0 Hz, 1H), 6.40 (s, 1H), 3.98 (s, 3H), 2.96 (s, 2H), 1.37 (s, 6H).

EXAMPLE 35

(Z)-2-(7-carboxy-6-chloro-3,3-dimethyl-3,4-dihydro-(2H)-isoquinolin-1-ylidene)-1-cyclohexylethan-1-one

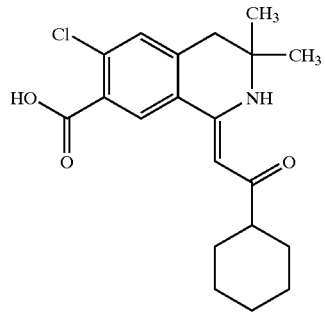

To tetrahydrofuran (1 ml) and methanol (1 ml) was added the compound prepared in example 19 (58 mg) and to the mixture was added 2N aqueous solution of sodium hydroxide (1 ml) and the mixture was stirred overnight at room temperature. The reaction mixture was neutralized with 1N hydrochloric acid and was extracted with ethyl acetate. The extract was washed with a saturated aqueous solution of sodium chloride, dried over anhydrous magnesium sulfate and was concentrated. The residue was washed with a mixture of hexane and ethyl acetate to give the compound of the present invention (45 mg) having the following physical data.

TLC: Rf 0.40 (water:methanol:chloroform=1:10:100);

NMR (CDCl$_3$): δ 11.24 (br., 1H), 8.35 (s, 1H), 7.33 (s, 1H), 5.66 (s, 1H), 2.86 (s, 2H), 2.34 (m, 1H), 1.95–1.65 (m, 5H), 1.55–1.20 (m, 5H), 1.31 (s, 6H).

EXAMPLE 35(1)~EXAMPLE 35(2)

By the same procedure as described in example 35 using the compound prepared in example 11(197) or example 11(198), the following compounds of the present invention were given.

EXAMPLE 35(1)

(Z)-2-(7-carboxy-6-chloro-3,3-dimethyl-3,4-dihydro-(2H)-isoquinolin-1-ylidene)-1-(adamantan-1-yl)ethan-1-one

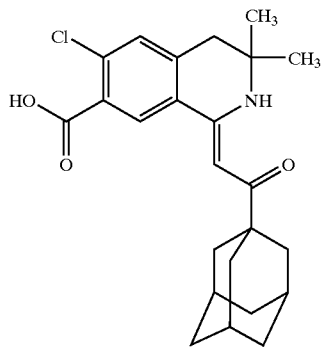

TLC: Rf 0.28 (hexane:ethyl acetate=1:1);

NMR (CDCl$_3$): δ 11.44 (brs, 1H), 8.33 (s, 1H), 7.33 (s, 1H), 5.80 (s, 1H), 2.86 (s, 2H), 2.10–2.03 (m, 3H), 1.93–1.89 (m, 6H), 1.77–1.72 (m, 6H), 1.31 (s, 6H).

EXAMPLE 35(2)

(Z)-2-(7-carboxy-6-chloro-3,3-dimethyl-3,4-dihydro-(2H)-isoquinolin-1-ylidene)-1-cycloheptylethan-1-one

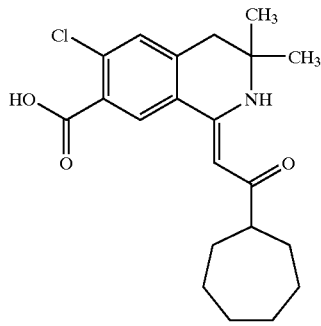

TLC: Rf 0.28 (hexane:ethyl acetate=1:1);

NMR (CDCl$_3$): δ 11.16 (brs, 1H), 8.34 (s, 1H), 7.32 (s, 1H), 5.63 (s, 1H), 2.85 (s, 2H), 2.50 (tt, J=9.9, 3.9 Hz, 1H), 1.97–1.42 (m, 12H), 1.31 (s, 6H).

EXAMPLE 36

(Z)-2-(3,3,4,4-tetramethyl-3,4-dihydro-(2H)-isoquinolin-1-ylidene)-1-(4-cyanophenyl)ethan-1-one

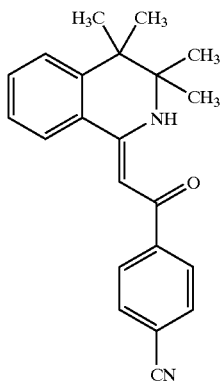

By the same procedure as described in example 3 using 1,3,3,4,4-pentamethyl-3,4-dihydroisoquinoline in place of the compound prepared in reference example 2 and 4-cyanobenzoyl chloride in place of 3-cyanobenzoyl chloride, the compounds of the present invention having the following physical data were given.

TLC: Rf 0.48 (hexane:ethyl acetate=2:1);

NMR (CDCl$_3$): δ 11.90 (br, 1H), 8.03 (d, J=8.5 Hz, 2H), 7.79 (dd, J=7.5, 1.0 Hz, 1H), 7.72 (d, J=8.5 Hz, 2H), 7.52 (dt, J=1.0, 7.5 Hz, 1H), 7.45 (dd, J=7.5, 1.0 Hz, 1H), 7.34 (dt, J=1.0, 7.5 Hz, 1H), 6.25 (s, 1H), 1.31 (br, 12H).

EXAMPLE 37

(Z)-2-(7-formylamino-3,3-dimethyl-3,4-dihydro-(2H)-isoquinolin-1-ylidene)-1-phenylethan-1-one

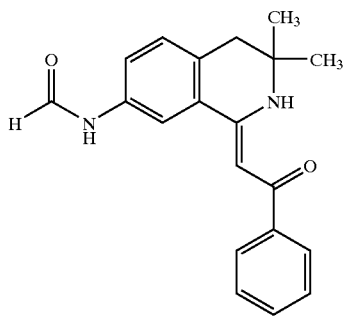

To a mixture of acetic anhydride (0.50 ml) and formic acid (5 ml) was added the compound prepared in example 14(3) (151 mg) and the mixture was stirred for 1 hour at 70° C. The reaction mixture was allowed to cool and to the mixture was added ice and the mixture was neutralized with a saturated aqueous solution of sodium bicarbonate and was extracted with ethyl acetate. The extract was washed with a saturated aqueous solution of sodium bicarbonate, water and a saturated aqueous solution of sodium chloride, dried over anhydrous magnesium sulfate and was concentrated. The residue was purified by column chromatography on silica gel (hexane:ethyl acetate=2:1) to give the compound of the present invention (131 mg) having the following physical data.

TLC: Rf 0.21 (hexane:ethyl acetate=1:1);

NMR (DMSO-d$_6$): δ 11.74 (brs, 1H), 10.26 (brs, 1H), 8.13 (d, J=1.8 Hz, 1H), 7.89–7.84 (m, 2H), 7.74 (dd, J=8.1, 1.8 Hz, 1H), 7.50–7.43 (m, 3H), 7.28 (d, J=8.1 Hz, 1H), 7.26 (s, 1H), 6.24 (s, 1H), 2.87 (s, 2H), 1.27 (s, 6H).

EXAMPLE 37(1)

(Z)-2-(6-formylamino-3,3-dimethyl-3,4-dihydro-(2H)-isoquinolin-1-ylidene)-1-phenylethan-1-one

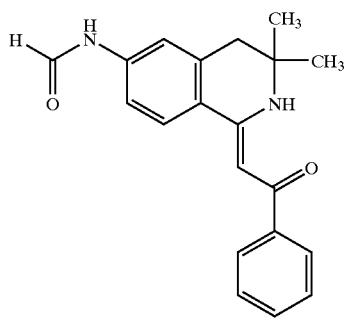

By the same procedure as described in example 37 using the compound prepared in example 40 in place of the compound prepared in example 14(3), the following compound of the present invention was given.

TLC: Rf 0.40 (hexane:ethyl acetate=1:4);

NMR (CDCl$_3$): δ 11.79 (brs, 1H), 8.43 (s, 1H), 7.97–7.92 (m, 2H), 7.80 (d, J=8.4 Hz, 1H), 7.63 (d, J=2.1 Hz, 1H), 7.47–7.39 (m, 3H), 7.37 (dd, J=8.4, 2.1 Hz, 1H), 6.27 (s, 1H), 2.89 (s, 2H), 1.36 (s, 6H).

EXAMPLE 38

(Z)-2-(7-methylamino-3,3-dimethyl-3,4-dihydro-(2H)-isoquinolin-1-ylidene)-1-phenylethan-1-one

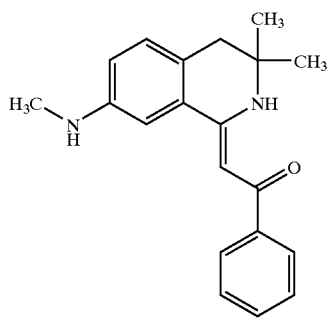

To a suspension of lithium aluminum hydride (77 mg) in tetrahydrofuran (1 ml) was added a solution of the compound prepared in example 37 (131 mg) in tetrahydrofuran (4 ml) and the mixture was stirred for 4 hours at room temperature. To the reaction mixture was added a saturated aqueous solution of sodium sulfate and was filtered over celite. The filtrate was concentrated. The residue was purified by column chromatography on silica gel (hexane:ethyl acetate=4:1) to give the compound of the present invention (73 mg) having the following physical data.

TLC: Rf 0.41 (hexane:ethyl acetate=2:1);

NMR (CDCl$_3$): δ 11.85 (brs, 1H), 7.97–7.91 (m, 2H), 7.46–7.40 (m, 3H), 7.03 (d, J=8.1 Hz, 1H), 7.03 (d, J=2.4

Hz, 1H), 6.71 (dd, J=8.1, 2.4 Hz, 1H), 6.25 (s, 1H), 2.91 (s, 3H), 2.78 (s, 2H), 1.35 (s, 6H).

EXAMPLE 38(1)~EXAMPLE 38(2)

By the same procedure as described in example 38 using the compound prepared in example 37(1) or example 30(4) in place of the compound prepared in example 37, the following compounds of the present invention were given.

EXAMPLE 38(1)

(Z)-2-(6-methylamino-3,3-dimethyl-3,4-dihydro-(2H)-isoquinolin-1-ylidene)-1-phenylethan-1-one

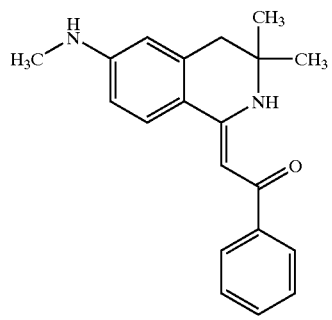

TLC: Rf 0.69 (hexane:ethyl acetate=1:4);

NMR (CDCl$_3$): δ 11.85 (brs, 1H), 7.97–7.91 (m, 2H), 7.66 (d, J=8.7 Hz, 1H), 7.44–7.38 (m, 3H), 6.51 (dd, J=8.7, 2.4 Hz, 1H), 6.35 (d, J=2.4 Hz, 1H), 6.21 (s, 1H), 4.14 (brs, 1H), 2.91 (s, 3H), 2.80 (s, 2H), 1.36 (s, 6H).

EXAMPLE 38(2)

(Z)-2-(7-methylaminomethyl-3,3-dimethyl-3,4-dihydro-(2H)-isoquinolin-1-ylidene)-1-phenylethan-1-one

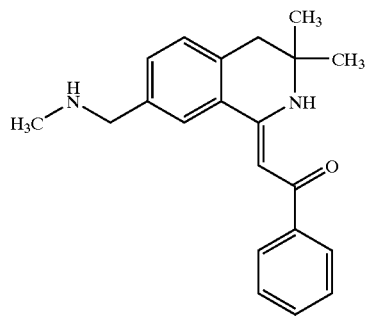

TLC: Rf 0.29 (hexane:ethyl acetate:isopropylamine= 10:2:1);

NMR (CDCl$_3$): δ 11.86 (br, 1H), 7.98–7.95 (m, 2H), 7.77 (s, 1H), 7.47–7.37 (m, 4H), 7.18 (d, J=8.0 Hz, 1H), 6.35 (s, 1H), 3.81 (s, 2H), 2.89 (s, 2H), 2.50 (s, 3H), 1.36 (s, 6H).

EXAMPLE 39

(Z)-2-(6-t-butoxycarbonylamino-3,3-dimethyl-3,4-dihydro-(2H)-isoquinolin-1-ylidene)-1-phenylethan-1-one

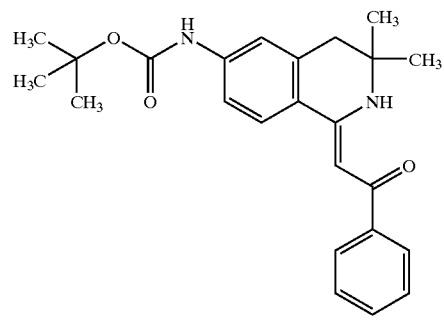

To a suspension of the compound prepared in example 15 (965 mg) in t-butanol (15 ml) were added triethylamine (0.460 ml) and diphenylphosphoryl azide (0.710 ml) and the mixture was stirred for 3 hours at 100° C. The reaction mixture was allowed to cool and it was diluted with ethyl acetate and then washed with water, a saturated aqueous solution of sodium bicarbonate and was a saturated aqueous solution of sodium chloride successively and was dried over anhydrous magnesium sulfate and was concentrated. The residue was purified by column chromatography on silica gel (hexane:ethyl acetate=9:1) to give the compound of the present invention (1.04 g) having the following physical data.

TLC: Rf 0.58 (hexane:ethyl acetate=1:1);

NMR (CDCl$_3$): δ 11.81 (brs, 1H), 7.96–7.91 (m, 2H), 7.74 (d, J=8.7 Hz, 1H), 7.46–7.40 (m, 4H), 7.16 (dd, J=8.7, 2.7 Hz, 1H), 6.64 (brs, 1H), 6.26 (s, 1H), 2.87 (s, 2H), 1.54 (s, 9H), 1.35 (s, 6H).

EXAMPLE 39(1)~EXAMPLE 39(4)

By the same procedure as described in example 39 using the compound prepared 15(3), example 15(4), example 15(13) or example 15(14) in place of the compound prepared in example 15, the following compounds of the present invention were given.

EXAMPLE 39(1)

(Z)-2-(6-t-butoxycarbonylamino-3,3-dimethyl-3,4-dihydro-(2H)-isoquinolin-1-ylidene)-1-cyclohexylethan-1-one

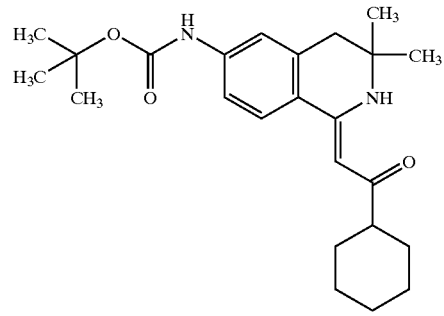

TLC: Rf 0.17 (hexane:ethyl acetate=5:1);

NMR (CDCl₃): δ 11.30 (br, 1H), 7.62 (d, J=8.5 Hz, 1H), 7.38 (d, J=2.0 Hz, 1H), 7.12 (dd, J=8.5, 2.0 Hz, 1H), 6.61 (br, 1H), 5.56 (s, 1H), 2.80 (s, 2H), 2.26 (m, 1H), 1.89–1.78 (m, 4H), 1.68 (m, 1H), 1.58–1.24 (m, 20H).

EXAMPLE 39(2)

(Z)-2-(6-t-butoxycarbonylamino-3,3-dimethyl-3,4-dihydro-(2H)-isoquinolin-1-ylidene)-1-cycloheptylethan-1-one

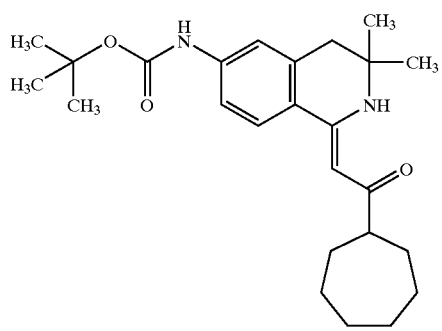

TLC: Rf 0.42 (hexane:ethyl acetate=3:1).

EXAMPLE 39(3)

(Z)-2-(6-t-butoxycarbonylamino-3,3-dimethyl-3,4-dihydro-(2H)-isoquinolin-1-ylidene)-1-(adamantan-1-yl)ethan-1-one

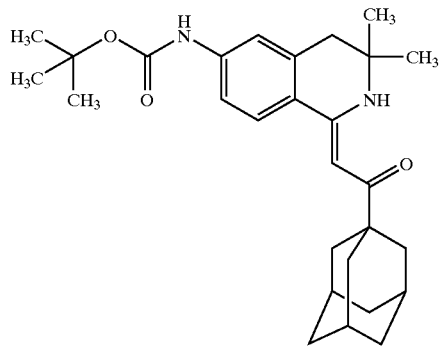

TLC: Rf 0.42 (hexane:ethyl acetate=3:1);

NMR (CDCl₃): δ 11.48 (br, 1H), 7.64 (d, J=9.0 Hz, 1H), 7.42 (d, J=2.0 Hz, 1H), 7.10 (dd, J=9.0, 2.0 Hz, 1H), 6.60 (br, 1H), 5.71 (s, 1H), 2.80 (s, 2H), 2.05 (br, 3H), 1.91 (br, 6H), 1.74 (br, 6H), 1.53 (s, 9H), 1.28 (s, 6H).

EXAMPLE 39(4)

(Z)-2-(6-t-butoxycarbonylamino-3,3-dimethyl-3,4-dihydro-(2H)-isoquinolin-1-ylidene)-1-(pyridin-3-yl)ethan-1-one

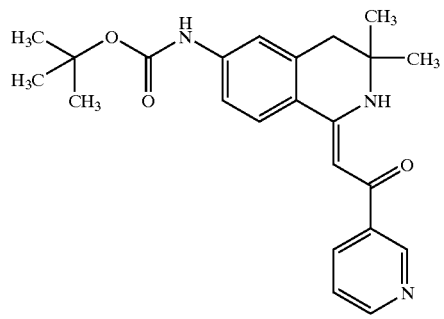

TLC: Rf 0.41 (methylene chloride:methanol=10:1);

NMR (CDCl₃): δ 11.84 (br, 1H), 9.14 (d, J=1.5 Hz, 1H), 8.65 (dd, J=5.0, 1.5 Hz, 1H), 8.21 (ddd, J=8.5, 1.5, 1.5 Hz, 1H), 7.74 (d, J=8.5 Hz, 1H), 7.49 (d, J=2.0 Hz, 1H), 7.36 (dd, J=8.5, 5.0 Hz, 1H), 7.17 (dd, J=8.5, 2.0 Hz, 1H), 6.67 (s, 1H), 6.21 (s, 1H), 2.88 (s, 2H), 1.54 (s, 9H), 1.37 (s, 6H).

EXAMPLE 40

(Z)-2-(6-amino-3,3-dimethyl-3,4-dihydro-(2H)-isoquinolin-1-ylidene)-1-phenylethan-1-one

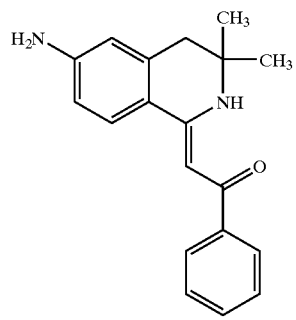

To the compound prepared in example 39 (1.04 g) was added 4N hydrochloric acid-dioxane (20 ml) and the mixture was stirred for 2 hours at room temperature. To the reaction mixture was added methanol until it became uniform, and the mixture was stirred for 1 hour at 50° C. To the reaction mixture was added a saturated aqueous solution of sodium bicarbonate and was extracted with a mixture of ethyl acetate and tetrahydrofuran. The extract was washed with a saturated aqueous solution of sodium chloride, dried over anhydrous sodium sulfate and concentrated. The residue was purified by column chromatography on silica gel (hexane:ethyl acetate=3:1→chloroform) to give the compound of the present invention (458 mg) having the following physical data.

TLC: Rf 0.29 (hexane:ethyl acetate=1:1);

NMR (CDCl₃): δ 11.84 (brs, 1H), 7.96–7.91 (m, 2H), 7.64 (d, J=8.4 Hz, 1H), 7.44–7.39 (m, 3H), 6.59 (dd, J=8.4, 2.4 Hz, 1H), 6.46 (d, J=2.4 Hz, 1H), 6.21 (s, 1H), 4.00 (brs, 2H), 2.78 (s, 2H), 1.35 (s, 6H).

EXAMPLE 40(1)–EXAMPLE 40(4)

By the same procedure as described in example 40 using one compound selected from the compounds prepared in example 39(1)~example 39(4) in place of the compound prepared in example 39, the compounds of the present invention were given.

EXAMPLE 40(1)

(Z)-2-(6-amino-3,3-dimethyl-3,4-dihydro-(2H)-isoquinolin-1-ylidene)-1-cyclohexylethan-1-one

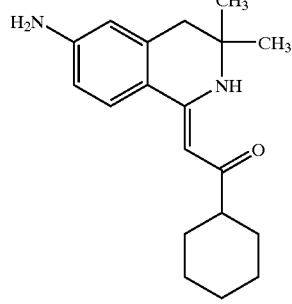

TLC: Rf 0.11 (hexane:ethyl acetate=31);

NMR (CDCl$_3$): δ 11.33 (br, 1H), 7.52 (d, J=8.5 Hz, 1H), 6.55 (dd, J=8.5, 2.5 Hz, 1H), 6.42 (d, J=2.5 Hz, 1H), 5.50 (s, 1H), 3.94 (br, 2H), 2.72 (s, 2H), 2.25 (tt, J=11.5, 3.5 Hz, 1H), 1.89–1.78 (m, 4H), 1.68 (m, 1H), 1.58–1.20 (m, 11H).

EXAMPLE 40(2)

(Z)-2-(6-amino-3,3-dimethyl-3,4-dihydro-(2H)-isoquinolin-1-ylidene)-1-cycloheptylethan-1-one

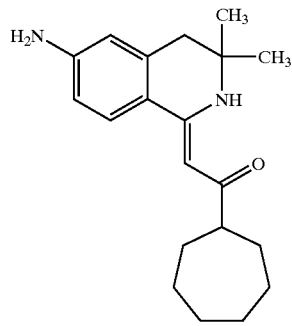

TLC: Rf 0.14 (hexane:ethyl acetate=3:1);

NMR (CDCl$_3$): δ 11.25 (br, 1H), 7.51 (d, J=8.5 Hz, 1H), 6.55 (dd, J=8.5, 2.5 Hz, 1H), 6.42 (d, J=2.5 Hz, 1H), 5.47 (s, 1H), 3.93 (br, 2H), 2.71 (s, 2H), 2.41 (tt, J=9.5, 4.0 Hz, 1H), 1.94–1.88 (m, 2H), 1.82–1.45 (m, 10H), 1.28 (s, 6H).

EXAMPLE 40(3)

(Z)-2-(6-amino-3,3-dimethyl-3,4-dihydro-(2H)-isoquinolin-1-ylidene)-1-(adamantan-1-yl)ethan-1-one

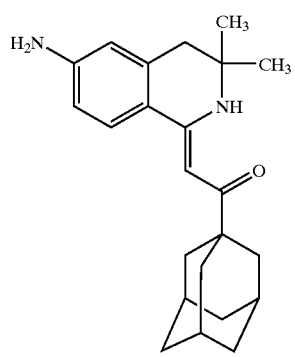

TLC: Rf 0.12 (hexane:ethyl acetate=3:1);

NMR (CDCl$_3$): δ 11.51 (br, 1H), 7.54 (d, J=8.5 Hz, 1H), 6.56 (dd, J=8.5, 2.5 Hz, 1H), 6.42 (d, J=2.5 Hz, 1H), 5.65 (s, 1H), 3.94 (br, 2H), 2.71 (s, 2H), 2.05 (br, 3H), 1.91 (br, 6H), 1.74 (br, 6H), 1.28 (s, 6H).

EXAMPLE 40(4)

(Z)-2-(6-amino-3,3-dimethyl-3,4-dihydro-(2H)-isoquinolin-1-ylidene)-1-(pyridin-3-yl)ethan-1-one

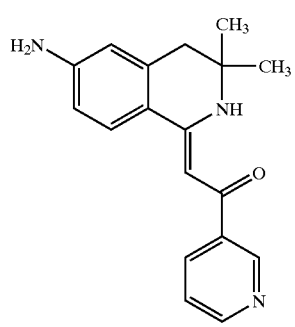

TLC: Rf 0.39 (methylene chloride:methanol=10:1);

NMR (CDCl$_3$): δ 11.86 (br, 1H), 9.13 (dd, J=2.0, 1.0 Hz, 1H), 8.64 (dd, J=4.5, 2.0 Hz, 1H), 8.21 (ddd, J=8.0, 2.0, 2.0 Hz, 1H), 7.63 (d, J=8.5 Hz, 1H), 7.35 (ddd, J=8.0, 4.5, 1.0 Hz, 1H), 6.61 (dd, J=8.5, 2.5 Hz, 1H), 6.47 (d, J=2.5 Hz, 1H), 6.16 (s, 1H), 4.04 (br, 2H), 2.80 (s, 2H), 1.37 (s, 6H).

EXAMPLE 41

(Z)-2-(7-dimethylamino-3,3-dimethyl-3,4-dihydro-(2H)-isoquinolin-1-ylidene)-1-phenylethan-1-one

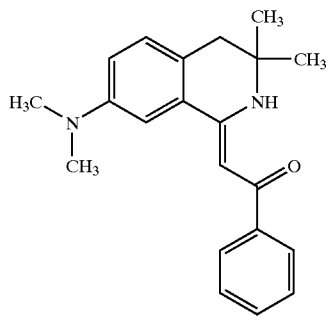

To a solution of the compound prepared in example 38 (49 mg) in tetrahydrofuran (2 ml) were added acetic acid (0.10 ml), 35% aqueous solution of formaldehyde (0.14 ml) and sodium triacetoxyborohydride (340 mg) and the mixture was stirred overnight at room temperature. The reaction mixture was added to a saturated aqueous solution of sodium bicarbonate, and was extracted with ethyl acetate. The extract was washed with a saturated aqueous solution of sodium chloride, dried over anhydrous magnesium sulfate and was concentrated. The residue was purified by column chromatography on silica gel (hexane:ethyl acetate=9:1) to give the compound of the present invention (25 mg) having the following physical data.

TLC: Rf 0.54 (hexane:ethyl acetate=2:1);

NMR (CDCl$_3$): δ 11.90 (brs, 1H), 7.97–7.90 (m, 2H), 7.46–7.41 (m, 3H), 7.13 (d, J=2.7 Hz, 1H), 7.07 (d, J=8.4 Hz, 1H), 6.84 (dd, J=8.4, 2.7 Hz, 1H), 6.28 (s, 1H), 3.01 (s, 6H), 2.79 (s, 2H), 1.35 (s, 6H).

EXAMPLE 41(1)~EXAMPLE 41(2)

By the same procedure as described in example 41 using the compound prepared in example 11(133) or example 11(134) in place of the compound prepared in example 38, the following compounds of the present invention were given.

EXAMPLE 41(1)

(Z)-2-(7-dimethylamino-6-methoxy-3,3-dimethyl-3,4-dihydro-(2H)-isoquinolin-1-ylidene)-1-(4-cyanophenyl)ethan-1-one

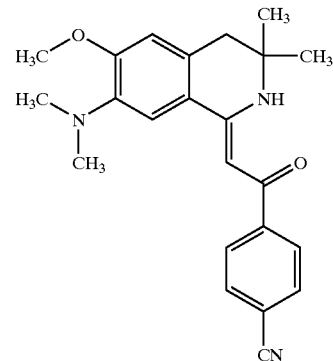

TLC: Rf 0.26 (hexane:ethyl acetate=1:1);

NMR (CDCl$_3$): δ 11.97 (br, 1H), 8.00 (d, J=8.5 Hz, 2H), 7.72 (d, J=8.5 Hz, 2H), 7.30 (s, 1H), 6.66 (s, 1H), 6.14 (s, 1H), 3.96 (s, 3H), 2.85 (s, 8H), 1.38 (s, 6H).

EXAMPLE 41(2)

(Z)-2-(7-dimethylamino-6-methoxy-3,3-dimethyl-3,4-dihydro-(2H)-isoquinolin-1-ylidene)-1-(adamantan-1-yl)ethan-1-one

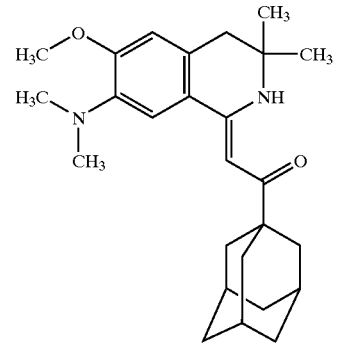

TLC: Rf 0.47 (hexane:ethyl acetate=1:1);

NMR (CDCl$_3$): δ 11.56 (br, 1H), 7.25 (s, 1H), 6.60 (s, 1H), 5.66 (s, 1H), 3.93 (s, 3H), 2.83 (s, 6H), 2.76 (s, 2H), 2.06 (br, 3H), 1.92 (br, 6H), 1.75 (br, 6H), 1.30 (s, 6H).

REFERENCE EXAMPLE 9

4-bromo-3,3-dimethyl-3,4-dihydro-(2H)-isoquinolin-1-one

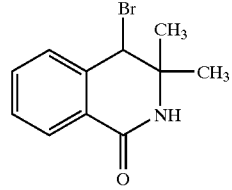

To carbon trioxide (5 ml) were added 3,3-dimethyl-3,4-dihydro-(2H)-isoquinolin-1-one (200 mg) and N-bromosuccinimide (223 mg) and to the mixture was added benzoyl peroxide (24 mg) and the mixture was stirred overnight at room temperature and refluxed for 1 hour. The reaction mixture was allowed to cool and the aggregate that appeared was filtered off. The filtrate was washed with water and a saturated aqueous solution of sodium chloride successively, and dried over anhydrous magnesium sulfate and was concentrated. The residue was washed with a mixture (hexane:ethyl acetate=4:1) to give the compound of the present invention (196 mg) having the following physical data.

TLC: Rf 0.37 (ethyl acetate:hexane=1:1);

NMR (CDCl$_3$): δ 8.10 (dd, J=7.5, 1.5 Hz, 1H), 7.54 (ddd, J=7.5, 7.5, 1.5 Hz, 1H), 7.46 (ddd, J=7.5, 7.5, 1.5 Hz, 1H), 7.39 (dd, J=7.5, 1.5 Hz, 1H), 5.98 (br., 1H), 5.11 (s, 1H), 1.59 (s, 3H), 1.37 (s, 3H).

REFERENCE EXAMPLE 10

4-hydroxy-3,3-dimethyl-3,4-dihydro-(2H)-isoquinolin-1-one

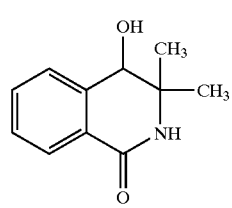

To a mixture of dioxane (100 ml) and water (20 ml), were added the compound prepared in reference example 9 (6.57 g) and sodium acetate (21.2 g) and the mixture was refluxed for 3 days. To the reaction mixture was added potassium carbonate (10.6 g) and the mixture was stirred overnight at room temperature. The reaction mixture was concentrated and to the residue was added ethyl acetate and was filtered off. The aqueous layer of the filtrate was extracted with ethyl acetate. The combined organic layer was washed with a saturated aqueous solution of sodium chloride and was dried over anhydrous magnesium sulfate and was concentrated. The residue was purified by column chromatography on silica gel (hexane:ethyl acetate=3:2) to give the compound of the present invention (2 g) having the following physical data.

TLC: Rf 0.28 (ethyl acetate:hexane=1:1).

REFERENCE EXAMPLE 11

4-t-butyldimethylsilyloxy-3,3-dimethyl-3,4-dihydro-(2H)-isoquinolin-1-one

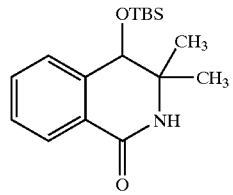

To methylene chloride (10 ml) were added the compound prepared in reference example 10 (1.0 g) and t-butyldimethylsilyl chloride (784 mg) and then was added imidazole (708 mg) and the mixture was stirred for 2 hours at room temperature. To the reaction mixture were added methylene chloride (10 ml), dimethylformamide (5 ml) and triethylamine (0.5 ml) and the mixture was stirred overnight. The reaction mixture was poured into ice-water and was extracted with a mixture of hexane and ethyl acetate (1:3). The extract was washed with water and a saturated aqueous solution of sodium chloride successively, dried over anhydrous magnesium sulfate and was concentrated. The residue was purified by column chromatography on silica gel (hexane:ethyl acetate=3:1) to give the compound of the present invention (632 mg) having the following physical data.

TLC: Rf 0.61 (ethyl acetate:hexane=1:1);

NMR (CDCl$_3$): δ 8.02 (dd, J=7.5, 1.5 Hz, 1H), 7.52 (ddd, J=7.5, 7.5, 1.5 Hz, 1H), 7.45–7.35 (m, 2H), 5.80 (br., 1H), 4.65 (s, 1H), 1.26 (s, 3H), 1.18 (s, 3H), 0.93 (s, 9H), 0.14 (s, 3H), 0.00 (s, 3H).

REFERENCE EXAMPLE 12

(Z)-2-(4-t-butyldimethylsilyloxy-3,3-dimethyl-3,4-dihydro-(2H)-isoquinolin-1-ylidene)-1-phenylethan-1-one

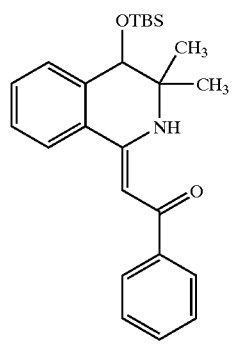

By the same procedure as described in reference example 6→example 11 using the compound prepared in reference example 11 in place of the compound prepared in reference example 5, the compound of the present invention having the following physical data was given.

TLC: Rf 0.56 (chloroform:hexane=1:5);

NMR (CDCl$_3$): δ 11.66 (br., 1H), 7.95 (m, 2H), 7.79 (d, J=8.0 Hz, 1H), 7.55–7.30 (m, 6H), 6.32 (s, 1H), 4.65 (s, 1H), 1.36 (s, 3H), 1.15 (s, 3H), 0.95 (s, 9H), 0.15 (s, 3H), 0.06 (s, 3H).

EXAMPLE 42

(Z)-2-(3,3-dimethyl-4-hydroxy-3,4-dihydro-(2H)-isoquinolin-1-ylidene)-1-phenylethan-1-one

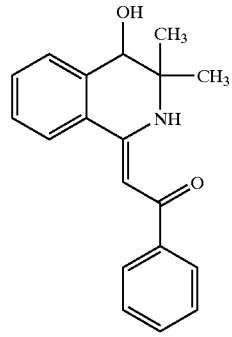

The compound prepared in reference example 12 (810 mg) was dissolved in tetrahydrofuran (10 ml) and to the mixture was added tetrabutylammonium fluoride (4.0 ml, 1.0M tetrahydrofuran solution) at 0° C. and the mixture was stirred for 3 hours at room temperature. The reaction mixture was poured into ice-water and was extracted with ethyl acetate. The extract was washed with hydrochloric acid, a saturated aqueous solution of sodium biscarbonate, water and a saturated aqueous solution of sodium chloride and was dried over anhydrous magnesium sulfate and was concentrated. The residue was purified by column chromatography on silica gel (hexane:ethyl acetate=4:1→3:2) to give the compound of the present invention (566 mg) having the following physical data.

TLC: Rf 0.52 (ethyl acetate:hexane=1:1);

NMR (CDCl$_3$): δ 11.65 (br., 1H), 7.94 (m, 2H), 7.85 (d, J=8.0 Hz, 1H), 7.60–7.40 (m, 6H), 6.37 (s, 1H), 4.55 (d, J=7.5 Hz, 1H), 2.11 (d, J=7.5 Hz, 1H), 1.37 (s, 3H), 1.33 (s, 3H).

EXAMPLE 43

(Z)-2-(3,3-dimethyl-4-oxo-3,4-dihydro-(2H)-isoquinolin-1-ylidene)-1-phenylethan-1-one

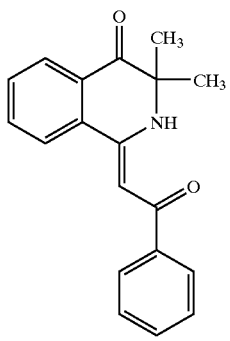

The compound prepared in example 42 (428 mg) was dissolved in methylene chloride (40 ml) and to the mixture was added pyridinium chlorochromate (2793 mg) at room temperature and the mixture was stirred for 6 hours at room temperature. The reaction mixture was filtered. The filtrate was concentrated. The residue was purified by column chromatography on silica gel (hexane:ethyl acetate= 9:1→5:1) to give the compound of the present invention (137 mg) having the following physical data.

TLC: Rf 0.31 (ethyl acetate:hexane=1:5);

NMR (CDCl$_3$): δ 12.22 (br., 1H), 8.17 (dd, J=7.5, 1.5 Hz, 1H), 8.06 (m, 1H), 7.97 (m, 2H), 7.76 (ddd, J=7.5, 7.5, 1.5 Hz, 1H), 7.68 (ddd, J=7.5, 7.5, 1.5 Hz, 1H), 7.55–7.40 (m, 3H), 6.60 (s, 1H), 1.60 (s, 6H).

EXAMPLE 44~EXAMPLE 44(4)

By converting to corresponding salts the compounds prepared in example 11 (80) or example 14 (8) by conventional method, the following compounds of the present invention were given.

EXAMPLE 44

(Z)-2-(6-chloro-3,3-dimethyl-3,4-dihydroisoquinolin-1-yl)-1-(adamantan-1-yl)ethan-1-one hydrochloride

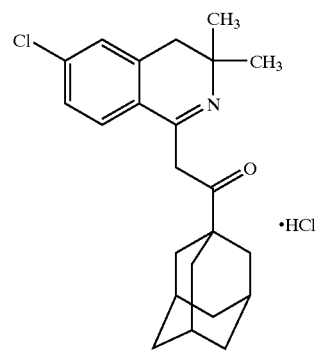

TLC: Rf 0.25 (ethyl acetate:hexane=1:10);

NMR (CDCl$_3$): δ 7.50 (d, J=8.0 Hz, 1H), 7.35 (dd, J=8.0, 2.0 Hz, 1H), 7.28 (d, J=2.0 Hz, 1H), 4.6 (br., 2H), 2.95 (s, 2H), 2.09 (m, 3H), 1.95 (m, 6H), 1.75 (m, 6H), 1.49 (s, 6H).

EXAMPLE 44(1)

(Z)-2-(6-chloro-3,3-dimethyl-3,4-dihydroisoquinolin-1-yl)-1-(adamantan-1-yl)ethan-1-one methanesulfonate

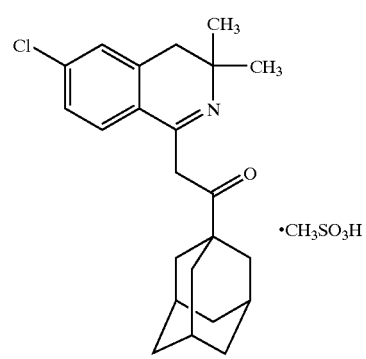

TLC: Rf 0.25 (ethyl acetate:hexane=1:10);

NMR (CDCl$_3$): δ 7.47 (d, J=8.5 Hz, 1H), 7.39 (dd, J=8.5, 2.0 Hz, 1H), 7.33 (s, 1H), 4.6 (br., 2H), 3.02 (s, 2H), 2.85 (s, 3H), 2.12 (m, 3H), 1.96 (m, 6H), 1.76 (m, 6H), 1.55 (s, 6H).

EXAMPLE 44(2)

(Z)-2-(7-amino-6-chloro-3,3-dimethyl-3,4-dihydroisoquinolin-1-yl)-1-(adamantan-1-yl)ethan-1-one bishydrochloride

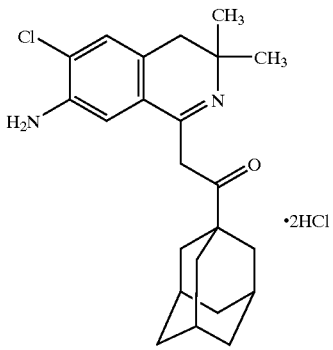

TLC: Rf 0.68 (ethyl acetate:hexane=1:2);

NMR (CDCl$_3$): δ 7.22 (s, 1H), 6.80 (s, 1H), 2.91 (s, 2H), 2.12 (m, 3H), 1.98 (m, 6H), 1.76 (m, 6H), 1.59 (s, 6H).

EXAMPLE 44(3)

(Z)-2-(7-amino-6-chloro-3,3-dimethyl-3,4-dihydroisoquinolin-1-yl)-1-(adamantan-1-yl)ethan-1-one bismethanesulfonate

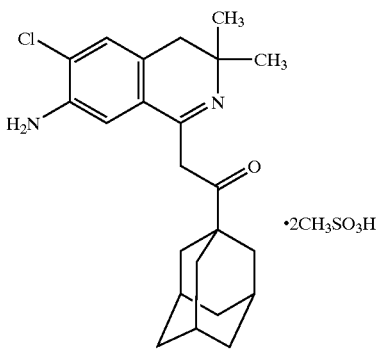

TLC: Rf 0.68 (ethyl acetate:hexane=1:2);

NMR (CDCl$_3$): δ 7.58 (s, 1H), 7.30 (s, 1H), 4.94 (br., 6H), 2.99 (s, 2H), 2.85 (s, 6H), 2.09 (m, 3H), 1.95 (m, 6H), 1.74 (m, 6H), 1.53 (s, 6H).

EXAMPLE 44(4)

(Z)-2-(7-amino-6-chloro-3,3-dimethyl-3,4-dihydroisoquinolin-1-yl)-1-(adamantan-1-yl)ethan-1-one methanesulfonate

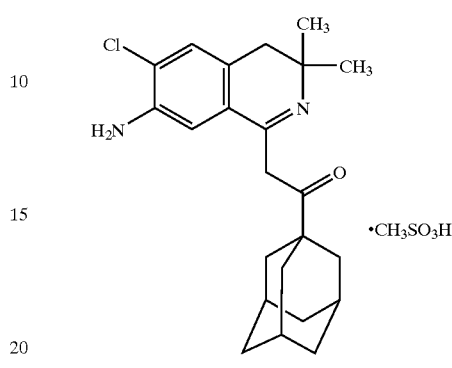

TLC: Rf 0.68 (ethyl acetate:hexane=1:2);

NMR (CDCl$_3$): δ 7.34 (s, 1H), 7.15 (s, 1H), 4.81 (br., 2H), 3.46 (br., 3H), 2.86 (s, 2H), 2.83 (s, 3H), 2.05 (m, 3H), 1.96 (m, 6H), 1.73 (m, 6H), 1.46 (s, 6H).

EXAMPLE 45

(Z)-2-(6-cyano-3,3-dimethyl-3,4-dihydro-(2H)-isoquinolin-1-ylidene)-1-cyclohexylethan-1-one

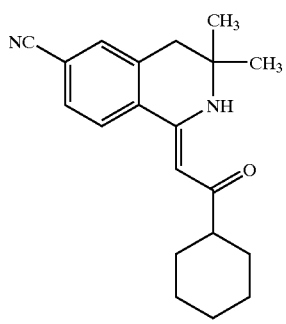

To a solution of the compound prepared in example 30 (9) (488 mg) in 1,4-dioxane (10 ml) was added pyridine (0.36 ml) and to the mixture was added trifluoroacetic anhydride (0.32 ml) under cooling with ice, and the mixture was stirred for 15 minutes, The mixture was dried over anhydrous magnesium sulfate and was concentrated. The residue was purified by column chromatography on silica gel (hexane:ethyl acetate=15:1→13:1) to give the compound of the present invention having the following physical data. (305 mg).

TLC: Rf 0.44 (hexane:ethyl acetate=3:1);

NMR (CDCl$_3$): δ 11.18 (br, 1H), 7.80 (d, J=8.5 Hz, 1H), 7.58 (dd, J=8.5, 1.5 Hz, 1H), 7.48 (d, J=1.5 Hz, 1H), 5.64 (s, 1H), 2.87 (s, 2H), 2.31 (tt, J=11.5, 3.5 Hz, 1H), 1.89–1.80 (m, 4H), 1.70 (m, 1H), 1.51–1.20 (m, 11H).

EXAMPLE 45(1)~EXAMPLE 45(2)

By the same procedure as described in example 45 using the compound prepared in example 30(10) or 30(11) in place of the compound prepared in example 30 (9), the following compounds of the present invention were obtained.

EXAMPLE 45(1)

(Z)-2-(6-cyano-3,3-dimethyl-3,4-dihydro-(2H)-isoquinolin-1-ylidene)-1-cycloheptylethan-1-one

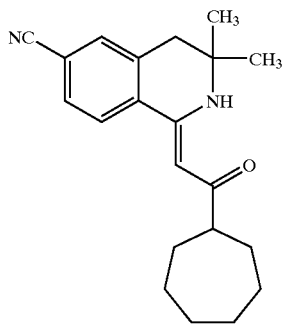

TLC: Rf 0.45 (hexane:ethyl acetate=3:1);

NMR (CDCl$_3$): δ 11.09 (br, 1H), 7.79 (d, J=8.0 Hz, 1H), 7.58 (dd, J=8.0, 1.5 Hz, 1H), 7.47 (d, J=1.5 Hz, 1H), 5.61 (s, 1H), 2.87 (s, 2H), 2.48 (tt, J=10.0, 4.0 Hz, 1H), 1.94–1.87 (m, 2H), 1.83–1.45 (m, 10H), 1.29 (s, 6H).

EXAMPLE 45(2)

(Z)-2-(6-cyano-3,3-dimethyl-3,4-dihydro-(2H)-isoquinolin-1-ylidene)-1-(adamantan-1-yl)ethan-1-one

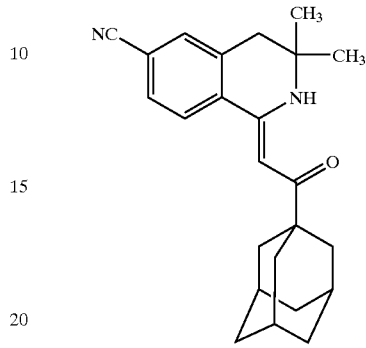

TLC: Rf 0.48 (hexane:ethyl acetate=3:1);

NMR (CDCl$_3$): δ 11.34 (br, 1H), 7.81 (d, J=8.0 Hz, 1H), 7.59 (dd, J=8.0, 1.5 Hz, 1H), 7.48 (d, J=1.5 Hz, 1H), 5.80 (s, 1H), 2.87 (s, 2H), 2.06 (br, 3H), 1.90 (br, 6H), 1.74 (br, 6H), 1.30 (s, 6H).

FORMULATION EXAMPLE 1

The following components were admixed in a conventional method, dried, and punched out to give 100 tablets each containing 50 mg of active ingredient.

| | |
|---|---|
| (Z)-2-(3,3-dimethyl-3,4-dihydro-(2H)-isoquinolin-1-ylidene)-1-cyclohexylethan-1-one | 5.0 g |
| carboxymethylcellulose calcium (disintegrating agent) | 0.2 g |
| magnesium stearate (lubricant) | 0.1 g |
| microcrystalline cellulose | 4.7 g |

FORMULATION EXAMPLE 2

The following components were admixed in a conventional method. The solution was sterilized in conventional method, placed 5 ml portions into each ampoule and freeze-dried to give 100 ampoules each containing 20 mg of the active ingredient.

| | |
|---|---|
| (Z)-2-(3,3-dimethyl-3,4-dihydro-(2H)-isoquinolin-1-ylidene)-1-cyclohexylethan-1-one | 2.0 g |
| mannitol | 20 g |
| distilled water | 1000 ml |

What is claimed is:

1. A 3,4-dihydroisoquinoline derivative compound of formula (I)

$$\text{(I)}$$

(wherein $R^1$ and $R^2$ are each independently
1) hydrogen, or
2) C1~8 alkyl or
$R^1$ and $R^2$ are taken together with the carbon atom to which they are attached to form Cyc1, with the proviso that $R^1$ and $R^2$ do not represent hydrogen at the same time;
Z is
1) —$CR^3R^4$—, or
2) —O—,
$R^3$ and $R^4$ are each independently,
1) hydrogen,
2) C1~8 alkyl,
3) C1~8 alkoxy or
4) hydroxy, or
$R^3$ and $R^4$ may be taken together with the carbon atom to which they are attached to form Cyc1 or —C(O)—,
$R^5$ and $R^6$ are each independently,
1) hydrogen or
2) C1~8 alkyl, or
$R^5$ and $R^6$ are taken together with the carbon atom to which they are attached to form Cyc1,
Cyc1 represented by $R^1$ and $R^2$, $R^3$ and $R^4$, and $R^5$ and $R^6$ are each independently,
1) C3~10 cycloalkyl or
2) 3~10 membered mono-cyclic heteroring comprising 1~2 of heteroatoms selected from the group consisting of oxygen, nitrogen and sulfur,
Cyc1 may be substituted with $R^{10}$;
$R^{10}$ is
1) C1~8 alkyl, 2) C1~8 alkoxy, 3) hydroxy, 4) —$COOR^{11}$, 5) keto, 6) —$SO_2R^{12}$, or 7) —$COR^{13}$,
$R^{11}$ is hydrogen or C1~8 alkyl,
$R^{12}$ and $R^{13}$ are, 1) C1~8 alkyl or 2) phenyl substituted with C1~8 alkyl,
$R^7$ and $R^8$ are each independently,
1) hydrogen,
2) C1~8 alkyl,
3) C1~8 alkoxy,
4) hydroxy,
5) cyano,
6) halogen,
7) —$COOR^{14}$,
8) —$CONR^{15}R^{16}$,
9) Cyc2,
10) C2~8 alkenyl,
11) C2~8 alkynyl,
12) —$NR^{51}R^{52}$,
13) nitro,
14) formyl,
15) C2~8 acyl,
16) hydroxy, C1~8 alkoxy, Cyc2, —$NR^{51}R^{52}$ or C1~8 alkyl substituted with —$NR^{53}$-Cyc2,
17) —$NR^{54}COR^{55}$,
18) —$NR^{56}SO_2R^{57}$,
19) —$SO_2NR^{58}R^{59}$,
20) C2~8 alkenyl substituted with —$COOR^{14}$,
21) —CH=N—OH,
22) —(C1~8 alkylene)—$NR^{60}$—(C1~8alkylene)—$R^{61}$ or
23) C1~8 alkylthio;
$R^{14}$ is hydrogen or C1~8 alkyl,
$R^{15}$ and $R^{16}$ are each independently, hydrogen or C1~8 alkyl,
$R^{51}$ and $R^{52}$, $R^{58}$ and $R^{59}$ are each independently, hydrogen or C1~8 alkyl,
$R^{53}$, $R^{54}$, $R^{56}$ and $R^{60}$ are each independently hydrogen or C1~8 alkyl,
$R^{55}$ is hydrogen, C1~alkyl, or C1~8 alkoxy,
$R^{57}$ is C1~8 alkyl,
$R^{61}$ is —$NR^{62}R^{63}$ or hydroxy,
$R^{62}$ and $R^{63}$ are each independently, hydrogen or C1~8alkyl;

(abbreviated as ring hereafter)
is Cyc2, but the atom which attaches to the carbonyl group in formula (I) is carbon;
Cyc2, represented by $R^7$, $R^8$ and ring, are each independently,
1) C3~15 mono-, bi- or tri-cyclic (fused or spiro) carbocyclic ring or
2) 3~15 membered mono-, bi- or tri-cyclic (fused or spiro) heterocyclic ring comprising 1~4 of hetero atoms selected from the group consisting of oxygen, nitrogen and sulfur,
Cyc2 may be substituted with 1~5 of $R^{17}$;
$R^{17}$ is
1) C1~8 alkyl, 2) C2~8 alkenyl, 3) C2~8 alkynyl, 4) C1~8 alkoxy, 5) C1~8 alkylthio, 6) hydroxy, 7) halogen, 8) nitro, 9) keto, 10) carboxy, 11) formyl, 12) cyano, 13) —$NR^{18}R^{19}$, 14) phenyl, phenoxy or phenylthio which may be substituted with 1~5 of $R^{20}$, 15) C1~8 alkyl, C2~8 alkenyl, C1~8 alkoxy or C1~8 alkylthio which may be substituted with 1~5 of $R^{21}$, 16) —$OCOR^{22}$, 17) —$CONR^{23}R^{24}$, 18) —$SO_2NR^{25}R^{26}$, 19) —$COOR^{27}$, 20) —$COCOOR^{28}$, 21) —$COR^{29}$, 22) —$COCOR^{30}$, 23) —$NR^{31}COR^{32}$, 24) —$SO_2R^{33}$, 25) —$NR^{34}SO_2R^{35}$, or 26) —$SOR^{64}$;
$R^{18}$ and $R^{19}$, $R^{31}$ and $R^{34}$ are each independently, hydrogen or C1~8alkyl,
$R^{20}$ and $R^{21}$ are, C1~8 alkyl, C1~8 alkoxy, hydroxy, halogen, nitro, or —$COOR^{36}$, $R^{22}$ and $R^{64}$ are each independently, C1~8 alkyl, $R^{23}$ and $R^{24}$, $R^{25}$ and $R^{26}$ are each independently, hydrogen, C1~8 alkyl, or phenyl, $R^{27}$, $R^{28}$, $R^{29}$, $R^{30}$, $R^{32}$, $R^{33}$ and $R^{35}$ are, 1) C1~8 alkyl, 2) C2~8 alkenyl, 3) C1~8 alkyl substituted with 1~5 of $R^{37}$, 4) diphenylmethyl, 5) triphenylmethyl, 6) Cyc3, 7) C1~8 alkyl or C2~8 alkenyl substituted with Cyc3, 8) C1~8 alkyl substituted with —O-Cyc3, —S-Cyc3 or —SO$_2$-Cyc3;

$R^{36}$ is hydrogen or C1~8 alkyl, $R^{37}$ is C1~8 alkoxy, C1~8 alkylthio, benzyloxy, halogen, nitro or —COOR$^{38}$, $R^{38}$ is hydrogen, C1~8 alkyl or C2~8 alkenyl, Cyc3 is 1) C3~15 mono-, bi- or tri-cyclic (fused or spiro) carbocycle, or 2) 3~15 membered mono-, bi- or tri-cyclic (fused or spiro) heteroring comprising 1~4 of heteroatoms selected from the group consisting of oxygen, nitrogen and sulfur, Cyc3 may be substituted with 1~5 of $R^{39}$;

$R^{39}$ is

1) C1~8 alkyl, 2) C2~8 alkenyl, 3) C2~8 alkynyl, 4) C1~8 alkoxy, 5) C1~8 alkylthio, 6) hydroxy, 7) halogen, 8) nitro, 9) keto, 10) cyano, 11) benzyl, 12) benzyloxy, 13) C1~8 alkyl, C1~8 alkoxy or C1~8 alkylthio substituted with 1~5 of $R^{40}$, 14) phenyl, phenoxy, phenylthio, phenylsulfonyl or benzoyl, which may be substituted with 1~5 of $R^{41}$, 15) —OCOR$^{42}$, 16) —SO$_2$R$^{43}$, 17) —NR$^{44}$COR$^{45}$, 18) —SO$_2$NR$^{46}$R$^{47}$, 18) —COOR$^{48}$, or 19) —NR$^{49}$R$^{50}$;

$R^{40}$ is halogen, $R^{41}$ is C1~8 alkyl, C1~8 alkoxy, halogen or nitro, $R^{42}$, $R^{43}$ and $R^{45}$ are C1~8 alkyl, $R^{44}$ and $R^{48}$ are hydrogen or C1~8 alkyl, $R^{46}$ and $R^{47}$, $R^{49}$ and $R^{50}$ are each independently, hydrogen or C1~8 alkyl;

Cyc4 is

1) C5~7 mono-cyclic carbocyclic ring, or 2) 5~7 membered mono-cyclic heterocyclic ring comprising 1–2 of heteroatom selected from the group consisting of oxygen, nitrogen and sulfur;

a
=====

(abbreviated as broken line a hereafter)
and b
=====

(abbreviated as broken line b hereafter)
is 1) a bond or 2) a double bond;

$R^9$ is 1) absent or 2) hydrogen;

with the proviso that, 1) when the broken line a is a bond, then the broken line b is a double bond and $R^9$ is absent, 2) when the broken line a is a double bond, then the broken line b is a bond and $R^9$ is hydrogen and $R^6$ is absent, and 3) 2-(3,3-dimethyl-3,4-dihydro-(2H)-isoquinolin-1-ylidene)-1-phenylethan-1-one is excluded), or a non-toxic salt thereof.

2. The compound or a non-toxic salt thereof according to claim 1, wherein Cyc4 is C5~7 mono-cyclic carbocyclic ring.

3. The compound or a non-toxic salt thereof according to claim 1, wherein Cyc4 is 5~7 membered mono-cyclic heterocyclic ring comprising 1~2 of heteroatoms selected from the group consisting of oxygen, nitrogen and sulfur.

4. The compound or a non-toxic salt thereof according to claim 2, wherein Z is —CR$^3$R$^4$— and ring is C3~15 membered mono-, bi- or tri-cyclic (fused or spiro) carbocyclic ring.

5. The compound or a non-toxic salt thereof according to claim 2, wherein Z is —CR$^3$R$^4$— and ring is 3~15 membered mono-, bi- or tri-cyclic (fused or spiro) heterocyclic ring comprising 1~4 of heteroatoms selected from the group consisting of oxygen, nitrogen and sulfur.

6. The compound or a non-toxic salt thereof according to claim 2, wherein Z is —O— and ring is C3~15 mono-, bi- or tri-cyclic (fused or spiro) carbocyclic ring.

7. The compound or a non-toxic salt thereof according to claim 2, wherein Z is —O— and ring is a 3~15 membered mono-, bi- or tri-cyclic (fused or spiro) ring comprising 1~4 of heteroatoms selected from group consisting of oxygen, nitrogen and sulfur.

8. The compound according to claim 4, which is (1) (Z)-2-(3,3-dimethyl-3,4-dihydro-(2H)-isoquinolin-1-ylidene)-1-cyclohexylethan-1-one, (2) (Z)-2-(3,3-dimethyl-3,4-dihydro-(2H)-isoquinolin-1-ylidene)-1-(4-methoxycarbonylphenyl)ethan-1-one, (3) (Z)-2-(3,3-dimethyl-3,4-dihydro-(2H)-isoquinolin-1-ylidene)-1-cyclopentylethan-1-one, (4) (Z)-2-(3,3-dimethyl-3,4-dihydro-(2H)-isoquinolin-1-ylidene)-1-(2-methylphenyl)ethan-1-one, (5) (Z)-2-(3,3-dimethyl-3,4-dihydro-(2H)-isoquinolin-1-ylidene)-1-(3-methylphenyl)ethan-1-one, (6) (Z)-2-(3,3-dimethyl-3,4-dihydro-(2H)-isoquinolin-1-ylidene)-1-(4-methylphenyl)ethan-1-one, (7) (Z)-2-(3,3-dimethyl-3,4-dihydro-(2H)-isoquinolin-1-ylidene)-1-(2-chlorophenyl)ethan-1-one, (8) (Z)-2-(3,3-dimethyl-3,4-dihydro-(2H)-isoquinolin-1-ylidene)-1-(3-chlorophenyl)ethan-1-one, (9) (Z)-2-(3,3-dimethyl-3,4-dihydro-(2H)-isoquinolin-1-ylidene)-1-cyclobutylethan-1-one,

(10) (Z)-2-(3,3-dimethyl-3,4-dihydro-(2H)-isoquinolin-1-ylidene)-1-cycloheptylethan-1-one,

(11) (Z)-2-(3,3-dimethyl-3,4-dihydro-(2H)-isoquinolin-1-ylidene)-1-(4-chlorophenyl)ethan-1-one,

(12) (Z)-2-(3,3-dimethyl-3,4-dihydro-(2H)-isoquinolin-1-ylidene)-1-(adamantan-1-yl)ethan-1-one,

(13) (Z)-2-(3,3,5-trimethyl-3,4-dihydro-(2H)-isoquinolin-1-ylidene)-1-phenylethan-1-one,

(14) (Z)-2-(3,3,6-trimethyl-3,4-dihydro-(2H)-isoquinolin-1-ylidene)-1-phenylethan-1-one,

(15) (Z)-2-(3,3-dimethyl-3,4-dihydro-(2H)-isoquinolin-1-ylidene)-1-(naphthalen-2-yl)ethan-1-one,

(16) (Z)-2-(3,3-dimethyl-3,4-dihydro-(2H)-isoquinolin-1-ylidene)-1-(4-methoxyphenyl)ethan-1-one,

(17) (Z)-2-(3,3-dimethyl-3,4-dihydro-(2H)-isoquinolin-1-ylidene)-1-(3-methoxyphenyl)ethan-1-one,

(18) (Z)-2-(3,3-dimethyl-3,4-dihydro-(2H)-isoquinolin-1-ylidene)-1-(4-fluorophenyl)ethan-1-one,

(19) (Z)-2-(3,3,7-trimethyl-3,4-dihydro-(2H)-isoquinolin-1-ylidene)-1-phenylethan-1-one,
(20) (Z)-2-(3,3-dimethyl-3,4-dihydro-(2H)-isoquinolin-1-yjidene)-1-(naphthalen-1-yl)ethan-1-one,
(21) (Z)-2-(3,3-dimethyl-3,4-dihydro-(2H)-isoquinolin-1-ylidene)-1-(2-methoxyphenyl)ethan-1-one,
(22) (Z)-2-(3,3-dimethyl-3,4-dihydro-(2H)-isoquinolin-1-ylidene)-1-(2-fluorophenyl)ethan-1-one,
(23) (Z)-2-(3,3-dimethyl-3,4-dihydro-(2H)-isoquinolin-1-ylidene)-1-(3-fluorophenyl)ethan-1-one,
(24) (Z)-2-(3,3-dimethyl-3,4-dihydro-(2H)-isoquinolin-1-ylidene)-2-methyl-1-phenylethan-1-one,
(25) (Z)-2-(spiro[3,4-dihydro-(2H)-isoquinolin-3,1'-cyclohexan]-1-ylidene)-1-phenylethan-1-one,
(26) (Z)-2-(spiro[3,4-dihydro-(2H)-isoquinolin-3,1'-cyclopentan]-1-ylidene)-1-phenylethan-1-one,
(27) (Z)-2-(spiro[3,4-dihydro-(2H)-isoquinolin-3,1'-cycloheptan]-1-ylidene)-1-phenylethan-1-one,
(28) (Z)-2-(3,3-diethyl-3,4-dihydro-(2H)-isoquinolin-1-ylidene)-1-phenylethan-1-one,
(29) (Z)-2-(3,3-dimethyl-3,4-dihydro-(2H)-isoquinolin-1-ylidene)-1-(3-methoxycarbonylphenyl)ethan-1-one,
(30) (Z)-2-(spiro[3,4-dihydro-(2H)-isoquinolin-3,1'-cyclobutan]-1-ylidene)-1-phenylethan-1-one,
(31) (Z)-2-(spiro[3,4-dihydro-(2H)-isoquinolin-3,4'-3,4,5,6-tetrahydropyran]-1-ylidene)-1-phenylethan-1-one,
(32) (Z)-2-(spiro[3,4-dihydro-(2H)-isoquinolin-3,4'-1'-methylpiperidin]-1-ylidene)-1-phenylethan-1-one,
(33) (Z)-2-(3,3-dimethyl-3,4-dihydro-(2H)-isoquinolin-1-ylidene)-1-(2-trifluoromethylphenyl)ethan-1-one,
(34) (Z)-2-(3,3-dimethyl-3,4-dihydro-(2H)-isoquinolin-1-ylidene)-1-(3-trifluoromethylphenyl)ethan-1-one,
(35) (Z)-2-(3,3-dimethyl-3,4-dihydro-(2H)-isoquinolin-1-ylidene)-1-(4-trifluoromethylphenyl)ethan-1-one,
(36) (Z)-2-(3,3,6,8-tetramethyl-3,4-dihydro-(2H)-isoquinolin-1-ylidene)-1-phenylethan-1-one,
(37) (Z)-2-(8-methoxy-3,3-dimethyl-3,4-dihydro-(2H)-isoquinolin-1-ylidene)-1-phenylethan-1-one,
(38) (Z)-2-(6-methoxy-3,3-dimethyl-3,4-dihydro-(2H)-isoquinolin-1-ylidene)-1-phenylethan-1-one,
(39) (Z)-2-(spiro[3,4-dihydro-(2H)-isoquinolin-3,4'-piperidin]-1-ylidene)-1-phenylethan-1-one,
(40) (Z)-2-(3,3-dimethyl-3,4-dihydro-(2H)-isoquinolin-1-ylidene)-1-(2,6-dimethylphenyl)ethan-1-one,
(41) (Z)-2-(spiro[3,4-dihydro-(2H)-isoquinolin-3,1'-4'-ethoxycarbonylcyclohexan]-1-ylidene)-1-phenylethan-1-one,
(42) (Z)-2-(3,3-dimethyl-3,4-dihydro-(2H)-isoquinolin-1-ylidene)-1-cyclododecylethan-1-one,
(43) (Z)-2-(3,3-dimethyl-3,4-dihydro-(2H)-isoquinolin-1-ylidene)-1-(4-t-butylphenyl)ethan-1-one,
(44) (Z)-2-(spiro[3,4-dihydro-(2H)-isoquinolin-3,1'-4'-oxocyclohexan]-1-ylidene)-1-phenylethan-1-one,
(45) (Z)-2-(3,3-dimethyl-3,4-dihydro-(2H)-isoquinolin-1-ylidene)-1-(4-isopropylphenyl)ethan-1-one,
(46) (Z)-2-(3,3-dimethyl-3,4-dihydro-(2H)-isoquinolin-1-ylidene)-1-cyclooctylethan-1-one,
(47) (Z)-2-(3,3-dimethyl-3,4-dihydro-(2H)-isoquinolin-1-ylidene)-1-(1-methylcyclohexyl)ethan-1-one,
(48) (Z)-2-(3,3-dimethyl-3,4-dihydro-(2H)-isoquinolin-1-ylidene)-1-(4-ethylphenyl)ethan-1-one,
(49) (Z)-2-(3,3-dimethyl-3,4-dihydro-(2H)-isoquinolin-1-ylidene)-1-(4-butylphenyl)ethan-1-one,
(50) (Z)-2-(3,3-dimethyl-3,4-dihydro-(2H)-isoquinolin-1-ylidene)-1-(1-phenylcyclohexyl)ethan-1-one,
(51) (Z)-2-(3,3-dimethyl-3,4-dihydro-(2H)-isoquinolin-1-ylidene)-1-(4-propylphenyl)ethan-1-one,
(52) 2-(3,3-dimethyl-3,4-dihydroisoquinolin-1-yl)-1-phenylbutan-1-one,
(53) 2-(3,3-dimethyl-3,4-dihydroisoquinolin-1-yl)-1-phenylpentan-1-one,
(54) (Z)-cis-2-(3,3-dimethyl-3,4-dihydro-(2H)-isoquinolin-1-ylidene)-1-(2-methylcyclohexyl)ethan-1-one,
(55) (Z)-trans-2-(3,3-dimethyl-3,4-dihydro-(2H)-isoquinolin-1-ylidene)-1-(2-methylcyclohexyl)ethan-1-one,
(56) (Z)-trans-2-(3,3-dimethyl-3,4-dihydro-(2H)-isoquinolin-1-ylidene)-1-(3-methylcyclohexyl)ethan-1-one,
(57) (Z)-cis-2-(3,3-dimethyl-3,4-dihydro-(2H)-isoquinolin-1-ylidene)-1-(3-methylcyclohexyl)ethan-1-one,
(58) (Z)-cis-2-(3,3-dimethyl-3,4-dihydro-(2H)-isoquinolin-1-ylidene)-1-(4-methylcyclohexyl)ethan-1-one,
(59) (Z)-trans-2-(3,3-dimethyl-3,4-dihydro-(2H)-isoquinolin-1-ylidene)-1-(4-methylcyclohexyl)ethan-1-one,
(60) (Z)-2-(3,3-dimethyl-3,4-dihydro-(2H)-isoquinolin-1-ylidene)-1-(4-trifluoromethoxyphenyl)ethan-1-one,
(61) (Z)-2-(6-chloro-3,3-dimethyl-3,4-dihydro-(2H)-isoquinolin-1-ylidene)-1-phenylethan-1-one,
(62) (Z)-2-(5-chloro-3,3-dimethyl-3,4-dihydro-(2H)-isoquinolin-1-ylidene)-1-phenylethan-1-one,
(63) (Z)-2-(7-chloro-3,3-dimethyl-3,4-dihydro-(2H)-isoquinolin-1-ylidene)-1-phenylethan-1-one,
(64) (Z)-2-(7-fluoro-3,3-dimethyl-3,4-dihydro-(2H)-isoquinolin-1-ylidene)-1-phenylethan-1-one,
(65) (Z)-2-(6-fluoro-3,3-dimethyl-3,4-dihydro-(2H)-isoquinolin-1-ylidene)-1-phenylethan-1-one,
(66) (Z)-2-(5-fluoro-3,3-dimethyl-3,4-dihydro-(2H)-isoquinolin-1-ylidene)-1-phenylethan-1-one,
(67) (Z)-2-(3,3-dimethyl-3,4-dihydro-(2H)-isoquinolin-1-ylidene)-1-(4-pentylbicyclo[2.2.2]octan-1-yl)ethan-1-one,
(68) (Z)-trans-2-(3,3-dimethyl-3,4-dihydro-(2H)-isoquinolin-1-ylidene)-1-(4-t-butylcyclohexyl)ethan-1-one,
(69) (Z)-2-(3,3,4,4-tetramethyl-3,4-dihydro-(2H)-isoquinolin-1-ylidene)-1-phenylethan-1-one,
(70) (Z)-2-(spiro[3,3-dimethyl-3,4-dihydro-(2H)-isoquinolin-4,1'-cyclohexan]-1-ylidene)-1-phenylethan-1-one,
(71) (Z)-2-(6,7-dimethoxy-3,3-dimethyl-3,4-dihydro-(2H)-isoquinolin-1-ylidene)-1-phenylethan-1-one,
(72) (Z)-2-(spiro[3,3-dimethyl-3,4-dihydro-(2H)-isoquinolin-4,1'-cyclopentan]-1-ylidene)-1-phenylethan-1-one,
(73) 2-(3,3-dimethyl-3,4-dihydroisoquinolin-1-yl)-1-cyclopentylethan-1-one,
(74) 2-(3,3-dimethyl-3,4-dihydroisoquinolin-1-yl)-1-cycloheptylethan-1-one,
(75) 2-(3,3-dimethyl-3,4-dihydroisoquinolin-1-yl)-1-phenylpropan-1-one,

(76) (Z)-2-(3,3-dimethyl-3,4-dihydro-(2H)-isoquinolin-1-ylidene)-1-(3-cyanophenyl)ethan-1-one,
(77) (Z)-2-(3,3-dimethyl-3,4-dihydro-(2H)-isoquinolin-1-ylidene)-1-(4-cyanophenyl)ethan-1-one,
(78) (Z)-2-(3,3-dimethyl-3,4-dihydro-(2H)-isoquinolin-1-ylidene)-1-(2-trifluoromethoxyphenyl)ethan-1-one,
(79) (Z)-2-(3,3-dimethyl-3,4-dihydro-(2H)-isoquinolin-1-ylidene)-1-(2-cyanophenyl)ethan-1-one,
(80) (Z)-2-(3,3-dimethyl-3,4-dihydro-(2H)-isoquinolin-1-ylidene)-1-(3-trifluoromethoxyphenyl)ethan-1-one,
(81) (Z)-2-(3,3-dimethyl-3,4-dihydro-(2H)-isoquinolin-1-ylidene)-1-(4-carboxyphenyl)ethan-1-one,
(82) (Z)-2-(3,3-dimethyl-3,4-dihydro-(2H)-isoquinolin-1-ylidene)-1-(3-carboxyphenyl)ethan-1-one,
(83) (Z)-2-(spiro[3,4-dihydro-(2H)-isoquinolin-3,1'-4'-carboxycyclohexan]-1-ylidene)-1-phenylethan-1-one,
(84) (Z)-2-(3,3-dimethyl-3,4-dihydro-(2H)-isoquinolin-1-ylidene)-1-(3-hydroxyphenyl)ethan-1-one,
(85) (Z)-2-(3,3-dimethyl-3,4-dihydro-(2H)-isoquinolin-1-ylidene)-1-(4-hydroxyphenyl)ethan-1-one,
(86) (Z)-2-(3,3-dimethyl-3,4-dihydro-(2H)-isoquinolin-1-ylidene)-1-(2-hydroxyphenyl)ethan-1-one,
(87) (Z)-2-(6-hydroxy-3,3-dimethyl-3,4-dihydro-(2H)-isoquinolin-1-ylidene)-1-phenylethan-1-one,
(88) 2-(3,3-dimethyl-3,4-dihydroisoquinolin-1-yl)-2-methyl-1-phenylpropan-1-one,
(89) 1-(3,3-dimethyl-3,4-dihydroisoquinolin-1-yl) cyclopentylphenylketone,
(90) 1-(3,3-dimethyl-3,4-dihydroisoquinolin-1-yl) cyclohexylphenylketone,
(91) 4-(3,3-dimethyl-3,4-dihydroisoquinolin-1-yl)-3,4,5,6-tetrahydropyran-4-ylphenylketone,
(92) (Z)-2-(spiro[3,4-dihydro-(2H)-isoquinolin-3,1'-4'-hydroxycyclohexan]-1-ylidene)-1-phenylethan-1-one,
(93) (Z)-2-(spiro[3,4-dihydro-(2H)-isoquinolin-3,4'-1'-acetylpiperidin]-1-ylidene)-1-phenylethan-1-one,
(94) (Z)-2-(6-phenyl-3,3-dimethyl-3,4-dihydro-(2H)-isoquinolin-1-ylidene)-1-phenylethan-1-one,
(95) (Z)-2-(6-(pyridin-3-yl)-3,3-dimethyl-3,4-dihydro-(2H)-isoquinolin-1-ylidene)-1-phenylethan-1-one,
(96) (Z)-2-(3,3-dimethyl-3,4-dihydro-(2H)-isoquinolin-1-ylidene)-1-(4-hydroxymethylphenyl)ethan-1-one,
(97) (Z)-2-(3,3-dimethyl-3,4-dihydro-(2H)-isoquinolin-1-ylidene)-1-(3-hydroxymethylphenyl)ethan-1-one,
(98) (Z)-2-(7-isopropyl-3,3-dimethyl-3,4-dihydro-(2H)-isoquinolin-1-ylidene)-1-phenylethan-1-one,
(99) (Z)-2-(7-methoxy-3,3-dimethyl-3,4-dihydro-(2H)-isoquinolin-1-ylidene)-1-phenylethan-1-one,
(100) (Z)-2-(7-ethyl-3,3-dimethyl-3,4-dihydro-(2H)-isoquinolin-1-ylidene)-1-phenylethan-1-one,
(101) (Z)-2-(7-t-butyl-3,3-dimethyl-3,4-dihydro-(2H)-isoquinolin-1-ylidene)-1-phenylethan-1-one,
(102) (Z)-2-(7-propyl-3,3-dimethyl-3,4-dihydro-(2H)-isoquinolin-1-ylidene)-1-phenylethan-1-one,
(103) (Z)-2-(7-butyl-3,3-dimethyl-3,4-dihydro-(2H)-isoquinolin-1-ylidene)-1-phenylethan-1-one,
(104) (Z)-2-(7-bromo-3,3-dimethyl-3,4-dihydro-(2H)-isoquinolin-1-ylidene)-1-phenylethan-1-one,
(105) (Z)-2-(7-methoxy-3,3-dimethyl-3,4-dihydro-(2H)-isoquinolin-1-ylidene)-1-cyclohexylethan-1-one,
(106) (Z)-2-(7-methoxy-3,3-dimethyl-3,4-dihydro-(2H)-isoquinolin-1-ylidene)-1-cycloheptylethan-1-one,
(107) (Z)-2-(7-methoxy-3,3-dimethyl-3,4-dihydro-(2H)-isoquinolin-1-ylidene)-1-(2-methoxyphenyl)-1-one,
(108) (Z)-2-(7-methoxy-3,3-dimethyl-3,4-dihydro-(2H)-isoquinolin-1-ylidene)-1-(4-cyanophenyl)-1-one,
(109) (Z)-2-(7-t-butyl-3,3-dimethyl-3,4-dihydro-(2H)-isoquinolin-1-ylidene)-1-cyclohexylethan-1-one,
(110) (Z)-2-(7-t-butyl-3,3-dimethyl-3,4-dihydro-(2H)-isoquinolin-1-ylidene)-1-cycloheptylethan-1-one,
(111) (Z)-2-(7-t-butyl-3,3-dimethyl-3,4-dihydro-(2H)-isoquinolin-1-ylidene)-1-(2-methoxyphenyl)ethan-1-one,
(112) (Z)-2-(7-t-butyl-3,3-dimethyl-3,4-dihydro-(2H)-isoquinolin-1-ylidene)-1-(4-cyanophenyl)ethan-1-one,
(113) (Z)-2-(7-fluoro-3,3-dimethyl-3,4-dihydro-(2H)-isoquinolin-1-ylidene)-1-(4-cyanophenyl)ethan-1-one,
(114) (Z)-2-(7-chloro-3,3-dimethyl-3,4-dihydro-(2H)-isoquinolin-1-ylidene)-1-(4-cyanophenyl)ethan-1-one,
(115) (Z)-2-(7-fluoro-3,3-dimethyl-3,4-dihydro-(2H)-isoquinolin-1-ylidene)-1-(2-methoxyphenyl)ethan-1-one,
(116) (Z)-2-(7-chloro-3,3-dimethyl-3,4-dihydro-(2H)-isoquinolin-1-ylidene)-1-(2-methoxyphenyl)ethan-1-one,
(117) (Z)-2-(7-fluoro-3,3-dimethyl-3,4-dihydro-(2H)-isoquinolin-1-ylidene)-1-cyclohexylethan-1-one,
(118) (Z)-2-(7-fluoro-3,3-dimethyl-3,4-dihydro-(2H)-isoquinolin-1-ylidene)-1-cycloheptylethan-1-one,
(119) (Z)-2-(7-chloro-3,3-dimethyl-3,4-dihydro-(2H)-isoquinolin-1-ylidene)-1-cyclohexylethan-1-one,
(120) (Z)-2-(7-chloro-3,3-dimethyl-3,4-dihydro-(2H)-isoquinolin-1-ylidene)-1-cycloheptylethan-1-one,
(121) (Z)-2-(3,3,7-trimethyl-3,4-dihydro-(2H)-isoquinolin-1-ylidene)-1-cyclohexylethan-1-one,
(122) (Z)-2-(3,3,7-trimethyl-3,4-dihydro-(2H)-isoquinolin-1-ylidene)-1-cycloheptylethan-1-one,
(123) (Z)-2-(3,3,7-trimethyl-3,4-dihydro-(2H)-isoquinolin-1-ylidene)-1-(2-methoxyphenyl)ethan-1-one,
(124) (Z)-2-(3,3,7-trimethyl-3,4-dihydro-(2H)-isoquinolin-1-ylidene)-1-(4-cyanophenyl)ethan-1-one,
(125) (Z)-2-(3,3-dimethyl-3,4-dihydro-(2H)-isoquinolin-1-ylidene)-1-(2-nitrophenyl)ethan-1-one,
(126) (Z)-2-(3,3-dimethyl-3,4-dihydro-(2H)-isoquinolin-1-ylidene)-1-(3-nitrophenyl)ethan-1-one,
(127) (Z)-2-(3,3-dimethyl-3,4-dihydro-(2H)-isoquinolin-1-ylidene)-1-(4-nitrophenyl)ethan-1-one,
(128) (Z)-2-(3,3-dimethyl-3,4-dihydro-(2H)-isoquinolin-1-ylidene)-1-(2,5-dimethoxyphenyl)ethan-1-one,
(129) (Z)-2-(3,3-dimethyl-3,4-dihydro-(2H)-isoquinolin-1-ylidene)-1-(2,4-dimethoxyphenyl)ethan-1-one,
(130) (Z)-2-(7-methoxy-3,3-dimethyl-3,4-dihydro-(2H)-isoquinolin-1-ylidene)-1-(naphthalen-1-yl)ethan-1-one,
(131) (Z)-2-(3,3-dimethyl-3,4-dihydro-(2H)-isoquinolin-1-ylidene)-1-(anthracen-9-yl)ethan-1-one,
(132) (Z)-2-(3,3,7-trimethyl-3,4-dihydro-(2H)-isoquinolin-1-ylidene)-1-(adamantan-1-yl)ethan-1-one,
(133) (Z)-2-(7-methoxy-3,3-dimethyl-3,4-dihydro-(2H)-isoquinolin-1-ylidene)-1-(adamantan-1-yl)ethan-1-one,
(134) (Z)-2-(7-bromo-3,3-dimethyl-3,4-dihydro-(2H)-isoquinolin-1-ylidene)-1-(naphthalen-1-yl)ethan-1-one, (135) (Z)-2-(6-chloro-3,3-dimethyl-3,4-dihydro-(2H)-isoquinolin-1-ylidene)-1-(4-cyanophenyl)ethan-1-one,
(136) (Z)-2-(8-chloro-3,3-dimethyl-3,4-dihydro-(2H)-isoquinolin-1-ylidene)-1-(4-cyanophenyl)ethan-1-one,
(137) (Z)-2-(8-chloro-3,3-dimethyl-3,4-dihydro-(2H)-isoquinolin-1-ylidene)-1-cyclohexylethan-1-one,
(138) (Z)-2-(7-fluoro-3,3-dimethyl-3,4-dihydro-(2H)-isoquinolin-1-ylidene)-1-(adamantan-1-yl)ethan-1-one,
(139) (Z)-2-(7-chloro-3,3-dimethyl-3,4-dihydro-(2H)-isoquinolin-1-ylidene)-1-(adamantan-1-yl)ethan-1-one,
(140) (Z)-2-(6-chloro-3,3-dimethyl-3,4-dihydro-(2H)-isoquinolin-1-ylidene)-1-(adamantan-1-yl)ethan-1-one,
(141) (Z)-2-(3,3-dimethyl-3,4-dihydro-(2H)-isoquinolin-1-ylidene)-1-(4-bromophenyl)ethan-1-one,
(142) (Z)-2-(3,3-dimethyl-3,4-dihydro-(2H)-isoquinolin-1-ylidene)-1-(4-methylthiophenyl)ethan-1-one,
(143) (Z)-2-(3,3-dimethyl-3,4-dihydro-(2H)-isoquinolin-1-ylidene)-1-(4-dimethylaminophenyl)ethan-1-one,
(144) (Z)-2-(3,3-dimethyl-3,4-dihydro-(2H)-isoquinolin-1-ylidene)-1-(4-mesylphenyl)ethan-1-one,
(145) (Z)-2-(8-chloro-3,3-dimethyl-3,4-dihydro-(2H)-isoquinolin-1-ylidene)-1-phenylethan-1-one,
(146) (Z)-2-(3,3-dimethyl-3,4-dihydro-(2H)-isoquinolin-1-ylidene)-1-(2,4-dichlorophenyl)ethan-1-one,
(147) (Z)-2-(6-fluoro-3,3-dimethyl-3,4-dihydro-(2H)-isoquinolin-1-ylidene)-1-(adamantan-1-yl)ethan-1-one,
(148) (Z)-2-(6-fluoro-3,3-dimethyl-3,4-dihydro-(2H)-isoquinolin-1-ylidene)-1-(4-cyanophenyl)ethan-1-one,
(149) (Z)-2-(3,3-dimethyl-3,4-dihydro-(2H)-isoquinolin-1-ylidene)-1-(4-methylnaphthalen-1-yl)ethan-1-one,
(150) (Z)-2-(3,3-dimethyl-3,4-dihydro-(2H)-isoquinolin-1-ylidene)-1-(4-fluoronaphthalen-1-yl)ethan-1-one,
(151) (Z)-2-(7-nitro-3,3-dimethyl-3,4-dihydro-(2H)-isoquinolin-1-ylidene)-1-phenylethan-1-one,
(152) (Z)-2-(spiro[6-chloro-3,4-dihydro-(2H)-isoquinolin-3,4'-3,4,5,6-tetrahydropyran]-1-ylidene)-1-phenylethan-1-one,
(153) (Z)-2-(spiro[6-chloro-3,4-dihydro-(2H)-isoquinolin-3,4'-3,4,5,6-tetrahydropyran]-1-ylidene)-1-(4-cyanophenyl)ethan-1-one,
(154) (Z)-2-(spiro[6-chloro-3,4-dihydro-(2H)-isoquinolin-3,4'-3,4,5,6-tetrahydropyran]-1-ylidene)-1-(adamantan-1-yl)ethan-1-one,
(155) (Z)-2-(3,3-dimethyl-3,4-dihydro-(2H)-isoquinolin-1-ylidene)-1-(noradamantan-1-yl)ethan-1-one,
(156) (Z)-2-(6-chloro-3,3-dimethyl-3,4-dihydro-(2H)-isoquinolin-1-ylidene)-1-(noradamantan-1-yl)ethan-1-one,
(157) (Z)-2-(3,3-dimethyl-3,4-dihydro-(2H)-isoquinolin-1-ylidene)-1-(2-chloro-4-mesylphenyl)ethan-1-one,
(158) (Z)-2-(6-methoxy-3,3-dimethyl-3,4-dihydro-(2H)-isoquinolin-1-ylidene)-1-(adamantan-1-yl)ethan-1-one,
(159) (Z)-2-(6-methoxy-3,3-dimethyl-3,4-dihydro-(2H)-isoquinolin-1-ylidene)-1-(4-cyanophenyl)ethan-1-one,
(160) (Z)-2-(7-bromo-6-chloro-3,3-dimethyl-3,4-dihydro-(2H)-isoquinolin-1-ylidene)-1-(adamantan-1-yl)ethan-1-one,
(161) (Z)-2-(5-methoxy-3,3-dimethyl-3,4-dihydro-(2H)-isoquinolin-1-ylidene)-1-phenylethan-1-one,
(162) (Z)-2-(3,3,6-trimethyl-3,4-dihydro-(2H)-isoquinolin-1-ylidene)-1-(adamantan-1-yl)ethan-1-one,
(163) (Z)-2-(3,3,6-trimethyl-3,4-dihydro-(2H)-isoquinolin-1-ylidene)-1-(4-cyanophenyl)ethan-1-one,
(164) (Z)-2-(7-nitro-3,3-dimethyl-3,4-dihydro-(2H)-isoquinolin-1-ylidene)-1-(4-cyanophenyl)ethan-1-one,
(165) (Z)-2-(6-chloro-7-nitro-3,3-dimethyl-3,4-dihydro-(2H)-isoquinolin-1-ylidene)-1-cyclohexylethan-1-one,
(166) (Z)-2-(6-chloro-7-nitro-3,3-dimethyl-3,4-dihydro-(2H)-isoquinolin-1-ylidene)-1-cycloheptylethan-1-one,
(167) (Z)-2-(6-chloro-7-nitro-3,3-dimethyl-3,4-dihydro-(2H)-isoquinolin-1-ylidene)-1-(4-cyanophenyl)ethan-1-one,
(168) (Z)-2-(6-chloro-7-nitro-3,3-dimethyl-3,4-dihydro-(2H)-isoquinolin-1-ylidene)-1-(adamantan-1-yl)ethan-1-one,
(169) (Z)-2-(7-dimethylaminomethyl-3,3-dimethyl-3,4-dihydro-(2H)-isoquinolin-1-ylidene)-1-(4-cyanophenyl)ethan-1-one,
(170) (Z)-2-(7-dimethylaminomethyl-3,3-dimethyl-3,4-dihydro-(2H)-isoquinolin-1-ylidene)-1-(adamantan-1-yl)ethan-1-one,
(171) (Z)-2-(7-amino-6-methoxy-3,3-dimethyl-3,4-dihydro-(2H)-isoquinolin-1-ylidene)-1-(4-cyanophenyl)ethan-1-one,
(172) (Z)-2-(7-amino-6-methoxy-3,3-dimethyl-3,4-dihydro-(2H)-isoquinolin-1-ylidene)-1-(adamantan-1-yl)ethan-1-one,
(173) (Z)-2-(6-chloro-7-dimethylamino-3,3-dimethyl-3,4-dihydro-(2H)-isoquinolin-1-ylidene)-1-cyclohexylethan-1-one,
(174) (Z)-2-(6-chloro-7-dimethylamino-3,3-dimethyl-3,4-dihydro-(2H)-isoquinolin-1-ylidene)-1-cycloheptylethan-1-one,
(175) (Z)-2-(6-chloro-7-dimethylamino-3,3-dimethyl-3,4-dihydro-(2H)-isoquinolin-1-ylidene)-1-(4-cyanophenyl)ethan-1-one,
(176) (Z)-2-(6-chloro-7-dimethylamino-3,3-dimethyl-3,4-dihydro-(2H)-isoquinolin-1-ylidene)-1-(adamantan-1-yl)ethan-1-one,
(177) (Z)-2-(7-dimethylamino-3,3,6-trimethyl-3,4-dihydro-(2H)-isoquinolin-1-ylidene)-1-(4-cyanophenyl)ethan-1-one,
(178) (Z)-2-(7-dimethylamino-3,3,6-trimethyl-3,4-dihydro-(2H)-isoquinolin-1-ylidene)-1-(adamantan-1-yl)ethan-1-one,
(179) (Z)-2-(7-dimethylamino-3,3,6-trimethyl-3,4-dihydro-(2H)-isoquinolin-1-ylidene)-1-cyclohexylethan-1-one,
(180) (Z)-2-(7-dimethylamino-3,3,6-trimethyl-3,4-dihydro-(2H)-isoquinolin-1-ylidene)-1-cycloheptylethan-1-one,
(181) (Z)-2-(7-dimethylaminomethyl-3,3-dimethyl-3,4-dihydro-(2H)-isoquinolin-1-ylidene)-1-cyclohexylethan-1-one,
(182) (Z)-2-(7-dimethylaminomethyl-3,3-dimethyl-3,4-dihydro-(2H)-isoquinolin-1-ylidene)-1-cycloheptylethan-1-one,
(183) (Z)-2-(6-methoxy-7-methylamino-3,3-dimethyl-3,4-dihydro-(2H)-isoquinolin-1-ylidene)-1-(4-cyanophenyl)ethan-1-one, (184) (Z)-2-(6-methoxy-7-methylamino-3,3-dimethyl-3,4-dihydro-(2H)-isoquinolin-1-ylidene)-1-(adamantan-1-yl)ethan-1-one, (185) (Z)-2-(7-dimethylamino-6-methoxy-3,3-dimethyl-3,4-dihydro-(2H)-isoquinolin-1-ylidene)-1-cyclohexylethan-1-one, (186) (Z)-2-(7-dimethylamino-6-methoxy-3,3-dimethyl-3,4-dihydro-(2H)-isoquinolin-1-ylidene)-1-cycloheptylethan-1-one, (187) (Z)-2-(7-dimethylamino-3,3-dimethyl-3,4-dihydro-(2H)-isoquinolin-1-ylidene)-1-(4-cyanophenyl)ethan-1-one, (188) (Z)-2-(7-dimethylamino-3,3-dimethyl-3,4-dihydro-(2H)-isoquinolin-1-ylidene)-1-(adamantan-1-yl)ethan-1-one, (189) (Z)-2-(7-amino-6-methoxy-3,3-dimethyl-3,4-dihydro-(2H)-isoquinolin-1-ylidene)-1-cyclohexylethan-1-one, (190) (Z)-2-(7-amino-6-methoxy-3,3-dimethyl-3,4-dihydro-(2H)-isoquinolin-1-ylidene)-1-cycloheptylethan-1-one, (191) (Z)-2-(7-bromo-6-chloro-3,3-dimethyl-3,4-dihydro-(2H)-isoquinolin-1-ylidene)-1-cyclohexylethan-1-one, (192) (Z)-2-(7-bromo-6-chloro-3,3-dimethyl-3,4-dihydro-(2H)-isoquinolin-1-ylidene)-1-cycloheptylethan-1-one, (193) (Z)-2-(7-nitro-3,3-dimethyl-3,4-dihydro-(2H)-isoquinolin-1-ylidene)-1-cyclohexylethan-1-one, (194) (Z)-2-(7-bromo-6-methoxy-3,3-dimethyl-3,4-dihydro-(2H)-isoquinolin-1-ylidene)-1-(adamantan-1-yl)ethan-1-one, (195) (Z)-2-(7-nitro-3,3-dimethyl-3,4-dihydro-(2H)-isoquinolin-1-ylidene)-1-(adamantan-1-yl)ethan-1-one, (196) (Z)-2-(7-dimethylamino-3,3-dimethyl-3,4-dihydro-(2H)-isoquinolin-1-ylidene)-1-cyclohexylethan-1-one, (197) (Z)-2-(7-dimethylamino-3,3-dimethyl-3,4-dihydro-(2H)-isoquinolin-1-ylidene)-1-cycloheptylethan-1-one, (198) (Z)-2-(7-methylamino-3,3-dimethyl-3,4-dihydro-(2H)-isoquinolin-1-ylidene)-1-cyclohexylethan-1-one, (199) (Z)-2-(7-methylamino-3,3-dimethyl-3,4-dihydro-(2H)-isoquinolin-1-ylidene)-1-cycloheptylethan-1-one, (200) (Z)-2-(7-methylamino-3,3-dimethyl-3,4-dihydro-(2H)-isoquinolin-1-ylidene)-1-(4-cyanophenyl)ethan-1-one, (201) (Z)-2-(7-cyano-6-methoxy-3,3-dimethyl-3,4-dihydro-(2H)-isoquinolin-1-ylidene)-1-(4-cyanophenyl)ethan-1-one, (202) (Z)-2-(7-methylamino-3,3-dimethyl-3,4-dihydro-(2H)-isoquinolin-1-ylidene)-1-(adamantan-1-yl)ethan-1-one, (203) (Z)-2-(7-cyano-6-methoxy-3,3-dimethyl-3,4-dihydro-(2H)-isoquinolin-1-ylidene)-1-(adamantan-1-yl)ethan-1-one, (204) (Z)-2-(7-cyano-6-methoxy-3,3-dimethyl-3,4-dihydro-(2H)-isoquinolin-1-ylidene)-1-cyclohexylethan-1-one, (205) (Z)-2-(7-cyano-6-methoxy-3,3-dimethyl-3,4-dihydro-(2H)-isoquinolin-1-ylidene)-1-cycloheptylethan-1-one, (206) (Z)-2-(7-bromo-3,3-dimethyl-3,4-dihydro-(2H)-isoquinolin-1-ylidene)-1-(adamantan-1-yl)ethan-1-one, (207) (Z)-2-(7-dimethylaminomethyl-6-methoxy-3,3-dimethyl-3,4-dihydro-(2H)-isoquinolin-1-ylidene)-1-cycloheptylethan-1-one, (208) (Z)-2-(7-bromo-6-methoxy-3,3-dimethyl-3,4-dihydro-(2H)-isoquinolin-1-ylidene)-1-cyclohexylethan-1-one, (209) (Z)-2-(7-dimethylaminomethyl-6-methoxy-3,3-dimethyl-3,4-dihydro-(2H)-isoquinolin-1-ylidene)-1-cyclohexylethan-1-one, (210) (Z)-2-(7-nitro-3,3,6-trimethyl-3,4-dihydro-(2H)-isoquinolin-1-ylidene)-1-(adamantan-1-yl)ethan-1-one, (211) (Z)-2-(6-methoxy-7-methylaminomethyl-3,3-dimethyl-3,4-dihydro-(2H)-isoquinolin-1-ylidene)-1-cyclohexylethan-1-one, (212) (Z)-2-(7-dimethylaminomethyl-6-methoxy-3,3-dimethyl-3,4-dihydro-(2H)-isoquinolin-1-ylidene)-1-(4-cyanophenyl)ethan-1-one, (213) (Z)-2-(7-nitro-3,3,6-trimethyl-3,4-dihydro-(2H)-isoquinolin-1-ylidene)-1-(4-cyanophenyl)ethan-1-one, (214) (Z)-2-(7-nitro-3,3,6-trimethyl-3,4-dihydro-(2H)-isoquinolin-1-ylidene)-1-cyclohexylethan-1-one, (215) (Z)-2-(7-nitro-3,3,6-trimethyl-3,4-dihydro-(2H)-isoquinolin-1-ylidene)-1-cycloheptylethan-1-one, (216) (Z)-2-(7-methylamino-3,3,6-trimethyl-3,4-dihydro-(2H)-isoquinolin-1-ylidene)-1-cyclohexylethan-1-one, (217) (Z)-2-(7-methylamino-3,3,6-trimethyl-3,4-dihydro-(2H)-isoquinolin-1-ylidene)-1-cycloheptylethan-1-one, (218) (Z)-2-(7-methylamino-3,3,6-trimethyl-3,4-dihydro-(2H)-isoquinolin-1-ylidene)-1-(adamantan-1-yl)ethan-1-one, (219) (Z)-2-(7-bromo-6-methoxy-3,3-dimethyl-3,4-dihydro-(2H)-isoquinolin-1-ylidene)-1-cycloheptylethan-1-one, (220) (Z)-2-(6,7-dicyano-3,3-dimethyl-3,4-dihydro-(2H)-isoquinolin-1-ylidene)-1-cyclohexylethan-1-one, (221) (Z)-2-(6,7-dicyano-3,3-dimethyl-3,4-dihydro-(2H)-isoquinolin-1-ylidene)-1-(adamantan-1-yl)ethan-1-one, (222) (Z)-2-(7-bromo-3,3,6-trimethyl-3,4-dihydro-(2H)-isoquinolin-1-ylidene)-1-(adamantan-1-yl)ethan-1-one, (223) (Z)-2-(6,7-dicyano-3,3-dimethyl-3,4-dihydro-(2H)-isoquinolin-1-ylidene)-1-cycloheptylethan-1-one, (224) (Z)-2-(6,7-dicyano-3,3-dimethyl-3,4-dihydro-(2H)-isoquinolin-1-ylidene)-1-(4-cyanophenyl)ethan-1-one, (225) (Z)-2-(7-methylamino-3,3,6-trimethyl-3,4-dihydro-(2H)-isoquinolin-1-ylidene)-1-(4-cyanophenyl)ethan-1-one, (226) (Z)-2-(7-bromo-3,3-dimethyl-3,4-dihydro-(2H)-isoquinolin-1-ylidene)-1-cyclohexylethan-1-one, (227) (Z)-2-(7-bromo-3,3,6-trimethyl-3,4-dihydro-(2H)-isoquinolin-1-ylidene)-1-cyclohexylethan-1-one, (228) (Z)-2-(6-chloro-7-methylamino-3,3-dimethyl-3,4-dihydro-(2H)-isoquinolin-1-ylidene)-1-cyclohexylethan-1-one, (229) (Z)-2-(6-chloro-7-methylamino-3,3-dimethyl-3,4-dihydro-(2H)-isoquinolin-1-ylidene)-1-cycloheptylethan-1-one, (230) (Z)-2-(6-chloro-7-methylamino-3,3-dimethyl-3,4-dihydro-(2H)-isoquinolin-1-ylidene)-1-(adamantan-1-yl)ethan-1-one,
(231) (Z)-2-(7-bromo-3,3-dimethyl-3,4-dihydro-(2H)-isoquinolin-1-ylidene)-1-cycloheptylethan-1-one,
(232) (Z)-2-(7-bromo-3,3,6-trimethyl-3,4-dihydro-(2H)-isoquinolin-1-ylidene)-1-cycloheptylethan-1-one,
(233) (Z)-2-(7-nitro-3,3-dimethyl-3,4-dihydro-(2H)-isoquinolin-1-ylidene)-1-cycloheptylethan-1-one,
(234) (Z)-2-(7-dimethylsulfamoyl-3,3-dimethyl-3,4-dihydro-(2H)-isoquinolin-1-ylidene)-1-(adamantan-1-yl)ethan-1-one,
(235) (Z)-2-(7-butoxycarbonyl-6-chloro-3,3-dimethyl-3,4-dihydro-(2H)-isoquinolin-1-ylidene)-1-(adamantan-1-yl)ethan-1-one,
(236) (Z)-2-(7-butoxycarbonyl-6-chloro-3,3-dimethyl-3,4-dihydro-(2H)-isoquinolin-1-ylidene)-1-cycloheptylethan-1-one,
(237) (Z)-2-(7-methylsulfamoyl-3,3-dimethyl-3,4-dihydro-(2H)-isoquinolin-1-ylidene)-1-(adamantan-1-yl)ethan-1-one,
(238) (Z)-2-(6-chloro-7-methoxy-3,3-dimethyl-3,4-dihydro-(2H)-isoquinolin-1-ylidene)-1-(adamantan-1-yl)ethan-1-one,
(239) (Z)-2-(7-methoxy-3,3,6-trimethyl-3,4-dihydro-(2H)-isoquinolin-1-ylidene)-1-(adamantan-1-yl)ethan-1-one,
(240) (Z)-2-(7-methoxy-3,3,6-trimethyl-3,4-dihydro-(2H)-isoquinolin-1-ylidene)-1-cyclohexylethan-1-one,
(241) (Z)-2-(7-methoxy-3,3,6-trimethyl-3,4-dihydro-(2H)-isoquinolin-1-ylidene)-1-cycloheptylethan-1-one,
(242) (Z)-2-(6-bromo-3,3-dimethyl-3,4-dihydro-(2H)-isoquinolin-1-ylidene)-1-phenylethan-1-one,
(243) (Z)-2-(6-fluoro-3,3-dimethyl-3,4-dihydro-(2H)-isoquinolin-1-ylidene)-1-cyclohexylethan-1-one,
(244) (Z)-2-(6-chloro-3,3-dimethyl-3,4-dihydro-(2H)-isoquinolin-1-ylidene)-1-cyclohexylethan-1-one,
(245) (Z)-2-(6-fluoro-3,3-dimethyl-3,4-dihydro-(2H)-isoquinolin-1-ylidene)-1-cycloheptylethan-1-one,
(246) (Z)-2-(6-chloro-3,3-dimethyl-3,4-dihydro-(2H)-isoquinolin-1-ylidene)-1-cycloheptylethan-1-one,
(247) (Z)-2-(8-methoxy-3,3-dimethyl-3,4-dihydro-(2H)-isoquinolin-1-ylidene)-1-cyclohexylethan-1-one,
(248) (Z)-2-(6-methoxy-3,3-dimethyl-3,4-dihydro-(2H)-isoquinolin-1-ylidene)-1-cyclohexylethan-1-one,
(249) (Z)-2-(8-methoxy-3,3-dimethyl-3,4-dihydro-(2H)-isoquinolin-1-ylidene)-1-cycloheptylethan-1-one,
(250) (Z)-2-(6-methoxy-3,3-dimethyl-3,4-dihydro-(2H)-isoquinolin-1-ylidene)-1-cycloheptylethan-1-one,
(251) (Z)-2-(3,3,4,4-tetramethyl-3,4-dihydro-(2H)-isoquinolin-1-ylidene)-1-(2-methoxyphenyl)ethan-1-one,
(252) (Z)-2-(3,3,4,4-tetramethyl-3,4-dihydro-(2H)-isoquinolin-1-ylidene)-1-cyclohexylethan-1-one,
(253) (Z)-2-(3,3,4,4-tetramethyl-3,4-dihydro-(2H)-isoquinolin-1-ylidene)-1-cycloheptylethan-1-one,
(254) (Z)-2-(6-chloro-3,3-dimethyl-3,4-dihydro-(2H)-isoquinolin-1-ylidene)-1-(2-methoxyphenyl)ethan-1-one,
(255) (Z)-2-(6-chloro-3,3-dimethyl-3,4-dihydro-(2H)-isoquinolin-1-ylidene)-1-(2-chlorophenyl)ethan-1-one,
(256) (Z)-2-(6,8-dichloro-3,3-dimethyl-3,4-dihydro-(2H)-isoquinolin-1-ylidene)-1-phenylethan-1-one,
(257) (Z)-2-(3,3-dimethyl-3,4-dihydro-(2H)-isoquinolin-1-ylidene)-1-(2-ethoxyphenyl)ethan-1-one,
(258) 2-(3,3-dimethyl-3,4-dihydroisoquinolin-1-yl)-1-(adamantan-1-yl)propan-1-one,
(259) (Z)-2-(3,3-dimethyl-3,4-dihydro-(2H)-isoquinolin-1-ylidene)-1-(4-chloro-2-methoxyphenyl)ethan-1-one,
(260) (Z)-2-(3,3-dimethyl-3,4-dihydro-(2H)-isoquinolin-1-ylidene)-1-(2-methoxy-4-methylthiophenyl)ethan-1-one,
(261) (Z)-2-(3,3-dimethyl-3,4-dihydro-(2H)-isoquinolin-1-ylidene)-1-(2-methoxy-4-mesylphenyl)ethan-1-one,
(262) 2-(6-fluoro-3,3-dimethyl-3,4-dihydroisoquinolin-1-yl)-1-phenylpropan-1-one,
(263) (Z)-2-(6,7-dichloro-3,3-dimethyl-3,4-dihydro-(2H)-isoquinolin-1-ylidene)-1-phenylethan-1-one,
(264) (Z)-2-(3,3-dimethyl-3,4-dihydro-(2H)-isoquinolin-1-ylidene)-1-(4-bromo-2-methoxyphenyl)ethan-1-one,
(265) (Z)-2-(3,3-dimethyl-3,4-dihydro-(2H)-isoquinolin-1-ylidene)-1-(4-bromo-2-chlorophenyl)ethan-1-one,
(266) (Z)-2-(6-bromo-3,3-dimethyl-3,4-dihydro-(2H)-isoquinolin-1-ylidene)-1-cyclohexylethan-1-one,
(267) (Z)-2-(6-bromo-3,3-dimethyl-3,4-dihydro-(2H)-isoquinolin-1-ylidene)-1-cycloheptylethan-1-one,
(268) (Z)-2-(6-bromo-3,3-dimethyl-3,4-dihydro-(2H)-isoquinolin-1-ylidene)-1-(adamantan-1-yl)ethan-1-one,
(269) (Z)-2-(6-formyl-3,3-dimethyl-3,4-dihydro-(2H)-isoquinolin-1-ylidene)-1-phenylethan-1-one,
(270) (Z)-2-(7-formyl-3,3-dimethyl-3,4-dihydro-(2H)-isoquinolin-1-ylidene)-1-phenylethan-1-one,
(271) (Z)-2-(7-formyl-3,3-dimethyl-3,4-dihydro-(2H)-isoquinolin-1-ylidene)-1-(naphthalen-1-yl)ethan-1-one,
(272) (Z)-2-(3,3-dimethyl-3,4-dihydro-(2H)-isoquinolin-1-ylidene)-1-(4-formylphenyl)ethan-1-one,
(273) (Z)-2-(3,3-dimethyl-3,4-dihydro-(2H)-isoquinolin-1-ylidene)-1-(4-formyl-2-methoxyphenyl)ethan-1-one,
(274) (Z)-2-(6-chloro-7-formyl-3,3-dimethyl-3,4-dihydro-(2H)-isoquinolin-1-ylidene)-1-(adamantan-1-yl)ethan-1-one,
(275) (Z)-2-(6-chloro-7-formyl-3,3-dimethyl-3,4-dihydro-(2H)-isoquinolin-1-ylidene)-1-cyclohexylethan-1-one,
(276) (Z)-2-(6-chloro-7-formyl-3,3-dimethyl-3,4-dihydro-(2H)-isoquinolin-1-ylidene)-1-cycloheptylethan-1-one,
(277) (Z)-2-(7-formyl-6-methoxy-3,3-dimethyl-3,4-dihydro-(2H)-isoquinolin-1-ylidene)-1-(adamantan-1-yl)ethan-1-one,
(278) (Z)-2-(7-formyl-3,3-dimethyl-3,4-dihydro-(2H)-isoquinolin-1-ylidene)-1-(adamantan-1-yl)ethan-1-one,
(279) (Z)-2-(7-formyl-6-methoxy-3,3-dimethyl-3,4-dihydro-(2H)-isoquinolin-1-ylidene)-1-cyclohexylethan-1-one,
(280) (Z)-2-(7-formyl-6-methoxy-3,3-dimethyl-3,4-dihydro-(2H)-isoquinolin-1-ylidene)-1-cycloheptylethan-1-one,
(281) (Z)-2-(7-formyl-3,3,6-trimethyl-3,4-dihydro-(2H)-isoquinolin-1-ylidene)-1-(adamantan-1-yl)ethan-1-one, (282) (Z)-2-(7-formyl-3,3-dimethyl-3,4-dihydro-(2H)-isoquinolin-1-ylidene)-1-cyclohexylethan-1-one,
(283) (Z)-2-(7-formyl-3,3,6-trimethyl-3,4-dihydro-(2H)-isoquinolin-1-ylidene)-1-cyclohexylethan-1-one,
(284) (Z)-2-(7-formyl-3,3-dimethyl-3,4-dihydro-(2H)-isoquinolin-1-ylidene)-1-cycloheptylethan-1-one,
(285) (Z)-2-(7-formyl-3,3,6-trimethyl-3,4-dihydro-(2H)-isoquinolin-1-ylidene)-1-cycloheptylethan-1-one,
(286) (Z)-2-(3,3-dimethyl-3,4-dihydro-(2H)-isoquinolin-1-ylidene)-1-(4-aminophenyl)ethan-1-one,
(287) (Z)-2-(3,3-dimethyl-3,4-dihydro-(2H)-isoquinolin-1-ylidene)-1-(2-aminophenyl)ethan-1-one,
(288) (Z)-2-(3,3-dimethyl-3,4-dihydro-(2H)-isoquinolin-1-ylidene)-1-(3-aminophenyl)ethan-1-one,
(289) (Z)-2-(7-amino-3,3-dimethyl-3,4-dihydro-(2H)-isoquinolin-1-ylidene)-1-phenylethan-1-one,
(290) (Z)-2-(7-amino-3,3-dimethyl-3,4-dihydro-(2H)-isoquinolin-1-ylidene)-1-(4-cyanophenyl)ethan-1-one,
(291) (Z)-2-(7-amino-6-chloro-3,3-dimethyl-3,4-dihydro-(2H)-isoquinolin-1-ylidene)-1-cyclohexylethan-1-one,
(292) (Z)-2-(7-amino-6-chloro-3,3-dimethyl-3,4-dihydro-(2H)-isoquinolin-1-ylidene)-1-cycloheptylethan-1-one,
(293) (Z)-2-(7-amino-6-chloro-3,3-dimethyl-3,4-dihydro-(2H)-isoquinolin-1-ylidene)-1-(4-cyanophenyl)ethan-1-one,
(294) (Z)-2-(7-amino-6-chloro-3,3-dimethyl-3,4-dihydro-(2H)-isoquinolin-1-ylidene)-1-(adamantan-1-yl)ethan-1-one,
(295) (Z)-2-(7-amino-3,3-dimethyl-3,4-dihydro-(2H)-isoquinolin-1-ylidene)-1-cyclohexylethan-1-one,
(296) (Z)-2-(7-amino-3,3-dimethyl-3,4-dihydro-(2H)-isoquinolin-1-ylidene)-1-(adamantan-1-yl)ethan-1-one,
(297) (Z)-2-(7-amino-3,3-dimethyl-3,4-dihydro-(2H)-isoquinolin-1-ylidene)-1-cycloheptylethan-1-one,
(298) (Z)-2-(7-amino-3,3,6-trimethyl-3,4-dihydro-(2H)-isoquinolin-1-ylidene)-1-(adamantan-1-yl)ethan-1-one,
(299) (Z)-2-(7-amino-3,3,6-trimethyl-3,4-dihydro-(2H)-isoquinolin-1-ylidene)-1-(4-cyanophenyl)ethan-1-one,
(300) (Z)-2-(7-amino-3,3,6-trimethyl-3,4-dihydro-(2H)-isoquinolin-1-ylidene)-1-cyclohexylethan-1-one,
(301) (Z)-2-(7-amino-3,3,6-trimethyl-3,4-dihydro-(2H)-isoquinolin-1-ylidene)-1-cycloheptylethan-1-one,
(302) (Z)-2-(6-carboxy-3,3-dimethyl-3,4-dihydro-(2H)-isoquinolin-1-ylidene)-1-phenylethan-1-one,
(303) (Z)-2-(7-carboxy-3,3-dimethyl-3,4-dihydro-(2H)-isoquinolin-1-ylidene)-1-phenylethan-1-one,
(304) (Z)-2-(7-carboxy-3,3-dimethyl-3,4-dihydro-(2H)-isoquinolin-1-ylidene)-1-(adamantan-1-yl)ethan-1-one,
(305) (Z)-2-(6-carboxy-3,3-dimethyl-3,4-dihydro-(2H)-isoquinolin-1-ylidene)-1-cyclohexylethan-1-one,
(306) (Z)-2-(6-carboxy-3,3-dimethyl-3,4-dihydro-(2H)-isoquinolin-1-ylidene)-1-cycloheptylethan-1-one,
(307) (Z)-2-(7-carboxy-3,3-dimethyl-3,4-dihydro-(2H)-isoquinolin-1-ylidene)-1-cyclohexylethan-1-one,
(308) (Z)-2-(7-carboxy-3,3-dimethyl-3,4-dihydro-(2H)-isoquinolin-1-ylidene)-1-cycloheptylethan-1-one,
(309) (Z)-2-(7-carboxy-6-methoxy-3,3-dimethyl-3,4-dihydro-(2H)-isoquinolin-1-ylidene)-1-cycloheptylethan-1-one,
(310) (Z)-2-(7-carboxy-6-methoxy-3,3-dimethyl-3,4-dihydro-(2H)-isoquinolin-1-ylidene)-1-(adamantan-1-yl)ethan-1-one,
(311) (Z)-2-(7-carboxy-3,3,6-trimethyl-3,4-dihydro-(2H)-isoquinolin-1-ylidene)-1-cyclohexylethan-1-one,
(312) (Z)-2-(7-carboxy-6-methoxy-3,3-dimethyl-3,4-dihydro-(2H)-isoquinolin-1-ylidene)-1-cyclohexylethan-1-one,
(313) (Z)-2-(7-carboxy-3,3,6-trimethyl-3,4-dihydro-(2H)-isoquinolin-1-ylidene)-1-(adamantan-1-yl)ethan-1-one,
(314) (Z)-2-(7-carboxy-3,3,6-trimethyl-3,4-dihydro-(2H)-isoquinolin-1-ylidene)-1-cycloheptylethan-1-one,
(315) (Z)-2-(6-carboxy-3,3-dimethyl-3,4-dihydro-(2H)-isoquinolin-1-ylidene)-1-(adamantan-1-yl)ethan-1-one,
(316) (Z)-2-(3,3,4,4-tetramethyl-3,4-dihydro-(2H)-isoquinolin-1-ylidene)-1-(2-hydroxyphenyl)ethan-1-one,
(317) (Z)-2-(7-hydroxy-3,3-dimethyl-3,4-dihydro-(2H)-isoquinolin-1-ylidene)-1-(naphthalen-1-yl)ethan-1-one,
(318) (Z)-2-(7-hydroxy-3,3-dimethyl-3,4-dihydro-(2H)-isoquinolin-1-ylidene)-1-phenylethan-1-one,
(319) (Z)-2-(5-hydroxy-3,3-dimethyl-3,4-dihydro-(2H)-isoquinolin-1-ylidene)-1-phenylethan-1-one,
(320) (Z)-2-(6-chloro-7-hydroxy-3,3-dimethyl-3,4-dihydro-(2H)-isoquinolin-1-ylidene)-1-(adamantan-1-yl)ethan-1-one,
(321) (Z)-2-(7-hydroxy-3,3-dimethyl-3,4-dihydro-(2H)-isoquinolin-1-ylidene)-1-(adamantan-1-yl)ethan-1-one,
(322) (Z)-2-(7-hydroxy-3,3-dimethyl-3,4-dihydro-(2H)-isoquinolin-1-ylidene)-1-cyclohexylethan-1-one,
(323) (Z)-2-(7-phenyl-3,3-dimethyl-3,4-dihydro-(2H)-isoquinolin-1-ylidene)-1-phenylethan-1-one,
(324) (Z)-2-(7-(pyridin-3-yl)-3,3-dimethyl-3,4-dihydro-(2H)-isoquinolin-1-ylidene)-1-phenylethan-1-one,
(325) (Z)-2-(6-(morpholin-4-yl)-3,3-dimethyl-3,4-dihydro-(2H)-isoquinolin-1-ylidene)-1-phenylethan-1-one,
(326) (Z)-2-(7-(morpholin-4-yl)-3,3-dimethyl-3,4-dihydro-(2H)-isoquinolin-1-ylidene)-1-phenylethan-1-one,
(327) (Z)-2-(6-chloro-7-propoxycarbonyl-3,3-dimethyl-3,4-dihydro-(2H)-isoquinolin-1-ylidene)-1-cyclohexylethan-1-one,
(328) (Z)-2-(3,3-dimethyl-3,4-dihydro-(2H)-isoquinolin-1-ylidene)-1-(4-methylsulfinylphenyl)ethan-1-one,
(329) (Z)-2-(6-cyano-3,3-dimethyl-3,4-dihydro-(2H)-isoquinolin-1-ylidene)-1-phenylethan-1-one,
(330) (Z)-2-(7-(1-hydroxy-1-methylethyl)-3,3-dimethyl-3,4-dihydro-(2H)-isoquinolin-1-ylidene)-1-phenylethan-1-one,
(331) (Z)-2-(7-(1-hydroxy-1-methylethyl)-3,3-dimethyl-3,4-dihydro-(2H)-isoquinolin-1-ylidene)-1-cyclohexylethan-1-one,
(332) (Z)-2-(7-(1-hydroxy-1-methylethyl)-3,3-dimethyl-3,4-dihydro-(2H)-isoquinolin-1-ylidene)-1-(adamantan-1-yl)ethan-1-one,
(333) (Z)-2-(6-acetyl-3,3-dimethyl-3,4-dihydro-(2H)-isoquinolin-1-ylidene)-1-phenylethan-1-one, (334) (Z)-2-(7-hydroxyiminomethyl-3,3-dimethyl-3,4-dihydro-(2H)-isoquinolin-1-ylidene)-1-phenylethan-1-one, (335) (Z)-2-(6-hydroxyiminomethyl-3,3-dimethyl-3,4-dihydro-(2H)-isoquinolin-1-ylidene)-1-phenylethan-1-one, (336) (Z)-2-(7-hydroxyiminomethyl-6-methoxy-3,3-dimethyl-3,4-dihydro-(2H)-isoquinolin-1-ylidene)-1-(adamantan-1-yl)ethan-1-one, (337) (Z)-2-(7-hydroxyiminomethyl-6-methoxy-3,3-dimethyl-3,4-dihydro-(2H)-isoquinolin-1-ylidene)-1-cyclohexylethan-1-one, (338) (Z)-2-(7-hydroxyiminomethyl-3,3-dimethyl-3,4-dihydro-(2H)-isoquinolin-1-ylidene)-1-(adamantan-1-yl)ethan-1-one, (339) (Z)-2-(7-hydroxyiminomethyl-6-methoxy-3,3-dimethyl-3,4-dihydro-(2H)-isoquinolin-1-ylidene)-1-cycloheptylethan-1-one, (340) (Z)-2-(7-hydroxyiminomethyl-3,3-dimethyl-3,4-dihydro-(2H)-isoquinolin-1-ylidene)-1-cyclohexylethan-1-one, (341) (Z)-2-(7-hydroxyiminomethyl-3,3,6-trimethyl-3,4-dihydro-(2H)-isoquinolin-1-ylidene)-1-(adamantan-1-yl)ethan-1-one, (342) (Z)-2-(7-hydroxyiminomethyl-3,3-dimethyl-3,4-dihydro-(2H)-isoquinolin-1-ylidene)-1-cycloheptylethan-1-one, (343) (Z)-2-(7-hydroxyiminomethyl-3,3,6-trimethyl-3,4-dihydro-(2H)-isoquinolin-1-ylidene)-1-cyclohexylethan-1-one, (344) (Z)-2-(7-hydroxyiminomethyl-3,3,6-trimethyl-3,4-dihydro-(2H)-isoquinolin-1-ylidene)-1-cycloheptylethan-1-one, (345) (Z)-2-(6-aminomethyl-3,3-dimethyl-3,4-dihydro-(2H)-isoquinolin-1-ylidene)-1-phenylethan-1-one, (346) (Z)-2-(7-aminomethyl-3,3-dimethyl-3,4-dihydro-(2H)-isoquinolin-1-ylidene)-1-phenylethan-1-one, (347) (Z)-2-(7-aminomethyl-6-methoxy-3,3-dimethyl-3,4-dihydro-(2H)-isoquinolin-1-ylidene)-1-(adamantan-1-yl)ethan-1-one, (348) (Z)-2-(7-aminomethyl-6-methoxy-3,3-dimethyl-3,4-dihydro-(2H)-isoquinolin-1-ylidene)-1-cyclohexylethan-1-one, (349) (Z)-2-(7-aminomethyl-3,3-dimethyl-3,4-dihydro-(2H)-isoquinolin-1-ylidene)-1-(adamantan-1-yl)ethan-1-one, (350) (Z)-2-(7-aminomethyl-6-methoxy-3,3-dimethyl-3,4-dihydro-(2H)-isoquinolin-1-ylidene)-1-cycloheptylethan-1-one, (351) (Z)-2-(7-aminomethyl-3,3,6-trimethyl-3,4-dihydro-(2H)-isoquinolin-1-ylidene)-1-(adamantan-1-yl)ethan-1-one, (352) (Z)-2-(7-aminomethyl-3,3-dimethyl-3,4-dihydro-(2H)-isoquinolin-1-ylidene)-1-cyclohexylethan-1-one, (353) (Z)-2-(7-aminomethyl-3,3-dimethyl-3,4-dihydro-(2H)-isoquinolin-1-ylidene)-1-cycloheptylethan-1-one, (354) (Z)-2-(7-aminomethyl-3,3,6-trimethyl-3,4-dihydro-(2H)-isoquinolin-1-ylidene)-1-cyclohexylethan-1-one, (355) (Z)-2-(7-aminomethyl-3,3,6-trimethyl-3,4-dihydro-(2H)-isoquinolin-1-ylidene)-1-cycloheptylethan-1-one, (356) (Z)-2-(7-cyano-3,3-dimethyl-3,4-dihydro-(2H)-isoquinolin-1-ylidene)-1-(adamantan-1-yl)ethan-1-one, (357) (Z)-2-(7-cyano-3,3-dimethyl-3,4-dihydro-(2H)-isoquinolin-1-ylidene)-1-cyclohexylethan-1-one, (358) (Z)-2-(7-cyano-3,3-dimethyl-3,4-dihydro-(2H)-isoquinolin-1-ylidene)-1-cycloheptylethan-1-one, (359) (Z)-2-(7-(morpholin-4-yl)methyl-3,3-dimethyl-3,4-dihydro-(2H)-isoquinolin-1-ylidene)-1-(naphthalen-1-yl)ethan-1-one, (360) (Z)-2-(7-(morpholin-4-yl)methyl-3,3-dimethyl-3,4-dihydro-(2H)-isoquinolin-1-ylidene)-1-phenylethan-1-one, (361) (Z)-2-(7-(piperidin-1-yl)methyl-3,3-dimethyl-3,4-dihydro-(2H)-isoquinolin-1-ylidene)-1-phenylethan-1-one, (362) (Z)-2-(7-(N-methyl-N-(2-dimethylaminoethyl)aminomethyl)-3,3-dimethyl-3,4-dihydro-(2H)-isoquinolin-1-ylidene)-1-phenylethan-1-one, (363) (Z)-2-(7-(N-(2-hydroxyethyl)-N-methylaminomethyl)-3,3-dimethyl-3,4-dihydro-(2H)-isoquinolin-1-ylidene)-1-phenylethan-1-one, (364) (Z)-2-(7-(N-cyclohexylaminomethyl)-3,3-dimethyl-3,4-dihydro-(2H)-isoquinolin-1-ylidene)-1-phenylethan-1-one, (365) (Z)-2-(6-(morpholin-4-yl)methyl-3,3-dimethyl-3,4-dihydro-(2H)-isoquinolin-1-ylidene)-1-phenylethan-1-one, (366) (Z)-2-(6-dimethylaminomethyl-3,3-dimethyl-3,4-dihydro-(2H)-isoquinolin-1-ylidene)-1-phenylethan-1-one, (367) (Z)-2-(6-methylaminomethyl-3,3-dimethyl-3,4-dihydro-(2H)-isoquinolin-1-ylidene)-1-phenylethan-1-one, (368) (Z)-2-(7-dimethylaminomethyl-3,3-dimethyl-3,4-dihydro-(2H)-isoquinolin-1-ylidene)-1-phenylethan-1-one, (369) (Z)-2-(7-dimethylaminomethyl-6-methoxy-3,3-dimethyl-3,4-dihydro-(2H)-isoquinolin-1-ylidene)-1-(adamantan-1-yl)ethan-1-one, (370) (Z)-2-(6-methoxy-7-methylaminomethyl-3,3-dimethyl-3,4-dihydro-(2H)-isoquinolin-1-ylidene)-1-(adamantan-1-yl)ethan-1-one, (371) (Z)-2-(7-methylaminomethyl-3,3-dimethyl-3,4-dihydro-(2H)-isoquinolin-1-ylidene)-1-(adamantan-1-yl)ethan-1-one, (372) (Z)-2-(6-methoxy-7-methylaminomethyl-3,3-dimethyl-3,4-dihydro-(2H)-isoquinolin-1-ylidene)-1-cycloheptylethan-1-one, (373) (Z)-2-(6-chloro-7-dimethylaminomethyl-3,3-dimethyl-3,4-dihydro-(2H)-isoquinolin-1-ylidene)-1-(adamantan-1-yl)ethan-1-one, (374) (Z)-2-(7-methylaminomethyl-3,3,6-trimethyl-3,4-dihydro-(2H)-isoquinolin-1-ylidene)-1-(adamantan-1-yl)ethan-1-one, (375) (Z)-2-(7-dimethylaminomethyl-3,3,6-trimethyl-3,4-dihydro-(2H)-isoquinolin-1-ylidene)-1-(adamantan-1-yl)ethan-1-one, (376) (Z)-2-(6-chloro-7-methylaminomethyl-3,3-dimethyl-3,4-dihydro-(2H)-isoquinolin-1-ylidene)-1-(adamantan-1-yl)ethan-1-one, (377) (Z)-2-(7-methylaminomethyl-3,3-dimethyl-3,4-dihydro-(2H)-isoquinolin-1-ylidene)-1-cyclohexylethan-1-one, (378) (Z)-2-(6-chloro-7-methylaminomethyl-3,3-dimethyl-3,4-dihydro-(2H)-isoquinolin-1-ylidene)-1-cycloheptylethan-1-one, (379) (Z)-2-(6-chloro-7-dimethylaminomethyl-3,3-dimethyl-3,4-dihydro-(2H)-isoquinolin-1-ylidene)-1-cycloheptylethan-1-one, (380) (Z)-2-(7-methylaminomethyl-3,3,6-trimethyl-3,4-dihydro-(2H)-isoquinolin-1-ylidene)-1-cyclohexylethan-1-one, (381) (Z)-2-(7-methylaminomethyl-3,3-dimethyl-3,4-dihydro-(2H)-isoquinolin-1-ylidene)-1-cycloheptylethan-1-one, (382) (Z)-2-(7-dimethylaminomethyl-3,3,6-trimethyl-3,4-dihydro-(2H)-isoquinolin-1-ylidene)-1-cyclohexylethan-1-one, (383) (Z)-2-(6-chloro-7-methylaminomethyl-3,3-dimethyl-3,4-dihydro-(2H)-isoquinolin-1-ylidene)-1-cyclohexylethan-1-one, (384) (Z)-2-(6-chloro-7-dimethylaminomethyl-3,3-dimethyl-3,4-dihydro-(2H)-isoquinolin-1-ylidene)-1-cyclohexylethan-1-one, (385) (Z)-2-(7-methylaminomethyl-3,3,6-trimethyl-3,4-dihydro-(2H)-isoquinolin-1-ylidene)-1-cycloheptylethan-1-one, (386) (Z)-2-(7-dimethylaminomethyl-3,3,6-trimethyl-3,4-dihydro-(2H)-isoquinolin-1-ylidene)-1-cycloheptylethan-1-one, (387) (Z)-2-(6-hydroxymethyl-3,3-dimethyl-3,4-dihydro-(2H)-isoquinolin-1-ylidene)-1-phenylethan-1-one, (388) (Z)-2-(7-hydroxymethyl-3,3-dimethyl-3,4-dihydro-(2H)-isoquinolin-1-ylidene)-1-phenylethan-1-one, (389) (Z)-2-(6-chloro-7-hydroxymethyl-3,3-dimethyl-3,4-dihydro-(2H)-isoquinolin-1-ylidene)-1-(adamantan-1-yl)ethan-1-one, (390) (Z)-2-(6-chloro-7-hydroxymethyl-3,3-dimethyl-3,4-dihydro-(2H)-isoquinolin-1-ylidene)-1-cyclohexylethan-1-one, (391) (Z)-2-(6-chloro-7-hydroxymethyl-3,3-dimethyl-3,4-dihydro-(2H)-isoquinolin-1-ylidene)-1-cycloheptylethan-1-one, (392) (Z)-2-(7-hydroxymethyl-6-methoxy-3,3-dimethyl-3,4-dihydro-(2H)-isoquinolin-1-ylidene)-1-(adamantan-1-yl)ethan-1-one, (393) (Z)-2-(7-hydroxymethyl-3,3-dimethyl-3,4-dihydro-(2H)-isoquinolin-1-ylidene)-1-(adamantan-1-yl)ethan-1-one, (394) (Z)-2-(7-hydroxymethyl-6-methoxy-3,3-dimethyl-3,4-dihydro-(2H)-isoquinolin-1-ylidene)-1-cyclohexylethan-1-one, (395) (Z)-2-(7-hydroxymethyl-6-methoxy-3,3-dimethyl-3,4-dihydro-(2H)-isoquinolin-1-ylidene)-1-cycloheptylethan-1-one, (396) (Z)-2-(7-hydroxymethyl-3,3,6-trimethyl-3,4-dihydro-(2H)-isoquinolin-1-ylidene)-1-(adamantan-1-yl)ethan-1-one, (397) (Z)-2-(7-hydroxymethyl-3,3-dimethyl-3,4-dihydro-(2H)-isoquinolin-1-ylidene)-1-cyclohexylethan-1-one, (398) (Z)-2-(7-hydroxymethyl-3,3,6-trimethyl-3,4-dihydro-(2H)-isoquinolin-1-ylidene)-1-cyclohexylethan-1-one, (399) (Z)-2-(7-hydroxymethyl-3,3-dimethyl-3,4-dihydro-(2H)-isoquinolin-1-ylidene)-1-cycloheptylethan-1-one, (400) (Z)-2-(7-hydroxymethyl-3,3,6-trimethyl-3,4-dihydro-(2H)-isoquinolin-1-ylidene)-1-cycloheptylethan-1-one, (401) (Z)-2-(3,3-dimethyl-3,4-dihydro-(2H)-isoquinolin-1-ylidene)-1-(4-acetylaminophenyl)ethan-1-one, (402) (Z)-2-(3,3-dimethyl-3,4-dihydro-(2H)-isoquinolin-1-ylidene)-1-(3-acetylaminophenyl)ethan-1-one, (403) (Z)-2-(3,3-dimethyl-3,4-dihydro-(2H)-isoquinolin-1-ylidene)-1-(3-mesylaminophenyl)ethan-1-one, (404) (Z)-2-(7-acetylamino-3,3-dimethyl-3,4-dihydro-(2H)-isoquinolin-1-ylidene)-1-phenylethan-1-one, (405) (Z)-2-(7-acetylamino-3,3-dimethyl-3,4-dihydro-(2H)-isoquinolin-1-ylidene)-1-(adamantan-1-yl)ethan-1-one, (406) (Z)-2-(7-mesylamino-3,3-dimethyl-3,4-dihydro-(2H)-isoquinolin-1-ylidene)-1-phenylethan-1-one, (407) (Z)-2-(7-mesylamino-3,3-dimethyl-3,4-dihydro-(2H)-isoquinolin-1-ylidene)-1-(adamantan-1-yl)ethan-1-one, (408) (Z)-2-(6-methylcarbamoyl-3,3-dimethyl-3,4-dihydro-(2H)-isoquinolin-1-ylidene)-1-phenylethan-1-one, (409) (Z)-2-(6-dimethylcarbamoyl-3,3-dimethyl-3,4-dihydro-(2H)-isoquinolin-1-ylidene)-1-phenylethan-1-one, (410) (Z)-2-(6-carbamoyl-3,3-dimethyl-3,4-dihydro-(2H)-isoquinolin-1-ylidene)-1-phenylethan-1-one, (411) (Z)-2-(7-carbamoyl-3,3-dimethyl-3,4-dihydro-(2H)-isoquinolin-1-ylidene)-1-phenylethan-1-one, (412) (Z)-2-(7-methylcarbamoyl-3,3-dimethyl-3,4-dihydro-(2H)-isoquinolin-1-ylidene)-1-phenylethan-1-one, (413) (Z)-2-(7-dimethylcarbamoyl-3,3-dimethyl-3,4-dihydro-(2H)-isoquinolin-1-ylidene)-1-phenylethan-1-one, (414) (Z)-2-(7-carbamoyl-3,3-dimethyl-3,4-dihydro-(2H)-isoquinolin-1-ylidene)-1-(adamantan-1-yl)ethan-1-one, (415) (Z)-2-(7-methylcarbamoyl-3,3-dimethyl-3,4-dihydro-(2H)-isoquinolin-1-ylidene)-1-(adamantan-1-yl)ethan-1-one, (416) (Z)-2-(7-dimethylcarbamoyl-3,3-dimethyl-3,4-dihydro-(2H)-isoquinolin-1-ylidene)-1-(adamantan-1-yl)ethan-1-one, (417) (Z)-2-(6-carbamoyl-3,3-dimethyl-3,4-dihydro-(2H)-isoquinolin-1-ylidene)-1-cyclohexylethan-1-one, (418) (Z)-2-(6-carbamoyl-3,3-dimethyl-3,4-dihydro-(2H)-isoquinolin-1-ylidene)-1-cycloheptylethan-1-one, (419) (Z)-2-(6-carbamoyl-3,3-dimethyl-3,4-dihydro-(2H)-isoquinolin-1-ylidene)-1-(adamantan-1-yl)ethan-1-one, (420) (Z)-2-(3,3-dimethyl-3,4-dihydro-(2H)-isoquinolin-1-ylidene)-1-(4-cyano-2-methoxyphenyl)ethan-1-one, (421) (Z)-2-(7-cyano-3,3-dimethyl-3,4-dihydro-(2H)-isoquinolin-1-ylidene)-1-phenylethan-1-one, (422) (Z)-2-(7-cyano-3,3,6-trimethyl-3,4-dihydro-(2H)-isoquinolin-1-ylidene)-1-(adamantan-1-yl)ethan-1-one, (423) (Z)-2-(7-cyano-3,3,6-trimethyl-3,4-dihydro-(2H)-isoquinolin-1-ylidene)-1-cyclohexylethan-1-one, (424) (Z)-2-(6-ethynyl-3,3-dimethyl-3,4-dihydro-(2H)-isoquinolin-1-ylidene)-1-phenylethan-1-one, (425) (Z)-2-(7-ethynyl-3,3-dimethyl-3,4-dihydro-(2H)-isoquinolin-1-ylidene)-1-phenylethan-1-one, (426) (Z)-2-(3,3-dimethyl-3,4-dihydro-(2H)-isoquinolin-1-ylidene)-1-(4-ethynylphenyl)ethan-1-one, (427) (Z)-2-(6-((E)-2-carboxyethenyl)-3,3-dimethyl-3,4-dihydro-(2H)-isoquinolin-1-ylidene)-1-phenylethan-1-one, (428) (Z)-2-(6-((E)-2-methoxycarbonylethenyl)-3,3-dimethyl-3,4-dihydro-(2H)-isoquinolin-1-ylidene)-1-phenylethan-1-one, (429) (Z)-2-(6-methoxycarbonyl-3,3-dimethyl-3,4-dihydro-(2H)-isoquinolin-1-ylidene)-1-phenylethan-1-one, (430) (Z)-2-(7-methoxycarbonyl-3,3-dimethyl-3,4-dihydro-(2H)-isoquinolin-1-ylidene)-1-phenylethan-1-one, (431) (Z)-2-(7-carboxy-6-chloro-3,3-dimethyl-3,4-dihydro-(2H)-isoquinolin-1-ylidene)-1-cyclohexylethan-1-one, (432) (Z)-2-(7-carboxy-6-chloro-3,3-dimethyl-3,4-dihydro-(2H)-isoquinolin-1-ylidene)-1-(adamantan-1-yl)ethan-1-one, (433) (Z)-2-(7-carboxy-6-chloro-3,3-dimethyl-3,4-dihydro-(2H)-isoquinolin-1-ylidene)-1-cycloheptylethan-1-one, (434) (Z)-2-(3,3,4,4-tetramethyl-3,4-dihydro-(2H)-isoquinolin-1-ylidene)-1-(4-cyanophenyl)ethan-1-one, (435) (Z)-2-(7-formylamino-3,3-dimethyl-3,4-dihydro-(2H)-isoquinolin-1-ylidene)-1-phenylethan-1-one, (436) (Z)-2-(6-formylamino-3,3-dimethyl-3,4-dihydro-(2H)-isoquinolin-1-ylidene)-1-phenylethan-1-one, (437) (Z)-2-(7-methylamino-3,3-dimethyl-3,4-dihydro-(2H)-isoquinolin-1-ylidene)-1-phenylethan-1-one, (438) (Z)-2-(6-methylamino-3,3-dimethyl-3,4-dihydro-(2H)-isoquinolin-1-ylidene)-1-phenylethan-1-one, (439) (Z)-2-(7-methylaminomethyl-3,3-dimethyl-3,4-dihydro-(2H)-isoquinolin-1-ylidene)-1-phenylethan-1-one, (440) (Z)-2-(6-t-butoxycarbonylamino-3,3-dimethyl-3,4-dihydro-(2H)-isoquinolin-1-ylidene)-1-phenylethan-1-one, (441) (Z)-2-(6-t-butoxycarbonylamino-3,3-dimethyl-3,4-dihydro-(2H)-isoquinolin-1-ylidene)-1-cyclohexylethan-1-one, (442) (Z)-2-(6-t-butoxycarbonylamino-3,3-dimethyl-3,4-dihydro-(2H)-isoquinolin-1-ylidene)-1-cycloheptylethan-1-one, (443) (Z)-2-(6-t-butoxycarbonylamino-3,3-dimethyl-3,4-dihydro-(2H)-isoquinolin-1-ylidene)-1-(adamantan-1-yl)ethan-1-one, (444) (Z)-2-(6-amino-3,3-dimethyl-3,4-dihydro-(2H)-isoquinolin-1-ylidene)-1-phenylethan-1-one, (445) (Z)-2-(6-amino-3,3-dimethyl-3,4-dihydro-(2H)-isoquinolin-1-ylidene)-1-cyclohexylethan-1-one, (446) (Z)-2-(6-amino-3,3-dimethyl-3,4-dihydro-(2H)-isoquinolin-1-ylidene)-1-cycloheptylethan-1-one, (447) (Z)-2-(6-amino-3,3-dimethyl-3,4-dihydro-(2H)-isoquinolin-1-ylidene)-1-(adamantan-1-yl)ethan-1-one, (448) (Z)-2-(7-dimethylamino-3,3-dimethyl-3,4-dihydro-(2H)-isoquinolin-1-ylidene)-1-phenylethan-1-one, (449) (Z)-2-(7-dimethylamino-6-methoxy-3,3-dimethyl-3,4-dihydro-(2H)-isoquinolin-1-ylidene)-1-(4-cyanophenyl)ethan-1-one, (450) (Z)-2-(7-dimethylamino-6-methoxy-3,3-dimethyl-3,4-dihydro-(2H)-isoquinolin-1-ylidene)-1-(adamantan-1-yl)ethan-1-one, (451) (Z)-2-(3,3-dimethyl-4-hydroxy-3,4-dihydro-(2H)-isoquinolin-1-ylidene)-1-phenylethan-1-one, (452) (Z)-2-(3,3-dimethyl-4-oxo-3,4-dihydro-(2H)-isoquinolin-1-ylidene)-1-phenylethan-1-one, (453) (Z)-2-(6-cyano-3,3-dimethyl-3,4-dihydro-(2H)-isoquinolin-1-ylidene)-1-cyclohexylethan-1-one, (454) (Z)-2-(6-cyano-3,3-dimethyl-3,4-dihydro-(2H)-isoquinolin-1-ylidene)-1-cycloheptylethan-1-one or (455) (Z)-2-(6-cyano-3,3-dimethyl-3,4-dihydro-(2H)-isoquinolin-1-ylidene)-1-(adamantan-1-yl)ethan-1-one, or a non-toxic salt thereof.

9. The compound according to claim 5, which is (1) (Z)-2-(3,3-dimethyl-3,4-dihydro-(2H)-isoquinolin-1-ylidene)-1-(furan-2-yl)ethan-1-one, (2) (Z)-2-(3,3-dimethyl-3,4-dihydro-(2H)-isoquinolin-1-ylidene)-1-(thiophen-2-yl)ethan-1-one, (3) (Z)-2-(3,3-dimethyl-3,4-dihydro-(2H)-isoquinolin-1-ylidene)-1-(quinolin-6-yl)ethan-1-one, (4) (Z)-2-(3,3-dimethyl-3,4-dihydro-(2H)-isoquinolin-1-ylidene)-1-(pyridin-3-yl)ethan-1-one, (5) (Z)-2-(3,3-dimethyl-3,4-dihydro-(2H)-isoquinolin-1-ylidene)-1-(pyridin-4-yl)ethan-1-one, (6) (Z)-2-(3,3-dimethyl-3,4-dihydro-(2H)-isoquinolin-1-ylidene)-1-(piperidin-4-yl)ethan-1-one, (7) (Z)-2-(3,3-dimethyl-3,4-dihydro-(2H)-isoquinolin-1-ylidene)-1-(3,5-dimethylisoxazol-4-yl)ethan-1-one, (8) (Z)-2-(3,3-dimethyl-3,4-dihydro-(2H)-isoquinolin-1-ylidene)-1-(5-methyl-2-phenyloxazol-4-yl)ethan-1-one, (9) (Z)-2-(3,3-dimethyl-3,4-dihydro-(2H)-isoquinolin-1-ylidene)-1-(4-methyl-2-phenylthiazol-5-yl)ethan-1-one,

(10) (Z)-2-(3,3-dimethyl-3,4-dihydro-(2H)-isoquinolin-1-ylidene)-1-(1-acetylpiperidin-4-yl)ethan-1-one,

(11) (Z)-2-(3,3-dimethyl-3,4-dihydro-(2H)-isoquinolin-1-ylidene)-1-(1-t-butoxycarbonylpiperidin-4-yl)ethan-1-one,

(12) (Z)-2-(3,3-dimethyl-3,4-dihydro-(2H)-isoquinolin-1-ylidene)-1-(1-mesylpiperidin-4-yl)ethan-1-one,

(13) (Z)-2-(3,3-dimethyl-3,4-dihydro-(2H)-isoquinolin-1-ylidene)-1-(thiazol-2-yl)ethan-1-one,

(14) (Z)-2-(3,3-dimethyl-3,4-dihydro-(2H)-isoquinolin-1-ylidene)-1-(pyrrol-2-yl)ethan-1-one,

(15) (Z)-2-(3,3-dimethyl-3,4-dihydro-(2H)-isoquinolin-1-ylidene)-1-(pyrazin-2-yl)ethan-1-one,

(16) (Z)-2-(3,3-dimethyl-3,4-dihydro-(2H)-isoquinolin-1-ylidene)-1-(thiophen-3-yl)ethan-1-one,

(17) (Z)-2-(3,3-dimethyl-3,4-dihydro-(2H)-isoquinolin-1-ylidene)-1-(5-methylfuran-2-yl)ethan-1-one,

(18) (Z)-2-(3,3-dimethyl-3,4-dihydro-(2H)-isoquinolin-1-ylidene)-1-(5-methylthiophen-2-yl)ethan-1-one,

(19) (Z)-2-(3,3-dimethyl-3,4-dihydro-(2H)-isoquinolin-1-ylidene)-1-(2,5-dimethylfuran-3-yl)ethan-1-one,

(20) (Z)-2-(3,3-dimethyl-3,4-dihydro-(2H)-isoquinolin-1-ylidene)-1-(5-cyanothiophen-2-yl)ethan-1-one,

(21) (Z)-2-(6-chloro-3,3-dimethyl-3,4-dihydro-(2H)-isoquinolin-1-ylidene)-1-(tetrahydropyran-4-yl)ethan-1-one,

(22) (Z)-2-(7-chloro-3,3-dimethyl-3,4-dihydro-(2H)-isoquinolin-1-ylidene)-1-(tetrahydropyran-4-yl) ethan-1-one,

(23) (Z)-2-(7-fluoro-3,3-dimethyl-3,4-dihydro-(2H)-isoquinolin-1-ylidene)-1-(tetrahydropyran-4-yl)ethan-1-one,

(24) (Z)-2-(3,3-dimethyl-3,4-dihydro-(2H)-isoquinolin-1-ylidene)-1-(2,5-dichlorothiophen-3-yl)ethan-1-one,

(25) (Z)-2-(3,3-dimethyl-3,4-dihydro-(2H)-isoquinolin-1-ylidene)-1-(tetrahydropyran-4-yl)ethan-1-one,

(26) (Z)-2-(3,3-dimethyl-3,4-dihydro-(2H)-isoquinolin-1-ylidene)-1-(isoquinolin-1-yl)ethan-1-one,

(27) (Z)-2-(3,3-dimethyl-3,4-dihydro-(2H)-isoquinolin-1-ylidene)-1-(quinolin-4-yl)ethan-1-one,

(28) (Z)-2-(3,3-dimethyl-3,4-dihydro-(2H)-isoquinolin-1-ylidene)-1-(quinolin-8-yl)ethan-1-one,

(29) (Z)-2-(6-bromo-3,3-dimethyl-3,4-dihydro-(2H)-isoquinolin-1-ylidene)-1-(pyridin-3-yl)ethan-1-one,

(30) (Z)-2-(6-carboxy-3,3-dimethyl-3,4-dihydro-(2H)-isoquinolin-1-ylidene)-1-(pyridin-3-yl)ethan-1-one,

(31) (Z)-2-(3,3-dimethyl-3,4-dihydro-(2H)-isoquinolin-1-ylidene)-1-(1-phenylsulfonylpiperidin-4-yl)ethan-1-one,

(32) (Z)-2-(3,3-dimethyl-3,4-dihydro-(2H)-isoquinolin-1-ylidene)-1-(1-ethylsulfonylpiperidin-4-yl)ethan-1-one,

(33) (Z)-2-(3,3-dimethyl-3,4-dihydro-(2H)-isoquinolin-1-ylidene)-1-(1-propylsulfonylpiperidin-4-yl)ethan-1-one,

(34) (Z)-2-(3,3-dimethyl-3,4-dihydro-(2H)-isoquinolin-1-ylidene)-1-(1-butylsulfonylpiperidin-4-yl)ethan-1-one,

(35) (Z)-2-(3,3-dimethyl-3,4-dihydro-(2H)-isoquinolin-1-ylidene)-1-(1-octylsulfonylpiperidin-4-yl)ethan-1-one,

(36) (Z)-2-(6-t-butoxycarbonylamino-3,3-dimethyl-3,4-dihydro-(2H)-isoquinolin-1-ylidene)-1-(pyridin-3-yl)ethan-1-one, or

(37) (Z)-2-(6-amino-3,3-dimethyl-3,4-dihydro-(2H)-isoquinolin-1-ylidene)-1-(pyridin-3-yl)ethan-1-one, or a non-toxic salt thereof.

10. The compound according to claim 6, which is (1) (Z)-2-(3,3-dimethyl-4-oxa-3,4-dihydro-(2H)-isoquinolin-1-ylidene)-1-phenylethan-1-one, (2) (Z)-2-(7-chloro-3,3-dimethyl-4-oxa-3,4-dihydro-(2H)-isoquinolin-1-ylidene)-1-cycloheptylethan-1-one, (3) (Z)-2-(7-chloro-3,3-dimethyl-4-oxa-3,4-dihydro-(2H)-isoquinolin-1-ylidene)-1-cyclohexylethan-1-one, (4) (Z)-2-(7-chloro-3,3-dimethyl-4-oxa-3,4-dihydro-(2H)-isoquinolin-1-ylidene)-1-(2-methoxyphenyl)ethan-1-one, (5) (Z)-2-(7-chloro-3,3-dimethyl-4-oxa-3,4-dihydro-(2H)-isoquinolin-1-ylidene)-1-(4-cyanophenyl)ethan-1-one, (6) (Z)-2-(3,3,7-trimethyl-4-oxa-3,4-dihydro-(2H)-isoquinolin-1-ylidene)-1-cyclohexylethan-1-one, (7) (Z)-2-(7-methoxy-3,3-dimethyl-4-oxa-3,4-dihydro-(2H)-isoquinolin-1-ylidene)-1-cyclohexylethan-1-one, (8) (Z)-2-(7-fluoro-3,3-dimethyl-4-oxa-3,4-dihydro-(2H)-isoquinolin-1-ylidene)-1-cyclohexylethan-1-one, (9) (Z)-2-(3,3,7-trimethyl-4-oxa-3,4-dihydro-(2H)-isoquinolin-1-ylidene)-1-(2-methoxyphenyl)ethan-1-one,

(10) (Z)-2-(7-methoxy-3,3-dimethyl-4-oxa-3,4-dihydro-(2H)-isoquinolin-1-ylidene)-1-(2-methoxyphenyl)ethan-1-one,

(11) (Z)-2-(7-fluoro-3,3-dimethyl-4-oxa-3,4-dihydro-(2H)-isoquinolin-1-ylidene)-1-(2-methoxyphenyl)ethan-1-one,

(12) (Z)-2-(3,3,7-trimethyl-4-oxa-3,4-dihydro-(2H)-isoquinolin-1-ylidene)-1-cycloheptylethan-1-one,

(13) (Z)-2-(7-methoxy-3,3-dimethyl-4-oxa-3,4-dihydro-(2H)-isoquinolin-1-ylidene)-1-cycloheptylethan-1-one,

(14) (Z)-2-(7-fluoro-3,3-dimethyl-4-oxa-3,4-dihydro-(2H)-isoquinolin-1-ylidene)-1-cycloheptylethan-1-one,

(15) (Z)-2-(3,3,7-trimethyl-4-oxa-3,4-dihydro-(2H)-isoquinolin-1-ylidene)-1-(4-cyanophenyl)ethan-1-one,

(16) (Z)-2-(7-methoxy-3,3-dimethyl-4-oxa-3,4-dihydro-(2H)-isoquinolin-1-ylidene)-1-(4-cyanophenyl)ethan-1-one,

(17) (Z)-2-(7-fluoro-3,3-dimethyl-4-oxa-3,4-dihydro-(2H)-isoquinolin-1-ylidene)-1-(4-cyanophenyl)ethan-1-one,

(18) (Z)-2-(3,3-dimethyl-4-oxa-3,4-dihydro-(2H)-isoquinolin-1-ylidene)-1-(2-methoxyphenyl)ethan-1-one,

(19) (Z)-2-(3,3-dimethyl-4-oxa-3,4-dihydro-(2H)-isoquinolin-1-ylidene)-1-(4-cyanophenyl)ethan-1-one,

(20) (Z)-2-(3,3-dimethyl-4-oxa-3,4-dihydro-(2H)-isoquinolin-1-ylidene)-1-cycloheptylethan-1-one,

(21) (Z)-2-(3,3-dimethyl-4-oxa-3,4-dihydro-(2H)-isoquinolin-1-ylidene)-1-cyclohexylethan-1-one,

(22) (Z)-2-(3,3,7-trimethyl-4-oxa-3,4-dihydro-(2H)-isoquinolin-1-ylidene)-1-phenylethan-1-one,

(23) (Z)-2-(7-methoxy-3,3-dimethyl-4-oxa-3,4-dihydro-(2H)-isoquinolin-1-ylidene)-1-phenylethan-1-one,

(24) (Z)-2-(7-chloro-3,3-dimethyl-4-oxa-3,4-dihydro-(2H)-isoquinolin-1-ylidene)-1-phenylethan-1-one,

(25) (Z)-2-(7-fluoro-3,3-dimethyl-4-oxa-3,4-dihydro-(2H)-isoquinolin-1-ylidene)-1-phenylethan-1-one,

(26) (Z)-2-(3,3-dimethyl-4-oxa-3,4-dihydro-(2H)-isoquinolin-1-ylidene)-1-(adamantan-1-yl)ethan-1-one,

(27) (Z)-2-(7-fluoro-3,3-dimethyl-4-oxa-3,4-dihydro-(2H)-isoquinolin-1-ylidene)-1-(adamantan-1-yl)ethan-1-one,

(28) (Z)-2-(7-chloro-3,3-dimethyl-4-oxa-3,4-dihydro-(2H)-isoquinolin-1-ylidene)-1-(adamantan-1-yl)ethan-1-one,

(29) (Z)-2-(7-methoxy-3,3-dimethyl-4-oxa-3,4-dihydro-(2H)-isoquinolin-1-ylidene)-1-(adamantan-1-yl)ethan-1-one,

(30) (Z)-2-(3,3,7-trimethyl-4-oxa-3,4-dihydro-(2H)-isoquinolin-1-ylidene)-1-(adamantan-1-yl)ethan-1-one,

(31) (Z)-2-(6-chloro-3,3-dimethyl-4-oxa-3,4-dihydro-(2H)-isoquinolin-1-ylidene)-1-(4-cyanophenyl)ethan-1-one,

(32) (Z)-2-(6-chloro-3,3-dimethyl-4-oxa-3,4-dihydro-(2H)-isoquinolin-1-ylidene)-1-phenylethan-1-one,

(33) (Z)-2-(6-chloro-3,3-dimethyl-4-oxa-3,4-dihydro-(2H)-isoquinolin-1-ylidene)-1-cyclohexylethan-1-one,

(34) (Z)-2-(6-chloro-3,3-dimethyl-4-oxa-3,4-dihydro-(2H)-isoquinolin-1-ylidene)-1-cycloheptylethan-1-one,

(35) (Z)-2-(6-chloro-3,3-dimethyl-4-oxa-3,4-dihydro-(2H)-isoquinolin-1-ylidene)-1-(adamantan-1-yl)ethan-1-one,

(36) (Z)-2-(6-methoxy-3,3-dimethyl-4-oxa-3,4-dihydro-(2H)-isoquinolin-1-ylidene)-1-(4-cyanophenyl)ethan-1-one,

(37) (Z)-2-(6-methoxy-3,3-dimethyl-4-oxa-3,4-dihydro-(2H)-isoquinolin-1-ylidene)-1-phenylethan-1-one,

(38) (Z)-2-(6-methoxy-3,3-dimethyl-4-oxa-3,4-dihydro-(2H)-isoquinolin-1-ylidene)-1-(adamantan-1-yl)ethan-1-one,

(39) (Z)-2-(3,3,6-trimethyl-4-oxa-3,4-dihydro-(2H)-isoquinolin-1-ylidene)-1-phenylethan-1-one,

(40) (Z)-2-(3,3,6-trimethyl-4-oxa-3,4-dihydro-(2H)-isoquinolin-1-ylidene)-1-(4-cyanophenyl)ethan-1-one, or (41) (Z)-2-(3,3,6-trimethyl-4-oxa-3,4-dihydro-(2H)-isoquinolin-1-ylidene)-1-(adamantan-1-yl)ethan-1-one, or a non-toxic salt thereof.

11. The compound according to claim 7, which is (Z)-2-(3,3-dimethyl-4-oxa-3,4-dihydro-(2H)-isoquinolin-1-ylidene)-1-(tetrahydropyran-4-yl)ethan-1-one, or a non-toxic salt thereof.

12. The compound according to claim 3, which is (1) (Z)-2-(6,6-dimethyl-4,5,6,7-tetrahydrothiopheno[3,2-c]pyridin-4-ylidene)-1-phenylethan-1-one, (2) (Z)-2-(6,6-dimethyl-4,5,6,7-tetrahydrothiopheno[3,2-c]pyridin-4-ylidene)-1-(adamantan-1-yl)ethan-1-one, (3) (Z)-2-(6,6-dimethyl-4,5,6,7-tetrahydrothiopheno[3,2-c]pyridin-4-ylidene)-1-(4-cyanophenyl)ethan-1-one, (4) (Z)-2-(2-chloro-6,6-dimethyl-4,5,6,7-tetrahydrothiopheno[3,2-c]pyridin-4-ylidene)-1-phenylethan-1-one, (5) (Z)-2-(2-chloro-6,6-dimethyl-4,5,6,7-tetrahydrothiopheno[3,2-c]pyridin-4-ylidene)-1-(adamantan-1-yl)ethan-1-one or (6) (Z)-2-(2-chloro-6,6-dimethyl-4,5,6,7-tetrahydrothiopheno[3,2-c]pyridin-4-ylidene)-1-(4-cyanophenyl)ethan-1-one, or a non-toxic salt thereof.

13. A cannabinoid (CB)2 receptor agonist comprising 3,4-dihydro isoquinoline derivative compound of formula (I) or a non-toxic salt thereof described in claim 1 as an active ingredient, and a carrier.

14. A method for the prophylaxis and/or treatment of asthma, nasal allergy, atopic dermatology, autoimmune diseases, rheumatoid arthritis, immune dysfunction, postoperative pain, or carcinomatous pain comprising administering to a subject in need thereof an effective amount of the compound of formula (I) or a non-toxic salt thereof described in claim 1 as an active ingredient.

* * * * *